(12) United States Patent
Barrangou et al.

(10) Patent No.: US 10,711,267 B2
(45) Date of Patent: Jul. 14, 2020

(54) RECOMBINANT TYPE I CRISPR-CAS SYSTEM

(71) Applicant: North Carolina State University, Raleigh, NC (US)

(72) Inventors: Rodolphe Barrangou, Raleigh, NC (US); Claudio Hidalgo-Cantabrana, Cary, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 16/582,269

(22) Filed: Sep. 25, 2019

(65) Prior Publication Data

US 2020/0102551 A1    Apr. 2, 2020

Related U.S. Application Data

(60) Provisional application No. 62/739,666, filed on Oct. 1, 2018.

(51) Int. Cl.
*C12N 15/10* (2006.01)
*C12N 15/90* (2006.01)
*C12N 9/22* (2006.01)

(52) U.S. Cl.
CPC ............. *C12N 15/102* (2013.01); *C12N 9/22* (2013.01); *C12N 15/90* (2013.01)

(58) Field of Classification Search
None
See application file for complete search history.

(56) References Cited

U.S. PATENT DOCUMENTS

| | | | |
|---|---|---|---|
| 9,023,649 B2 | 5/2015 | Mali et al. | |
| 9,260,723 B2 | 2/2016 | Mali et al. | |
| 2006/0199190 A1* | 9/2006 | Russell | C12Q 1/689 435/6.11 |
| 2009/0007301 A1 | 1/2009 | Wintz et al. | |
| 2013/0288251 A1 | 10/2013 | Horvath et al. | |
| 2014/0068797 A1 | 3/2014 | Doudna et al. | |
| 2014/0113376 A1 | 4/2014 | Sorek et al. | |
| 2014/0186958 A1 | 7/2014 | Zhang et al. | |
| 2014/0273233 A1 | 9/2014 | Chen et al. | |
| 2014/0356867 A1 | 12/2014 | Peter et al. | |
| 2014/0356956 A1 | 12/2014 | Church et al. | |
| 2015/0050699 A1 | 2/2015 | Siksnys et al. | |
| 2015/0056628 A1 | 2/2015 | Russell et al. | |
| 2015/0064138 A1 | 3/2015 | Lu et al. | |
| 2015/0093473 A1 | 4/2015 | Barrangou et al. | |
| 2015/0098954 A1 | 4/2015 | Hyde et al. | |
| 2015/0132263 A1 | 5/2015 | Liu et al. | |
| 2015/0291961 A1 | 10/2015 | Siksnys et al. | |
| 2015/0315576 A1 | 11/2015 | Caliando et al. | |
| 2015/0353901 A1 | 12/2015 | Liu et al. | |
| 2016/0017366 A1 | 1/2016 | Chen et al. | |
| 2016/0024510 A1 | 1/2016 | Bikard et al. | |
| 2016/0186152 A1 | 6/2016 | Brouns et al. | |
| 2016/0186213 A1 | 6/2016 | Zhang et al. | |
| 2016/0289700 A1 | 10/2016 | Barrangou et al. | |
| 2016/0298096 A1 | 10/2016 | Charpentier et al. | |
| 2016/0333348 A1 | 11/2016 | Clube et al. | |
| 2016/0345578 A1* | 12/2016 | Barrangou | C12N 15/1034 |
| 2017/0002339 A1 | 1/2017 | Barrangou et al. | |
| 2017/0028083 A1 | 2/2017 | Beisel et al. | |
| 2017/0196225 A1 | 7/2017 | Clube et al. | |
| 2017/0246221 A1 | 8/2017 | Clube et al. | |
| 2018/0064114 A1 | 3/2018 | Clube | |
| 2018/0064115 A1 | 3/2018 | Clube et al. | |
| 2018/0070594 A1 | 3/2018 | Clube et al. | |
| 2018/0084785 A1 | 3/2018 | Clube | |
| 2018/0084786 A1 | 3/2018 | Clube | |
| 2018/0146681 A1 | 5/2018 | Clube | |
| 2018/0155729 A1 | 6/2018 | Beisel et al. | |
| 2018/0200387 A1 | 7/2018 | Porteus | |
| 2018/0273937 A1 | 9/2018 | Beisel et al. | |

FOREIGN PATENT DOCUMENTS

| | | |
|---|---|---|
| EP | 2860267 | 4/2015 |
| WO | 2006/113709 | 10/2006 |
| WO | 2010/054154 | 1/2010 |
| WO | 2010/075424 | 7/2010 |
| WO | 2013/098244 | 7/2013 |
| WO | 2013/141680 | 9/2013 |
| WO | 2013/176772 | 11/2013 |
| WO | 2013/188522 | 12/2013 |
| WO | 2013/188638 | 12/2013 |
| WO | 2014/022702 | 2/2014 |
| WO | 2014/065596 | 5/2014 |

(Continued)

OTHER PUBLICATIONS

Ajdic et al. "hypothetical protein SMU_1405c [*Steptococcus mutans* UA159]", Proc. Natl. Acad. Sci. U.S.A. 99 (22), 14434-14439 (2002) URL: https://www.ncbi.nlm.nih.gov/protein/NP_721764.1/, retrieved Jul. 20, 2018.
Barrangou R. "CRISPR-Cas systems and RNA-guided interference", Wiley interdisciplinary reviews, RNA (2013) 4: pp. 267-278.
Barrangou R., et al. "CRISPR-Cas systems: prokaryotes upgrade to adaptive immunity", Mol. Cell (2014) 54(2): pp. 234-244.
Barrangou R., et al. "CRISPR: new horizons in phage resistance and strain identification" Annu Rev Food Sci Technol (2012) 3, pp. 143-162.
Barrangou, R. "Diversity of CRISPR-Cas Immune systems and molecular machines", Genome Biology (2015) 16:247, 11 pages.
Barrangou, R., et al. "CRISPR provides acquired resistance agains viruses in prokaryotes", Science (2007) 315(5819): pp. 1709-1712.
Beisel CL et al. A CRISPR design for next-generation antimicrobials. Genome Biology, 2014; 15: 516, 4 pages.

(Continued)

*Primary Examiner* — Mindy G Brown
(74) *Attorney, Agent, or Firm* — Myers Bigel, P.A.

(57) ABSTRACT

This invention relates to recombinant Clustered Regularly Interspaced Short Palindromic Repeats (CRISPR) arrays and recombinant nucleic acid constructs encoding Type I-E CASCADE complexes as well as plasmids, retroviruses and bacteriophage comprising the same.

19 Claims, 25 Drawing Sheets

Specification includes a Sequence Listing.

(56) References Cited

FOREIGN PATENT DOCUMENTS

| | | |
|---|---|---|
| WO | 2014/071235 | 5/2014 |
| WO | 2014/093479 | 6/2014 |
| WO | 2014/110006 | 7/2014 |
| WO | 2014/113493 | 7/2014 |
| WO | 2014/124226 | 8/2014 |
| WO | 2014/144155 | 9/2014 |
| WO | 2014/144592 | 9/2014 |
| WO | 2014/150624 | 9/2014 |
| WO | 2014/186686 | 11/2014 |
| WO | 2014/191128 | 12/2014 |
| WO | 2014/191518 | 12/2014 |
| WO | 2014/201015 | 12/2014 |
| WO | 2014/204727 | 12/2014 |
| WO | 2015/021353 | 2/2015 |
| WO | 2015/026886 | 2/2015 |
| WO | 2015/034872 | 3/2015 |
| WO | 2015/035139 | 3/2015 |
| WO | 2015/040402 | 3/2015 |
| WO | 2015/053995 | 4/2015 |
| WO | 2015/066119 | 5/2015 |
| WO | 2015/070193 | 5/2015 |
| WO | 2015/077290 | 5/2015 |
| WO | 2015/089277 | 6/2015 |
| WO | 2015/089406 | 6/2015 |
| WO | 2015/089486 | 6/2015 |
| WO | 2015/112896 | 7/2015 |
| WO | 2015/116686 | 8/2015 |
| WO | 2015/119941 | 8/2015 |
| WO | 2015/139139 | 9/2015 |
| WO | 2015/148680 | 10/2015 |
| WO | 2015/153791 | 10/2015 |
| WO | 2015/153889 | 10/2015 |
| WO | 2015/153940 | 10/2015 |
| WO | 2015/155686 | 10/2015 |
| WO | 2015/159068 | 10/2015 |
| WO | 2015/159086 | 10/2015 |
| WO | 2015/159087 | 10/2015 |
| WO | 2015/160683 | 10/2015 |
| WO | 2015/189693 | 12/2015 |
| WO | 2015/200555 | 12/2015 |
| WO | 2016/084088 | 6/2016 |
| WO | 2016/177682 | 11/2016 |
| WO | 2016/196361 | 12/2016 |
| WO | 2016/205276 | 12/2016 |
| WO | 2017/027423 | 2/2017 |
| WO | 2017/058751 | 4/2017 |
| WO | 2017/066497 | 4/2017 |
| WO | 2017/112620 | 6/2017 |
| WO | 2017/147507 | 8/2017 |

OTHER PUBLICATIONS

Beloglazova et al. "Structure and activity of the Cas3 HD nuclease MJ0384, an effector enzyme of the CRISPR interference" The EMBO Journal, 30:4616-4627 (2011).

Bhaya et al. "CRISPR-Cas Systems in Bacteria and Acrhaea: Versatile Small RNAs for Adaptive Defence and Regulation", Annu. Rev. Genet. (2011) 45: pp. 273-297.

Bikard D. et al. "Programmable repression and activation of bacterial gene expression using an engineered CRISPR-Cas system" Nucleic Acids Res (2013) 41(15): pp. 7429-7437.

Bikard D., et al. "CRISPR interference can prevent natural transformation and virulence acquisition during in vivo bacterial infection", Cell Host & Microbe (2012), 10 pages.

Bikard D., et al. "Exploiting CRISPR-Cas nucleases to produce sequence-specific antimicrobial", Nature Biotechnology 2014, 6 pages.

Briner AE, Barrangou R. "Lactobacillus buchneri Genotyping on the Basis of Clustered Regularly Interspaced Short Palindromic Repeat (CRISPR) Locus Diversity", Appl Environ Microbiol. 80:994-1001, (2014).

Briner et al. "Guide RNA Functional Modules Direct Cas9 Activity and Orthogonality", Molecular Cell. (2014) 56(2): pp. 333-339.

Brouns SJJ, et al. "Small CRISPR RNAs guide antiviral defense in prokaryotes", Science (2008) 321:5891, pp. 960-964.

Carte et al. "The three major types of CRISPR-Cas systems function independently in CRISPR RNA biogenesis in *Streptococcus thermophilus*", Molecular Microbiology, 93(1), pp. 98.112 (2014).

Chylinski et al. "Classification and evolution of type II CRISPR-Cas Systems", Nucleic Acids Research, (2014) 15 pages.

Chylinski Krzysztof et al., "The tracrRNA and Cas9 families of type II CRISPR-Cas immunity systems", RNA biology, 10.5, 13 pages (2013).

Citorik R., et al. "Sequence-specific antimicrobials using efficiently delivered RNA-guided nucleases", Nature Biotechnology 2014, 7 pages.

Claesson MJ et al. NCBI reference sequence NC_007929, direct submission Dec. 16, 2005, p. 1 (2005).

Cochrane Kyla et al., "Complete genome sequences and analysis of the *Fusobacterium nucleatum* subspecies animals 7-1 bacteriophage PHIFunu1 and PHIFunu2", Anaerobe, 38:125-129 (2016).

Cong et al. "Multiplex Genome Engineering Using CRISPR/Cas Systems" Science (2013) vol. 339 (6121): pp. 819-823.

Cong et al. Supplementary Materials for "Multiplex Genome Engineering Using CRISPR/Cas Systems" Science (2013) vol. 339 (6121): pp. 819-823.

Crawley et al. "Characterizing the activity of abundant, diverse and olive CRISPR-Cas systems in lactobacilli" Scientific Reports, 8.1-12(2018).

Darmon E, Leach DF "Bacterial Genome Instability", Micorbiol. Mol. Biol. Rev. (2014) vol. 78, pp. 1-39.

Database GenBank [online]. NBI, U.S. National Library of Medcine, Aug. 5, 2014. "CRISPR-associated protein, Csn1 family [Bifidobacterium bombi DSM 19703]," XP002785852, retrieved from NCBI accession No. GenBank: KFF31259, Database accession No. KFF31259. 1 page.

Deltcheva, E. et al. "CRISPR RNA maturation by trans-encoded small RNA and host factor RNase III", Nature, vol. 471, (Mar. 2011) pp. 602-607.

Doench et al. "Rational design of highly active sgRNAs for CRISPR-Cas9-mediated gene inactivation", Nature Biotechnology, 32:12 (2014) 8 pages.

Dupuis ME et al., "CRISPR-Cas and restriction-madificatson systems are compatible and increase phage resistance" Nat Commun., vol. 4, p. 2087 (2013).

Edgar R., et al. "The *Escherichia coli* CRISPR System Protects from Lysogenization, Lysogens, and Prophage Induction", Journal of Bacteriology (2010), vol. 192, No. 23, pp. 6292-6294.

Estvelt et al. "Orthogonal Cas9 proteins for RNA-guided gene regulation and editing", Nature Methods, 10:11 (2013) pp. 1116-1121.

Final Office Action, U.S. Appl. No. 15/032,985, dated Feb. 5, 2019 31 pages.

Final Office Action, U.S. Appl. No. 15/113,655, dated Jul. 30. 2018, 8 pages.

Final Office Action, U.S. Appl. No. 15/302,655, dated Nov. 2, 2018, 21 pp.

Fonfara, I. et al, "Phylogeny of Cas9 determines functional exchangeability of dual-RNA and Cas9 among orthologous type II CRISPR-Cas systems", Nucleic Acids Res (2013) 14 pages.

Fu et al. "Improving CRISPR-Cas nuclease specificity using truncated guide RNAs", Nature Biotechnology, 32:3 (2013) 9 pages.

Garneau JE, et al. "The CRISPR/Cas bacterial immune systems cleaves bacteriophage and plasmid DNA" Nature (2010) 468(7320): pp. 67-71.

Gasiunas et al. "Cas9-crRNA ribonucleoprotein complex mediates specific DNA cleavage for adaptive immunity in bacteria", Proc. Natl. Acad. Sci. (2012), 109:E2579-E2586.

Gilbert et al. "Genome-Scale CRISPR-Mediated Control of Gene Repression and Activation", Cell, 159 (2014) pp. 647-661.

Gilbert, L. A. et al. "CRISPR-Mediated Modular RNA-Guided Regulaton of Transcription in Eukanirotes", Cell 154, (2013) pp. 444-451.

Gomaa AA, et al. "Programmable Removal of Bacterial Strains by Use of Genome-Targeting CRISPR-Cas Systems", mBio (2014), 5(1):e00928-13.

(56) References Cited

OTHER PUBLICATIONS

Grissa et al. "The CRISPRdb database and tools to display CRISPIRs and to generate dictionaries of spacers and repeats" BMC Bioinformatics, 8(172):1-10 (2007).
Haurwitz et al. "Sequence- and Structure-Specific RNA Processing by a CRISPR Endonuclease", Science (2010) 329: pp. 1355-1358.
Heinl, Stefan et al. "Insights into the completely annotated genome of Lactobacillus buchneri CD034, a strain isolated from stable grass silage", Journal of Biotechnology, 161:153-166 (2012).
Horvath and Barrangou "CRISPR/Cas, the immune system of Bacteria and Archaea", Science (2010) 327, pp. 167-170.
Horvath, P. et al. "Diversity, Activity, and Evolution of CRISPR Loci in *Streptococcus thermophilus*", J Bacteriol. 190 (2008) pp. 1401-1412.
Hsu et al. "DNA targeting specificity of RNA-guided Cas9 nucleases", Nature Biotechnology, 31:9 (2013) pp. 827-834.
International Search Report and Written Opinion for PCT/US2015/047138 dated Nov. 26, 2015, 10 pages.
International Search Report and Written Opinion, PCT/US2018/034322, dated Sep. 13, 2018, 7 pages.
Jiang, W. et al. "Dealing with the Evolutionary Downside of CRISPR Immunity: Bacteria and Beneficial Plasmids". PLOS Genetics (2013) vol. 9, issue 9, 13 pages.
Jiang, W. et al. "RNA-guided editing of bacterial genemas using CRISPR-Cas systems", Nat. Biotechnol. (2013) vol. 31, pp. 233-239.
Jinek et al. "A Programmable Dual-RNA-Guide DNA Endonuclease in Adaptive Bacterial Immunity", Science (2012) vol. 337, pp. 816-821.
Jineic, M. et al.,"Structures of Cas9 endonucleases reveal RNA-mediated conformational activation", Science (2014) vol. 343, 6176, 28 pages.
Karvelis, Tautvydas et al., "crRNA and tracerRNK guide Cas9-mediated DNA interference in *Streptococcus thermophilus*," RNA Biology, 2013, vol. 10. Issue 5, pp. 841-851.
Karvelis, Tautvydas et al., "Programmable DNA cleavage in vitro by Cas9," Biochem. Soc. Trans. 2013, vol. 41, part 6, pp. 1401-1406.
Kobayashi K. et al. "Essential Bacillus subtilis genes", Proc. Natl. Acad. Sci. U.S.A. (2003) vol. 100, pp. 4678-4683.
Labrie SJ et al. "Bacteriphage resistance mechanisms" Nat. Rev. Microbiol (2010) vol. 8, pp. 317-327.
Liu S et al. Complete genome sequence of Lactobacillus buchneri NRRL B-30929, a novel strain from a commercial ethanol plant. Journal of Bacteriology. Aug. 2011; 193(15): 4019-4020.
Liu S et al. NCBI (2011) CRISPR-associated protein, Csn1 family [Lactobacillus buchneri], pp. 1-3.
Luo, M. et al., "Repurposing endogenous type I CRISPR-Cas systems for programmable gene repression", Nucleic Acid Research (2014) 8 pages.
Magadan et al. "Cleavage of Phage DNA by the *Streptococcus thermophilus* CRISPR3-Cas System", PloS One (2012) 7:e40913. 8 pages.
Mahillon J. et al. "Insertion sequences", Microbiol Mol Biol Rev (1998) vol. 62(3): pp. 725-774.
Makarova and Koonin "Annotation and Classification of CRISPR-Cas Systems", Methods Mol Biol. (2015), 1311: pp. 47-75.
Makarova et al. "An updated evolutionary classification of CRISPR-Cas systems", Nat Rev Microbiol. 13:722-736 (2015), 15 pages.
Makarova et al. "Unification of Cas protein families and a simple scenario for the origin and evolution of CRISPRCas systems", Biol Direct. (2011) vol. 6:38, 27 pages.
Makarova, K. S. et al. "Evolution and classification of the CRISPR-Cas system", Nat Rev Microbiol (2011) vol. 9, pp. 467-477.
Marcotte, H. et al. "Proteomes—Lactobacillus gasseri DSM 14869", NCBI Reference Sequence CP006803, (2013) URL: https://www.uniprot.org/proteomes/UP000217220, retrieved Jul. 20, 2018.
Marraffini and Sontheimer "CRISPR Interference Limits Horizontal Gene Transfer in Staphylococci by Targeting DNA", Science (2008) vol. 322: pp. 1843-1845.
Milani C et al. Genomic encyclopedia of type strains of the genus Bifidobacterium. Applied and Environmental Microbiology. Oct. 2014; 80(20): 6290-6302.
Mofica, F. et al. "Short motif sequences determine the targets of the prokaryotic CRISPR defence system", Microbiology (2009) vol. 155, 8 pages.
Nale Janet Y. et al., "Diverse temperate bacteriophage carriage in Clostridium difficile 027 strains", PloS One, 7(5) 1-9 (2012).
Nishimasu, H., et al. "Crystal Structure of Cas9 in Complex with Guide RNA and Target DNA", Cell (2014) vol. 156, pp. 935-949.
Notification and Transmittal of International Search Report and Written Opinion of the International Searching Authority for International Application No. PCT/IB2015/052515; dated Oct. 1, 2015, 12 pages.
Notification of International Preliminary Report on Patentability corresponding to International Application No. PCT/IB2015/052515; dated Oct. 12, 2016, 7 pages.
International Search Report and Written Opinion of the International Searching Authority, or the Declaration, PCT/US2016/034812, dated Sep. 15, 2016, 9 pages.
Novagen "pCDF-1b Vector" Sep. 10, 2003, Retrieved from the Internet on Sep. 1, 2015, at http://www.helmholtz-muenchen.de/fieadmin/PEPF/pCDF_vectors/pCDF-1b_map.pdf, 2 pages.
Oh JH and van Pijkeren JP "CRISPR-Cas9-assisted recombineering in Lactobacillus reuteri", Nucleic Acids Res (2014) vol. 10.1093/nar/gku623.
Qi, L. S. et al. "Repurposing CRISPR as an RNA-Guided Platform for Sequence-Specific Control of Gene Expression", Cell 152, 1173-1183 (2013), 11 pages.
Ramakrishna Suresh et al. "Gene disruption by cell-penetrating peptide-mediated delivery of Cas9 protein and guide RNA", Genome Research, 24:1020-1027 (2014).
Rath et al. "The CRISPR-Cas immune system: Biology, mechanisms and applications" Biochimie, 117:119-128 (2015).
Sander JD, and Joung JK. "CRISPR-Cas systems for editing, regulating and targeting genomes", Nat. Biotechnol. (2014) vol. 32, pp. 347-355.
Sapranauskas et al. "The *Streptococcus thermophilus* CRISPR/Cas system provided immunity in *Escherichia coli*", Nucleic Acid Res. (2011) vol. 39: pp. 9275-9282.
Seed Kimberley D. et al., "A bacteriophage encodes its own CRISPR/Cas adaptive response to evade host innate Immunity", Nature, 494:7438, pp. 489-491 (2013).
Selle K. Brrangou R. "Harnessing CRISPR-Cas systems for bacterual genome editing", Cell Press: Trends Microbiol. (2015) vol. 23(4): pp. 225-232.
Selle, K. et al. "CRISPR-based screening of genomic island excision events in bacteria", Proc Natl Acad Sci USA, (2015); 112(26): pp. 8076-8081.
Selle, K. et al., "CRISPR-Based Technologies and the Future of Food Science", Journal of Food Science (2015) vol. 80, 6 pages.
Semenova et al. "Interference by clustered regularly interspaced short palindormic repeat (CRISPR) RNA is governed by a seed sequence", PNAS, 108:205 (2011) 6 pages.
Sinkuna, T. et al. "In vitro reconstitution of Cascade-mediated CRISPR Immunity in *Streptococcus thermophilus*", The EMBO Journal (2013) vol. 32, pp. 385-394.
Spath et al. "Lactobacillus plantarum and Lactobacillus buchneri as Expression Systems: Evaluation of Different Origins of Replication for the Design of Suitable Shuttle Vectors" Mol. Biotechnol., 52:40-48 (2012).
Stern, A. et al., "Self-targeting by CRISPR: gene regulation or autoimmunity", Cell Press: Trend in Genetics, (2010) vol. 26, No. 8, 6 pages.
Sternberg et al. "DNA interrogation by the CRISPR RNA-guided endonuclease Cas9", Nature, vol. 507, (2014) 17 pages.
Terns and Terns "CRISPR-based adaptive immune systems", Curr. Opin. Microbiol. (2011) vol. 14: pp. 321-327.
Uchiyama Jumpei et al., "Characterization of Helicobacter pylori bacteriophage KHP30", Applied and environmental microbiology, 79(10):3176-3184 (2013).

(56) References Cited

OTHER PUBLICATIONS

Vercoe RB, et al. "Cytotoxic chromosomal targeting by CRISPR/Cas systems can reshape bacterial genomes and expel or remodel pathogenicity island", PloS Genet (2013) vol. 9(4):e1003454.
Westra et al. "The CRISPRs, They are A-Changin': How Prokaryotes Generate Adaptive Immunity", Annu. Rev. Genet. (2012) vol. 46: pp. 311-339.
Wiedenheft et al. "RNA-guided complex from a bacterial immune system enhances target recognition through seed sequence interactions", PNAS, 108:36 (2011) 7 pages.
International Search Report and Written Opinion corresponding to International Application No. PCT/US2016/037493.
International Search Report and Written Opinion regarding International Application No. PCT/US2016/067657, dated Mar. 6, 2017, 9 pages.
Beloglazova et al. "Structure and activity of the Cas3 HD nuclease MJ0384, an effector enzyme of the CRISPR Interference" The EMBO Journal, 30(22):4616-4627 (2011).
Final Office Action, U.S. Appl. No. 15/507,176, dated Jan. 16, 2019, 30 pages.
Gasiunas et al. "Molecular mechanisms of CRISPR-mediated microbial immunity" Cellular and Molecular Life Sciences, 71:449-465 (2014).
GenBank Accession No. FN692037.1, "Lactobacillus crispatus ST1 complete genome, strain ST1" Feb. 27, 2015.
Hidalgo-Cantabrana et al. "Genome editing using the endogenous type I CRISPR-Cas system in Lactobacillus crispatus" PNAS, 116)32):15774-15783 (2019).
International Preliminary Report on Patentability Notification, PCT/US2018/034322, dated Dec. 5, 2019, 7 pages.
International Serach Report and Written Opinion corresponding to PCT/US2019/52883, dated Dec. 23, 2019, 9 pages.
International Search Report and Written Opinion corresponding to PCT/US2019/52878, dated Dec. 27, 2019, 14 pages.
International Search Report and Written Opinion corresponding to PCT/US2019/52864, dated Dec. 17, 2019, 15 pages.
International Search Report and Written Opinion corresponding to PCT/US219/52861, dated Feb. 1, 2020, 18 pages.
Ojala et al. "Comparative genomics of Lactobacillus cirspatus suggest novel mechanisms for the competitive exclusion of Garnerella vaginalis" BNC Genomics, 15:1070 (2014).
Westra et al. "CRISPR Immunity Relies on the Consecutive Binding and Degradation of Negatively Supercoiled Invader DNA by Cascade and Casts" Molecular Cell, 46:595-605 (2012).
Yosef et al. "High-temperature protein G is essential for activity of the *Escherichia coli* clustered regularly interspaced short palindromic repeats (CRISPR)/Cas system" Proc Natl Acad Sci, 108(50):20136-20141 (2011).
Sanozky-Dawes et al. "Occurrence and activity of a type II CRISPR-Cas system in Lactobacillus gasseri" Microbiology, 161:1752-1761 2015.
Anderson et al. "Lactobacillus gasseri CRISPR-Cas9 characterization In Vitro reveales a flexible mode of protospacer-adjacent motif recognition" PLOS ONE, 13(2) 14 pages 2018.

\* cited by examiner

Fig. 9 (con't)
C
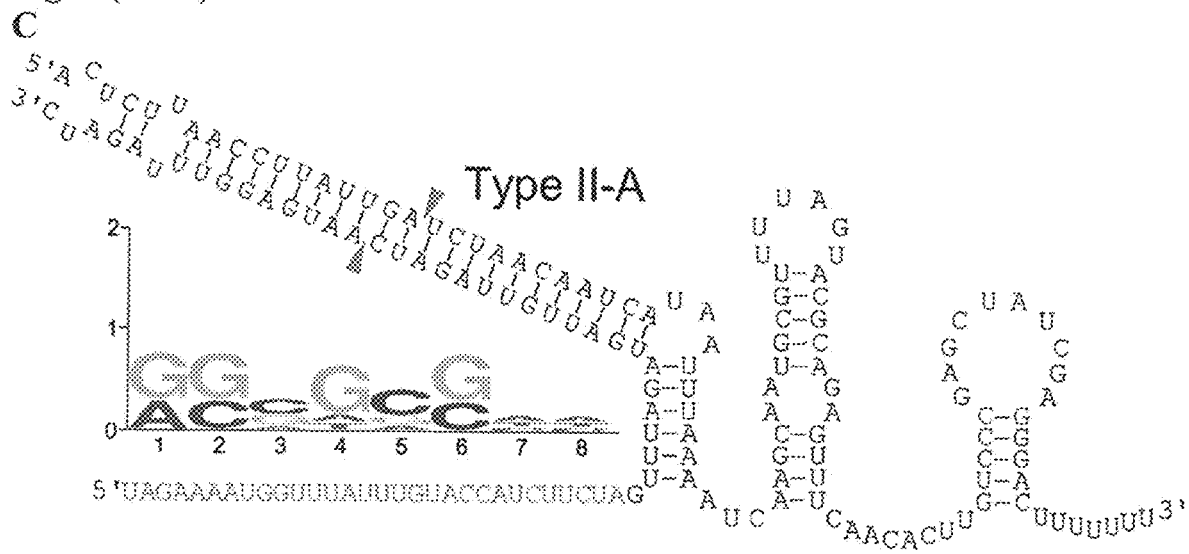
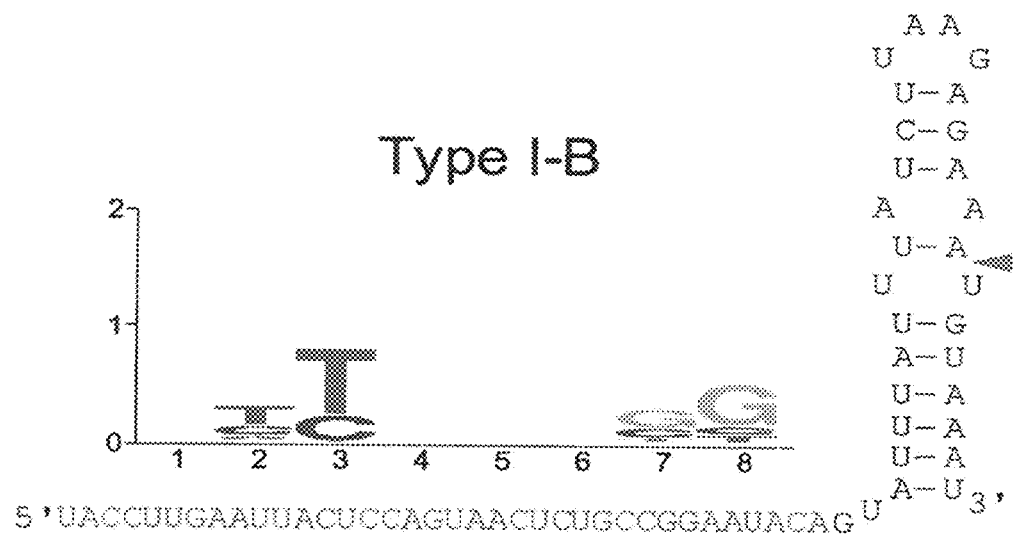
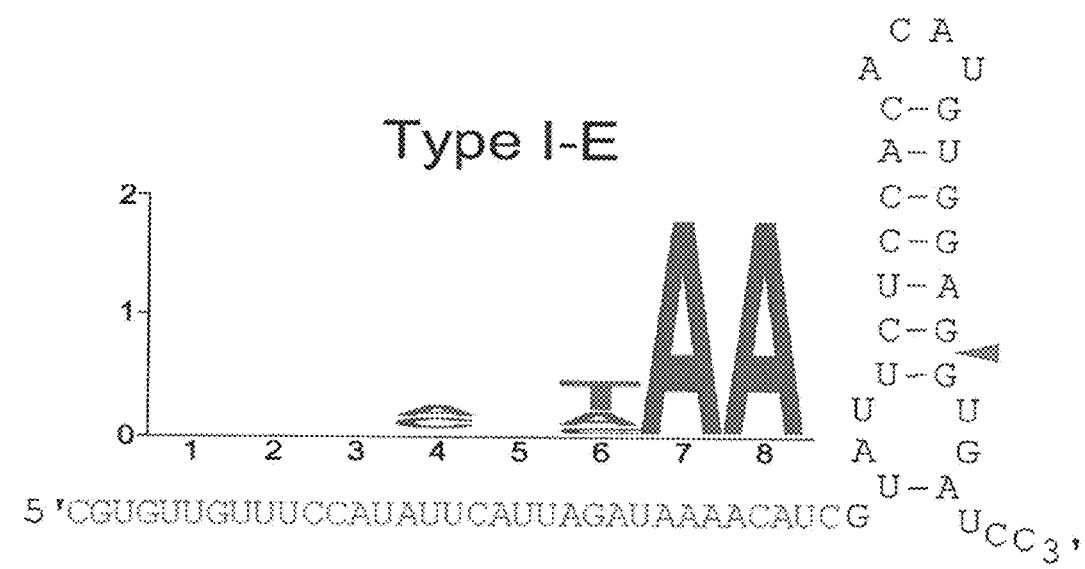

Fig. 10 (con't)
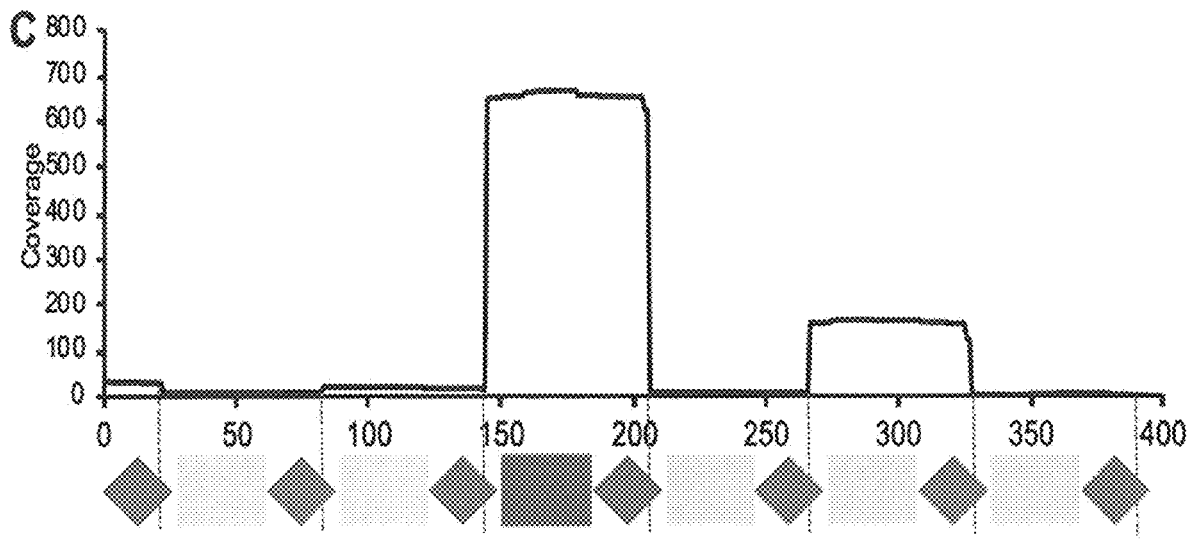
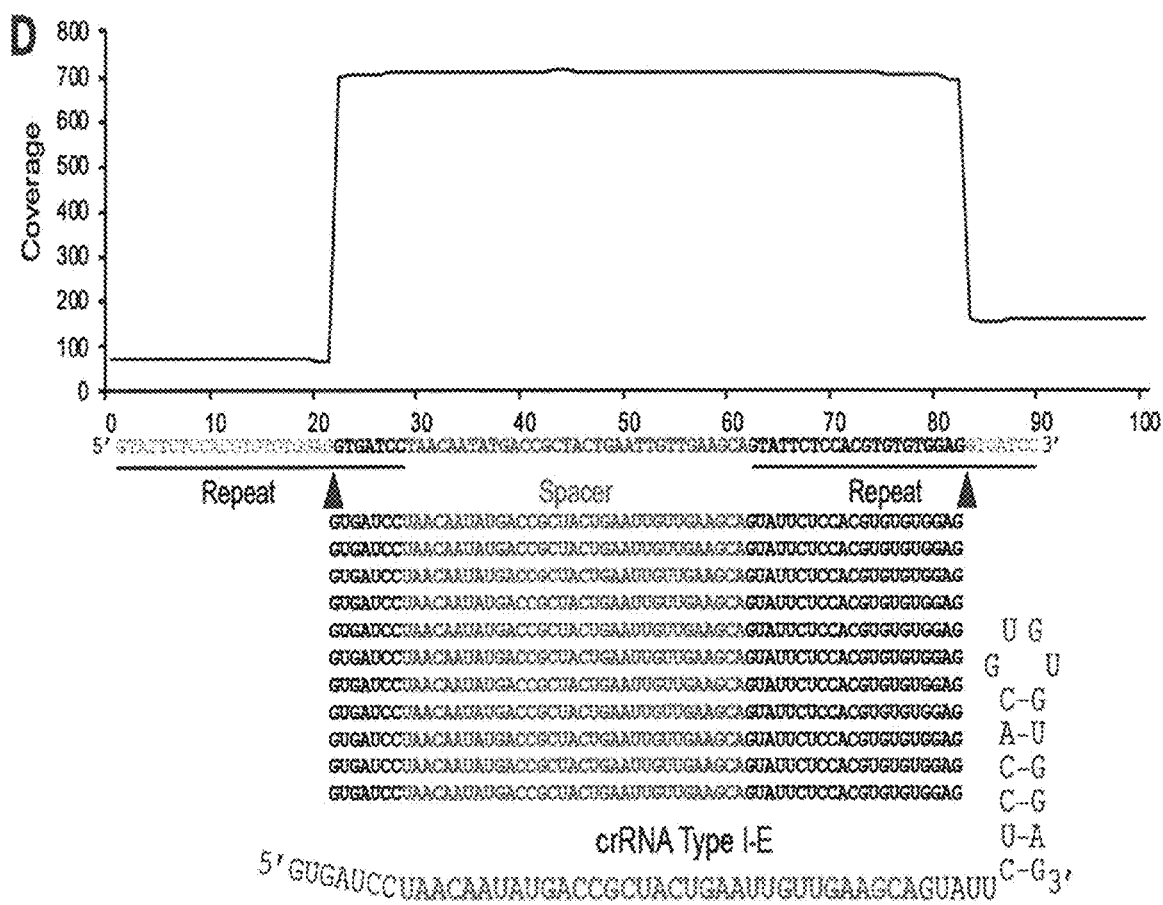

Fig. 10 (con't)
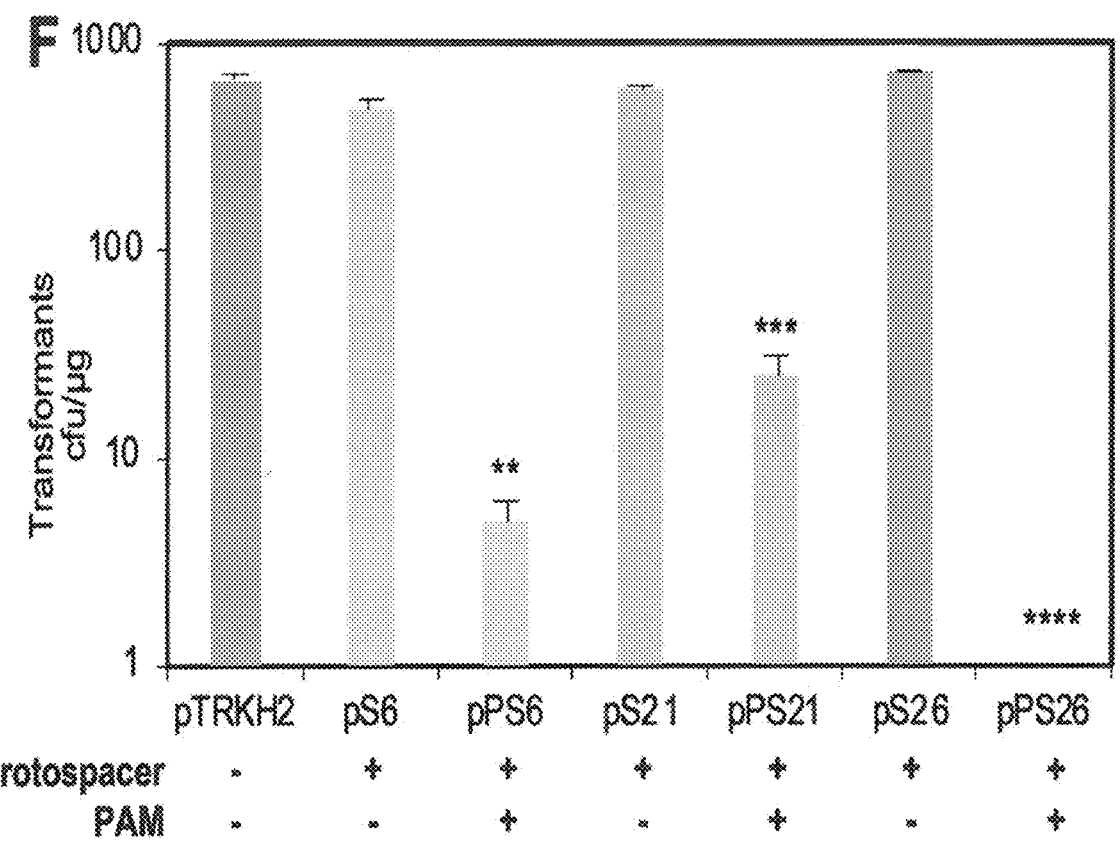

Fig. 12 (con't)
A (con't)
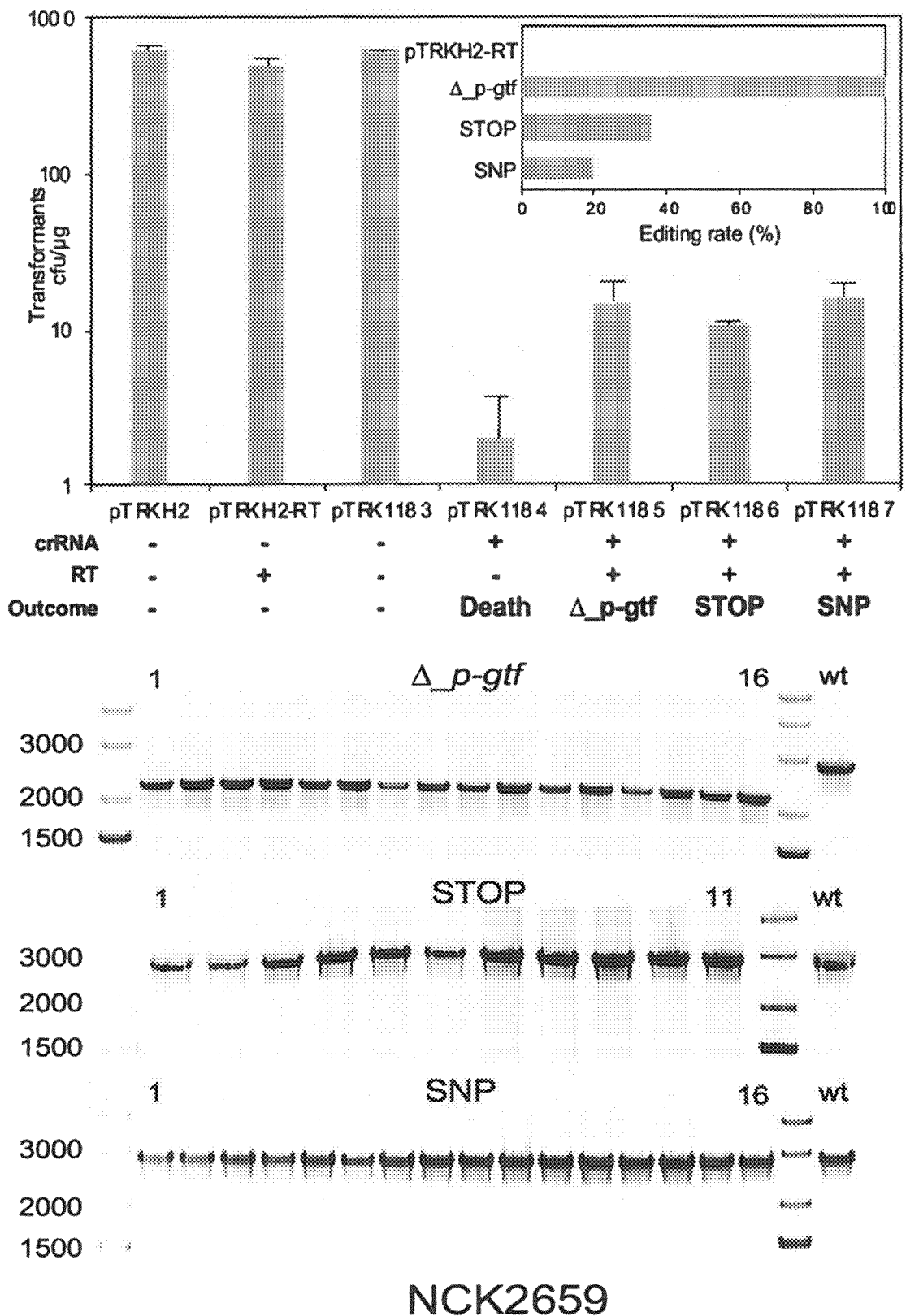
NCK2659

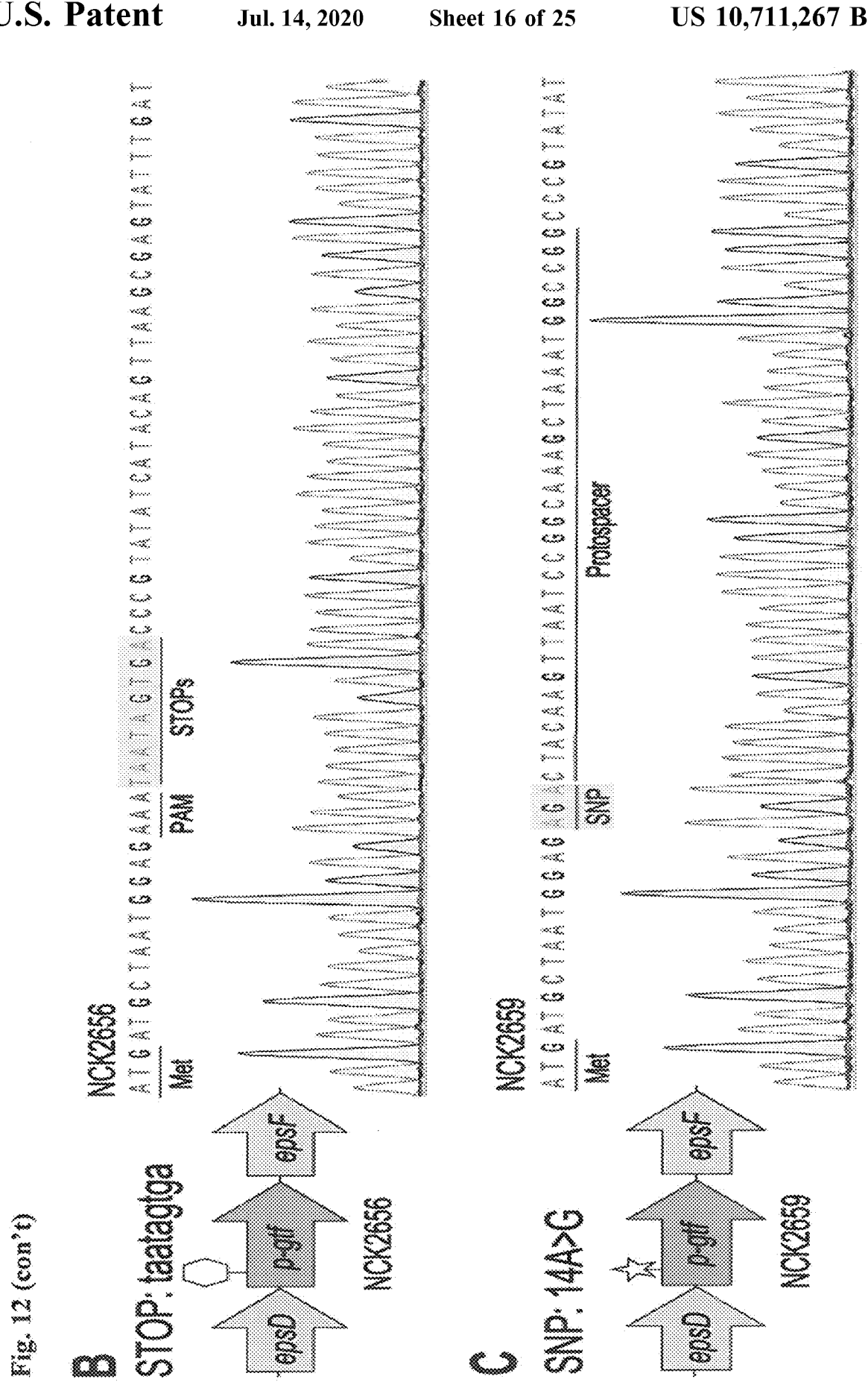
Fig. 12 (con't)

Fig. 12 (con't)
D
NCK1350
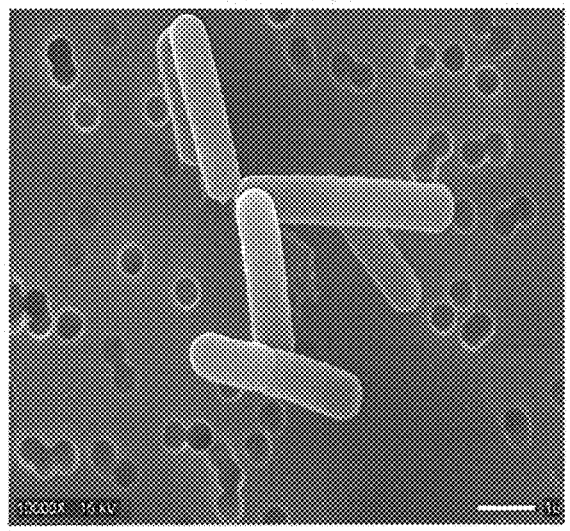
NCK2635
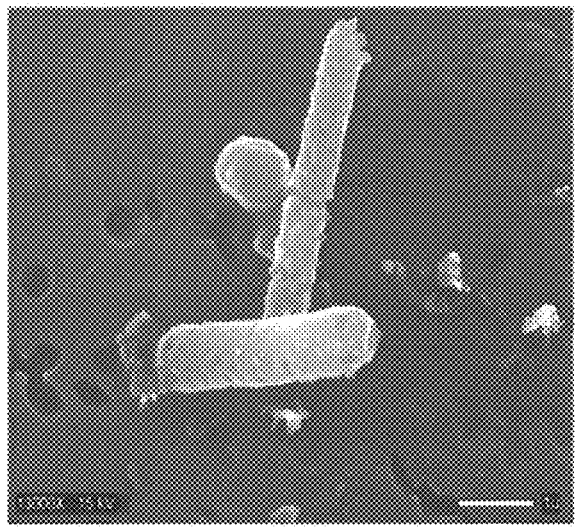
NCK2656
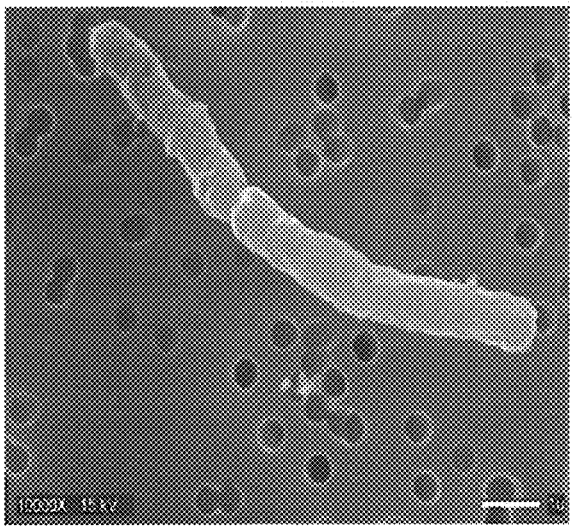
NCK2659
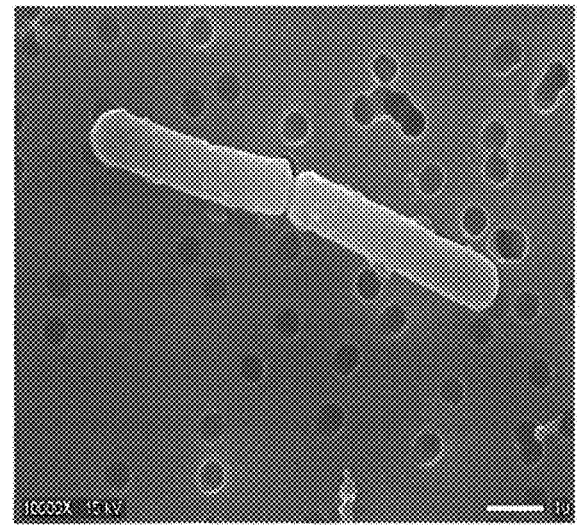

Fig. 13 (con't)
A (con't)
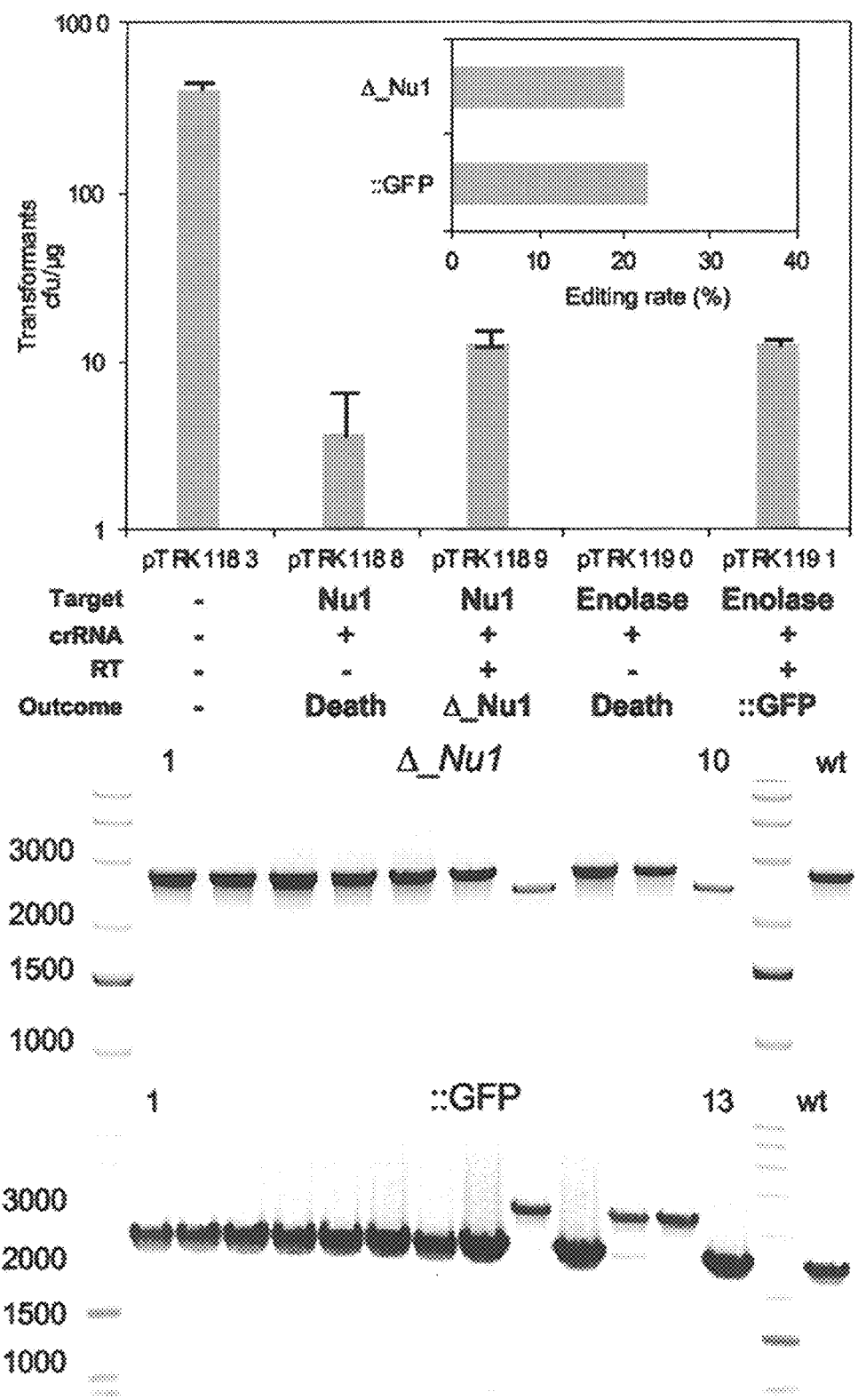

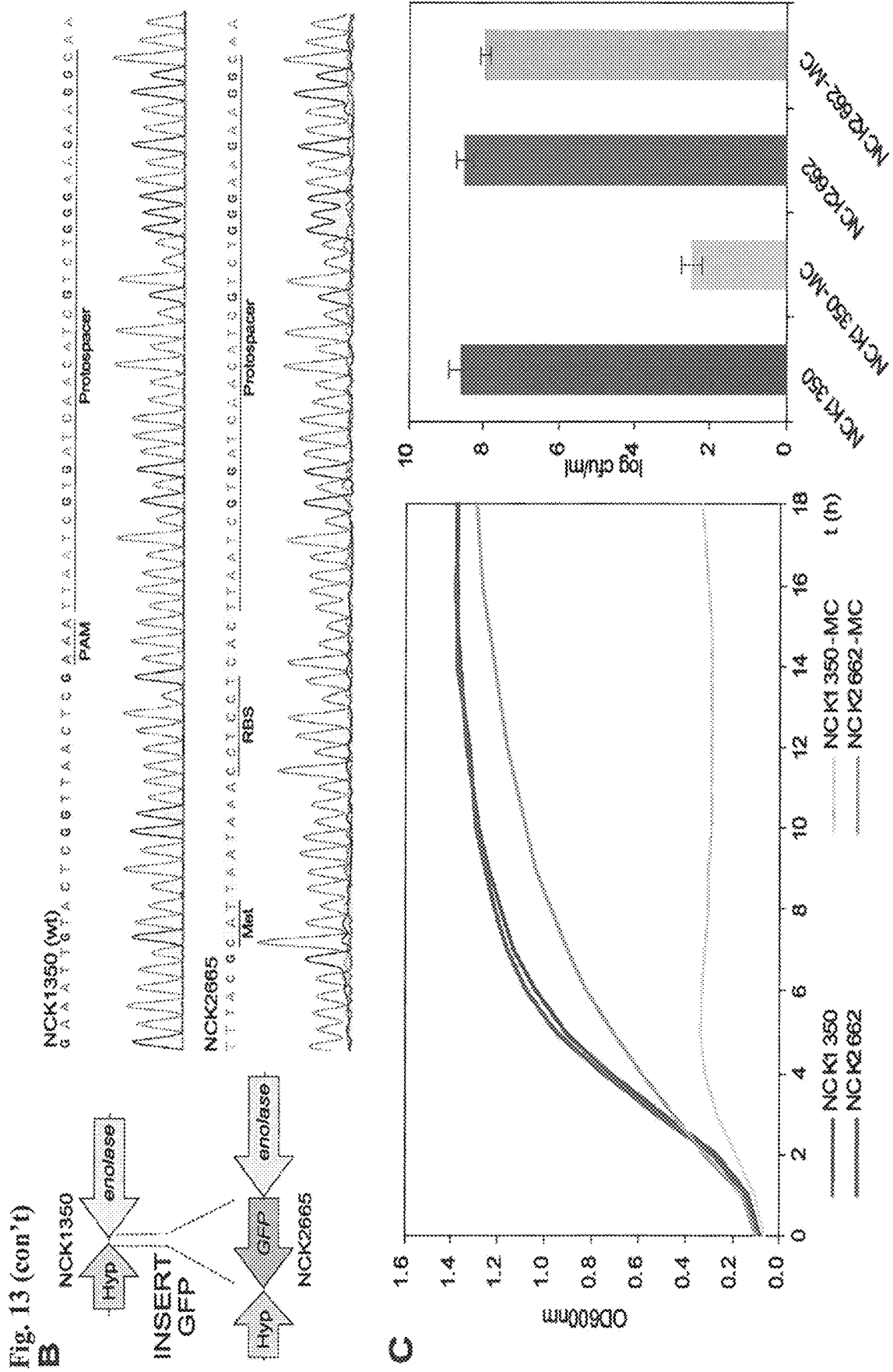
Fig. 13 (con't)

Fig. 13 (con't)
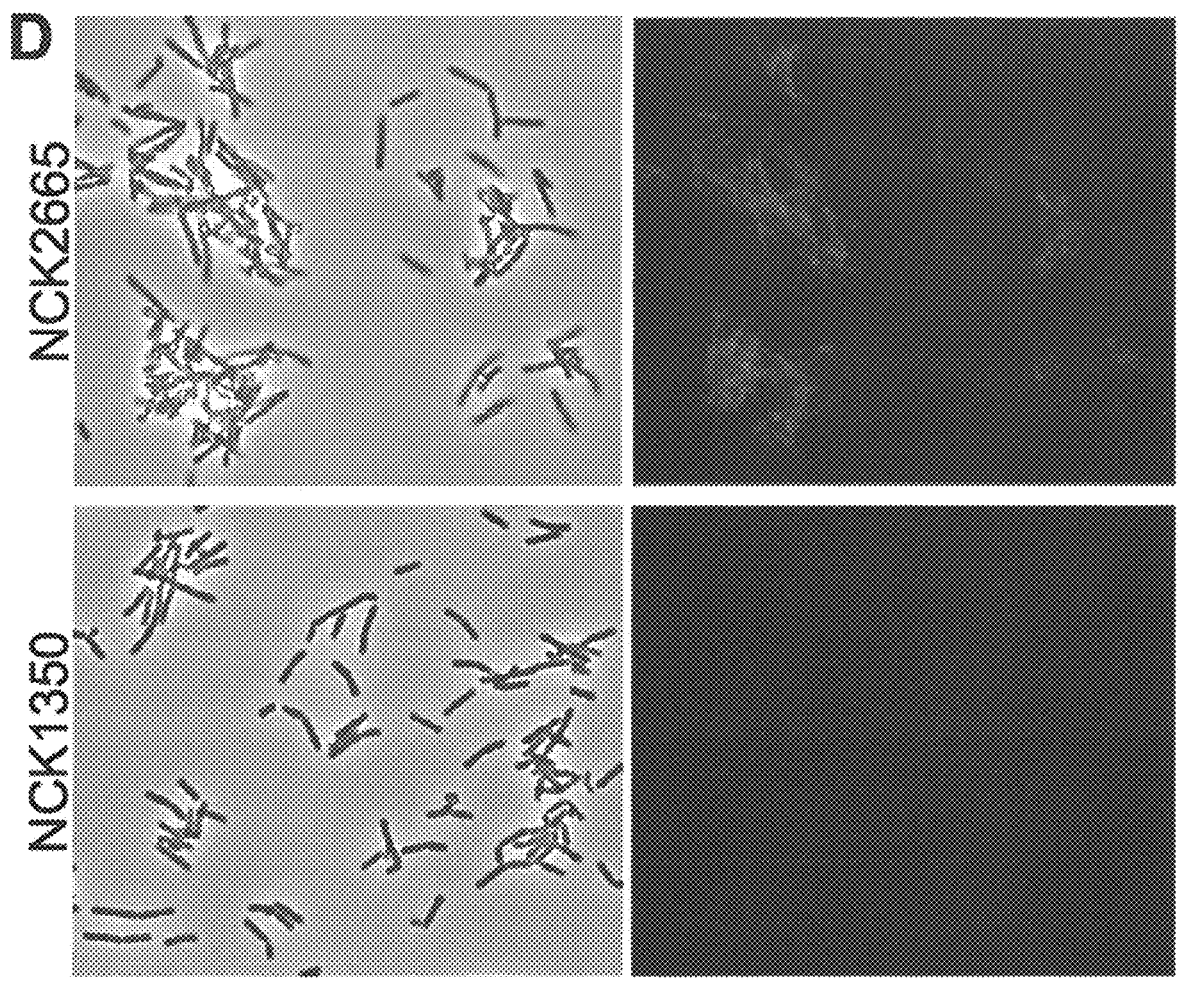

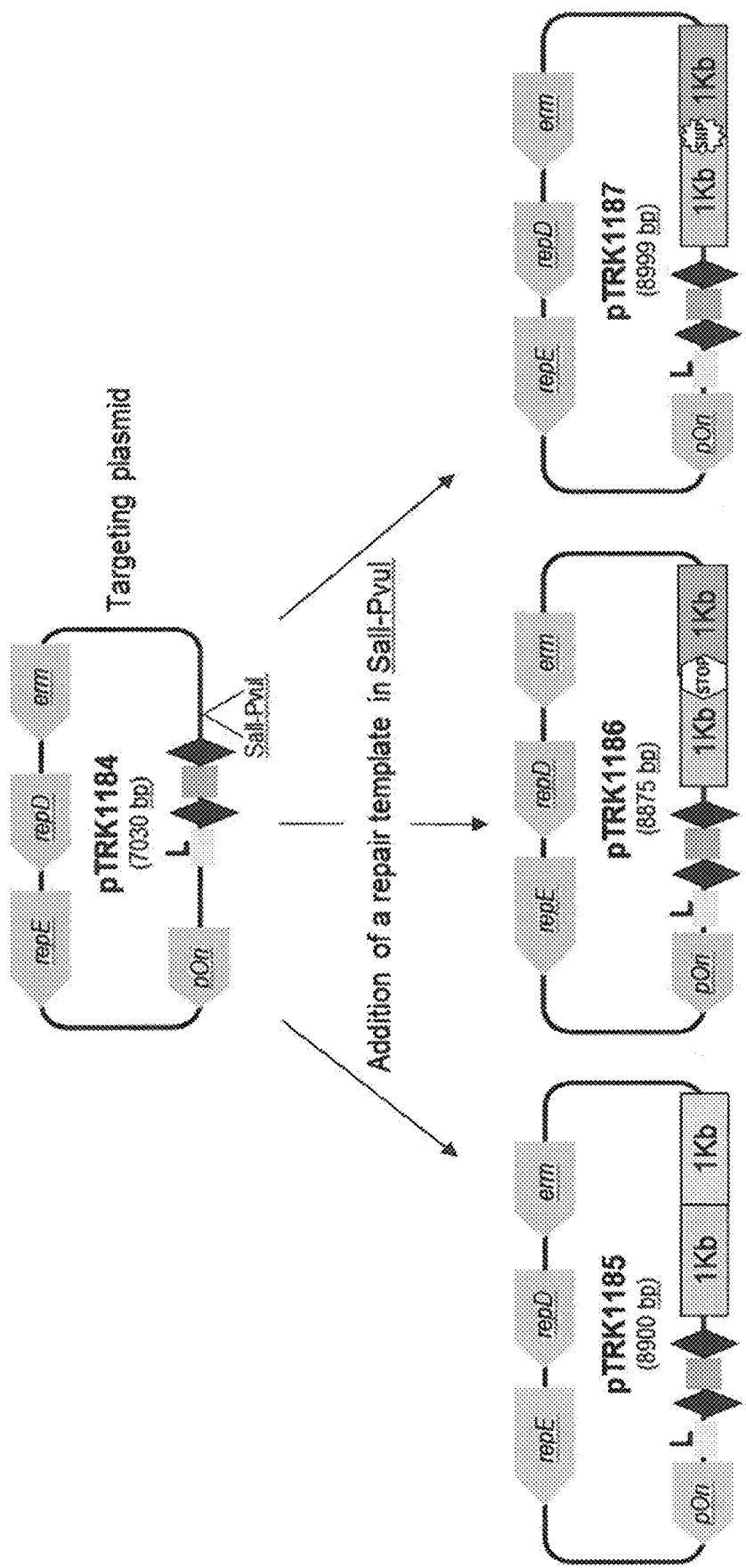
Fig. 14 (con't)

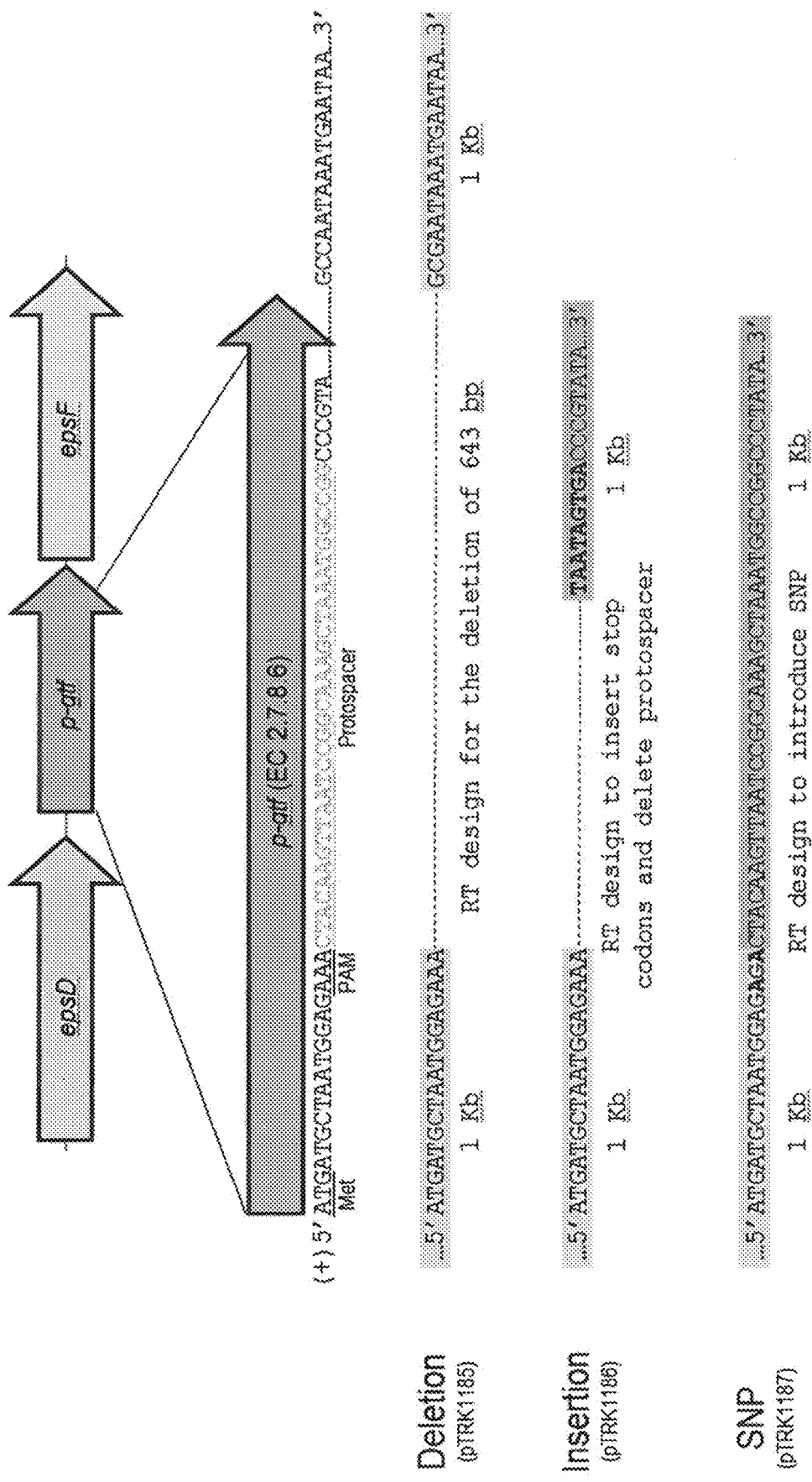

Fig. 15 (con't)
B
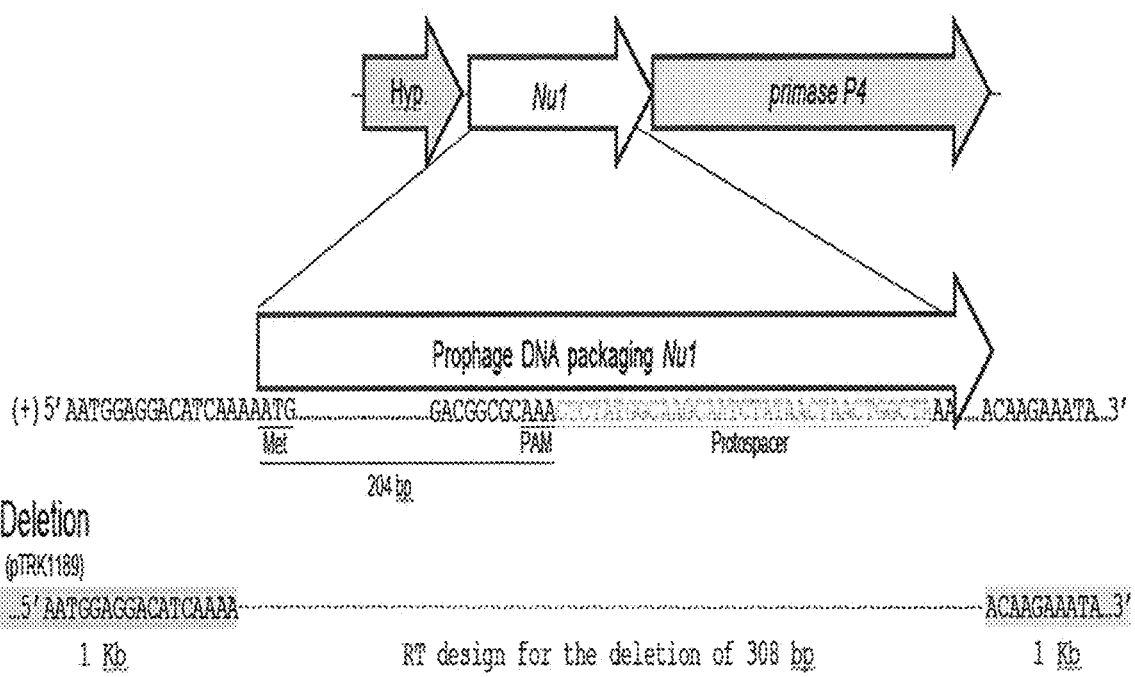
C
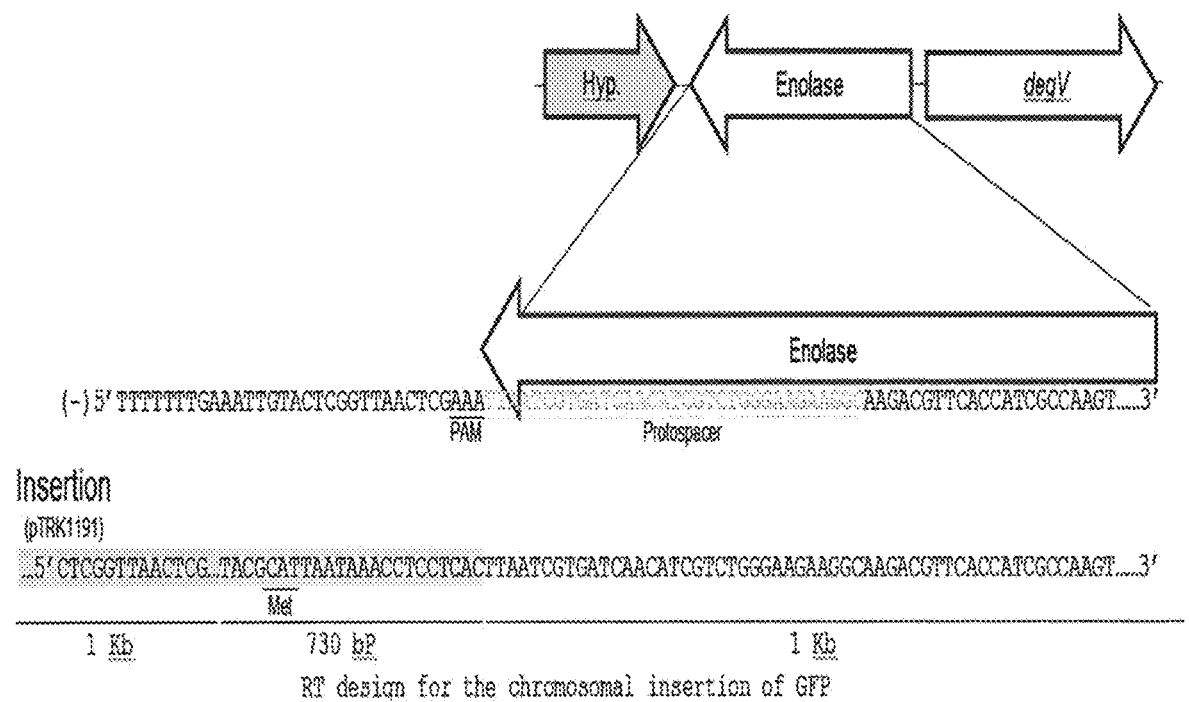

RECOMBINANT TYPE I CRISPR-CAS SYSTEM

STATEMENT OF PRIORITY

This application claims the benefit, under 35 U.S.C. § 119 (e), of U.S. Provisional Application No. 62/739,666 filed on Oct. 1, 2018, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 5051-940_ST25 txt, 72,136 bytes in size, generated on Sep. 19, 2019 and filed via EFS-Web, is provided in lieu of a paper copy. This Sequence Listing is hereby incorporated herein by reference into the specification for its disclosures.

FIELD OF THE INVENTION

This invention relates to recombinant Clustered Regularly Interspaced Short Palindromic Repeats (CRISPR) arrays and recombinant nucleic acid constructs encoding Type I-E CASCADE complexes as well as plasmids, retroviruses and bacteriophage comprising the same.

BACKGROUND OF THE INVENTION

Clustered Regularly Interspaced Short Palindromic Repeats (CRISPR), in combination with CRISPR associated genes (cas) constitute the CRISPR-Cas system, which confers adaptive immunity in many bacteria and most archaea. CRISPR-mediated immunization occurs through the integration of DNA from invasive genetic elements such as plasmids and phages that can be used to thwart future infections by invaders containing the same sequence.

CRISPR-Cas systems consist of CRISPR arrays of short DNA "repeats" interspaced by hypervariable "spacer" sequences and a set of flanking cas genes. The system acts by providing adaptive immunity against invasive genetic elements such as phage and plasmids through the sequence-specific targeting and interference of foreign nucleic acids (Barrangou et al. 2007. *Science* 315:1709-1712; Brouns et al. 2008. *Science* 321:960-4; Horvath and Barrangou. 2C10. *Science* 327:167-70; Marraffini and Sontheimer. 2008. *Science*. 322:1843-1845; Bhaya et al. 2011. *Annu. Rev. Genet.* 45:273-297; Terns and Terns 2011. *Curr. Opin. Microbiol.* 14:321-327; Westra et al. 2012 *Annu. Rev. Genet.* 46:311-339; Barrangou R. 2013. *RNA*. 4:267-278). Typically, invasive DNA sequences are acquired as novel "spacers" (Barrangou et al. 2007. *Science*. 315:1709-1712), each paired with a CRISPR repeat and inserted as a novel repeat-spacer unit in the CRISPR locus. The "spacers" are acquired by the Cas1 and Cas2 proteins that are universal to all CRISPR-Cas systems (Makarova et al. 2011. *Nature Rev. Microbiol.* 9:467-477; Yosef et al. 2012. *Nucleic Acids Res.* 40:5569-5576), with involvement by the Cas4 protein in some systems (Plagens et al. 2012. *J. Bact.* 194: 2491-2500; Zhang et al. 2012. *PLoS One* 7:e47232). The resulting repeat-spacer array is transcribed as a long pre-CRISPR RNA (pre-crRNA) (Brouns et al. 2008. *Science* 321:960-4), which is processed into CRISPR RNAs (crRNAs) that drive sequence-specific recognition of DNA or RNA. Specifically, crRNAs guide nucleases towards complementary targets for sequence-specific nucleic acid cleavage mediated by Cas endonucleases (Garneau et al. 2010. *Nature* 468:67-71; Haurwitz et al. 2010 *Science* 329:1355-1358; Sapranauskas et al. 2011. *Nucleic Acid Res.* 39:9275-9282; Jinek et al. 2012. *Science*. 337:816-821; Gasiunas et al. 2012. *Proc. Natl. Acad. Sci.* 109:E2579-E2586; Magadan et al. 2012. *PLoS One.* 7:e40913; Karvelis et al. 2013. *RNA Biol.* 10:841-851).

These widespread systems occur in nearly half of bacteria (~46%) and the large majority of archaea (~90%). CRISPR/Cas are subdivided in classes and types based on the cas gene content, organization and variation in the biochemical processes that drive crRNA biogenesis, and Cas protein complexes that mediate target recognition and cleavage. Class 1 uses multiple Cas proteins in a cascade complex to degrade nucleic acids (see, FIG. 1). Class 2 uses a single large Cas protein to degrade nucleic acids. The type I systems are the most prevalent in bacteria and in archaea (Makarova et al. 2011. *Nature Rev. Microbiol.* 9:467-477) and target DNA (Brouns et al. 2008. *Science* 321:960-4). A complex of 3-8 Cas proteins called the CRISPR associated complex for antiviral defense (Cascade) processes the pre-crRNAs (Brouns et al. 2008. *Science* 321:960-4), retaining the crRNA to recognize DNA sequences called "protospacers" that are complementary to the spacer portion of the crRNA. Aside from complementarity between the crRNA spacer and the protospacer, targeting requires a protospacer-adjacent motif (PAM) located at the 5' end of the protospacer (Mojica et al. 2009. *Microbiology* 155:733-740; Sorek et al. 2013. *Ann. Rev. Biochem.* 82:237-266). For type I systems, the PAM is directly recognized by Cascade (Sashital et al. 2012. *Mol. Cell* 46:606-615; Westra et al. 2012. *Mol. Cell* 46:595-605). The exact PAM sequence that is required can vary between different type I systems. Once a protospacer is recognized, Cascade generally recruits the endonuclease Cas3, which cleaves and degrades the target DNA (Sinkunas et al. 2011. *EMBO J.* 30:1335-1342; Sinkunas et al. 2013. *EMBO J.* 32:385-394).

SUMMARY OF THE INVENTION

One aspect of the invention provides a recombinant nucleic acid construct comprising a Clustered Regularly Interspaced Short Palindromic Repeats (CRISPR) array comprising two or more repeat sequences and one or more spacer sequence(s), wherein each spacer sequence is linked at its 5' end and at its 3' end to a repeat sequence, and the spacer sequence is complementary to a target sequence (protospacer) in a target DNA of a target organism that is located immediately adjacent (3') to a protospacer adjacent motif (PAM).

A second aspect provides a recombinant nucleic acid construct comprising a CRISPR array comprising two or more repeat sequences and one or more spacer sequence(s), wherein each spacer sequence is linked at its 5' end and at its 3' end to a repeat sequence, and the spacer sequence is complementary to a target sequence (protospacer) in a target DNA of a target organism that is located immediately adjacent (3') to a protospacer adjacent motif (PAM); and a recombinant nucleic acid construct encoding a Type I-E CRISPR associated complex for antiviral defense complex (Cascade complex) comprising a Cse1 polypeptide, a Cse2 polypeptide, a Cas7 polypeptide, a Cas5 polypeptide and a Cas6 polypeptide.

A third aspect provides a recombinant nucleic acid construct comprising a CRISPR array comprising two or more repeat sequences and one or more spacer sequence(s), wherein each spacer sequence is linked at its 5' end and at its 3' end to a repeat sequence, and the spacer sequence is complementary to a target sequence (protospacer) in a target DNA of a target organism that is located immediately adjacent (3') to a protospacer adjacent motif (PAM); and a recombinant nucleic acid construct encoding (a) a Type I-E CRISPR associated complex for antiviral defense complex (Cascade complex) comprising a Cse1 polypeptide, a Cse2 polypeptide, a Cas7 polypeptide, a Cas5 polypeptide and a Cas6 polypeptide; and (b) a polynucleotide encoding a Cas3 polypeptide.

Further provided are the recombinant plasmids, bacteriophages, and/or retroviruses comprising a recombinant nucleic acid construct of the invention. Additionally provided are cells comprising recombinant nucleic acid constructs of the invention, and/or comprising plasmids, bacteriophages, and/or retroviruses comprising the recombinant nucleic acid constructs of the invention.

These and other aspects of the invention are set forth in more detail in the description of the invention below.

(F) Interference assays with a reduction of between 2-3 log units compared to the vector pTRKH2 or the non-PAM containing plasmids. Bar graphs represent the mean of three independent biological replicates and the error bars represent the standard deviation. p-value<0.01, *p-value<0.001, ****p-value<0.001 after Welch's t-test to compare each sample with the non-PAM containing control.

Figure 11:
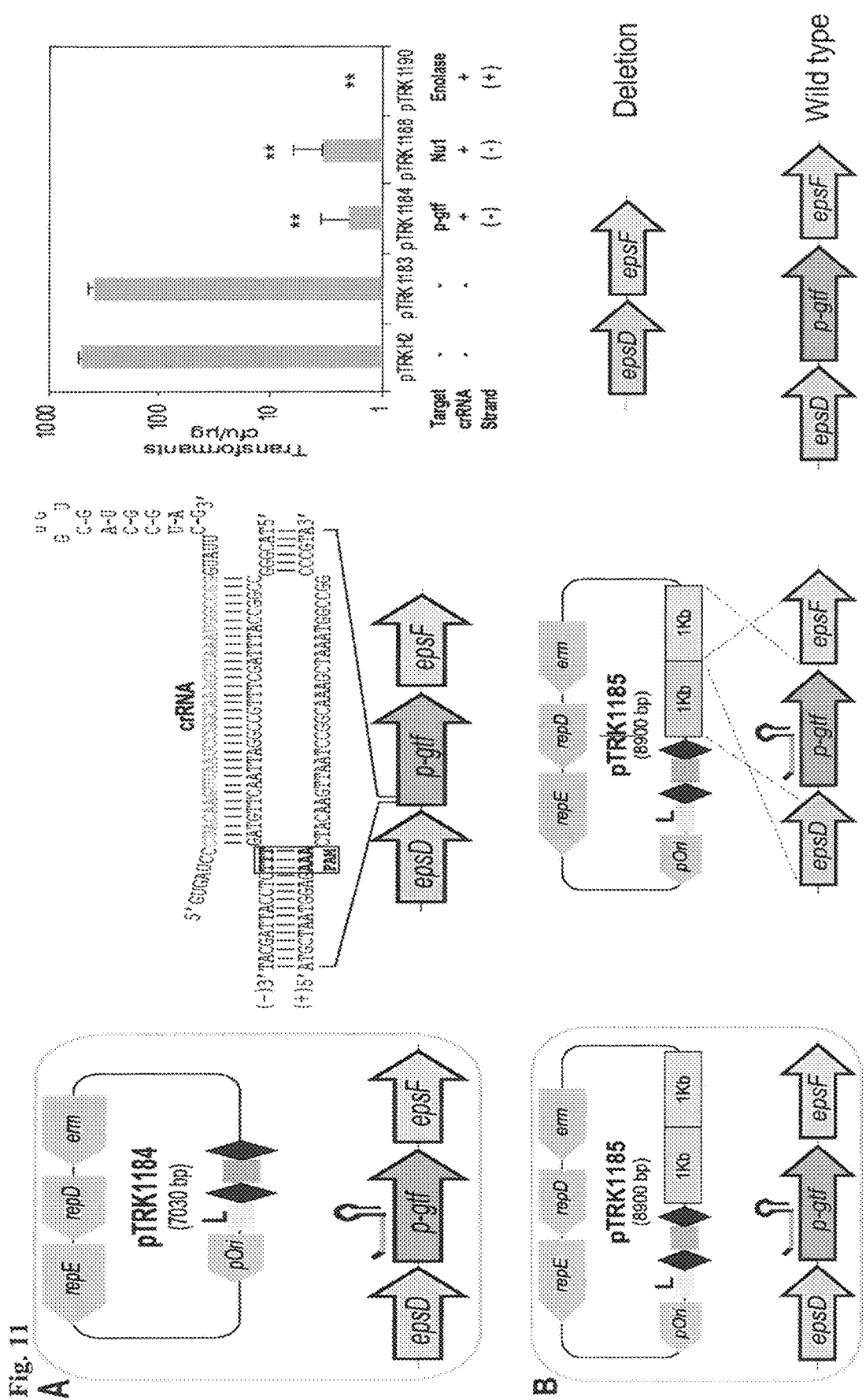

FIG. 11. Repurposing the endogenous Type I-E CRISPR-Cas system. (A) An artificial crRNA is expressed with a plasmid-based system (see FIG. 14; Table 1) to repurpose the endogenous Type I-E against the desired chromosomal target (middle panel of (A)) causing cell death (right panel of (A)). The base pair of the crRNA (SEQ ID NO:107) with the protospacer target located on the negative (−) or the positive (+) strand (SEQ ID NO:108 and complement, respectively) is indicated (right panel). The bar graphs represent the mean of three independent biological replicates and the error bars represent the standard deviation. **p-value<0.01 after Welch's t-test to compare each sample with the control pTRK1183. (B) Cloning a 2 kb homologous repair template in the targeting plasmid (see FIG. 14, 15) allowed generation of a marker-less technology to perform genome editing in *L. crispatus* NCK1350 with different applications.

Figure 12:
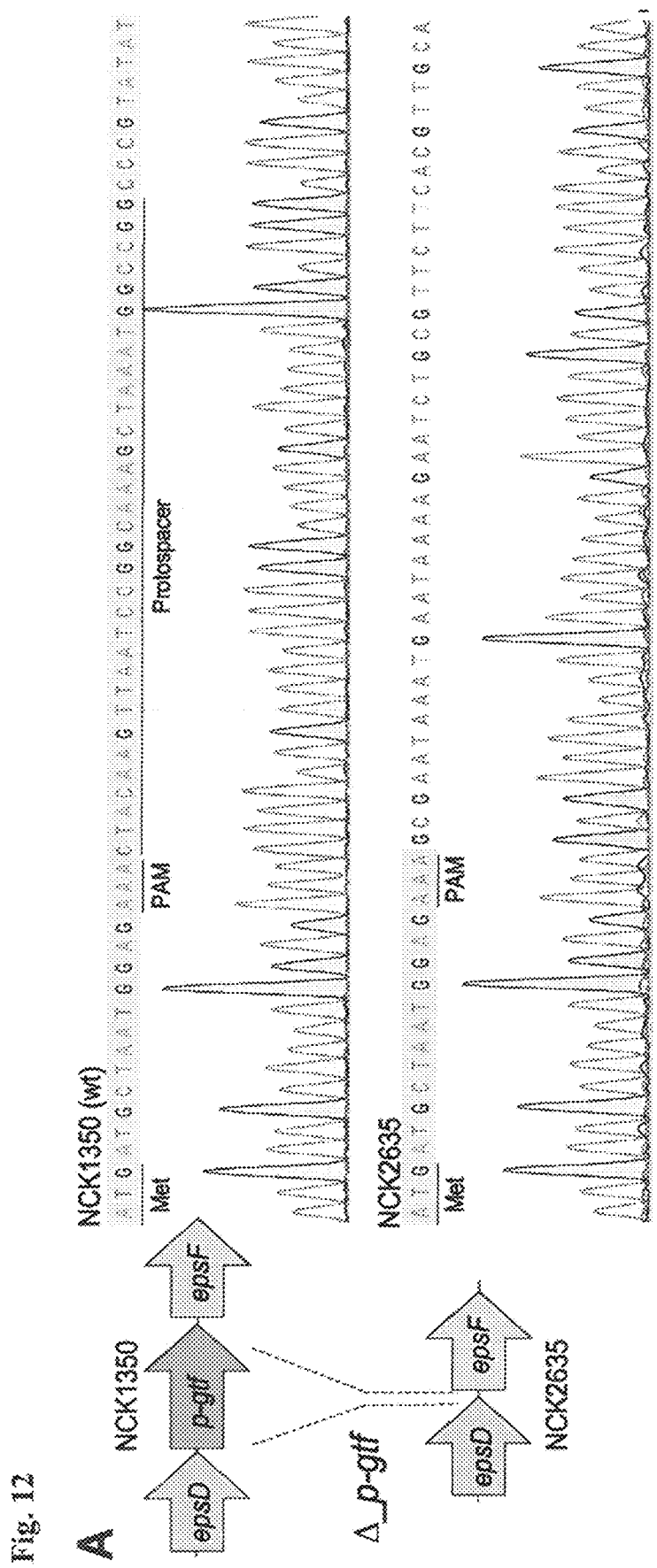

FIG. 12. Diversity of genome editing outcomes achieved by repurposing the endogenous Type I-E system in *L. crispatus* NCK1350. Different editing strategies can be achieved based on the repair template cloned in the targeting plasmid (see FIGS. 14, 15 (panel A)). Transformation efficiencies and editing rates (%) are shown in graph in (A) (middle panel) with the corresponding gels in (A) bottom panel. (A) Deletion of 643 bp in the exopolysaccharide p-gtf gene with the chromatogram showing the sequence of NCK1350 wild type strain (wt) (SEQ ID NO:130) and the deletion mutant NCK2635 (SEQ ID NO:131). (B) Insertion of stop codons while deleting the protospacer region in the p-gtf gene to generate the mutant NCK2656 (eps15_16:: taatagtga (SEQ ID NO:132)). (C) Single base editing performed as single base substitution to altered the PAM sequence (14A>G) creating a missense mutation (K5R) in the derivative mutant NCK2659 (SEQ ID NO:133). (D) scanning electron microscopy of the wild type strain *L. crispatus* NCK1350 and the derivative mutants NCK2635, NCK2656 and NCK2659 harboring a deletion, interruption or single base substitution in the exopolysaccharide priming-glycosyltransferase (p-gtf) gene, respectively. Pictures were taken at 10,000-13,000× magnification and scale bar represents 1 μm.

Figure 13:
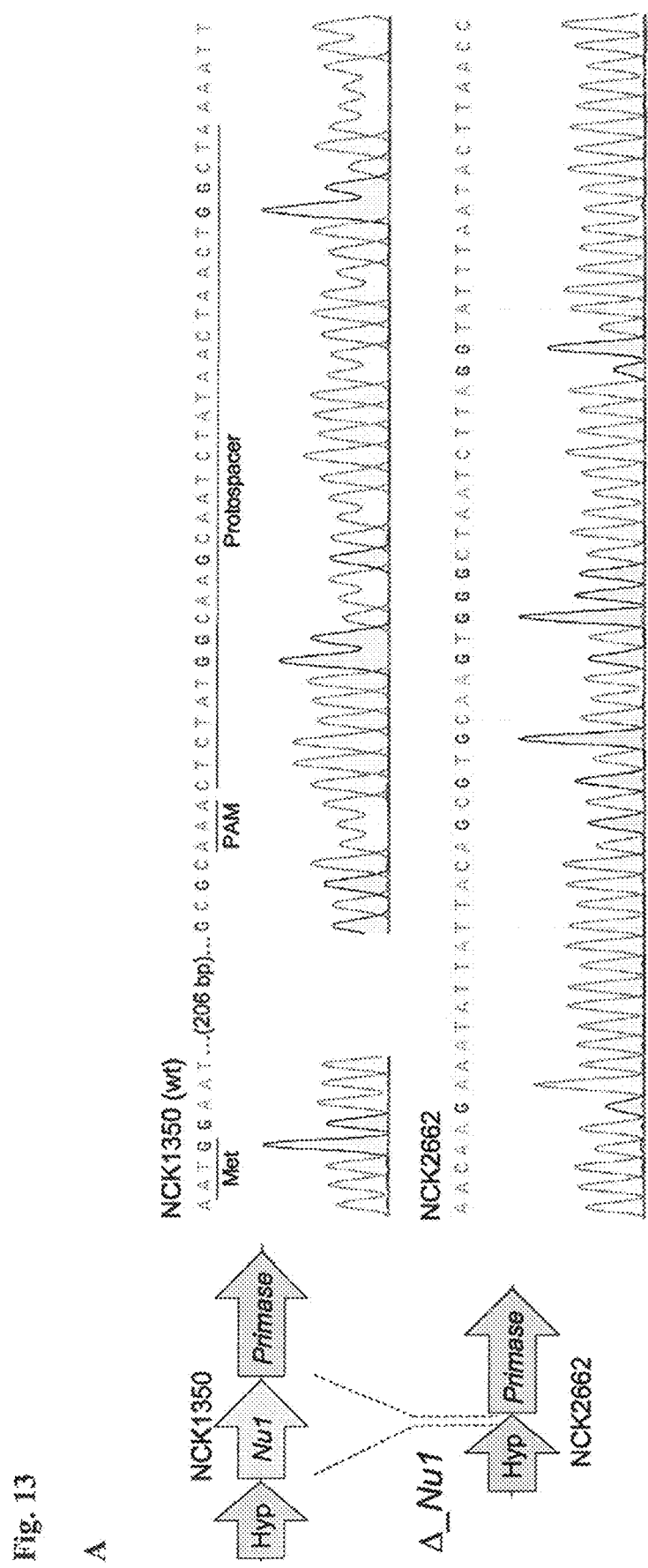

FIG. 13. Diversity of genome editing too achieved by repurposing the endogenous Type I-E system in *L. crispatus* NCK1350. Transformation efficiencies and editing rate (%) is shown in (A) (middle panel) with the corresponding gels in (A), bottom panel. (A) Deletion of the prophage DNA packaging Nu1 gene (308 bp) with the chromatogram showing the sequence of NCK1350 wild type strain (wt) (first 8 and last 45 nucleotides of SEQ ID NO:134 shown) and the derivative mutant NCK2662 (SEQ ID NO:135). Notice the repair template was designed 206 bp upstream from the PAM to delete the complete gene (see FIG. 15). (B) Chromosomal insertion of the GFP (730 bp) downstream the enolase gene with the chromatogram showing the sequence of the wild type strain (SEQ ID NO:136) and the derived mutant NCK2665 (SEQ ID NO:137). (C) Growth curve ($OD_{600nm}$) of NCK1350 and derivative mutant NCK2662 in the presence of Mitomycin-C (MC) for prophage induction. (D) Fluorescence microscopy of NCK1350 and derivative mutant NCK2665 expressing the green fluorescent protein inserted in the chromosome, using white filter (left) and FITC filter (right) under the Nikon Eclipse E600 microscope and 40× magnification.

Figure 14:
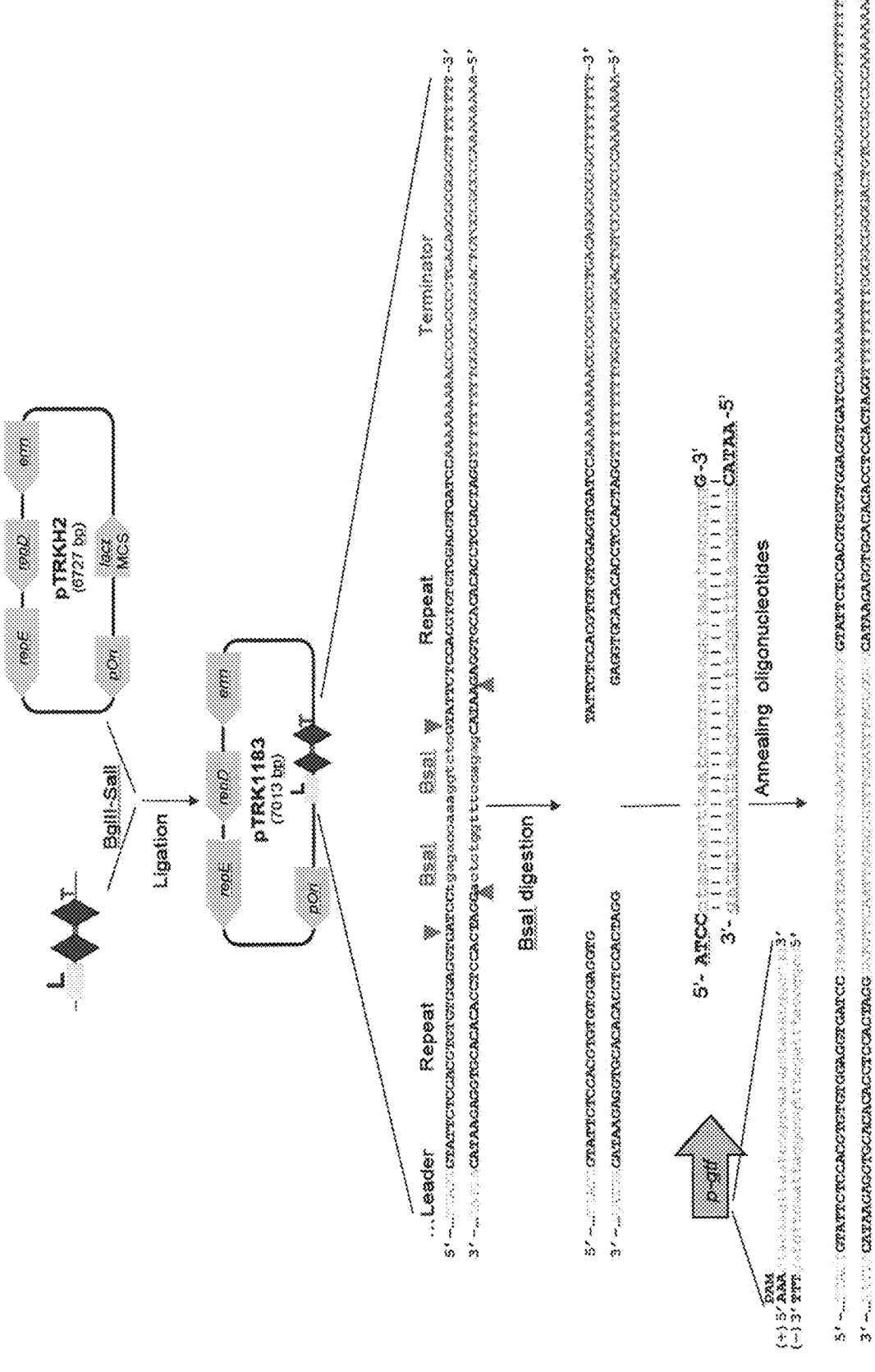

FIG. 14. Cloning strategy to generate the plasmid based technology to repurpose the endogenous CRISPR system Type I-E in *L. crispatus* NCK1350. (A) An artificial crRNA containing the native leader (L) of the CRISPR-3 of *L. crispatus* NCK1350 as promoter, together with two repeats (native repeat sequence of NCK1350) and a Rho-terminator were synthesized as a gene block and cloned into BglII-SalI digested pTRKH2 to generate the plasmid-based technology pTRK1183. (B) The pTRK1183 plasmid allows cloning a spacer (target) using annealing oligonucleotides with overhand ends to the BsaI-digested pTRK1183 generating the targeting plasmid pTRK1184, that will express the crRNA to repurpose the endogenous CRISPR systems I-E against the desire target (SEQ ID NO:98 and complement, SEQ ID NOs:99, 100, 101, 102, 103, 104, 105 and complement, and SEQ ID NO: 106 and complement). (C) The generated targeting plasmid contains SalI-PvuI restriction sites for convenient and easy cloning of different repair templates to perform different genome editing outcomes as deletion (pTRK1185), insertion (pTRK1186) or single base editing (pTRK1187).

FIG. 15. Cloning strategy to design the repair templates for the different genome editing outcomes. A total of five different edits were performed in three different chromosomal targets with different designs associated with the homologous repair template (RT). For each design, the homologous arms were designed with an average length of 1 kb each. For each target, the chromosomal architecture, the gene of interest and the nucleotide sequence is displayed, with the protospacer targeted (T) region in center (p-gtf). (A) Design for the deletion, insertion of stop codons or single base substitution is shown for the exopolysaccharide priming-glycosyl transferase p-gtf (EC 2.7.8.6). Each template was cloned into the targeting plasmid pTRK1184 to generate pTRK1185, pTRK1186 and pTRK1187 respectively (see, Table 7). The homologous arm for the upstream region (light shading at 5'end) was designed until the PAM (5'-AAA-3') sequence (homologous arm placed 5' of the PAM sequence), while the downstream arm was designed according to the desire mutation to be introduced for the deletion or the insertion of stop codons. To perform single base editing, the upstream homologous arm contains the single base substitution in the PAM sequence, while the downstream region remains as the chromosomal sequence, including the protospacer sequence (SEQ ID NOs:138, 139, 140, 141, 142, 143, and 144). (B) Repair template designed to delete the prophage DNA packaging Nu1 gene. The PAM motif detected in the prophage DNA packaging Nu1 gene is located closer to the 3' end of the gene. In this scenario the upstream arm was designed until the start codon of the Nu1 gene, located 204 bp upstream from PAM motif (SEQ ID NOs:145, 146, and 147). This designed repair template was cloned into pTRK1188 (also referred to as pcrRNA_T1) to generate pTRK1189 (SEQ ID NOs:148 and 149). (C) Repair template designed to perform a chromosomal insertion of the GFP in the downstream region of the highly expressed enolase gene. The upstream arm was designed until the PAM but without including the PAM sequence, followed by the GFP gene to be inserted (730 bp) carrying its own ribosomal binding site followed by the downstream arm that includes the protospacer region (SEQ ID NO: 150). The designed repair template was cloned into pTRK1190 to generate pTRK1191 (SEQ ID NOs:151 and 152).

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition composes components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass vacations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancement," "improve" and "improvement" (and the like and grammatical variations thereof) describe an elevation of at least about 5%, 10%, 15%, 20%, 25%, 50%, 75%, 100%, 150%, 200%, 300%, 400%, 500%, 750%, 1000%, 2500%, 5000%, 10,000%, 20,000% or more as compared to a control (e.g., a CRISPR array targeting a particular gene having, for example, more spacer sequences targeting different regions of that gene and therefore having increased repression of that gene as compared to a CRISPR array targeting the same gene but having, for example, fewer spacer sequences targeting different regions of that gene).

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount. As an example, a mutation in a Cas3 nuclease can reduce the nuclease activity of the Cas3 by at least about 90%, 95%, 97%, 98%, 99%, or 100% as compared to a control (e.g., wild-type Cas3).

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity with the comparator nucleotide sequence or it can mean less than 100% complementarity (e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

As used herein, the phrase "substantially complementary," or "substantial complementarity" in the context of two nucleic acid molecules, nucleotide sequences or protein sequences, refers to two or more sequences or subsequences that are at least about 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue complementary, when compared and aligned for maximum correspondence, as measured using one of the following sequence comparison algorithms or by visual inspection. In some embodiments, substantial complementarity can refer to two or more sequences or subsequences that have at least about 80%, at least about 85%, at least about 90%, at least about 95, 96, 96, 97, 98, or 99% complementarity (e.g., about 80% to about 90%, about 80% to about 95%, about 80% to about 96%, about 80% to about 97%, about 80% to about 98%, about 80% to about 99% or more, about 85% to about 90%, about 85% to about 95%, about 85% to about 96%, about 85% to about 97%, about 85% to about 98%, about 85% to about 99% or more, about 90% to about 95%, about 90% to about 96%, about 90% to about 97%, about 90% to about 98%, about 90% to about 99% or more, about 95% to about 97%, about 95% to about 98%, about 95% to about 99% or more). Two nucleotide sequences can be considered to be substantially complementary when the two sequences hybridize to each other under stringent conditions. In some representative embodiments, two nucleotide sequences considered to be substantially complementary hybridize to each other under highly stringent conditions.

As used herein, "contact," "contacting," "contacted," and grammatical variations thereof, refers to placing the components of a desired reaction together under conditions suitable for carrying out the desired reaction (e.g., integration, transformation, site-specific cleavage (nicking, cleaving), amplifying, site specific targeting of a polypeptide of interest and the like). The methods and conditions for carrying out such reactions are well known in the art (See, e.g., Gasiunas et al. (2012) *Proc. Natl. Acad. Sci.* 109: E2579-E2586, M. R. Green and J. Sambrook (2012) Molecular Cloning: A Laboratory Manual 4th Ed., Cold Spring Harbor Laboratory Press, Cold Spring Harbor, N.Y.).

As used herein, type I Clustered Regularly Interspaced Short Palindromic Repeats (CRISPR)-associated complex for antiviral defense (Cascade) refers to a complex of polypeptides involved in processing of pre-crRNAs and subsequent binding to the target DNA in type I CRISPR-Cas systems. Exemplary type I-E polypeptides useful with this invention include Cse1 (CasA) (SEQ ID NO:82), Cse2 (CasB) (SEQ ID NO:83), Cas7 (CasC) (SEQ ID NO:84), Cas5 (CasD) (SEQ ID NO:85) and/or Cas6 (CasE) (SEQ ID NO:86). In some embodiments of this invention, a recombinant nucleic acid construct may comprise, consist essentially of, or consist of a recombinant nucleic acid encoding a subset of type-IE Cascade polypeptides that function to process a CRISPR array and subsequently bind to a target DNA using the spacer of the processed CRISPR RNA as a guide. In some embodiments of this invention, a recombinant nucleic acid construct may comprise, consist essentially of, or consist of a recombinant nucleic acid encoding Cse1 (CasA) (SEQ ID NO:82), Cse2 (CasB) (SEQ ID NO:83), Cas7 (CasC) (SEQ ID NO:84), Cas5 (CasD) (SEQ ID NO:85) and Cas6 (CasE) (SEQ ID NO:86).

A "fragment" or "portion" of a nucleic acid will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising a nucleotide sequence of contiguous nucleotides that are identical or almost identical (e.g., 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. In some embodiments, a fragment of a polynucleotide can be a fragment that encodes a polypeptide that retains its function (e.g., encodes a fragment of a Type-1E Cascade polypeptide that is reduce in length as compared to the wild type polypeptide but which retains at least one function of a Type-1E Cascade protein (e.g., processes CRISPR RNAs, bind DNA and/or form a complex). In some embodiments, a fragment of a polynucleotide can be a fragment of a native repeat sequence (e.g., a native repeat sequence from *L. crispatus* that is shortened by about 1 nucleotide to about 8 nucleotides from the 3' end of a native repeat sequence).

As used herein, "chimeric" refers to a nucleic acid molecule or a polypeptide in which at least two components are derived from different sources (e.g., different organisms, different coding regions).

A "heterologous" or a "recombinant" nucleic acid is a nucleic acid not naturally associated with a host cell into which it is introduced, including non-naturally occurring multiple copies of a naturally occurring nucleic acid.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual, 4th Ed., Cold Spring Harbor Laboratory Press, Cold Spring Harbor, N.Y.)

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is a mRNA that is naturally occurring in or endogenous to the organism. A "homologous" nucleic acid is a nucleic acid naturally associated with a host cell into which it is introduced.

As used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme paring. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "synthetic" nucleic acid or nucleotide sequence, as used herein, refers to a nucleic acid or nucleotide sequence that is not found in nature but is constructed by human intervention and as a consequence is not a product of nature.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide," and "polynucleotide" are also used interchangeably herein to refer to a heteropolymer of nucleotides. Except as otherwise indicated, nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3'end. Thus, for example, an element in the 3' region of a polynucleotide can be located anywhere from the first nucleotide located at the 3' end of the polynucleotide to the nucleotide located halfway through the polynucleotide. An element that is described as being "at the 5'end" or "at the 3'end" of a polynucleotide (5' to 3') refers to an element located immediately adjacent to (upstream of) the first nucleotide at the 5' end of the polynucleotide, or immediately adjacent to (downstream of) the last nucleotide located at the 3' end of the polynucleotide, respectively.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, a "hairpin sequence" is a nucleotide sequence comprising hairpins. A hairpin (e.g., stem-loop, fold-back) refers to a nucleic acid molecule having a secondary structure that includes a region of nucleotides that form a single strand that are further flanked on either side by a double stranded-region. Such structures are well known in the art. As known in the art, the double stranded region can comprise some mismatches in base pairing or can be perfectly complementary. In some embodiments, a repeat sequence may comprise, consist essentially of, consist of a hairpin sequence that is located within the repeat nucleotide sequence (i.e., at least one nucleotide (e.g., one, two, three, four, five, six, seven, eight, nine, ten, or more) of the repeat nucleotide sequence is present on either side of the hairpin that is within the repeat nucleotide sequence).

A "CRISPR array" as used herein means a nucleic acid molecule that comprises at least two CRISPR repeat nucleotide sequences, or a portion(s) thereof, and at least one spacer sequence, wherein one of the two repeat nucleotide sequences, or a portion thereof, is linked to the 5' end of the spacer sequence and the other of the two repeat nucleotide sequences, or portion thereof, is linked to the 3' end of the spacer sequence. In a recombinant CRISPR array of the invention, the combination of repeat nucleotide sequences and spacer sequences is synthetic and not found in nature. The CRISPR array may be introduced into a cell or cell free system as RNA, or as DNA in an expression cassette or vector (e.g., plasmid, retrovirus, bacteriophage).

As used herein, the term "spacer sequence" refers to a nucleotide sequence that is complementary to a targeted portion (i.e., "protospacer") of a nucleic acid or a genome.

The term "genome," as used herein, refers to both chromosomal and non-chromosomal elements (i.e., extrachromosomal (e.g., mitochondrial, plasmid, a chloroplast, and/or extrachromosomal circular DNA (eccDNA))) of a target organism. The spacer sequence guides the CRISPR machinery to the targeted portion of the genome, wherein the targeted portion of the genome may be, for example, modified (e.g., a deletion, an insertion, a single base pair addition, a single base pair substitution, a single base pair removal, a stop codon insertion, and/or a conversion of one base pair to another base pair (base editing)).

A "target sequence" or "protospacer" refers to a targeted portion of a genome or of a cell free nucleic acid that is complementary to the spacer sequence of a recombinant CRISPR array. A target sequence or protospacer useful with this invention is located immediately adjacent to the 3' end of a PAM (protospacer adjacent motif) (e.g., 5'-PAM-Protospacer-3'). In some embodiments, a PAM may comprise, consist essentially of, or consist of a sequence of 5'-NAA-3', 5'-AAA-3' and/or 5'-AA-3' that is located immediately adjacent to and 5' of the protospacer. A non-limiting example of a PAM associated with a protospacer may be the following: . . . ATGCTAATGGAG AAA CTACAAGT-TAATCCGGCAAAGCTAAATGGCCGG CCCGT (SEQ ID NO:88).

As used herein, the terms "target genome" or "targeted genome" refer to a genome of an organism of interest.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin. H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the phrase "substantially identical," or "substantial identity" in the context of two nucleic acid molecules, nucleotide sequences or protein sequences, refers to two or more sequences or subsequences that have at least about 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In particular embodiments, substantial identity can refer to two or more sequences or subsequences that have at least about 80%, at least about 85%, at least about 90%, at least about 95, 96, 96, 97, 98, or 99% identity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W. T. and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

Any polynucleotide and/or nucleic acid construct useful with this invention may be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 98%, 97%, 98%, 99%, and the like) to the native nucleotide sequence but which still encodes a polypeptide having the same function (and in some embodiments, the same structure) as that encoded by the original nucleotide sequence. Thus, in some embodiments of the invention, polynucleotides and/or nucleic acid constructs useful with the invention may be codon optimized for expression in the particular organism/species of interest.

In some embodiments, the polynucleotides and polypeptides of the invention are "isolated". An "isolated" polynucleotide sequence or an "isolated" polypeptide is a polynucleotide or polypeptide that, by human intervention, exists apart from its native environment and is therefore not a product of nature. An isolated polynucleotide or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated polynucleotide and/or the isolated polypeptide may be at least about 1%, 5%, 10%, 20%, 30%, 40%, 50%, 60%, 70%, 80%, 90%, 95%, or more pure.

In other embodiments, an isolated polynucleotide or polypeptide may exist in a non-natural environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, through human intervention, they exist apart from their native environment and therefore are not products of nature, however, in some embodiments, they can be introduced into and exist in a recombinant host cell.

In some embodiments of the invention, a recombinant nucleic acid of the invention comprising/encoding a CRISPR array, a Cascade complex, and/or a Cas3 may be operatively associated with a variety of promoters, terminators and other regulatory elements for expression in various organisms or cells. Thus, in some embodiments, at least one promoter and/or at least one terminator may be operably linked to a recombinant nucleic acid of the invention comprising/encoding a CRISPR array, a Cascade complex, and/or a Cas3. In some embodiments, when comprised in the same nucleic acid construct (e.g., expression cassette), the CRISPR array, recombinant nucleic acid encoding a Cascade complex, and/or recombinant nucleic acid encoding a Cas3 polypeptide may be operably linked to separate (independent) promoters that may be the same promoter or a different promoter. In some embodiments, when comprised in the same nucleic acid construct, the recombinant nucleic acid comprising CRISPR array, recombinant nucleic acid encoding Cascade, and/or recombinant nucleic acid encoding Cas3 may be operably linked to a single promoter.

Any promoter useful with this invention can be used and includes, for example, promoters functional with the organism of interest. A promoter useful with this invention can include, but is not limited to, constitutive, inducible, developmentally regulated, tissue-specific/preferred-promoters, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid. In some embodiments, promoters useful with the constructs of the invention may be any combination of heterologous and/or endogenous promoters.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

Any promoter that initiates transcription of a recombinant nucleic acid construct of the invention, for example, in an organism/cell of interest may be used. A promoter useful with this invention can include, but is not limited to, a constitutive, inducible, developmentally regulated, tissue-specific/preferred-promoter, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature (e.g., a different position in a chromosome or in a plasmid), thereby producing a recombinant or non-native nucleic acid.

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." These various types of promoters are known in the art. Thus, expression can be made constitutive, inducible, temporally regulated, developmentally regulated, chemically regulated, tissue-preferred and/or tissue-specific promoters using the recombinant nucleic acid constructs of the invention operatively linked to the appropriate promoter functional in an organism of interest. Expression may also be made reversible using the recombinant nucleic acid constructs of the invention operatively linked to, for example, an inducible promoter functional in an organism of interest.

The choice of promoter will vary depending on the quantitative, temporal and spatial requirements for expression, and also depending on the host cell of interest. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

Exemplary promoters include, but are not limited to, promoters functional in eukaryotes and prokaryotes including but not limited to, plants, viruses, bacteria, fungi, archaea, animals, and mammals. For example, promoters useful with archaea include, but are not limited to, *Haloferax volcanii* tRNA (Lys) promoter (Palmer et al. *J. Bacteriol.* 1995. 177(7): 1844-1849), *Pyrococcus furiosus* gdh promoter (Waege et al. 2010. *Appl. Environ. Microbiol.* 76:3308-3313), *Sulfolobus sulfataricus* 16S/23S rRNA gene core promoter (DeYoung et al. 2011. *FEMS Microbiol. Lett.* 321:92-99).

Exemplary promoters useful with yeast can include a promoter from phosphoglycerate kinase (PGK), glyceraldehyde-3-phosphate dehydrogenase (GAP), triose phosphate isomerase (TPI), galactose-regulon (GAL1, GAL10), alcohol dehydrogenase (ADH1, ADH2), phosphatase (PHO5), copper-activated metallothionine (CUP1), MFα1, PGK/α2 operator, TPI/α2 operator, GAP/GAL, PGK/GAL, GAP/ADH2, GAP/PHO5, iso-1-cytochrome c/glucocorticoid response element (CYC/GRE), phosphoglycerate kinase/angrogen response element (PGK/ARE), transcription elongation factor EF-1α (TEF1), those phosphate dehydrogenase (TDH3), phosphoglycerate kinase 1 (PGK1), pyruvate kinase 1 (PYK1), and/or hexose transporter (HXT7) (See, Romanos et al. *Yeast* 8:423-488 (1992); and Partow et al. *Yeast* 27:955-964 (2010).

In additional embodiments, a promoter useful with bacteria can include, but is not limited to, L-arabinose inducible (araBAD, $P_{BAD}$) promoter, any lac promoter, L-rhamnose inducible ($rhaP_{BAD}$) promoter, T7 RNA polymerase promoter, trc promoter, tac promoter, lambda phage promoter ($p_L$, $p_L$-9G-50), anhydrotetracycline-inducible (tetA) promoter, trp, lpp, phoA, recA, proU, cst-1, cadA, nar, lpp-lac, cspA, T7-lac operator, T3-lac operator, T4 gene 32, T5-lac operator, nprM-lac operator, Vhb, Protein A, corynebacterial-*Escherichia coli* like promoters, thr, hom, diphtheria toxin promoter, sig A, sig B, nusG, SoxS, katb, α-amylase (Pamy), Ptms, P43 (comprised of two overlapping RNA polymerase σ factor recognition sites, σA; σB), Ptms, P43, rplK-rplA, ferredoxin promoter, and/or xylose promoter.

(See, K. Terpe *Appl. Microbiol. Biotechnol.* 72:211-222 (2006); Hannig et al. Trends in Biotechnology 16:54-60 (1998); and Srivastava Protein Expr Purif 40:221-229 (2005)).

Translation elongation factor promoters may be used with the invention. Translation elongation factor promoters may include but are not limited to elongation factor Tu promoter (Tuf) (e.g., Ventura et al., *Appl. Environ. Microbiol.* 69:6908-6922 (2003)), elongation factor P (Pefp) (e.g., Tauer et al., *Microbial Cell Factories,* 13:150 (2014), rRNA promoters including but not limited to a P3, a P6 a P15 promoter (e.g., Djordjevic et al., *Canadian Journal Microbiology,* 43:61-69 (1997); Russell and Klaenhammer, *Appl. Environ. Microbiol.* 67:1253-1261 (2001)) and/or a P11 promoter. In some embodiments, a promoter may be a synthetic promoter derived from a natural promoter (e.g., Rud et al., Microbiology, 152:1011-1019 (2006). In some embodiments, a sakacin promoter may be used with the recombinant nucleic acid constructs of the invention (e.g., Mathiesen et al. *J. Appl. Microbial.,* 96:819-827 (2004).

A promoter useful with the recombinant nucleic acid constructs of the invention may be a promoter from any bacterial species. In some embodiments, a promoter from a *Lactobacillus* spp. (e.g., *L. reuteri, L. buchneri, L. casei, L. paracasei, L. rhamnosus, L. pentosus, L. crispatus, L. gasseri,* and the like) may be operably linked to a recombinant nucleic acid construct of the invention (e.g., recombinant nucleic acid construct comprising a CRISPR array, recombinant nucleic acid construct encoding a Cascade complex and/or a recombinant nucleic acid construct encoding a Cas3 polypeptide). In some embodiments, an endogenous promoter from *L. crispatus* may be operably linked to a recombinant nucleic acid construct of the invention (e.g., a CRISPR array, a Cascade complex and/or a polynucleotide encoding a Cas3 polypeptide). In some embodiments, the promoter from *L. crispatus* may comprise the nucleotide sequence of SEQ ID NOs:69 to 73. Thus, for example, an *L. crispatus* promoter may include, but is not limited to, the sequence (5' to 3') of a native CRISPR array promoter:

SEQ ID NO: 69
ACAAAAAAGAACTTTAGTTGAATTACTGTTGTATAAGCGTTGTCGAAAGA

TGACGTCTTTTTTGTATGTTTAGGGAGACAAGAAAATTCTATTCGTTGGA

TGACTAATGAGACAGAAATAGATACAATAGTAATTGACAAAGTGATGAAA

TTTTGGGATCTATTGTTTTGTGATTGTTGTTATATTGGGATTTGTTTAC

T;

SEQ ID NO: 70
CTTGATATATAAGGATTTATAAATGAAATTTGAATCCTAGGGGCACTTTG

GGAGCAAAACTATTCAAAAAGAAGCAGAAATGCTTCTTTTTTATTTGGAG

TGGCTTTTTGTAATTATGGCTTTATTATTGGTCTTTGTTAAAAGTGATTA

AAAATGATATTATTTCGATTGAGCGATGCTGATATATTGTGGATCATTT

A;
and/or

SEQ ID NO: 71
GCAGACAAATAATATTTTTCTTTATTTGTTTAGGAGGAATCATAGCAGAA

TGATATTATGATTCCTCTTTTTATTTGAATATTATGTCTAGCAGATATTG

TCTATTTAATAAAAATCGATATACTTGGTAGTAGGATCAAAGTGATGAAA

AAATGGTGTTTGCGTATTTTCATTTGGCGCTATAAAGGGATTTGTTTAC

T.

In some embodiments, a *L. crispatus* promoter may include, but is not limited to, the sequence (5'-3') of a cas3 promoter in *L. crispatus*:

SEQ ID NO: 72
ATATTCCCAAACCAATCCAGCACCACTTGATGGTTCATCTAAGGGCGGAA

AATGGGAAGATTTTAGCATTTGGGATTATGATAAATATGATCAAGTAATA

AAAGACATCGATTATCCTATGTATATAAATAAAAATAGATTGTAAAATAA

AAAGTAATTATAAATATTAGATTAAGCAGATAGTATAAATTTAGGAGAAA

C, or the sequence (5'-3') of a Cascade complex promoter in *L. crispatus*:

SEQ ID NO: 73
TAAACTGTATTAAGTGTATTCCTCACTTAGGTGAGGGTGATCCTGTTAAT

TATTTATTTATTGAAGTAATCCCCATGAAAGTGGGGTTTAGCGGTTTCAG

TATATGAAACCGCTTTTTATTTTATTGAAAAAGTATTGTAAATAAAATAA

ATAAGCTTTAATATAAATATGAATGTTAAATATTTATTTAATGAGGAAAG

AAACGGTGATAT.

In some embodiments, a promoter from *L. crispatus* may be operably linked to a recombinant nucleic acid construct of the invention for expression in an *L. crispatus* cell. In some embodiments, a promoter from *L. crispatus* may be operably linked to a recombinant nucleic acid construct of the invention for expression in the cell of a different bacterial species.

In some embodiments, a promoter useful with the invention includes, but is not limited to, a translation elongation factor Tu promoter (Tuf) having the sequence of (5' to 3') of (SEQ ID NO: 74)
AAAATAAGTAAAAAGGTTTACATTTTCAAACTATTTAGTATAATTAGC

AAAGGATATTTTCGTTAGGCAATTTCGCTTAAGCTTTTTTACTAGGCAT

TTGCCGAAGAAAGTAGTACAATATTCAACAGAGAATTATCCGTTAACTT

ATCTCAACGGACTTCTTGCAAATTTACAGGAGGGTCATTTTA;

an Enolase promoter having the sequence of (5' to 3') of (SEQ ID NO: 75)
TTTAGATTCCTTATTTTTTGTATTTATTTTAATACATATATTATAGTCCT

TTGATATAGAGTTTTTTAGGCTGCTTTACTAATTTTTAAAATGTAAACCG

CTTTCATATGTTTACACCGTCACAAAGTTAGGCTAAAATTTGAGATGTAA

-continued

AGCGGAGCATTGTTCCGTATGGTATGAAAAACATACCATAATTTTTGAGG

AGGTTTATTA;

and/or a P6 promoter having the sequence of (5' to 3') of (SEQ ID NO: 76)
ATCTTAAGGAATTAGCTAATGAAGCTTGTTTTGTTTCAGAAACTGCTGAA

GAAAACGAAAAATTAGTTAACGACTTAATGAAGAAAATTAACAAGTAATT

TTCAAAAAGAGACCATCTGGTCTCTTTTTTTATATTTTTAAGTAAAACAA

ATAATTTCTTCACAAATAATTCACGCTTTATTTTTAGAATATAAGTAGTT

GTAAGTATAAAAGATAAAATGAGTACTTACAAAAAAGAAGTTAGTATGTT

ATACTGATTATAAGTTAAAGAACGTATACAAATATTTGTTCTGAGGAGCG

TGATTTTTATGGTAGATTTATATGTCTCTCCTAGTTGTACCTCATGTCGT

AAGGCAAGAGCATGGCTTGAAAAACATAATATTCCATTTAAGGAAAGAAA

CATTTTTCTGAGCCATTAACTAAAGAAGAATTATTAAAGATCCTCTAGA

G.

Thus, in some embodiments, a promoter operably linked to a CRISPR array may be an endogenous *L. crispatus* CRISPR-Cas system promoter (native to the *L. crispatus* repeat sequences) (e.g., SEQ ID NOs:69 to 71). In some embodiments, the promoter may be a heterologous promoter (non-native to the *L. crispatus* repeat sequences) (e.g., SEQ ID NOs:72 to 76).

In some embodiments, a promoter operably linked to a polynucleotide encoding a Cascade complex of the invention may be a *L. crispatus* CRISPR-Cas system promoter (native to the *L. crispatus* Cascade complex; e.g., SEQ ID NO:73) or it may be a heterologous promoter (non-native to the *L. crispatus* Cascade complex; e.g., SEQ ID NOs:69 to 72, or 74 to 76).

In some embodiments, a promoter operably linked to a polynucleotide encoding a Cas3 polypeptide may be a *L. crispatus* CRISPR-Cas system promoter (native to the *L. crispatus* Cas3; e.g., SEQ ID NO:72) or it may be a heterologous promoter (non-native to the *L. crispatus* Cas3; e.g., SEQ ID NOs:69 to 71 or 73 to 76).

Non-limiting examples of a promoter functional in a plant include the promoter of the RubisCo small subunit gene 1 (PrbcS1), the promoter of the actin gene (Psctin), the promoter of the nitrate reductase gene (Pnr) and the promoter of duplicated carbonic anhydrase gene 1 (Pdca1)(See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403: 132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812). CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), and/or S-adenosyl-L-methionine synthetase (SAMS)(Vander Mijnsbrugge et al. (1996) *Plant and Cell Physiology,* 37(8):1108-1115).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the RNAs and/or the polypeptides of the invention to be synthesized only when, for example, a crop of plants are treated with the inducing chemicals. Depending upon the objective, the promoter may be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induces gene expression (Levskaya et al. 2005. *Nature* 438:441-442). In other aspects, a promoter can include a light-repressible promoter, where application of specific wavelengths of light repress gene expression (Ye et al. 2011. *Science* 332:1565-1568).

Chemically inducible promoters useful with plants are known in the art and include, but are not limited to, the maize In2-2 promoter, which is activated by benzenesulfonamide herbicide safeners, the maize GST promoter, which activated by hydrophobic electrophilic compounds that are used as pre-emergent herbicides, and the tobacco PR-1a promoter, which is activated by salicylic acid (e.g., the PR1a system), steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

In some embodiments, promoters useful with algae include, but are not limited to, the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1)(See, Walker et al. *Plant Cell Rep.* 23:727-735 (2005); Li et al. *Gene* 403:132-142 (2007); Li et al. *Mol Biol. Rep.* 37:1143-1154 (2010)), the promoter of the $\sigma^{70}$-type plastid rRNA gene (Prrn), the promoter of the psbA gene (encoding the photosystem-II reaction center protein D1)(PpsbA), the promoter of the psbD gene (encoding the photosystem-II reaction center protein D2)(PpsbD), the promoter of the psaA gene (encoding an apoprotein of photosystem I)(PpsaA), the promoter of the ATPase alpha subunit gene (PatpA), and promoter of the RuBisCo large subunit gene (PrbcL), and any combination thereof (See, e.g., De Cosa et al. *Nat. Biotechnol.* 19:71-74 (2001); Daniell et al. *BMC Biotechnol.* 9:33 (2009); Muto et al. *BMC Biotechnol.* 9:26 (2009); Surzycki et al. *Biologicals* 37:133-138(2009)).

In some embodiments, a promoter useful with this invention can include, but is not limited to, pol III promoters such as the human U6 small nuclear promoter (U6) and the human H1 promoter (H1)(Mäkinen et al. *J Gene Med.* 8(4):433-41 (2006)), and pol II promoters such as the CMV (Cytomegalovirus) promoter (Barrow et al. *Methods in Mol. Biol.* 329:283-294 (2006)), the SV40 (Simian Virus 40)-derived initial promoter, the EF-1α (Elongation Factor-1α) promoter, the Ubc (Human Ubiquitin C) promoter, the PGK (Murine Phosphoglycerate Kinase-1) promoter and/or constitutive protein gene promoters such as the β-actin gene promoter, the tRNA promoter and the like.

Moreover, tissue-specific regulated nucleic acids and/or promoters as well as tumor-specific regulated nucleic acids and/or promoters have been reported. Thus, in some embodiments, tissue-specific or tumor-specific promoters can be used. Some reported tissue-specific nucleic acids include, without limitation, B29 (B cells), CD14 (monocytic cells), CD43 (leukocytes and platelets), CD45 (hematopoietic cells), CD68 (macrophages), desmin (muscle), elastase-1 (pancreatic acinar cells), endoglin (endothelial cells), fibronectin (differentiating cells and healing tissues), FLT-1 (endothelial cells), GFAP (astrocytes), GPIIb (megakaryocytes), ICAM-2 (endothelial cells), INF-β (hematopoietic cells), Mb (muscle), NPHSI (podocytes), OG-2 (osteoblasts), SP-B (lungs), SYN1 (neurons), and WASP (hematopoietic cells). Some reported tumor-specific nucleic acids and promoters include, without limitation, AFP (hepatocellular carcinoma), CCKAR (pancreatic cancer), CEA (epithelial cancer), c-erbB2 (breast and pancreatic cancer), COX-2, CXCR4, E2F-1, HE4, LP, MUC1 (carcinoma), PRC1 (breast cancer), PSA (prostate cancer), RRM2 (breast cancer), survivin, TRP1 (melanoma), and TYR (melanoma).

In some embodiments, inducible promoters can be used. Examples of inducible promoters include, but are not limited to, tetracycline repressor system promoters, Lac repressor system promoters, copper-inducible system promoters, salicylate-inducible system promoters (e.g., the PR1a system), glucocorticoid-inducible promoters, and ecdysone-inducible system promoters.

In some embodiments of this invention, one or more terminators may be operably linked to a polynucleotide encoding a Cascade complex, a polynucleotide encoding Cas3 polypeptides, and/or a CRISPR arrays of the invention. In some embodiments, a terminator sequence may be operably linked to the 3' end of a terminal repeat in a CRISPR array.

In some embodiments, when comprised in the same nucleic acid construct (e.g., expression cassette), each of the CRISPR array, recombinant nucleic acid encoding a Cascade complex, and/or recombinant nucleic acid encoding a Cas3 polypeptide may be operably linked to separate (independent) terminators (that may be the same terminator or a different terminator) or to a single terminator. In some embodiments, only the CRISPR array may be operably linked to a terminator. Thus, in some embodiments, a terminator sequence may be operably linked to the 3' end of a CRISPR array (e.g., linked to the 3' end of the repeat sequence located at the 3' end of the CRISPR array).

Any terminator that is useful for defining the end of a transcriptional unit (such as the end of a CRISPR array, a Cas 3, or a Cascade) and initiating the process of releasing the newly synthesized RNA from the transcription machinery may be used with this invention (e.g., an terminator that is functional with a polynucleotide composing a CRISPR array, a polynucleotide encoding a Cascade complex and/or polynucleotide encoding a Cas3 of the inventor may be utilized (e.g., that can define the end of a transcriptional unit (such as the end of a CRISPR array, Cascade complex or Cas3) and initiate the process of releasing the newly synthesized RNA from the transcription machinery).

A non-limiting example of a terminator useful with this invention may be a Rho-independent terminator sequence. In some embodiments, a Rho-independent terminator sequence from *L. crispatus* may be the nucleotide sequence of (5'-3') AAAAAAAAACCCCGCCCCTGACA-GGGCGGGGTTTTTTTT (SEQ ID NO:77). Further, non-limiting examples of useful *L. crispatus* terminator sequences (5'-3') include:

(SEQ ID NO: 78)
CAAAAAAAGCATGAGAATTAATTTTCTCATGCTTTTTTG;

(SEQ ID NO: 79)
AAAAAAGATGCACTTCTTCACAGGAGCGCATCTTTTTT;

(SEQ ID NO: 80)
CAAAAAGAGCGGCTATAGGCCGCTTTTTTTGC;
and/or (SEQ ID NO: 81)
GTAAAAATGGCTTGCGTGTTGCAAGCCATTTTTTTAC.

In some embodiments, a recombinant nucleic acid construct of the invention may be an "expression cassette" or may be comprised within an expression cassette. As used herein, "expression cassette" means a recombinant nucleic acid construct comprising a polynucleotide of interest (e.g., the Cascade complexes, polynucleotides encoding Cas3 polypeptides, and/or CRISPR arrays of the invention), wherein said polynucleotide of interest is operably associated with at least one control sequence (e.g., a promoter). Thus, some aspects of the invention provide expression cassettes designed to express the polynucleotides of the invention (e.g., the Cascade complexes, polynucleotides encoding Cas3 polypeptides, and/or CRISPR arrays of the invention).

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette may also optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked polynucleotide of interest, may be native to the host cell, or may be derived from another source (i.e., foreign or heterologous to the promoter, to the polynucleotide of interest, to the host, or any combination thereof).

An expression cassette (e.g., recombinant nucleic acid constructs and the like) may also include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Of course, many examples of suitable selectable markers are known in the art and can be used in the expression cassettes described herein. In some embodiments, a selectable marker useful with this invention includes polynucleotide encoding a polypeptide conferring resistance to an antibiotic. Non-limiting examples of antibiotics useful with this invention include tetracycline, chloramphenicol, and/or erythromycin. Thus, in some embodiments, a polynucleotide encoding a gene for resistance to an antibiotic may be introduced into the organism, thereby conferring resistance to the antibiotic to that organism.

In addition to expression cassettes, the nucleic acid construct and nucleotide sequences described herein may be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). A nucleic acid construct in the vector may be under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the recombinant nucleic acid constructs of this invention and/or expression cassettes comprising the recombinant nucleic acid constructs of this invention may be comprised in vectors as described herein and as known in the art. In some embodiments, the constructs of the invention may be delivered in combination with polypeptides (e.g., Cas3 and/or Cascade complex polypeptides) as ribonucleoprotein particles (RNPs). Thus, for example, Cas9 can be introduced as a DNA expression plasmid, e.g., in vitro transcripts, or as a recombinant protein bound to the RNA portion in a ribonucleoprotein particle (RNP), whereas the sgRNA can be delivered either expressed as a DNA plasmid or as an in vitro transcript.

Accordingly, in some embodiments, the invention provides a recombinant nucleic acid construct comprising a Clustered Regularly Interspaced Short Palindromic Repeats (CRISPR) array comprising two or more repeat sequences and one or more spacer sequence(s), wherein each spacer sequence and each repeat sequence have a 5' end and a 3' end and each spacer sequence is linked at its 5' end and at its 3' end to a repeat sequence, and the spacer sequence is complementary to a target sequence (protospacer) in a target DNA of a target organism that is located immediately adjacent (3') to a protospacer adjacent motif (PAM). A CRISPR array of the present invention comprises a minimum of two repeats, flanking a spacer, to be expressed as a premature CRISPR RNA (pre-crRNA) that will be processed internally in the cell to constitute the final mature CRISPR RNA (crRNA). As an example, FIG. 10D shows a precrRNA (GUAUU-CUCCACGUGUGUGGAGGUGAUCC *CUACAAGUCUUCCUGGCAAGCC CUAACGGCUGG*GUAUUCUCCACGUGUGUGGAG-GUGAUCC)(RNA equivalent of SEQ ID NO:89) and processed crRNA (GUGAUCC*CUACAAGUCUUCC GGCAAGCUAAUG GCCUGG* GUAUUCUCCACGUG UGUGGAG)(RNA equivalent of SEQ ID NO:90), wherein the crRNA is processed generating the mature crRNA with a 5' handle consisting of 7-nt (5'GUGAUCC-tag). The spacer region (italicized nucleotides) is exchangeable to target a nucleic acid of interest).

In some embodiments, a repeat sequence (i.e., CRISPR repeat sequence) as used herein may comprise any known repeat sequence of a wild-type *Lactobacillus crispatus* CRISPR Type I loci. In some embodiments, a repeat sequence useful with the invention may include a synthetic repeat sequence having a different nucleotide sequence than those known in the art for *L. crispatus* but sharing similar structure to that of the wild-type *L. crispatus* repeat sequences of a hairpin structure with a loop region. Thus, in some embodiments, a repeat sequence may be identical to (i.e., having 100% identity) or substantially identical (e.g., having 80% to 99% identity (e.g., 80, 81, 82, 83, 84, 85, 88, 87, 88, 89, 90, 91, 92, 93, 94, 95, 96, 97, 98, 99% identity)) to a repeat sequence from a wild-type *L. crispatus* CRISPR Type I loci.

The length of a CRISPR repeat sequence useful with this invention may be the full length of a *L. crispatus* repeat (i.e., 28 nucleotides)(see, e.g., SEQ ID NOs:1, 10, 19, 28, 37, 42, 51, or 60). In some embodiments, a repeat sequence may comprise a portion of a wild type *L. crispatus* repeat nucleotide sequence, the portion being reduced in length by as much as 7 or 8 nucleotides from the 3' end as compared to a wild type *L. crispatus* repeat (e.g., comprising about 21 to 28 contiguous nucleotides from the 5' end of a wild type *L. crispatus* CRISPR Type I loci repeat sequence; e.g., about 21, 22, 23, 24, 25, 26, 27 or 28 contiguous nucleotides from the 5' end, or any range or value therein). In some embodiments, a repeat sequence may be reduced in length by 7 nucleotides from the 3' end as compared to a wild type *L. crispatus* repeat and therefore, may be about 21 nucleotides in length (e.g., GTATTCTCCACGTGTGTGGAG)(nucleotides 1-21 of SEQ ID NO:1).

Thus, in some embodiments, a repeat sequence may comprise, consist essentially of, or consist of any of the nucleotide sequences of GTATTCTCCACGTGTGTGGAG-GTGATCC (SEQ ID NO:1), GTATTCTCCAC*ACA*TGTG-GAGGTGATCC (SEQ ID NO:10), GTATTCTCCAC *GCA*TGTGGAGGTGATCC (SEQ ID NO:19), GTAT-TCTCCAC*GTA*TGTGGAGGTGATCC (SEQ ID NO:28), GTATTCTCCAC*GTA*TGTGGAGGT*C*ATCC (SEQ ID NO:37), GTATTCTCCAC*GAG*TGTGG*G*G*A*T *CCTAT* (SEQ ID NO:42), GTATTCTCCACG*TAT*GTG-GAGGTGATCC*C* (SEQ ID NO:51), GTATTCTCCAC *GTG*TGTGGAGGTGATCC*T* (SEQ ID NO:60) (the bole and italicize nucleotides indicate the single nucleotide polymorphisms (SNPs) as compared to SEQ ID NO:1). In some embodiments, a repeat sequence may comprise, consist essentially of, or consist of a portion of contiguous nucleotides (e.g., about 20 to 27 contiguous nucleotides) of any of the nucleotide sequences of SEQ ID NOs:1, 10, 19, 28, 37, 42, 51, or 60 (see, e.g., SEQ ID NOs:2-9, 11-18, 20-27, 29-36, 38-41, 43-50, 52-59, 61-68). In some embodiments, a repeat sequence useful with the invention may comprise, consist essentially of, or consist of the nucleotide sequence of SEQ ID NOs:1 to 68 (100% identical). In some embodiments, the repeat sequence may comprise a "handle" or portion of a repeat sequence. In some embodiments, a handle may comprise 7 nucleotides from the 3' end of a wild type repeat sequence. In some embodiments, a handle may comprise, consist essentially of, or consist of the nucleotide sequence of GTGATCC (GUGAUCC).

In some embodiments, the two or more repeat sequences in a CRISPR array may comprise the same repeat sequence, may comprise different repeat sequences, or any combination thereof. In some embodiments, each of the two or more repeat sequences in a single CRISPR array may comprise, consist essentially of, or consist of the same repeat sequence. In some embodiments, each of the two or more repeat sequences in a single array may comprise, consist essentially of, or consist of the same sequence with the exception of the sequence of the terminal (most 3') repeat, which may be mutated at its 3' end (most 3' nucleotide of the terminal repeat). As a non-limiting example of such a mutation, the last nucleotides of the CRISPR repeat may be mutated from a C to a T/A/G, or the mutation may consist of an addition of a nucleotide, such as a C (sec SEQ ID NO:51) or T (see SEQ ID NO:52).

A CRISPR array of the invention may comprise one spacer sequence or more than one spacer sequence, wherein each spacer sequence is flanked by a repeat sequence. When more than one spacer sequence is present in a CRISPR array of the invention, each spacer sequence is separated from the next spacer sequence by a repeat sequence (or portion thereof (e.g., a handle). Thus, each spacer sequence is linked at the 3' end and at the 5' end to a repeat sequence. The repeat sequence that is linked to each end of the one or more spacers may be the same repeat sequence or it may be a different repeat sequence or any combination thereof.

In some embodiments, the one or more spacer sequences of the present invention may be about 25 nucleotides to about 40 nucleotides in length (e.g., about 25, 26, 27, 28, 29, 30, 31, 32, 33, 34, 35, 36, 37, 38, 39, 40 nucleotides in length, and any value or range therein). In some embodiments, a spacer sequence may be a length of about 25 to about 35 nucleotides (e.g., about 25, 26, 27, 28, 29, 30, 31, 32, 33, 34, 35 nucleotides in length, and any value or range therein) or about 30 to about 35 nucleotides (e.g., about 30, 31, 32, 33, 34, 35 nucleotides in length, and any value or range therein). In some embodiments, a spacer sequence may comprise, consist essentially of, or consist of a length of about 33 nucleotides.

In some embodiments, a spacer sequence may be fully complementary to a target sequence (e.g., 100% complementary to a target sequence across its full length). In some embodiments, a spacer sequence may be substantially complementary (e.g., at least about 80% complementary (e.g., about 80%, 81%, 82%, 83%, 84%, 85%, 86%, 87%, 88%, 89%, 90%, 91%, 92%, 93%, 94%, 95%, 96%, 97%, 98%, 98.5%, 99%, 99.5%, or more complementary)) to a target sequence from a target genome. Thus, in some embodiments, a spacer sequence may have one, two, three, four, five or more mismatches that may be contiguous or noncontiguous as compared to a target sequence from a target genome. In some embodiments, a spacer sequence may be about 80% to 100% (e.g., about 80%, 81%, 82%, 83%, 84%, 85%, 86%, 87%, 88%, 89%, 90%, 91%, 92%, 93%, 94%, 95%, 96%, 97%, 98%, 99%, or 100)) complementary to a target sequence from a target genome. In some embodiments, a spacer sequence may be about 85% to 100% (e.g., about 85%, 86%, 87%, 88%, 89%, 90%, 91%, 92%, 93%, 94%, 95%, 96%, 97%, 98%, 99%, or 100%)) complementary to a target sequence from a target genome. In some embodiments, a spacer sequence may be about 90% to 100% (e.g., about 90%, 91%, 92%, 93%, 94%, 95%, 96%, 97%, 98%, 99%, or 100%)) complementary to a target sequence from a target genome. In some embodiments, a spacer sequence may be about 95% to 100% (e.g., about 95%, 96%, 97%, 98%, 98.5%, 99%, 99.5% or 100%) complementary to a target sequence from a target genome.

In some embodiments, the 5' region of a spacer sequence may be fully complementary to a target sequence while the 3' region of the spacer sequence may be substantially complementary to the target sequence. Accordingly, in some embodiments, the 5' region of a spacer sequence (e.g., the first 8 nucleotides at the 5' end the first 10 nucleotides at the 5' end, the first 15 nucleotides at the 5' end, the first 20 nucleotides at the 5' end) may be about 100% complementary to a target sequence, while the remainder of the spacer sequence may be about 80% or more complementary to the target sequence.

In some embodiments, at least the first eight contiguous nucleotides at the 5' end of a spacer sequence of the invention are fully complementary to the portion of the target sequence adjacent to the PAM (termed a "seed sequence"). Thus, in some embodiments, the seed sequence may comprise the first 8 nucleotides of the 5' end of each of one or more spacer sequence(s), which first 8 nucleotides are fully complementary (100%) to the target sequence, and the remaining portion of the one or more spacer sequence(s) (3' to the seed sequence) may be at least about 80% complementarity (e.g., about 80, 81, 82, 83, 84, 85, 86, 87, 88, 89, 90, 91, 92, 93, 94, 95, 96, 97, 98, 99, or 100% complementarity) to the target sequence. Thus, for example, a spacer sequence having a length of 28 nucleotides may comprise a seed sequence of eight contiguous nucleotides located at the 5' end of the spacer sequence, which is 100% complementary to the target sequence, while the remaining 20 nucleotides may be about 80% to about 100% complimentary to the target sequence (e.g., 0 to 4 non-complementary nucleotides out of the remaining 20 in the spacer sequence). As another example, a spacer sequence having a length of 33 nucleotides may comprise a seed sequence of eight nucleotides from the 5' end, which is 100% complementary to the target sequence, while the remaining 25 nucleotides may be at least about 80% (e.g., 0 to 5 non-complementary nucleotides out of the remaining 25 nucleotides in the spacer sequence).

A CRISPR array of the invention comprising more than one spacer sequence may be designed to target one or more than one target sequence (protospacer). Thus, in some embodiments, when a recombinant nucleic acid construct of the invention comprises a CRISPR array that comprises at least two spacer sequences, the at least two spacer sequences may be complementary to two or more different target sequences. In some embodiments, when a recombinant nucleic acid construct of the invention comprises a CRISPR array that comprises at least two spacer sequences, the at least two spacer sequences may be complementary to the same target sequence. In some embodiments, a CRISPR array comprising at least two spacer sequences, the at least two spacer sequences may be complementary different portions of one gene.

A target sequence may be any sequence immediately adjacent to a PAM sequence (e.g., 5'-NAA-3', 5'-AAA-3' and/or 5'-AA-3'). Accordingly, a recombinant nucleic acid construct of the invention may target, for example, coding regions, non-coding legions, intragenic regions, and intergenic regions for genome modification and other uses. In some embodiments, a target sequence may be located in a target DNA of a target organism. In some embodiments, a target sequence may be located on a chromosome. In some embodiments, a target sequence may be located on an extrachromosomal nucleic acid.

In some embodiments, a target sequence may be located in a gene, which can be in the upper (sense, coding) strand or in the bottom (antisense, non-coding) strand. In some embodiments, a target sequence may be located in an intragenic region of a gene (e.g., an intron), optionally located in the upper (sense, coding) strand or in the bottom (antisense, non-coding) strand. In some embodiments, a gene that is targeted by constructs of this invention may encode a transcription factor or a promoter. In some embodiments, a gene that is targeted may encode non-coding RNA, including, but not limited to, miRNA, siRNA, piRNA (piwi-interacting RNA) and lncRNA (long non-coding RNA). In some embodiments, a target sequence may be located in an intergenic region, optionally in the upper (plus) strand or in the bottom (minus) strand. In some embodiments, a target sequence may be located in an intergenic region wherein the DNA is cleaved and a gene inserted that may be expressed under the control of the promoter of the previous open reading frame.

As used herein, "extrachromosomal nucleic acid" refers to nucleic acid from a mitochondrion, a plasmid, a plastid (e.g., chloroplast, amyloplast, leucoplast, proplastid, chromoplast, etioplast, elaiosplast, proteinoplast, tannosome), and/or an extrachromosomal circular DNA (eccDNA)). In some embodiments, an extrachromosomal nucleic acid may be referred to as "extranuclear DNA" or "cytoplasmic DNA." In some embodiments, a plasmid may be targeted (e.g., the target sequence is located on a plasmid), for example, for plasmid curing to eliminate undesired DNA like antibiotic resistance genes or virulence factors.

In some embodiments, a target sequence may be located on a mobile element (e.g., a transposon, a plasmid, a bacteriophage element (e.g., Mu), a group I and group II intron). Thus, for example, mobile elements located in the chromosome or transposons may be targeted to force the mobile elements to jump out of the chromosome.

In some embodiments, a recombinant nucleic acid construct of the invention may further encode a Type I-E CRISPR associated complex for antiviral defense complex (Cascade complex) comprising: a Cse1 polypeptide, a Cse2 polypeptide, a Cas7 polypeptide, a Cas5 polypeptide and a Cas6 polypeptide.

In some embodiments, a Cse1 polypeptide may be encoded by a nucleotide sequence of:

```
                                    (SEQ ID NO: 82)
ATGAATAATGATTTAAGCTTCAACTGGTTACTGATCCTTGGATTAAAGTC

CTGAAAAAGGATTATACCGAAAGTGAGGTCTCTTTGAATGAACTTTTTAG

TAATTCTGAAGAGTATCTTCAGCTTGCTGGTGATATGAAATCACAAGACT

TAGCGATTCTCAGATTATTGTTGGCTATTTTACTGTCAGTTTATACTAGA

TTCGATGCAGATGATACGCCATACTCATGGCTGGATTTAGATGACAAATG

GCGAGTGACTCGGACAGATAATGATGGCTTCAACTCTCAAAAACTAAAAC

TGGGAGACACTTGGAGAAGTCTATATGATCAAAAAACTTTTTCAAAAAAA

GTATTTGATTATCTAAATCTTTATCAGGCTAAGTTTAATTTATTTGGTGA

AGATCCTTTTTATCAAGTTAATCGTCAAGTCTATGACCAAAATGTGCCGG

AAAATAAAAAGGTAGCTAAAGGTGCGGGTACAGTATCAGTTAAACAAATT

AATCGACTTATTTCTGAAAGCAATAACAGCCCGGCACTGTTTTCACCTAA

ATCAGGTATTGAAAAAGATAGTGTTAATAATGCGGAATTAGTTCGCTGGT

TAATTACTTACCAAAACTTCACAGGTGTTACTGATAAGACCAAAGTTAAG

TCAAAGGATAAGTTCTCTGTTTCTCCTGGTTGGTTGTATTCAATTAATCC

TGTTTATATTAAAGGTAAAACTTTATTTGACACGTTGATGTTAAATCTAA

GCTTAGTTACCAATGATTCTGCAGATGGAACAAACTGGCTAAACTCACAA

AGACCAGTGTGGGAATACGATGATATTAATGATTATCTTCAACAAAGATT

GAATGGAGTGTATCCTGACAATTTGTCTGAATTATATACTGTCTGGTCTA

GAATGATTCATATTGATTGGCAAAATGGTCAGCCAGTTATATTTAGCGCA

GGACTGCCTAAGTTAGATAGTGAAAAACAATTCCTAGAGCCAATGACGAC
```

-continued

TTGGCGTAAAAATAAAGATGGTGTTGTATATCCAGCTGCCAAGAATAAAA

ATAATATAAATGTCGCTATGTGGCGTAATTTTGGTCAGTATATAAGGACT

AAAGAAGATAATAACAACGAAAAAAGATAAAAATAATCACAGAATTCCA

GGAGTTATTGGTTGGATTCAGGAATTGAAAATGCATAATCAAATTTCCAA

GCATACTAACATCAATATAGTTACAGTAGCTATGATAAGTGATGGAAATG

CTACATCTCAATCACCTTATGCGGAAATCACTGATAATATGCAAGCTAAG

GCAGGGATCCTTTTTGATGATGAGCCTATGTTTGAAAATCGGTGGCAAGA

TAAGATTGAAGAAGAAGTATTATTAGCACAAAAGGTTGTGGCTTATTTCT

ATTGGTTTGCAAAAGATATATCGAACATTCAAACCCATAGCGAGAAGAAA

AAAAGTAATGATGATTGGGCAAGTCGAAAGGTAGCGCAACTTTATGACGA

ACTGAATCAGCCATTTTACACTTGGCTTTCTGGATTAGATATAAATCAAG

ACCGTAATGTCAAAATTAAAGAATGGCGTGAAACTTTAAATCGTCTTGTT

GCAACGCAAGCTAAAAATATTTTTATCAATGCAACTGCTGATGAAATCAT

TGGCGGGAAGGAAGACAATATTTTTACAATTTATAATAAACTACGCAGAA

ACGTCTATGTTTGTCTCGGATTAAAATAA.

In some embodiments, a Cse1 polypeptide may comprise the amino acid sequence of SEQ ID NO:112.

In some embodiments, a Cse2 polypeptide may be encoded by a nucleotide sequence of:

(SEQ ID NO: 83)
ATGAGTGATGCTTATACTGCTACGGCACGAATAATTAATCAGCTGTATGG

TGATGGAACTCCTGATAAAGGTGCTTTGGCTGAACTTAGAAGGACAACAG

CTATCACCGATAAAGGCGCTGAAAAAATCTGGCCTTTAATTTTTTCAGTC

GTGCCTAAATTAAGTACAAATGGAAAGCCTACAAAGCTTGAAACAGCAGT

TTATACTGCTCTTCACTGTTATGCTGCATTTCAACAAGGGAATGATTCAT

TTGTCTTTGGTCAAATTCCTAGATCAAAAGATAAGGAAGAATCTGGAGAA

AATGGTGTATCTCTTTTTACTGCACTGAGGAAAATGAAAATAAACGACTC

TAACGAAAAGAAGGCTTTAGATAGGCGAGTAACAGCTTTATTAGCAACTA

CAAATATCAGCAGTGCCACCAATTCAATTAATCATCTAGTAAGTATTCTT

AAAGGAAAGAAAATGGGTGAAAAGATTGACTTTGCTCAATTGGCGGAAGA

CTTGTATAACTTTCAGTGGAGTACGAAAAATGCAAGATTCGTTGCCTTGA

AGTGGGGAAAAGATTACTACTGGAACGTTTATAAGCTGGCATCAGACAAC

GATTAG.

In some embodiments, a Cse2 polypeptide may comprise the amino acid sequence of SEQ ID NO:113.

In some embodiments, a Cas7 polypeptide may be encoded by a nucleotide sequence of:

(SEQ ID NO: 84)
ATGAATAAGAATCTTTATATGGACATTAATGTATTGCAAACTGTACCATC

ATCAAATATCAATAGAGATGACACTGGTTCACCTAAAACAGCTATTTATG

GTGGCGTGACTCGGTCAAGAGTTTCTTCACAAAGCTGGAAGAGAGCAATG

CGTTTAGCCTTTAAACAAGACTCAGAAAATGAAGAGTGGCTTAAGAGCTA

TAGAACTTTGAAAACAGCTAGTCTTTTGGCGAATAAGTTACAAGAACTAG

ATTCAAATTTAAGTGAAGAAGATGCTTTAAAGAAAGTTGAAGAAGTCTTT

AAAGTAGCTGGAATCAAATTAAAAAAGGACAAGAAAACGGGCGAAATGTT

AACTGGAGCACTACTACTAGTAAGTGAAGGGCAACTCGAAAAGATCGCTA

AACTTGCTTTGTCTGTTGATCAAATAGATAAAGATACAGCTAAAGAAATT

AAGAAAAATTTGATGGAAGATCAATCTCTAGATTTAGCTTTATTTGGAAG

AATGGTGGCAGATAATCCAGAATTGAATGTGGATGCTTCTAGTCAAGTGG

CTCATGCAATTTCCACTCATGAAGTTACTCCAGAATTTGATTATTACACT

GCAGTTGATGATGCAAATACGAAAAGCCAAACAGGTTCTGCAATGCTTGG

TACGATTGAATATAATTCATCTACTTTATACAGATATGCCAATGTTAACA

TTCTTGATTTATTGCACAATCTTGGTAATAAAGATTTGACTATTGAGGGA

ATTAAGCTTTTTATCAAAGAATTTGTTTTGACAATGCCGACTGGTAAGGA

AAATACTTTTGCTAATAAAACACTCCCTCAATACGTTATGATTAATGTTC

GTACTGATACACCTGTTAACCTAGTATCTGCATTTGAAACACCAGTTAGA

TCTGAAGGCGGATACGTTGATAAATCTATCAATCGATTAGAGGATGAATA

TAAAAATTCTTTGAAATTTGTAGATAAGCCTGTGTTTAATGTCGAATTGA

CGAATAGTGAGAATATAGTCGACAATCAGGCTGAAAATATTGATGATTTA

ATTAATCAAACTGCTGAATTCGTAAAACAGGAGTTAGAAAATGAAGACAG

CAACGATTAG.

In some embodiments, a Cas7 polypeptide may comprise the amino acid sequence of SEQ ID NO:114.

In some embodiments, a Cas5 polypeptide may be encoded by a nucleotide sequence of:

(SEQ ID NO: 85)
ATGAAGACAGCAACGATTAGATTGACTGCGCCACTTCAGTCTTATGGCAA

TCCCGCATCTTTTAACCAAAGAACTAGTGATAGTTATCCAACTAAAAGCG

CTATTGTAGGTATGATTGCAGCTGCATTGGGCTACGCAAGAGAAGATAAT

GAAAAAACTTTGGAGCTAAATAATTTATTATTTGCTGTTCGAATTGAGCA

ATCAGGCAAAATGTTGACAGAGTTTCAAACAGTGGAATACAGAAAGAGTG

CAAGCAAGACTGCTCGAAAGTTAACGTATCGTGATTTTATTCAAGATGGA

GTTTTCATGGTAGCAATTGGCAGCGATGATGATCAATTGATCGAAAACAT

CAAAGAAGCACTTGAACATCCAAAATTTCAGCTTTATTTAGGAAGACGGT

CTAATCCGCCAGCTGGTCCACTTAAAATTGATATTTTAATGGAAGAAAT

CCCTTACAAGTACTAGAAGATTTGCCTTGGCAAGCTTCAGATTGGTATAA

GAGGAGCTTTAAGACGTCACAATTTCTAACTAGAATAATTGCTGATGCTA

GTTTAGATTCTGAAAGTACCCCCTTAATGAAAAAGATAAAGTGGGCTCT

TTTGATCAAAAAGATAGATATTATCAATATCGTCCTGTCGTAATCAAAAA

AGCAGTTAAACTTAAAAATTCAGAAAATAATCAGACAGCAGATAATACTG

ATTGGGATTTTTGGTCATTTGTGTAG.

In some embodiments, a Cas5 polypeptide may comprise the amino acid sequence of SEQ ID NO:115.

In some embodiments, a Cas6 polypeptide may be encoded by a nucleotide sequence of:

(SEQ ID NO: 86)
ATGTATATTTCGAGAGTTGAAATTGATACTAACAACCGACAAAAAATTAG

GGATTTGTATCATTTAGGTGCTTATCATAATTGGGTTGAAAATTGCTTTC

CAGATGAATTAAAGAAAAAAGTAAGATTACGCCATTTATGGAGAATTGAT

GAATTAAATGGTAAAAAGTATTTACTTGTTTTAAGTGAAGAAAAGCCAAA

ATTAGATAAGCTTGAAAGATATGGTCTTGCCAATACGGCAGAGACGAAAG

ACTATGATCATTTTTTAAGTAGTTTAAATCAAGGAAAAAAATATCGCTTT

AAACTAACGGCTAATCCTTCATATAGAATTACAGATGCAAAAACCGGTAA

ATCAAAAGTAGTACCGCATATTACTGTTTTGCAGCAAACTAAGTGGTTAT

TAGATCGATCAGAAAAATATGGTTTTGATTTAGTTAAATCAGAAGATGAC

GAAGAAACATATGAAATGAATATTACGTCAAGAGATTGGCCACGATTACG

CCGCAAGGGCAATAAAATAGTAAAATTAAGTCGTGTTACTTTTGAAGGCT

TATTAGAGATTAAGGATTTGCAACAATTTAAGCAGGCAATGGTAACTGGT

ATAGGGCGTGAAAAAGCTTTTGGGATGGGACTACTCACTGTAATTCCAAT

GGAATAA.

In some embodiments, a Cas6 polypeptide may comprise the amino acid sequence of SEQ ID NO:116.

In contrast to the recombinant nucleic acid constructs of the present invention, a wild type Cascade complex (e.g., a wild type *L. crispatus* Cascade complex) further comprises Cas1 and Cas2 (see, SEQ ID NOs:117 and 118, respectively), which are responsible for spacer acquisition in wild type CRISPR-Cas systems.

In some embodiments, a recombinant nucleic acid construct of the invention may further comprise a polynucleotide encoding a Cas3 polypeptide. In some embodiments, a Cas3 polypeptide may be encoded by a nucleotide sequence of:

(SEQ ID NO: 87)
ATGACAAATTTATCAAATACCACCCTGTCTTTATGGGGTAAAAAGAATAT

TAATGAAGATAGCGAAGAAGTATGGTTACCCTTAATCGCTCACTTAATTG

ACACAAAAAATGTTATTGGATGGTTATATAATCATTGGCTTAATGACGGC

CAAAGATGCATTTTGAGTCAGGGTTTTGAAAACTCAAATGAAGTTCAGAA

TCTTGTTGAATTTATTGGATACATTCATGATATTGGTAAGGCTACGCCTG

CTTTTCAAATTAAGCAATCGTTTATCCATAATGAAGATTTAGACCAGGAT

CTGTTAGAGAGATTATTACAAAATGGATTTGATAATTTAGAAGAATTAAA

GGCAAATATGGATACTAGACACTGGCTCCACGCTCTGGCTGGTGAAGTGA

TCTTAGAAAATAGTGGGCTAAATGAAAGTATTGGCGCTATAGTTGGCGGG

CACCATGGTAAACCACAAAATAAGTATTTTGACTATGAAGATCAACTGAT

GGATGATACTTCTAAATATTATCAATCAGATTCTTGGGCCGAAAATCCAA

CTAGAGAAAATGGGAAATGTACAAAAAGAGATCATCAATTATGGTTTA

GATTTGTGTAATTTTAAAAATTTAGAAGATATACCTACAGTTACTGACTC

ACAAGCAGTAATTTTAGAAGGCCTAGTCATTATGGCCGACTGGTTGGCAT

CTAGTGAATATACAATTAAAGATGGTAAGCGTGTTAGCATGTTTCCATTA

ATCTCGATGGATCAAGGTTTTAGCGATATTGATATGACATCAAGATATCA

ACAAGGAATTTTAAATTGGCTTAAAACAGATTCCTGGACGCCTCAATTGA

TAGTCGATACTAAAGAGCAATATCAAAAACGCTGGAATTTTGATCCAAGA

CAAGTTCAGGAACAAATGTCTCAAGCAATCGGAGATAGTGTGGATCCTAG

CATGATTATCGTTGAAGCCCCGATGGGTATTGGTAAAACTGAAATAGCTT

TAACCGCTGTTGAGCAATTAGCTGCTAAGACCGGTATCAATGGCCTGTTT

TTTGGCTTGCCAACTCAGGCTACTGCAAATGCAATGTTTGATAGAGTAGA

TAACTGGCTGGGGAATATTGCCAAAGAACAGAGCGAAAATCTTTCTATTA

AATTGATGCATGGAAAGGCACAGTTTAATCAAAAATATCACAATATTCCT

GATGCTGATGATATTGAAACCGATGAAGGTCAGTTGTTGTTAATCAGTG

GTTTAATGGTAAAAAGTCAATATTAACTGACTTTGTAATTGGAACTATTG

ATCAATTGCTTTTGATGGGCTTGAAGCAAAAGCATCTGGCCTTAAGACAT

TTAGGGCTAAGCGGAAAAATAGTTGTAATTGACGAGGTTCATGCTTATGA

CGTATATATGAGTTCCTATCTTGAAAAGGCAATAGAGTGGTTGGGGGCAT

ATCATGTACCAGTTGTTGCTTTGTCGGCTACGCTTCCAGTTGATAAAAGA

AATGAACTTCTTACAGCATATTGTAGAGGAAAATATGGCAGTGAAAAATT

TAAAGCTCAAAATACTAATTGGCAAACTTGTCAAGCATATCCCTTATTAA

GTATTTTGGATGGCAAAGTTTTAAAACAAAAGTCAGACTTTTCTACTAAA

GCTGATGATACTACAGTTAAAGTTACTCGCTTAAGCATTGAAAATTACGA

TTTAATTGAAAAGATTAATGATCAAATTGAAGATGGCGGTGTCGCAGGTG

TCATAGTTAATACGGTAAAGCGAGCACAAGAATTGGCAAAAATTGCTGAA

AAAGAGTGCTCTGAAGATACGCAAATTTTGGTGCTTCATTCCGCATTTTT

GGCTAATGATCGTAGTAATTTAGAGTCCAAATTGGAAAAGTCAATTGGAA

ATCACCAAAAACGTCCAAAGAAAATGATAGTAATTGGCACGCAAGTGCTC

GAACAATCTTTGGATATCGATTTTGATGTTATGTATACGGATATTGCACC

AATAGACTTGATTTTACAAAGAGCGGGTCGTTTGCATCGTCATCAAGTTA

AGCGCCCAGACAAATTAATTGAGCCTCAACTATTCATTATGGGTATTAAT

TCTAATGGGACTATGGGGATGCAAATCAAGCAATATATGAGAAATATCT

TTTAATTAAGACGGATCATTTCTTAAAAGACAATATCAAATTACCTAGTG

ATATTTCTAATTTGGTTCAAAAGGTATATTCAGCGGATACTGATAATGAA

GTACAAGATCTTCAGGAAGCGGAAGTTAAGAAATTCAACATTGATCAGGA

AAAGGCAGAACAAAAATCGAAAGGGTATCAAATTAGAGCCCCAAGAGTTG

AAAAAACTTTACACGGTTGGCTTGATAATGATAGTGACACTGATCTAAAT

GATGTTAAAGCAGAGGCTGCTGTCAGAGATACGAATGAAACAATCGAGGT

TCTTTTGCTAAAAAAGATGCCGATGGATTTTATTTAATGGATGGGCGAA

AAGTGGATGAAGAAGTTCCTGATAGCGTTGTTGCTCAGCAGTTGATTAGG

CTGCCCCATGCATTAACGATGGATATAAACCAATCTATACGAAATTTGGA

ACGAGATACTATTAGTAATTTTCCTGAATGGCAGAACAGTTCCTGGTTAA

-continued

AGGGCTCGGTAGCTTTAATTCTTGATGCCAATAATGAGACAGAATTTAAT

GGATATAAAATTAAGTATTCATCTGACTTGGGGTTATCGTACGAAAAATA

G.

In some embodiments, a Cas3 polypeptide may comprise the amino acid sequence of SEQ ID NO:119.

In some embodiments, the recombinant nucleic acid constructs of the invention may be comprised in a vector (e.g., a plasmid, a bacteriophage, and/or a retrovirus. Thus, in some embodiments, the invention further provides vectors, plasmids, bacteriophage, and/or retroviruses comprising the recombinant nucleic acid constructs of the invention.

Plasmids useful with the invention may be dependent on the target organism, that is, dependent on where the plasmid is to replicate. Non-limiting examples of plasmids that express in *Lactobacillus* include pNZ and derivatives, pGK12 and derivatives, pTRK687 and derivatives, pTRKH2 and derivatives pIL252, and/or pIL253. Additional, non-limiting plasmids of interest include pORI-based plasmids or other derivatives and homologs.

The compositions (e.g., recombinant nucleic acid constructs) of the present invention may be used in methods for modifying nucleic acids such as modifying the genome of a target organism or a cell thereof. In some embodiments, the nucleic acid modification may be carried out in a cell free system. In some embodiments, the nucleic acid or genome modification may be directed to targeted gene silencing, repression of expression and/or modulation of the repression of expression in an organism of interest or cell thereof or in a cell free system. Other methods include selection of variants in a population of cells or selected killing of cells in a population.

Accordingly for use in such methods, the recombinant nucleic acid constructs of the invention may be introduced into a cell of an organism or contacted with a target nucleic acid in a cell free system. In some embodiments, the recombinant nucleic acid constructs of the invention may be stably or transiently introduced into a cell of an organism of interest.

"Introducing," "introduce" "introduced" (and grammatical variations thereof) in the context of a polynucleotide of interest and a cell of an organism means presenting the polynucleotide of interest to the host organism or cell of said organism (e.g., host cell) in such a manner that the nucleotide sequence gains access to the interior of a cell and includes such terms as transformation," "transfection," and/or "transduction." Where more than one nucleotide sequence is to be introduced these nucleotide sequences can be assembled as part of a single polynucleotide or nucleic acid construct, or as separate polynucleotide or nucleic acid constructs, and can be located on the same or different expression constructs or transformation vectors. Accordingly, these polynucleotides can be introduced into cells in a single transformation event, in separate transformation events, or, for example, they can be incorporated into an organism by conventional breeding protocols. Thus, in some aspects of the present invention one or more recombinant nucleic acid constructs of this invention may be introduced into a host organism or a cell of said host organism.

The terms "transformation," "transfection," and "transduction" as used herein refer to the introduction of a heterologous nucleic acid into a cell. Such introduction into a cell may be stable or transient. Thus, in some embodiments, a host cell or host organism is stably transformed with a nucleic acid construct of the invention. In other embodiments, a host cell or host organism is transiently transformed with a recombinant nucleic acid construct of the invention.

As used herein, the term "stably introduced" means that the introduced polynucleotide is stably incorporated into the genome of the cell, and thus the cell is stably transformed with the polynucleotide. When a nucleic acid construct is stably transformed and therefore integrated into a cell, the integrated nucleic acid construct is capable of being inherited by the progeny thereof, more particularly, by the progeny of multiple successive generations.

"Transient transformation" in the context of a polynucleotide means that a polynucleotide is introduced into the cell and does not integrate into the genome of the cell.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant, a mammal, an insect, an archaea, a bacterium, and the like). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, the nucleotide sequences, constructs, expression cassettes may be expressed transiently and/or they may be stably incorporated into the genome of the host organism. In some embodiments, when transient transformation is desired, the loss of the plasmids and the recombinant nucleic acids comprised therein may achieved by removal of selective pressure for plasmid maintenance.

A recombinant nucleic acid construct of the invention can be introduced into a cell by any method known to those of skill in the art. Exemplary methods of transformation or transfection include biological methods using viruses and bacteria (e.g., *Agrobacterium*), physicochemical methods such as electroporation, floral dip methods, particle or ballistic bombardment, microinjection, whiskers technology, pollen tube transformation, calcium-phosphate-mediated transformation, nanoparticle-mediated transformation, polymer-mediated transformation including cyclodextrin-mediated and polyethyleneglycol-mediated transformation, sonication, infiltration, as well as any other electrical, chemical, physical (mechanical) and/or biological mechanism that results in the introduction of nucleic acid into a cell, including any combination thereof.

In some embodiments of the invention, transformation of a cell comprises nuclear transformation. In other embodiments, transformation of a cell comprises plastid transformation (e.g., chloroplast transformation). In still further embodiments, the recombinant nucleic acid construct of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one polynucleotide is to be introduced, they can be assembled as part of a single nucleic acid construct, or as separate nucleic acid constructs, and can be located on the same or different nucleic acid constructs. Accordingly, the polynucleotides can be introduced into the cell of interest in a single transformation event, or in separate transformation events, or, alternatively, where relevant, a nucleotide sequence can be incorporated into a plant, as part of a breeding protocol.

A target organism useful with this invention may be any organism. In some embodiments, a target organism may be a prokaryote or a eukaryote. In some embodiments, a target organism may be a virus, a bacterium, an archaeon, a fungus, plant, or an animal (e.g., a mammal, a bird, a reptile, an amphibian, a fish, an arthropod (an insect or a spider), a nematode, a mollusk, etc.).

In some embodiments, the invention further comprises a recombinant cell or organism comprising the recombinant nucleic acid constructs of the invention, and/or comprising the recombinant plasmid, bacteriophage, and/or retrovirus comprising the recombinant nucleic acid constructs of the invention. In some embodiments, the recombinant cell or organism may be a prokaryotic cell or a eukaryotic cell, optionally a bacterial cell, an archaeon cell, a fungal cell, a plant cell, an animal cell, a mammalian cell, a fish cell, a nematode cell, or an arthropod cell. In some embodiments, a recombinant cell of the invention may be a recombinant *Lactobacillus crispatus* cell.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. CRISPR-Cas System Identification and Characterization in *Lactobacillus crispatus*

The 55 *Lactobacillus crispatus* genomes available from GenBank database (NCBI) (as of December 2017) were used to characterize the occurrence and diversity of CRISPR-Cas systems in this species. The in silico analyses were performed using Cas proteins (Cas 1, Cas 3, Cas 9) previously identified in other lactobacilli species (Sun et al., 2015, *Nat Commun* 6, 8322, doi: 10.1038/ncomms9322.) as templates to find the Cas proteins in the query *L. crispatus* strains, using the BLAST algorithm. (Altschul et al., 1997, *Nucleic Acids Res* 25(17), 3389-3402). Potential CRISPR array(s) of each genome were identified using CRISPR Recognition Tool (CRT) (Bland et al., 2007, *BMC Bioinformatics* 8, 209. doi: 10.1186/1471-2105-8-209) implemented in Geneious 10.0.6 software (Kearse, 2012, *Bioinformatics* 28, 1647-1649). The CRISPR-Cas systems of each strain were then manually curated, annotated and depicted. The CRISPR subtypes designation was performed based on the signature Cas proteins (Cas3-TypeI, Cas9-TypeII) and associated ones as previously reported (Makarova et al., 2011, *Nat Rev Microbiol* 9(6), 467-477. doi: 1.1038/nrmicro2577; Makarova et al., 2015, Nat Rev Microbiol 13(11), 722-736. doi: 10.1038/nrmicro3569; Koonin et al., 2017, *Curr Opin Microbiol* 37, 67-78. doi: 10.1016/j.mib.2017.05.008).

Example 2. PAM Prediction

Figure 1:
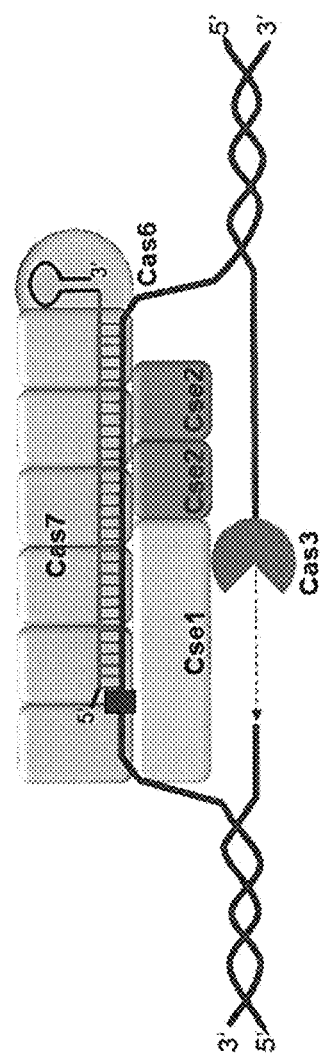
FIG. 1. Schematic representation of CRISPR-Cas system Class 1-Type I.
Figure 2:
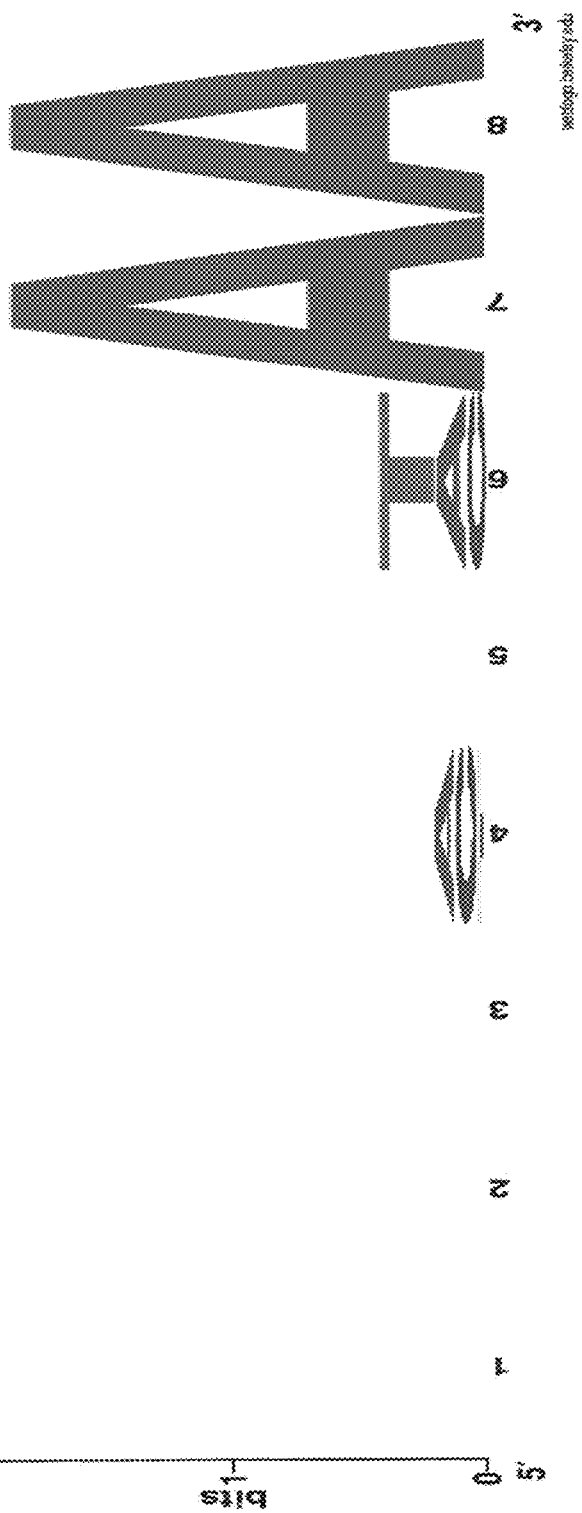
FIG. 2. Frequency plot representing the consensus predicted protospacer adjacent motif (PAM) for *L. crispatus* CRISPR-Cas system Type I-E (5'-NAA-3') based on in silico analyses.

Computational studies were performed with the spacers of each *L. crispatus* strain against several databases, using CRISPRTarget Webserver (Biswas et al., 2013, *RNA Biol* 10(5), 817-827 doi: 10.4161/rna 24046), to characterize the targets and the protospacers and protospacer adjacent motif (PAM) (Deveau, 2008, *J Bacteriol* 190(4), 1390-1400. doi 10.1128/JB.01412-07; Mojica, 2009, *Microbiology* 155(Pt 3), 733-740. doi: 10.1099/mic.0.023960-0). WebLogo server was used to represent the PAM sequence based on a frequency chart where the height of each nucleotide represents the conservation of that nucleotide at each position (Crooks et al., 2004, *Genome Res* 14(6), 1188-1190. doi: 10.1101/gr.849004). The PAM sequence for Type I-E in *L. crispatus* was predicted as 5'-NAA-3' as showed in FIG. 2. The PAM 5'-AAA-3' was further validated with plasmid interference assays in the strain *L. crispatus* NCK1350, and then used for self-targeting and genome editing purpose Example 3. Bacterial Strains and Growth Conditions The *Lactobacillus crispatus* NCK1350 and derivative strains used in this study were propagated in MRS (de Man Rogosa and Sharpe, Difco) broth or in MRS agar (1.5%, w/v) plates, both at 37° C. under anaerobic conditions. *Escherichia coli* DH10B was used as a host for all plasmid constructions *E. coli* strains were grown in BHI (Brain Heart Infusion, Difco) broth at 37° C. with stirring conditions (250 rpm) or in BHI agar plates at 37° C. aerobically. Transformants were selected in the presence of erythromycin (Erm) 2.5 μg ml$^{-1}$ for *L. crispatus* NCK1350 or Erm 150 μg ml$^{-1}$ for *E. coli* DH10B.

Example 4. Transcriptomic Analyses with RNAseq mRNA of *L. crispatus* NCK1350 was isolated from a 10 ml MRS culture grown under anaerobic conditions until about 0.6 OD$_{600}$. Cells were harvested by centrifugation (about 4,000 g for about 10 min at about 4° C.) and the pellet was freeze dried and stored at about −80° C. until RNA extraction was performed. The RNA isolation was performed using Zymo Direct-Zol RNA Miniprep kit (Zymo Research, Irvine, Calif.). The library preparation and RNA sequencing were performed in Roy J. Carver Biotechnology Centre from the University of Illinois (Urbana-Champaign, Ill.) and data analysis was performed as described (Theilmann, 2017, *MBio* 8(6). doi: 10.1128/mBio.01421-17). The RNAseq reads were mapped to *L. crispatus* NCK1350 using Geneious software (Kearse, 2012 #253) with default settings and the expression level for each coding DNA sequence (CDS) was calculated based on the normalized transcripts per million (TPM) (Wagner, 2012, *Theory Biosci* 131(4), 281-285 doi: 10.1007/s12064-012-0162-3).

The mRNA data probed the activity of cas genes and the smRNA (smallRNA) data displayed differential transcription level for the different CRISPR arrays. The smRNA data also showed the boundaries of the crRNA when processed in the cell. In this regard, from a repeat-spacer-repeat construct that is being expressed in the cell, the final mature crRNA processed will be as displayed in FIG. 3.

Example 5. DNA Manipulations

Chromosomal DNA from *L. crispatus* was isolated using the UltraClean microbial DNA isolation kit (MOBIO) and plasmid DNA from *E. coli* was obtained using QIAprep Spin miniprep kit (Qiagen) following manufacturer instructions. PCR primers, double strand synthetic DNA for interference assays and single strand DNA for annealing oligonucleotides were synthesized by Integrated DNA Technologies (IDT, Raleigh, N.C., USA). Synthetic DNA for the artificial crRNA was synthesized by Genewiz (China). PCR amplicons used for screening were generated using standard protocols and Taq blue DNA polymerase from Derville Scientific. The Q5 Hot Start High-Fidelity polymerase from New England Biolabs was used to amplify the DNA to be cloned. The PCR products were analysed in 0.8-1.5% agarose gels using 1 Kb Plus or 100 bp ladder (Invitrogen). DNA sequencing was performed at Genewiz (Raleigh, N.C., USA). Restriction digestions were performed with 1 μg of DNA in a final volume of 50 μl, at 37° C. for 1 h. Purification of digested products for ligation were performed using Monarch PCR&DNA Cleanup kit or Monarch DNA Gel extraction kit from New England Biolabs. Ligation reactions were performed in a ratio 3:1 (insert:vector) using 50 ng of vector and a final volume of 20 μl. The restrict-on enzymes and the Instant Sticky-end Ligase Master Mix were obtained from New England Biolabs.

Single strand DNA oligonucleotides were resuspended in IDT Duplex Buffer (IDT) to a final concentration of 100 μM. Equal amounts (2 μg) of each strand (A+B) were mixed and the final volume was increase up to about 50 μl with Duplex Buffer. Both strands were annealed at 95° C. for 2 min, followed by a cooling down step to 25° C. for 45 min. The annealed oligonucleotides were stored at −20° C.

Example 6. Construction of Interference Plasmids

The pTRKH2 plasmid (O'Sullivan, 1993, *Gene* 137(2), 227-231), replicating shuttle vector for *E. coli* and *Lactobacillus*, was used for all plasmid constructions. The interference plasmid was constructed by ligation of the synthetic double strand DNA protospacers, with and without the protospacer adjacent motif (PAM), into BglII-SalI digested pTRKH2 to check the functionality of the endogenous CRISPR system, and validate the PAM (5'-AAA3') based on plasmid interference assays (see, FIG. 4, top panel). The constructs were transformed into rubidium chloride competent (Hanahan, 1985, Techniques for transformation of *E. coli*. Oxford, United Kingdom: IRL Press 1, 109-135) *E. coli* DH10B cells using heat shock at 42° C. for 1 min, followed by another 2 min incubation on ice. Cells were recover in 400 μl of SOC medium (e.g., Super Optimal Broth with glucose) (New England Biolabs) at 37° C., aerobically for 3 hours and then plated in BHI with Erm 150 μg ml$^{-1}$. The resulting interference plasmids were isolated from *E. coli* transformants, checked by PCR with M13 primers for the presence of the insert and sequenced to confirm correct sequence.

Figure 4:
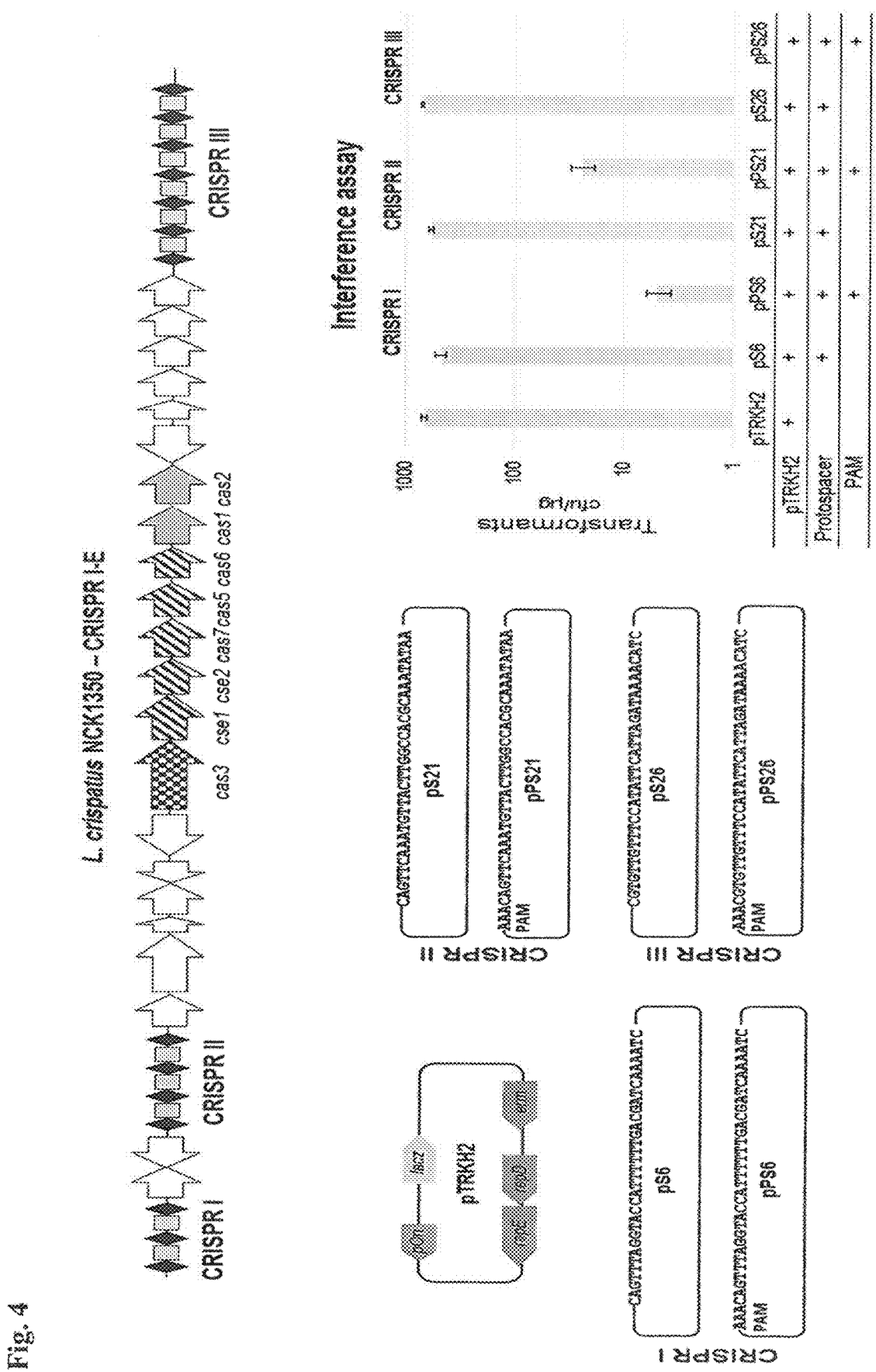
FIG. 4. Plasmid interference assay to check the functionality of the CRISPR-Cas system Type I-E in *L. crispatus* NCK1350. The CRISPR locus I-E of *L. crispatus* NCK1350 contains three different CRISPR arrays, CRISPR I-III (top panel). One spacer of each CRISPR array was cloned, with and without the PAM, into BglI-SalI digested pTRKH2 plasmid to check the functionality of the endogenous CRISPR system, and validate the PAM (5'-AAA3') based on plasmid interference assays. The spacer-protospacer match and PAM recognition by the endogenous systems lead in plasmid targeting and cleavage, reducing the transformants (cfu/µg) obtained in the presence of the selective marker (erm (erythromycin)). CRISPRI pS6 (SEQ ID NO:92); CRISPRI pPS6 (SEQ ID NO:93); CRISPRII pS21 (SEQ ID NO:94); CRISPRII pPS21 (SEQ ID NO:95); CRISPRIII pS26 (SEQ ID NO:96); CRISPRIII pPS26 (SEQ ID NO:97).

As shown in the bottom right panel of FIG. 4, the spacer-protospacer match and PAM recognition by the endogenous systems lead in plasmid targeting and cleavage, reducing the transformants (cfu/μg) obtained in the presence of the selective marker (erm). The plasmid interference experiments unraveled the functionality of the CRISPR loci, validated the predicted PAM and displayed differential activity among the three CRISPR arrays, with CRISPR III being the most active one.

Figure 3:
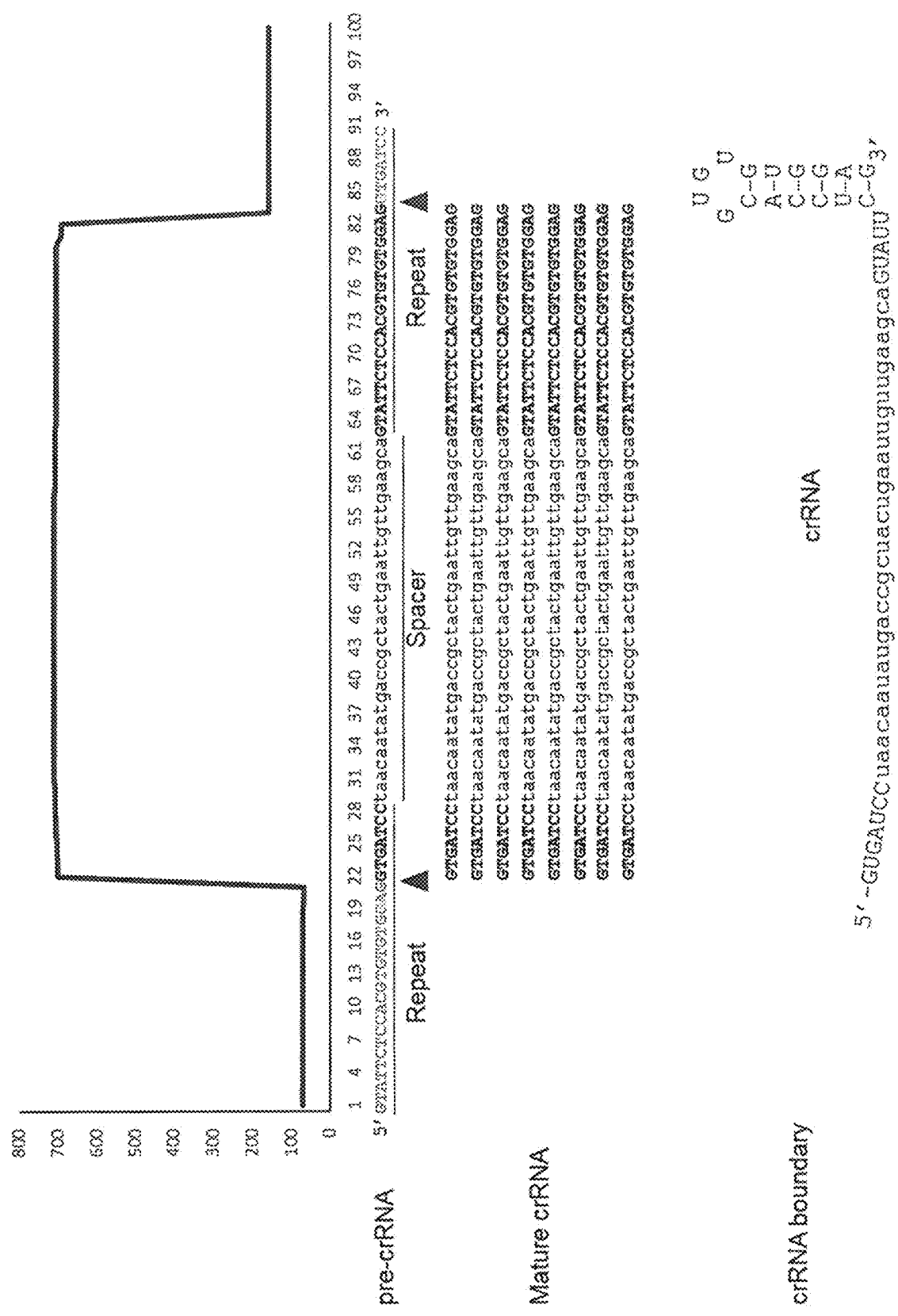
FIG. 3. Small RNA-seq data displaying the expression of an example CRISPR array (Repeat-Spacer-Repeat) from the Type I-E system in *L. crispatus* NCK1350. The premature crRNA (pre-crRNA) (SEQ ID NO:89) is processed to generate the mature crRNA (SEQ ID NO:90) containing 7 nt of the repeat (Bold uppercase; i.e., "handle") in the 5'end of the spacer (lowercase) and another 21 nt of the repeat on the 3'end of the spacer. The boundaries of the mature crRNA with the hairpin (SEQ ID NO:91) performed due to the palindromic sequence contain in the repeat, which is shown in the bottom panel.

Example 7. Construction of pcrRNA Plasmid and Subsequent Self-Targeting Plasmids The pcrRNA plasmid (also referred to as pTRK1183) was constructed by ligation of the synthetic double strand DNA that represents the crRNA of NCK1350, into BglII-SalI digested pTRKH2 (FIG. 3). The crRNA1350 contains the leader sequence (the same leader that is present in the CRISPR array in *L. crispatus* NCK1350 chromosome) together with two repeats and a rho-independent terminator (BBa_B1006, registry of standard biological pads). The constructs were transformed in rubidium chloride competent *E. coli* DH10B cells as described above. The resulting pcrRNA plasmids were isolated from *E. coli* transformants, checked by PCR with M13 primers for the presence of the insert and sequenced to confirm correct sequence. Plasmid construction of the engineer plasmid pcrRNA (pTRK1183) that contain the promoter, the two repeat sequence and the Rho-independent terminator cloned in pTRKH2 is shown in FIG. 4.

Figure 5:
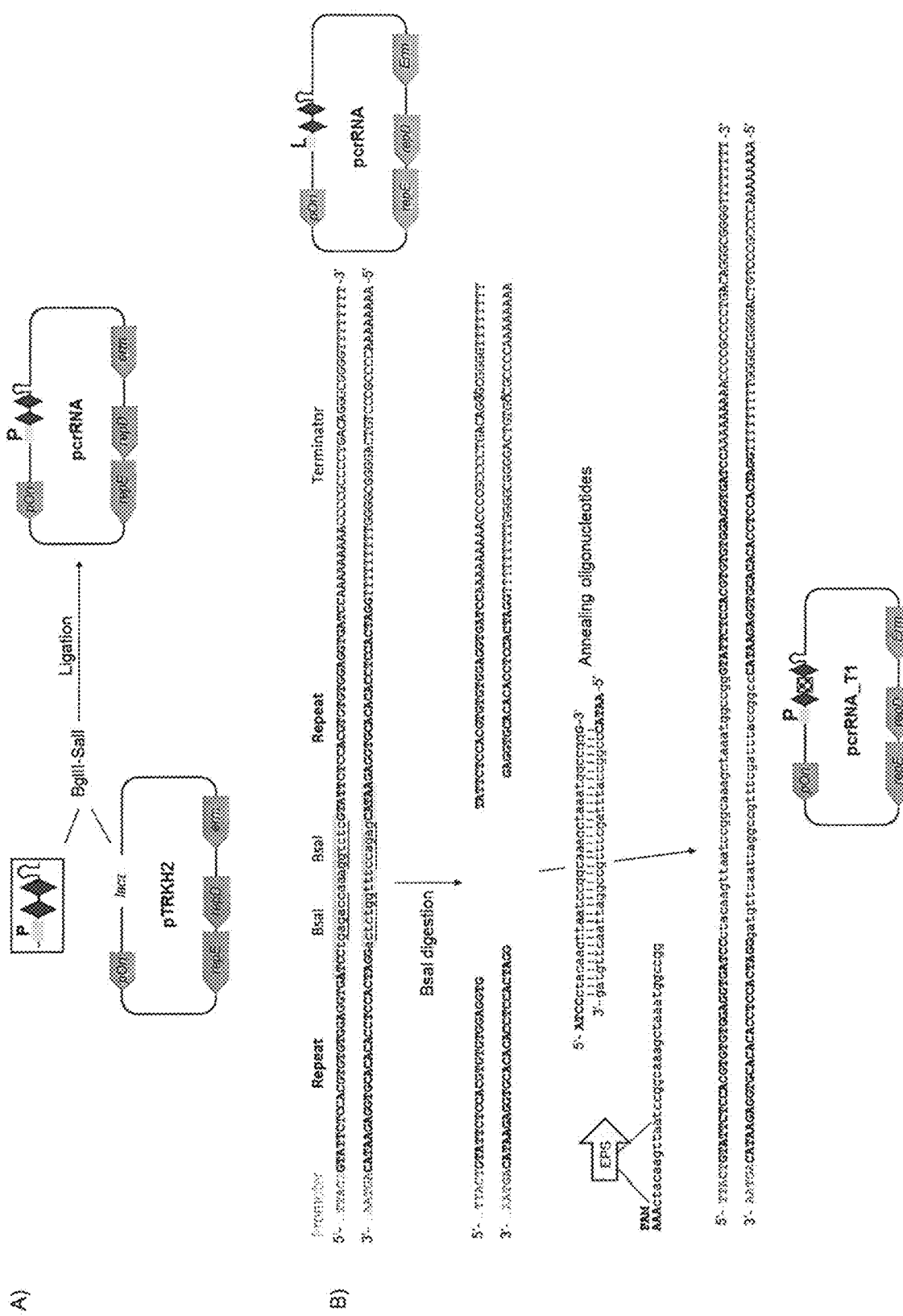
FIG. 5. A schematic representation of the cloning strategy to generate a pcrRNA plasmid and successive targeting plasmids. (panel A) A synthetic gblock, containing two repeats (Bold Uppercase) from Type I-E *L. crispatus* under the expression of specific promoter in 5' end and a terminator in 3' end, was cloned into BglII-SalI digested pTRKH2 plasmid to generate the pcrRNA plasmid. (panel B) The pcrRNA plasmid (SEQ ID NO:98 (5' to 3') and complement) contains two BsaI sites (underlined) between the repeats that allow the insertion of the designed targeting spacer (e.g. EPS gene)(lowercase)(SEQ ID NO:105) using annealing oligonucleotides (upper SEQ ID NO:103, lower SEQ ID NO:104) with overhanging ends to the BsaI digested pcrRNA plasmid (upper and lower fragments: SEQ ID NOs:99 to 102, respectively) generating the targeting plasmid pcrRNA-T1 (also referred to as pTRK1184) (SEQ ID NO:106 and its complement).

Two BsaI sites are located between the two direct repeats of pcrRNA to allow insertion of spacers using annealing oligonucleotides. The pcrRNA1350 plasmid was isolated from *E. coli* host, digested with BsaI, and ligated with the annealing oligonucleotides carrying overhand ends (FIG. 4). The constructs were transformed in rubidium chloride competent *E. coli* DH10B cells as described above. The resulting plasmid is a pcrRNA1350 derivative containing the target defined by the spacer cloned with the annealing oligonucleotides, thereof named as pcrRNA1350_TargetX. The resulting plasmids were isolated from *E. coli* transformants, checked by PCR with M13 primers for the presence of the insert and sequenced to confirm correct sequence. FIG. 5 shows an exemplary cloning strategy used to introduce the spacer using annealing oligonucleotides into the plasmid pcrRNA digested with BsaI:

Example 8. Construction of Genome Editing Plasmids

The plasmids used to perform self-targeting pcrRNA-Tx were used as the backbone to done the repair template to perform genome in a programmable and efficient manner based on the design donor DNA. In this regard, the pcrRNA_T1 plasmid (also referred to as pTRK1184), targeting the eps gene priming-GTF (EC.2.7.8.6) was used as a backbone to clone a repair template containing 1 kb upstream and 1 kb downstream of the target gene (for modification, e.g., deletion). For this purpose a double strand DNA synthetic gblock containing the 2 kb was PCR amplified with primers EPS_RT1-SalI and EPS_RT1-PvuI and cloned into SalI-PvuI digested pcrRNA_T1 generating the plasmid pcrRNA_T1-6PS_RT1 containing the crRNA guide to target the selective gene and the repair template to perform a deletion of 620 bp. A similar strategy has been used to perform the other outcomes previously mentioned, e.g., a knockout of a prophage protein or insertion of three stop codons in the eps gene.

Example 9. Transformation of L. crispatus NCK1350

The transformation of L. crispatus NCK1350 was optimized based on a modification of a previously described transformation protocol for lactobacilli (Goh, 2009, Appl Environ Microbiol 75(10), 3093-3105. doi: 10.1128/AEM.02502-08). Stationary cells grew anaerobically were inoculated (1% v/v) into MRS broth, previously reduced to anaerobic conditions, and grew until about 0.3 $OD_{600}$ (about 3 h) was achieved. Filter-sterilized water solution of Penicillin G was added to a final concentration of 10 µg $ml^{-1}$ and cells were incubated another hour. Then, cells were harvested by centrifugation (4000 rpm, 10 min, 4° C.) and washed three times with electroporation buffer containing 1 M sucrose and 3.5 mM $MgCl_2$. Cells were resuspended in 1 ml electroporation buffer and aliquoted in 200 µl for direct use For each transformation, 2 µg of plasmid was combined with 200 µl of cells, and 2 mm cuvettes were used for electro-transformation under 2.5 kV, 25 µF and 400Ω conditions. Cells were recovered in 1 ml MRS broth previously reduced to anaerobic conditions, and incubated at 37° C., under anaerobic conditions for 18 h. Transformants were selected using MRS plates with Erm 2.5 µg $ml^{-1}$ at 37° C. under anaerobic conditions for 72 hours.

Example 10. Repurposing for Endogenous Killing

Figure 6:
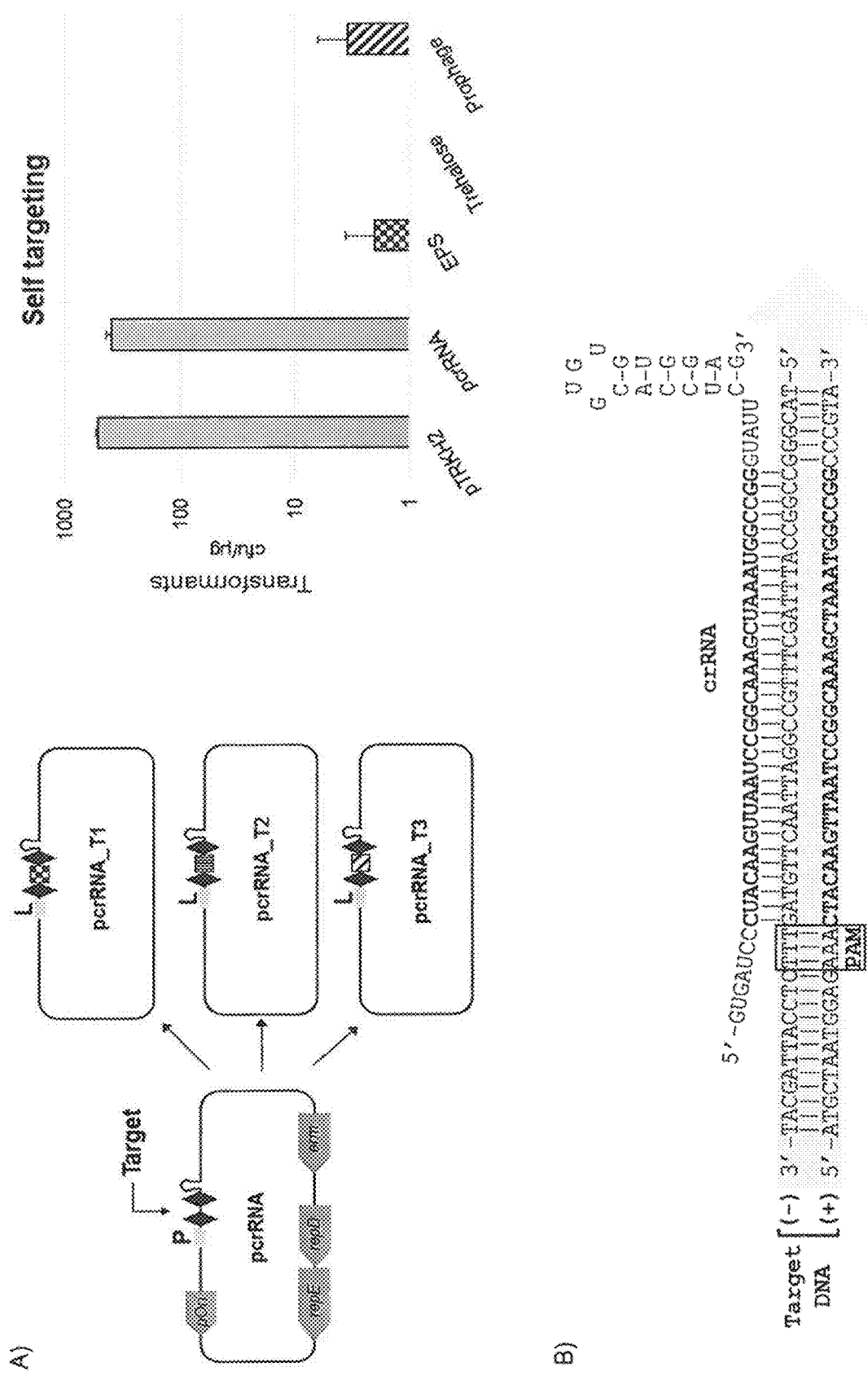
FIG. 6. Repurposing of endogenous CRISPR Type I-E system in *L. crispatus* NCK1350 for self-targeting. (panel A) The pcrRNA plasmid previously described (FIG. 5) is used to clone differently designed spacers to perform self-targeting in *L. crispatus* NCK1350 chromosome reprogramming the endogenous Type I-E system. As shown, plasmid-based delivery allowed repurposing the endogenous system to cleave the desire target location leading to cell suicide. Targeting EPS, trehalose or prophage genes leads to a 2-3 log reduction of transformants under a selective marker (erm). (panel B) Schematic representation of the interaction between the designed crRNA containing the targeting sequence (Bold) for the EPS gene. crRNA (SEQ ID NO:107); Target DNA (SEQ ID NO:108 and its complement).

The use of pTRKH2-based plasmids encompassing CRISPR arrays with spacers targeting chromosomal sequences to kill the host was developed. Specifically, a portion of the eps genes flanked by a PAM was cloned between repeats and delivered to L. crispatus via electroporation to repurpose the endogenous CRISPR-Cas machinery and drive lethal self-targeting, killing the bacterial population (see FIG. 6).

Example 11. Repurposing for Endogenous Genome Editing

Figure 7:
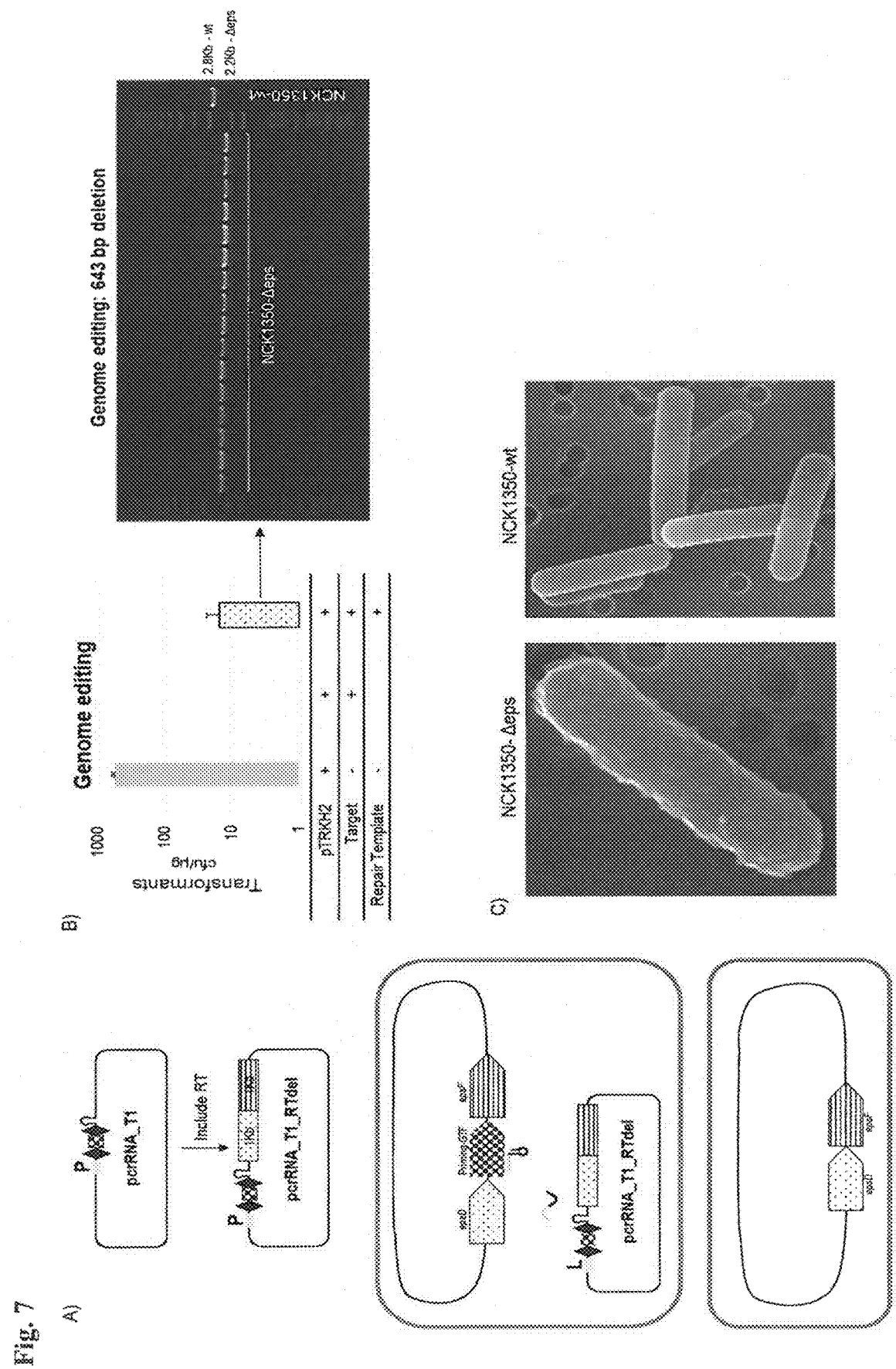
FIG. 7. Repurposing endogenous CRISPR Type I-E system in *L. crispatus* NCK1350 for genome editing. (panel A) A repair template (2 kb) that is cloned into SalI-PvuI sites of the targeting plasmid, previously described (FIG. 6), is used to assist *L. crispatus* NCK1350 to overcome DNA damage generated by Type I-E cleavage, resulting in genome editing based on the designed donor DNA. (panel B) Genome editing was achieved by repurposing the endogenous Type I-E system to delete 643 bp of the EPS gene priming-GTF with a 100% editing efficiency in the 16 surviving colonies, which display a different cell phenotype due to the knock out performed (panel C).

The use of pTRKH2-based plasmids encompassing CRISPR arrays with spacers targeting chromosomal sequences to edit the host genome was developed. Specifically, a portion of the eps genes flanked by a PAM was cloned between repeats and co-delivered with a repair template devoid of the target sequence and designed to create an internal deletion into the eps gene was delivered to L. crispatus via electroporation to repurpose the endogenous CRISPR-Cas machinery and drive lethal self-targeting, killing the wiki type bacterial population and driving homologous recombination with the repair template, generating a deletion within eps (see FIG. 7).

Example 12. Repurposing for Endogenous Genome Editing

Figure 8:
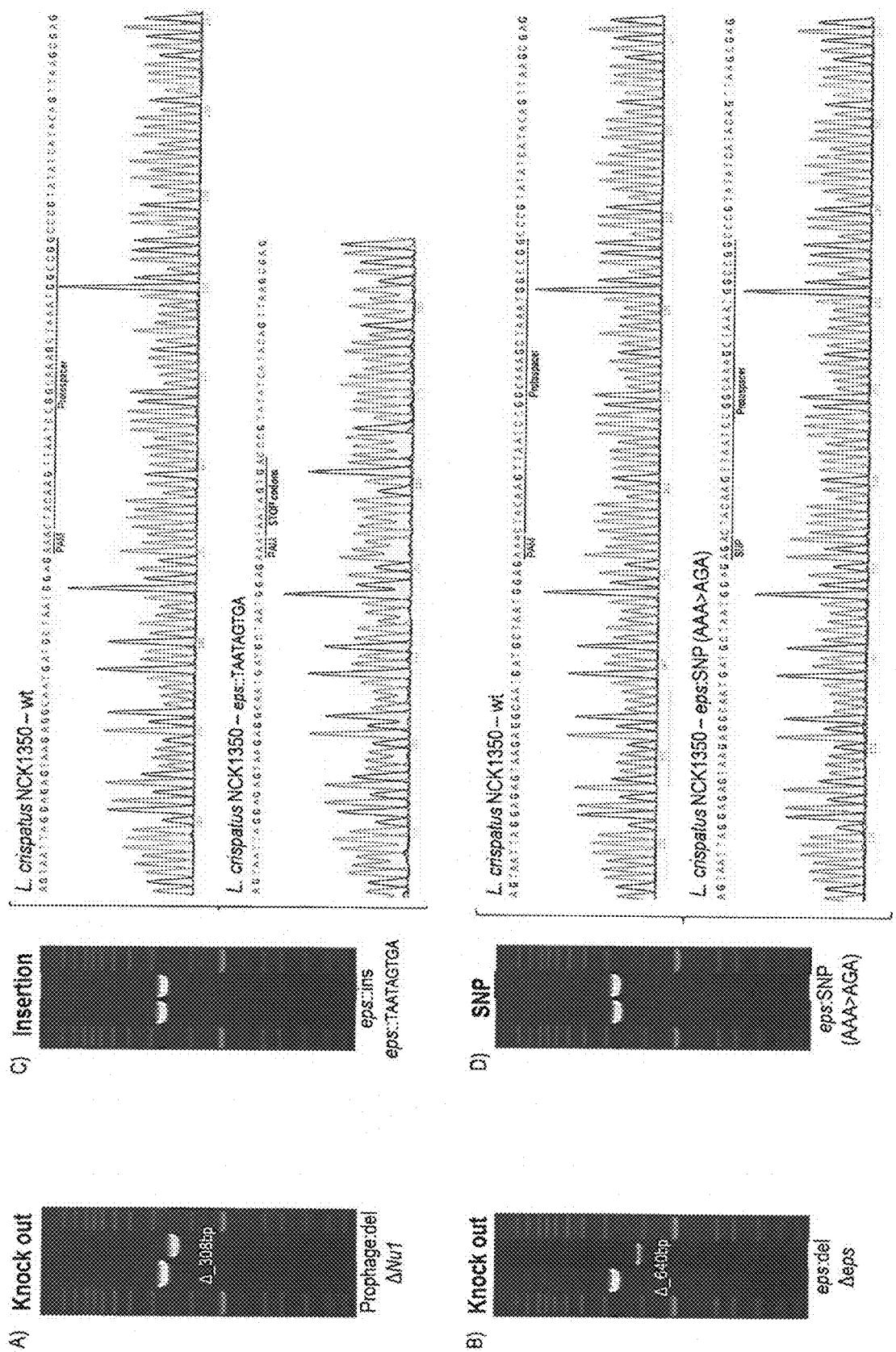
FIG. 8. Repurposing the endogenous CRISPR Type I-E system in *L. crispatus* NCK1350 for genome editing results in several outcomes. The endogenous Type I-E system of *L. crispatus* NCK1350 can be repurpose for efficient and precise genome editing based on the designed donor DNA provided as a repair template. Using the strategy previously described (see FIG. 7) deletions of different sizes were performed on different targets: deletion of 308 bp of the prophage DNA packaging Nu1 (panel A) and deletion of 640 bp of the EPS gene priming-GTF (panel B). Similarly, the gene sequence of the EPS gene priming-GTF was disrupted by the insertion of stop codons, while deleting the protospacer region (panel C), both at the same time. Also, single base editing may be performed to alter the nucleotide sequence, including altering the PAM sequence (panel D). *L. crispatus* NCK1350 wt (SEQ ID NO:109); *L. crispatus* NCK1350-eps::TAATAGTGA (SEQ ID NO:110); *L. crispatus* NCK1350-eps:SNP (AAA≤AGA)(SEQ ID NO:111).

The use of pTRKH2-based plasmids encompassing CRISPR arrays with spacers targeting chromosomal sequences to edit the host genome was developed. Specifically, various alternatives were used, cloning a portion of the eps genes flanked by a PAM, or a portion of the prophage nu1 DNA packaging gene, were cloned between repeats and co-delivered with various repair templates devoid of the target sequence and designed to create an internal deletion into the eps gene, or an internal deletion into the nu1 gene, or insert a series of stop codons, or generate a single base change (a base substitution) in the targeted PAM in eps. These various constructs were delivered to L. crispatus via electroporation to repurpose the endogenous CRISPR-Cas machinery and drive lethal self-targeting, killing the wild type bacterial population and driving homologous recombination with these four repair templates, generating a deletion within eps, a deletion in nu1 disruption and shortening of the eps coding frame, and substitution of a nucleotide (and corresponding amino acid) in eps (see FIG. 8).

Prophage nu1 DNA packaging gene AATGGAATT-TAAATTAGATGAATCACAAGAAACC GAGAT-TAAAACTTTTGTTATGGGCGTGGTTAAAGACGCT-ATTAAACAAGCCACTACCACCA GCAAACCATATTTGAACCGCAAAGAAATTGCTAAG-TATTTTGGCGTGGCTGAATCAACTAT TACATAT-TGGGCTTCTTAGGGATGCCTGTCGCTGTCATA-GACGGGCGC AAA CTCTATG GCAAGCAATCTATAACTAACTGGCTAAAATT (SEQ ID NO: 195)

Example 13. Genome Editing Using the Endogenous Type I CRISPR-Cas System in Lactobacillus crispatus In the present study, we detail how the native Type I-E CRISPR-Cas system, with a 5'-AAA-3' protospacer adjacent motif (PAM) and a 61-nt guide CRISPR RNA (crRNA), can be repurposed for efficient chromosomal targeting and genome editing in Lactobacillus crispatus, an important commensal and beneficial microbe in the vaginal and intestinal tracts.

Clustered Regularly Interspaced Short Palindromic Repeats (CRISPR) and associated proteins (Cas) provide adaptive immunity in prokaryotes against invasive nucleic acids (1). CRISPR-Cas systems are widespread in bacteria (46%) and archaea (90%), though distribution and classification vary greatly within and across phylogenetic clades (2). Currently, two major CRISPR-Cas system classes have been described, encompassing six types and thirty-four subtypes (3). Class 1 includes Type I, III and IV, which are defined by the presence of a multi-protein effector complex, such as the CRISPR-associated complex for antiviral defense (Cascade). In contrast, Class 2 systems are comprised of Type II, V and VI, which rely on single effector nucleases such as Cas9, Cas12 or Cas13 (3). Despite these distinctions, all types carry out DNA-encoded, RNA-mediated, nucleic acid targeting (4, 5), but vary in their mechanisms of action, molecular targets (DNA or RNA) and specific sequence biases as determined by the protospacer adjacent motif (PAM) (6-8). Exogenous Class 2 effector nucleases such as Cas9 and Cas12 are widely exploited for genome editing in a plethora of eukaryotes (9, 10), hinging on the programmable nature of synthetic guide RNA technology (11-13). Remarkably, few native systems have been harnessed for in situ editing in bacteria, including Type I CRISPR-Cas systems and the signature Cas3 helicase-nuclease (14) which constitute the most abundant and widespread CRISPR-Cas system in bacteria and archaea (2).

Currently, there is a lack of fundamental understanding regarding Type I CRISPR arrays, accompanying Cas proteins, and corresponding guide CRISPR RNAs (crRNAs) and targeting PAMs, necessary for molecular tool development in these systems (15). To date, only a handful of Type I CRISPR Cas systems have been characterized, including Type I-E CRISPR-Cas system from *E. coli*, which was actually the first observed CRISPR locus over 3 decades ago (16), and more recently used to demonstrate the dependency of CRISPR immunity on crRNA-targeting (17, 18). The Cascade complex, encompassing the crRNA and Cas proteins, constitutes a double-stranded DNA recognition machinery that drives the selective nucleotide base-pairing between the crRNA and the complementary DNA strand (target strand), looping out the nontarget strand generating the 'R-loop' structure (19-21). Then, the Cas3 helicase-nuclease is recruited by Cascade to unwind and degrade the nontarget strand in a 3' to 5' direction (22, 23), via nuclease- and helicase-dependent activities (14, 24). This processive single-strand DNA degradation, combined with inefficient DNA repair mechanisms, renders self-targeting lethal in bacteria (25) unless a repair template is provided to drive RecA-dependent recombination (26).

The microbiome composition, complexity and diversity have been the focus of extensive studies over the past decade to understand its impact on health and disease in humans (27, 28) and animals (29, 30). The human vaginal microbiome is dominated by lactobacilli with *Lactobacillus crispatus* as one of the predominant species (31), which also plays a key role in poultry intestinal health (29), and has been implicated in the maintenance of a healthy status, whereas its absence is correlated with a higher risk of infectious disease (32, 33). Moreover, *L. crispatus* has become an emerging probiotic for women's and poultry health, due to its ability to fend off invasive pathogenic bacteria through competitive exclusion, production of antimicrobial compounds and exopolysaccharides (34-36), as well as eliciting a beneficial host immune response (37). However, the genetic basis of the *L. crispatus* probiotic features remain unknown due to its recalcitrance to transformation and the lack of molecular tools available for this genetically refractory species.

Here, we characterized a novel Type I-E CRISPR-Cas system in the genetically recalcitrant *L. crispatus* species, in a strain isolated from a healthy human endoscopy. We show how the endogenous Type I-E CRISPR-Cas system of *L. crispatus* can be harnessed for flexible and efficient genetic engineering outcomes such as insertions, deletions and single base substitutions. Specifically, we generated diverse mutations encompassing a 643-bp deletion (100% efficiency), a stop codon insertion (36%) and a single nucleotide substitution (19%) in the exopolysaccharide priming-glycosyl transferase p-gtf. Additional genetic targets included a 308-bp deletion (20%) in the prophage DNA packaging protein Nu1 and a 730-bp insertion of the green fluorescent protein gene downstream of enolase (23%). This approach enables flexible alteration of the formerly genetically recalcitrant species *L. crispatus*, with potential for probiotic enhancement, biotherapeutic engineering and mucosal vaccine delivery. These results also provide a framework for repurposing endogenous CRISPR-Cas systems for flexible genome targeting and editing, while expanding the toolbox to include one of the most abundant and diverse CRISPR-Cas systems found in nature.

Methods

CRISPR-Cas system detection and characterization in silico—The 52 *L. crispatus* genomes (Table 2) available in GenBank (NCBI) on December 2017 were mined to determine the occurrence and diversity of CRISPR-Cas systems in this species. The in silico analyses were performed using Cas proteins (Cas1, Cas3, Cas9), previously identified in other lactobacilli species (38), as queries using BLAST® (82) to retrieve the Cas proteins among *L. crispatus* strains. Then, the putative CRISPR array(s) of each genome were identified using CRISPR Recognition Tool (CRT) (83) implemented in Geneious 10.0.6 software (84). Thereafter, the CRISPR-Cas systems of each strain were manually curated and annotated. The CRISPR subtypes were designated based on the occurrence of signature Cas proteins (Cas9-TypeII, Cas3-TypeI) and associated ones as previously reported (39).

Spacers analyses, PAM prediction, and guide RNA identification—CRISPR spacers represent an iterative vaccination record for bacteria. Computational analyses were performed with the spacers of each strain against several databases using the CRISPRtarget webserver (85) to identify their putative targets, the protospacer and predict the protospacer adjacent motif (PAM) (6, 8). The WebLogo server was used to represent the PAM sequence based on a frequency chart where the height of each nucleotide represents the conservation of that nucleotide at each position (86).

In Type I systems, the crRNA represents the guide RNA that interacts with the Cascade complex to define the complementary sequence. The crRNA encompasses the repeat-spacer pair, so a repeat-spacer nucleotide sequence was used to predict the structure of the crRNA of Type I-B and Type I-E using the NUPACK Webserver (87), and then manually depicted In Type II systems, the tracrRNA has a complementary region to the CRISPR repeat sequence of the crRNA allowing creation of the duplex crRNA:tracrRNA. Therefore, the repeat sequence of Type II-A was used to identify the tracrRNA in the CRISPR locus, as previously described (15) and then the interaction between crRNA:tracrRNA was predicted using NUPACK and depicted manually.

Bacterial strains and growth conditions—*Lactobacillus crispatus* NCK1350 and derivative strains used in this study (Table 1) were propagated in MRS (de Man Rogosa and Sharpe, Difco) broth or on MRS agar (1.5%, w/v) plates, at 37° C. under anaerobic conditions. *Escherichia coli* DH10B and MC1061 were used as cloning hosts. *E. coli* strains were grown in BHI (Brain heart infusion, Difco) broth at 37° C. with aeration (250 rpm) or on BHI agar plates at 37° C. aerobically. Transformants were selected in the presence of erythromycin (Erm) at 150 µg ml$^{-1}$ for *E. coli* or 2.5 µg ml$^{-1}$ for *L. crispatus*.

Genome sequencing and assembly—Total DNA of *L. crispatus* NCK1350 was isolated using the UltraClean® microbial DNA isolation kit (MOBIO) and whole genome sequencing was performed using a MiSeq system (Illumina®) at Roy J. Carver Biotechnology Centre from the University of Illinois (Urbana-Champaign, Ill.) following the supplier's protocol (Illumina®). Libraries were prepared with the Hyper Library construction kit from Kapa Biosystems. The libraries were pooled as instructed, quantitated by qPCR and sequenced on one lane per pool for 301 cycles from each end of the fragments on a MiSeq flowcell using a MiSeq 600-cycle sequencing kit version 3. Fastq files of the pair-end reads were generated and demultiplexed with the bcl2fastq v2.17.1.14 Conversion Software (Illumina). The adaptors were trimmed from the sequencing reads and sequences were quality retained. The fastq flies of the pair-end reads were used as input for the genome assembly through PATRIC Webserver (patricbrc.org) and also for the protein-encoding open reading frames (ORFs) prediction and annotation. Then, the genome annotations were manually curated in Geneious 11.0.5.

RNA extraction and RNA sequencing analysis—Total RNA of L. crispatus NCK1350 was isolated from a 10 ml MRS culture, with two independent biological replicates, grown under anaerobic conditions until $OD_{600nm}$ about 0.6. Cells were harvested by centrifugation (3,200 g; 10 min; 4° C.) and the cell pellets were flash frozen and stored at −80° C. until RNA extraction was performed. Total RNA was isolated using Zymo Direct-Zol™ RNA Miniprep kit (Zymo Research, Irvine, Calif.) following the protocol previously described (88). The mRNA and smRNA library preparation and sequencing were performed at the Roy J. Carver Biotechnology Centre of the University of Illinois (Urbana-Champaign, Ill.) and data analysis was performed as previously described (88). Finally, the RNA-seq reads were mapped onto the L. crispatus NCK1350 genome using Geneious 11.0.5 software (84) with default settings and the expression level for each CDS was calculated based on the normalized transcripts per million (TPM)(89).

DNA manipulations—Chromosomal DNA from L. crispatus was isolated using the UltraClean® microbial DNA isolation kit (MOBIO) and plasmid DNA from E. coli was obtained using QIAprep® Spin Miniprep kit (Qiagen) following the manufacturers instructions. PCR primers double-stranded synthetic DNA for plasmid Interference assays, and single-strand DNA for annealing oligonucleotides were synthesized by Integrated DNA Technologies (IDT, Morrisville, N.C. USA). Synthetic DNA for the target-specific crRNA was synthesized by Genewiz (China). PCR amplicons for colony screening were generated using standard PCR protocols and Taq blue DNA polymerase (Denville Scientific). Q5 Hot Start High-Fidelity polymerase (New England Biolabs [NEB], Ipswich, Mass., USA) was used to PCR-amplify DNA for cloning purpose. PCR products were analyzed on 0.8-1.5% agarose gels. DNA sequencing was performed by Genewiz (Morrisville, N.C. USA) to confirm sequence content. Restriction digestions were performed with 1 µg of plasmid DNA in a final volume of 50 µl, at 37° C. for 1 h, using high fidelity restriction enzymes (NEB). Purification of digested products for ligation were performed using Monarch® PCR&DNA Cleanup kit or Monarch® DNA Gel extraction kit (NEB). Ligation reactions were performed at a 3:1 insert:vector ratio using 50 ng of vector in a final volume of 10 µl, using Instant Sticky-end Ligase Master Mix (NEB) based on the manufacturer's instruction.

Single-strand DNA oligonucleotides were resuspended in IDT Duplex Buffer (IDT) to a final concentration of 100 µM. Then, equal amounts (2 µg) of each strand (A+B) were mixed and the final volume was adjusted to 50 µl with Duplex Buffer. Both strands were annealed at 95° C. for 2 min. followed by incubation at 25° C. for 45 min. All annealed oligonucleotides were stored at −20° C.

Construction of interference plasmids—The pTRKH2 plasmid (90), a replicating shuttle vector for E. coli and Lactobacillus, was used for all plasmid constructions. The interference plasmids were constructed by ligation of the synthetic double-stranded DNA protospacers, with or without the PAM into BglII-SalI digested pTRKH2 (Table 7). The constructs were transformed into rubidium chloride-treated competent E. coli DH10B cells using heat-shock at 42° C. for 1 min. followed by another 2 min incubation on ice. Cells were recovered in 900 µl of SOC medium (NEB) at 37° C., aerobically for 3 hours and then plated on BHI with Erm 150 µg $ml^{-1}$. The resulting interference plasmids were PCR-screened in E. coli transformants with M13 primers (Table 7) for the presence of the insert and sequenced to confirm sequence content.

Construction of the CRISPR-based editing vector pTRK1183 to repurpose the endogenous Type I-E system in L. crispatus NCK1350—The plasmid-based technology pTRK1183 was constructed by ligation of the synthetic double strand gene block that represents the artificial crRNA of NCK1350, into BglII-SalI digested pTRKH2 (Table 1). The artificial crRNA contains a promoter that is the native leader (L) of the CRISPR-3 array of L. crispatus NCK1350, together with two repeats and a rho-independent terminator (BBa_B1006, registry of standard biological parts)(FIG. 14). The ligation was transformed in rubidium chloride competent E. coli DH10B cells as described above. The resulting pTRK1183 plasmid were isolated from E. coli transformants, and checked by PCR with M13 primers (Table 7) for the presence of the insert and sequenced to confirm sequence composition.

Two BsaI sites are located between the two direct repeats of the artificial crRNA in pTRK1183 to allow the insertion of spacers (targets) using annealing oligonucleotides. The pTRK1183 plasmid was isolated from E. coli, digested with BsaI, and ligated with the annealing oligonucleotides carrying overhang ends. The constructs were transformed in rubidium chloride competent E. coli DH10B cells as described above. The resulting plasmid is a pTRK1183 derivative containing a spacer to target the exopolysaccharide gene p-gtf (EC.2.7.8.6) generating the plasmid pTRK1184, a spacer to target the prophage DNA packaging gene Nu1 generating pTRK1188, or a spacer to target the enolase gene (EC 4.2.1.11) generating the plasmid pTRK1190 (Table 1). The resulting plasmids were isolated from E. coli transformants, checked by PCR with M13 primers (Table 7) for the presence of the insert and sequenced to confirm sequence content.

pTRK1183 and derived targeting plasmids (pTRK1184, pTRK1188, pTRK1190) present a SalI-PvuI restriction site ideal to clone a designed repair template to perform genome editing repurposing the endogenous Type I-E system in L. crispatus NCK1350. For this purpose, a double strand DNA synthetic gene block containing 2-kb homologous arms to the p-gtf gene (FIG. 15, panel A) was PCR amplified with primers p-gtf_$RT_{KO}$_SalI_F and p-gtf_$RT_{KO}$_PvuI_R (Table 7) and cloned into SalI-PvuI digested pTRK1184 generating the plasmid pTRK1185 (also referred to as pcrRNA_T1_RTdel) (Table 1) that contains both, the crRNA guide to target the gene and the repair template to perform a deletion of 643 bp. The same repair template was cloned into SalI-PvuI digested pTRKH2 generating the plasmid pTRKH2-RT (Table 1), containing the repair template but not the targeting CRISPR array, that serves as a control plasmid for spontaneous homologous recombination. Similarly, a different gene block (2 Kb) designed to introduce three stop codons in the p-gtf gene (FIG. 15, panel A) was amplified by PCR using the primers p-gtf_$RT_{STOP}$_PvuI_R p-gtf_$RT_{STOP}$_PvuI_R and cloned into SalI-PvuI digested pTRK1184 generating the plasmid pTRK1186.

Another repair template (2 Kb) was designed to introduce a single base substitution in the p-gtf gene to alter the PAM. In this case, the primers p-gtf_$RT_{SNP}$_Up_SalI_F and p-gtf_$RT_{SNP}$_Up_R were used to perform a chromosomal amplification of the upstream homologous arm introducing the mutation in the repair template; and the primers p-gtf_$RT_{SNP}$_Dw_SOE-PCR_F and p-gtf_$RT_{SNP}$_Dw_PvuI_R amplified the downstream region. Then, both repair templates were overlapped using SOE-PCR with the primers p-gtf_$RT_{SNP}$_Up_SalI_F and gtf_$RT_{SNP}$_Dw_PvuI_R, to generate the final 2 Kb repair template that was cloned into SalI-PvuI digested pTRK1184 generating plasmid pTRK1167.

To delete the prophage DNA packaging gene Nu1, a double stranded DNA synthetic gene block containing 2 kb homologous arms (FIG. 15, panel B) was amplified using the primers Nu1_RT$_{KO}$_SalI_F and Nu1_RT$_{KO}$_SalI_R and cloned into SalI-PvuI digested pTRK1188 (also referred to as pcrRNA_T3) generating plasmid pTRK1189.

To perform the chromosomal insertion of the GFP at the 3'end of the enolase gene a repair template containing 730 bp corresponding to the GFP and 2 kb homologous arms to the enolase gene region was designed (FIG. 15, panel C). For this purpose, the enolase downstream region was amplified using the primers enolase_RT$_{GFP}$_Dw_SalI_F and enolase_RT$_{GFP}$_Dw_R, the upstream region was amplified using the primers enolase_RT$_{GFP}$_Up_F and enolase_RT$_{GFP}$_Up_PvuI_R, and the gene block containing the GFP was amplified using the primers RT$_{GFP}$_GFP_SOE-PCR_F and RT$_{GFP}$_GFP_SOE-PCR_R. Then, the three PCR fragments were overlapped using SOE-PCR with the primers enolase_RT$_{GFP}$_Dw_SalI_F and enolase_RT$_{GFP}$_Up_PvuI_R and the resulting amplicon (2.73 kb) was cloned into SalI-PvuI digested pTRK1190 generating plasmid pTRK1191.

The final plasmid constructs were PCR screened using the general primers M13_F and lacZ_Rev primers, or M13_F and 253_R primers (Table 7) to check plasmid content.

Transformation of *L. crispatus* NCK1350—Transformation of *L. crispatus* NCK1350 was optimized based on a slight modification of a previously described transformation protocol for lactobacilli (60). Stationary cells grown anaerobically were inoculated (1% v/v) into MRS broth previously reduced to anaerobic conditions, and grown until OD$_{600nm}$ about 0.3 was achieved. At this point, penicillin G was added to a final concentration of 10 µg ml$^{-1}$ and cells were incubated for another hour. Then, cells were harvested by centrifugation (3,200 g, 10 min, 4° C.) and washed three times with electroporation buffer containing 1 M sucrose and 3.5 mM MgCl$_2$. Finally, cells were resuspended in 1 ml electroporation buffer and aliquoted in 200 µl for direct use. For each transformation, 2 µg of plasmid was combined with 200 µl of cells and 2 mm cuvettes were used for electro-transformation under 2.5 kV, 25 µF and 400Ω conditions. Cells were recovered in 1 ml MRS broth previously reduced to anaerobic conditions, and incubated at 37° C. In anaerobic conditions for 18 h. Transformants were selected on MRS plates with Erm 2.5 µg ml$^{-1}$ for 48-72 hours.

The transformants obtained were PCR-screened and sequenced to confirm the presence of desired mutations. For the exopolysaccharide gene p-gtf, the primers KO_p-gtf_F and KO_p-gtf_R were used for the chromosomal PCR amplification (2.8 kb wild type and 2.2 kb in deletion mutant) and the primers p-gtf_F and p-gtf_R were used to sequence the p-gtf region, for the three different editing outcomes performed in this target. For the deletion of the prophage DNA packaging Nu1 gene the primers KO_Nu1_F KO_Nu1_R, we checked the chromosomal deletion (2.8 Kb wild type, 2.5 kb deletion mutant) and the primers Nu1_F and Nu1_R were used for sequencing. To check the insertion of the GFP in the enolase region the primers GFP_Insertion_F and GFP_Insertion_R were used for PCR amplification (2.4 kb wild type or 3.1 Kb insertion mutant) of the chromosomal location and the primers GFP_F and GFP_R were used to check the sequence.

Scanning electron microscopy—*L. crispatus* NCK1350 and derived exopolysaccharide mutants (NCK2635, NCK2656, NCK2659) were grown for 16 h as described above. Bacterial cells from 10 ml culture were harvested by centrifugation (10 min, 2,500 rpm) and resuspended in 10 ml of 3% glutaraldehyde in 0.1M Na cacodylate buffer pH 5.5 and stored at 4° C. until processed. Bacterial suspensions were filtered using a 0.4 µm pore polycarbonate Nucleopore filter. Filters containing bacteria were washed with three, 30-minute changes of 0.1M Na cacodylate buffer pH 5.5 and then dehydrated with a graded series of ethanol to 100% ethanol and then critical point dried (Tousimis Samdri-795, Tousimis Research Corp, Rockville, Md.) in liquid CO$_2$. Dried filters were mounted on stubs with double-stick tape and silver paint and sputter coated (Hummer 6.2 sputtering system, Anatech USA, Union City, Calif.) with 50 Å Au/Pd. Samples were held in a vacuum desiccator until viewed using a JEOL JSM-5900LV SEM (JEOL USA, Peabody, Mass.). Images were acquired at a resolution of 1,280×960 pixels. Sample preparation and scanning electron microscopy pictures were performed at CALS Center for Electron Microscopy at NC Slate University (Raleigh, N.C.).

Prophage induction—*L. crispatus* NCK1350 and the NCK2662 mutant, lacking the prophage DNA packaging Nu1 (Table 1), were grown for 16 h as described above. Then, 10 ml fresh broth was inoculated (1%) and mitomycin C (Sigma) was added (0.75 µg/ml) when the cultures reached OD$_{600nm}$ 0.2-0.3. Bacterial growth was monitored (OD$_{600nm}$) over eighteen hours and cell counts where performed on regular media at the final time point. Three independent biological replicates were performed with two technical replicates in each experiment.

Fluorescence microscopy—The *L. crispatus* NCK1350 and NCK2665 derivative mutant expressing the chromosomal inserted green fluorescent protein (GFP) were grown for 16 h as described above. Then, bacterial cells were washed, placed on a microscope slide and covered with a cover slip (Fisher Scientific, Hampton, USA). The preparations were observed with the microscope Nikon® eclipse E600 (Nikon®, Melville, USA) using 40× magnification. The FITC filter (excitation 480, emission 585) was used for visualization of the GFP signal.

Statistical analyses—In all figures, the bar graphs represent the mean of three independent biological replicates and the error bars represent the standard deviation. Data distribution was analyzed with Welch's t-test, used to compare unpaired two groups (sample vs control) under the hypothesis that the two groups contains equal means. Comparisons with a p-value<0.05 were considered statistically significant. The statistical analyses were performed in R studio v1.1.463.

Accession numbers—The chromosomal sequence and the RNA-seq data of *L. crispatus* NCK1350 reported in this manuscript have been deposited in the NCBI database under the BioProject ID PRJNA521996. The whole genome sequence has been deposited under the accession number SGWL00000000. The mRNA sequences have been deposited under the accession numbers SRR8568636-SRR8568637, and the smRNA sequences under the accession number SRR8568722-SRR8568723.

Results and Discussion

Occurrence and Diversity of CRISPR-Cas Systems in *L. crispatus*

Figure 9:
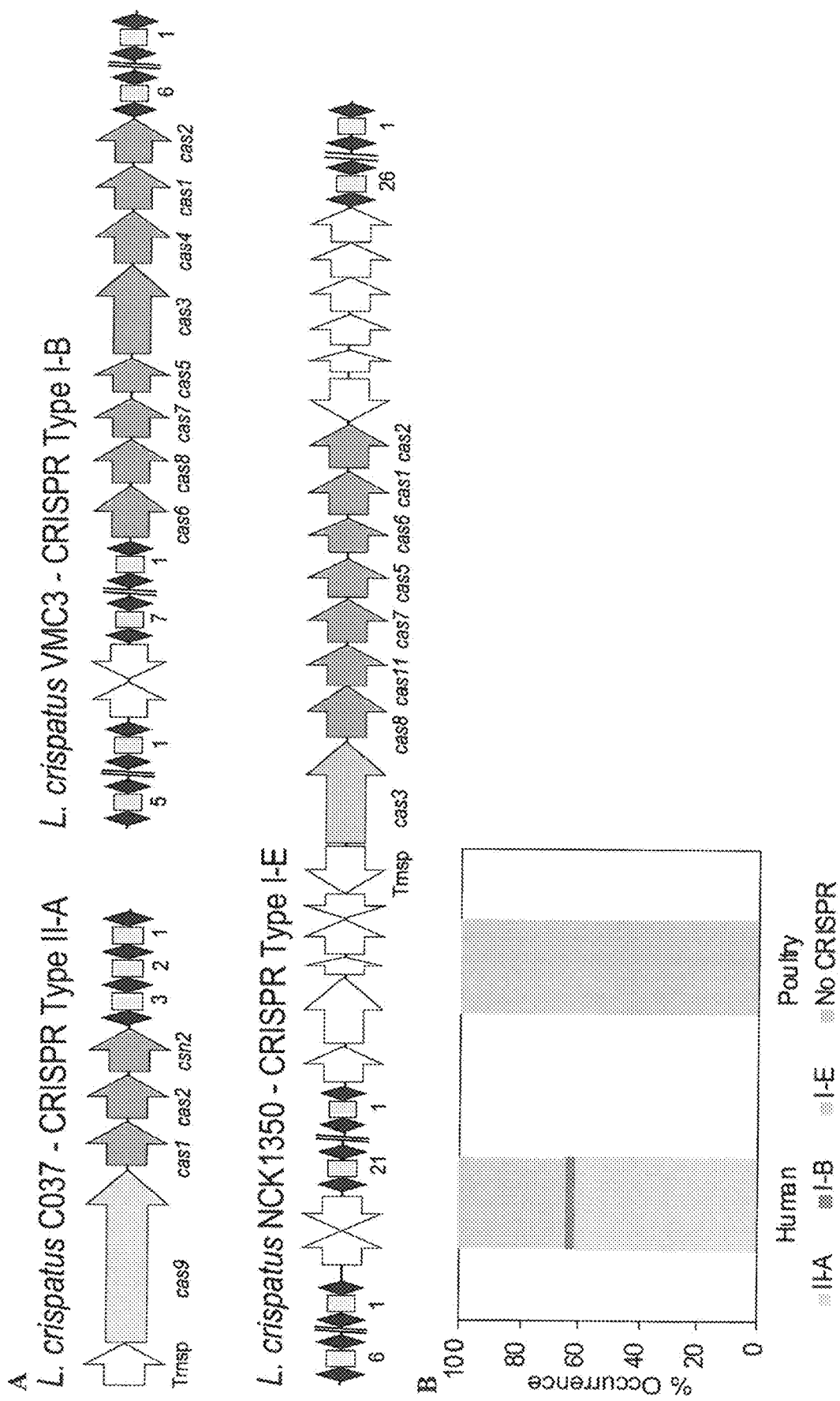
FIG. 9. CRISPR-Cas systems in *L. crispatus*. (A) Architecture of the CRISPR loci II-A, I-B and I-E detected in *L. crispatus* strains, with the signature cas genes—long arrows (Cas9, Type II-A), (Cas3, Type I-B) and (Cas3, Type I-E); cas genes short dark grey arrows; repeats are represented as black diamonds and spacers as grey squares with the number of total spacers in each CRISPR array indicated below. Trnsp. transposase (two white arrows). (B) Occurrence and diversity of CRISPR-Cas systems in *L. crispatus* strains from human (gut and urogenital tract) and poultry (gut) isolates. (C) Protospacer adjacent motif (PAM) prediction and representation using the frequency plot of WebLogo for each CRISPR subtype crRNA:tracrRNA predicted interaction in Type II-A system with the RNase III predicted processing sites indicated with grey arrows (SEQ ID NO:121); crRNA predicted structure for Type I-B (SEQ ID NO:122) and Type I-E (SEQ ID NO:123) with the putative Cas6 processing site indicated with grey arrow.

We first investigated the occurrence of CRISPR-Cas systems in 52 available genomes of *L. crispatus* (Table 2) and characterized the architecture of the CRISPR loci using in silico analyses. Overall, we identified CRISPR loci in 51 of the 52 genomes (98% occurrence rate) and found Type I-B, I-E and II-A CRISPR-Cas systems (FIG. 9, Table 3). This is a rather high level of occurrence and diversity, even for the CRISPR-enriched *Lactobacillus* genus, in which CRISPR loci occur in ~63% of genomes (38). The widespread abundance of Type I systems, and ~15% occurrence of Type II systems reflect their relative amounts in bacteria (39). In details, a total of 30 CRISPR-Cas systems were identified in the 24 human-associated strains, with 19 Type II-A, 10 Type I-E and a unique Type I-B (Table 3). In poultry isolates, all Type I-E loci seemed complete with CRISPR arrays typically accompanied by a canonical set of cas genes (40), whereas only 3 human isolates (DSM20584, NCK1350, VMC3) displayed a complete system. Interestingly, strains with degenerate Type I-E systems did harbor complete Type II-A systems (C037, FB049-03, OAB24-B, VMC1, VMC5, VMC6), except DISK12 (Table 3). Noteworthy, all strains with complete Type I-E systems carried multiple CRISPR arrays, typically two arrays located upstream of the cas locus, and a third array located downstream (FIG. 9, panel A). A single I-B system was also detected in human strain VMC3, which also carried a complete Type I-E system, in many incomplete sets, we observed the occurrence of transposases, which have been previously observed in CRISPR loci (41, 42). The coexistence of several CRISPR-Cas systems in the same genome has been previously described in several gut lactobacilli and bifidobacteria, (41, 43), as well as in *Streptococcus thermophilus* starter cultures (44, 45). Overall, we determined widespread occurrence of CRISPR-Cas systems in *Lactobacillus crispatus*, notably complete Type I-E systems (FIG. 9, panel B).

PAM and Guide RNA Characterization

Once we determined the occurrence and diversity of CRISPR-Cas systems in *L. crispatus* and selected Type I-E as the most widespread and promising candidate, we next determined the sequences that guide Cas nucleases, namely the PAM and the crRNAs. By nature, CRISPR spacers represent a vaccination record of immunization events over time. Therefore, we first analyzed CRISPR spacer sequences to elucidate the flanking protospacer sequences in their matching targets, to predict the PAM, which is essential for target DNA recognition and binding (6, 8). In silica analysis of the CRISPR spacers revealed sequence homology to plasmids, phages and bacterial chromosomes (Tables 4-6), allowing us to identify 5'-AA-3' as a conserved PAM upstream of the protospacer for the Type I-E LcrCRISPR-Cas3 (FIG. 9, panel C).

Using NUPACK to depict the predicted guides (46, 47), we determined the consensus repeat sequence for each CRISPR subtype, and predicted the crRNA sequence and structure, for Type I, and crRNA:tracrRNA for Type II, using previously established molecular rules about guide RNA composition and complementarity (48) (FIG. 9, panel C). Variations in repeat sequences did not alter the predicted crRNA structures, since polymorphisms occurred in predicted bulges (Table 3).

The Native Type I-E System is Active in *L. crispatus* NCK1350

Figure 10:
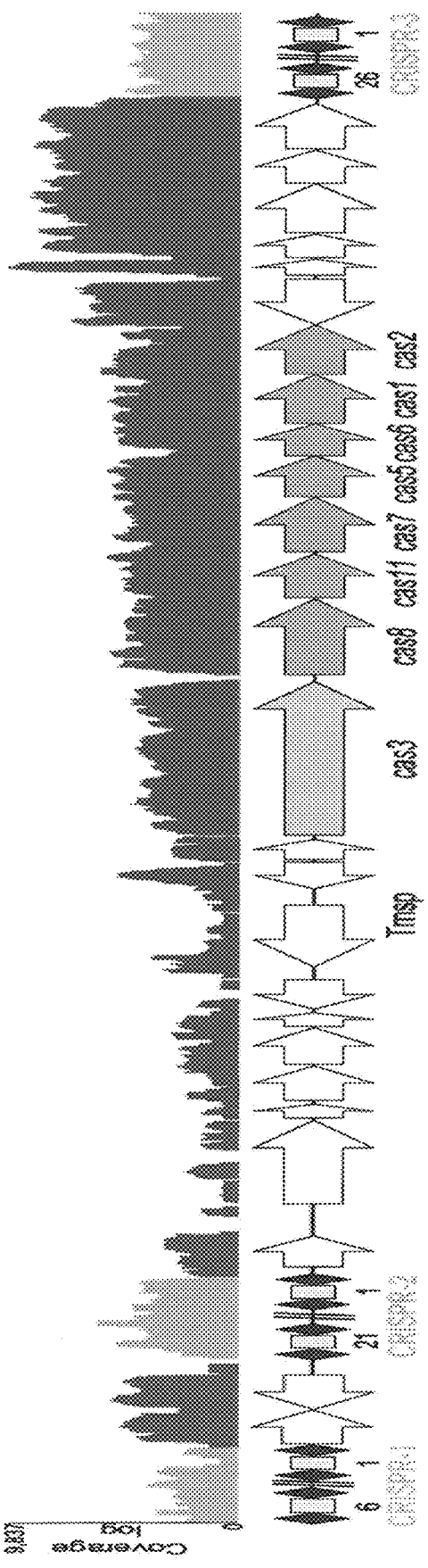
FIG. 10. CRISPR locus expression and functionality. (A) RNA-seq coverage displaying the transcriptional profile of the CRISPR locus Type I-E in *L. crispatus* NCK1350, with mRNA in dark grey and smRNA for the three CRISPR arrays in light grey. (B) smRNA-seq expression profiles of the CRISPR arrays displaying the coverage for each spacer in each array and (C) detailed representation of CRISPR-1 to display the coverage for each spacer-repeat. (D) smRNA-seq displayed the crRNA maturation with the generation of the 5' handle consisting of 7-nt (5'GUGAUCC-tag). The premature crRNA (pre-crRNA) (SEQ ID NO:89) is processed to generate the mature crRNA (SEQ ID NO:90). The crRNA boundaries with the terminal hairpin at the 3'end (SEQ ID NO:91) was manually depicted. (E) A protospacer corresponding to the most recently acquired spacer of each CRISPR array was cloned into the shuttle vector pTRKH2, with and without the PAM 5'-AAA-3', for plastic interference assays. Lowercase sequence displays the plasmid sequence upstream the protospacer. In each case the sequences for each plasmid are CRISPRI pS6 (SEQ ID NO:124); CRISPRI pPS6 (SEQ ID NO:125); CRISPRII pS21 (SEQ ID NO:126); CRISPRII pPS21 (SEQ ID NO:127); CRISPRIII pS26 (SEQ ID NO:128); CRISPRIII pPS26 (SEQ ID NO:129).
Figure 10:
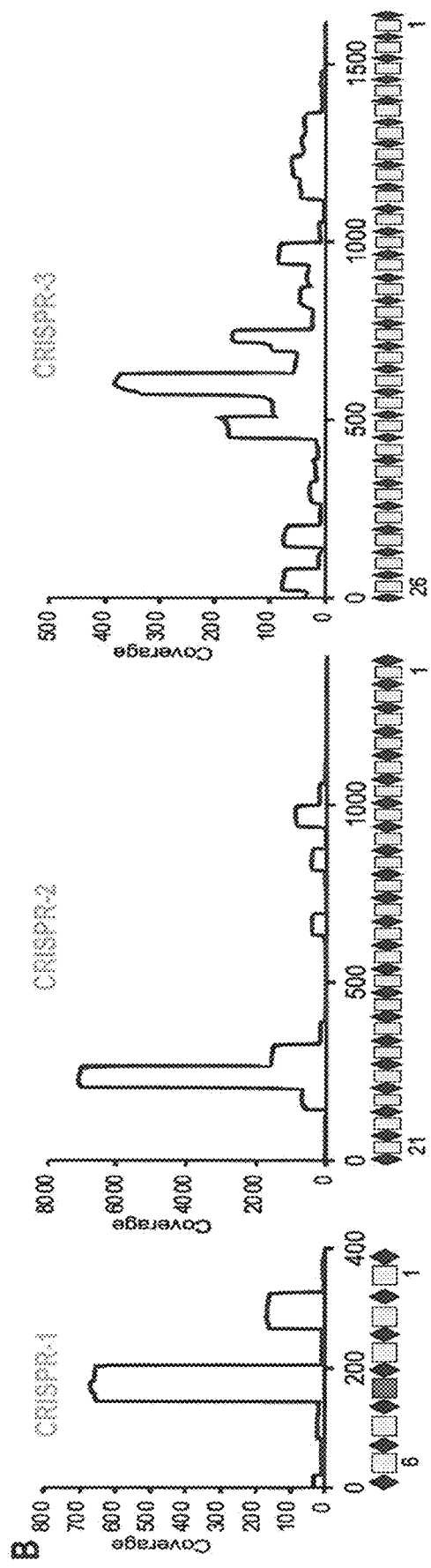

Once we established the widespread occurrence of complete Type I-E CRISPR-Cas systems in *L. crispatus*, and predicted the necessary guide RNA and targeting PAM, we selected a human endoscopy isolate, NCK1350 to validate our predictions and test the functionality of the endogenous system. RNA-seq data revealed constitutive expression of the cas genes encompassing a monocistronic transcript for cas3 and polycistronic expression for cascade (FIG. 10, panel A), while the small RNA (smRNA-seq) analyses probed the transcription profiles of all three associated CRISPR arrays (FIG. 10, panel B), enabling the determination of mature crRNA composition (FIG. 10, panels C-D). The mature crRNA structure is unique with a 5' handle consisting of 7-nt (FIG. 10, panel D), which differs from the canonical crRNA processing by Cas6 generating a 5' handle of 8-nt (49, 50).

Next, we used a plasmid interference assay to test the ability of the native system to prevent uptake of a plasmid carrying a sequence complementary to a native CRISPR spacer, flanked by the predicted PAM. Analysis of the NCK1350 spacer matches revealed 5'-AAA-3' (an extension of the aforementioned 5'-AA-3' PAM) as the likely PAM (Table 6). We tested all three endogenous CRISPR loci, using a protospacer corresponding to the most recently acquired spacer within each CRISPR array (5' end of the array, closest to the leader sequence), by cloning the corresponding protospacer into the shuttle vector pTRKH2 with, or without a flanking predicted PAM (FIG. 15, panel E, Table 7). Results showed that all three CRISPR loci can drive interference against plasmids that carry a target protospacer flanked by the predicted PAM. Specifically, the transformation efficiency was reduced by 10×, 100× and over 1,000× for loci 2, 1 and 3, respectively (FIG. 15, panel F), reflecting high activity and specificity of this Type I-E system. Overall, these results validated the predicted PAM 5'-AAA-3', determined the guide RNA sequences and confirmed activity of the native system in standard laboratory conditions.

Repurposing the Endogenous Type I-E CRISPR-Cas3 System for Genome Editing

Once the functionality of the endogenous Type I-E CRISPR-Cas was demonstrated in *L. crispatus* NCK1350, we next repurposed this endogenous system for genome editing by co-delivering a self-targeting CRISPR array with editing templates. We first surveyed the *L. crispatus* NCK1350 genome (~2.0 Mbp) for potential PAM sequences and found 56,591 instances of the 5'-AAA-3' motif and 181,672 occurrences of 5'-AA-3' on the coding strand, and 55,061 for 5'-AAA-3' and 182,194 for 5'-AA-3' on the non-coding strand. This high frequency of PAM sequences within the NCK1350 genome suggests that the endogenous Type I-E can be used to target and potentially alter every single gene in the genome, with a canonical PAM occurring on average every thirty-five nucleotides, virtually enabling widespread genome editing across this chromosome.

A plasmid-based tool was developed to reprogram the endogenous Type I-E machinery based on the expression of an artificial and programmable CRISPR array carrying a self-targeting CRISPR spacer. For this purpose, a double stranded gene block containing a promoter, two CRISPR repeats and a rho-independent terminator was cloned into BglII-SalI digested pTRKH2, to generate a flexible plasmid, pTRK1183, in which self-targeting spacers can readily be cloned (FIG. 14, Table 1). For the promoter, the native leader of the CRISPR-3 array (AT content ~70%) was chosen to drive the expression of the artificial CRISPR array. Conveniently, we designed pTRK1183 with two BsaI sites between the two CRISPR repeats, allowing flexible and easy insertion of spacers (33 bp) as programmable self-targeting guides, using annealing oligonucleotides with overhang ends compatible with the BsaI-digested plasmid (FIG. 14). Thus, the artificial guide expressed from the plasmid will mimic the native Type I-E crRNA from NCK135C. We used this tool to clone various self-targeting spacers close to the target gene start codon (FIG. 15), redirecting the endogenous Cascade-Cas3 machinery against select chromosomal locations. For this purpose, we engineered the plasmids pTRK1184, pTRK1188 and pTRK1190 targeting the nonessential exopolysaccharide priming-glycosyltransferase (p-gtf), the prophage DNA packaging Nu1, and the essential and highly transcribed enolase, respectively (Table 1). In all instances, self-targeting was lethal, with constructs killing over 99% of the cells across the three target sites (FIG. 11, panel A).

In order to trigger genome editing, we co-delivered a repair template cloned into the self-targeting plasmid containing the CRISPR array, to enable the host to overcome Cas3-based targeting and damage. First, we used the p-gtf target to generate a knock out, since the mutants will conveniently display a visibly distinct phenotype due to the altered exopolysaccharide content (51-53), which can also lead to altered probiotic features such as adherence, stress resistance and modulation of the host immune system (54-57). We designed the repair template to encompass sequences 1-kb upstream and 1-kb downstream of the target protospacer, and cloned into SalI-PvuI digested pTRK1184 to generate pTRK1185 (FIG. 15, panel A). All tested transformants generated a smaller PCR product, revealing the 643-bp expected deletion in the NCK2635 mutant (100% efficiency), confirmed by sequencing (FIG. 12, panel A). Similarly a control plasmid was generated containing the same repair template but lacking the targeting guide (pTRKH2-RT). Indeed, when this plasmid was transformed into *L. crispatus* NCK1350, hundreds of transformants were obtained (FIG. 12, panel A, right) and none of the PCR-screened colonies presented the deletion, indicating low-efficiency recombination without CRISPR selective pressure. This result suggests the deletion mutant NCK2635 was the consequence of Cascade-Cas3 targeting followed by homologous direct repair (HDR) based on the repair template provided on the plasmid, rather than naturally-occurring homologous recombination (HR). Also, these results confirmed the lethality of Cas3-based DNA damage when a self-targeting array is delivered to repurpose the endogenous system and trigger lethal cleavage without a repair template.

We then used a similar strategy to generate other genome editing outcomes to illustrate the versatility of the technology. We used the same targeting plasmid (pTRK1184), in which we cloned different repair templates to perform various editing outcomes within the p-gtf gene (FIG. 15, panel A). We introduced a stop codon in the p-gtf gene while simultaneously deleting the protospacer region (see pTRK1186 in Table 1, FIG. 15, panel A). When the plasmid was transformed into *L. crispatus* NCK1350, eleven transformants were obtained and PCR screening confirmed the insertion of the stop codon at the desired location with 36% efficiency (4/11 colonies), generating NCK2656 (FIG. 12, panel B Table 1). The other survivors appeared to carry defective plasmids, in which the targeting spacer had been excised, presumably by homologous recombination between the CRISPR repeats. Next, we carried out a single base substitution (14A>G) yielding a missense mutation (K5R) in the p-gtf target (see pTRK1187 in Table 1, FIG. 15, panel A). In this case, sixteen transformants were obtained and the PCR screening confirmed the genesis of the desired single base substitution in NCK2659 (FIG. 12, panel C), with an efficiency of 19% (3/16 colonies). The EPS-derivative mutants NCK2635 and NCK2656 displayed a rough phenotype due to the p-gtf deletion or interruption, visually distinguishable from the smooth phenotype of the wild type strain NCK1350, when using scanning electron microscopy (FIG. 12, panel D). The EPS-derivative mutant NCK2659 displayed an intermediate surface phenotype between the parental strain NCK1350 and the deletion mutant NCK2635 (FIG. 12, panel D) as the amino acid change K5R did show features of both the smooth and rough morphologies of *L. crispatus*. These results showed that this approach can be used to generate deletions, insert stop codons or precisely mutate a single base efficiently in the p-gtf gene.

Next, to illustrate the versatility of this approach, we targeted another chromosomal location, and deleted the prophage DNA packaging Nu1 gene, to provide a proof of concept for prophage curing. The NCK1350 wild type sequence is AATGGAATTTAAATTAGATGAATC ACAAGAAACCGAGATTAAAACTTTTGT-TATGGGCGTGGTTAAAGACGCTATTAAACAAGCC ACTACCACCACCAAACCATATTTGAACCG-CAAAGAAATTGCTAAGTATTTTGGCGTGGCTG AAT-CAACTATTACATATTGGGCTTCTTTAGGGATGCCT-GTCGCTGTCATAGACGGGCGC A AA CTCTATGGCAAGCAATCTATAACTAACTG-GCTAAAATT (SEQ ID NO:134) of which the first 8 and last 45 nucleotides are depicted in FIG. 13, panel A. Using the aforementioned vector, we designed a repair template completely ablating the Nu1, cloned it into SalI-PvuI digested pTRK1186 (see pTRK1189 in Table 1, FIG. 15, panel B), and generated a 308-nt deletion mutant NCK2662 with 20% efficiency (2/10 colonies) (FIG. 13, panel A). Finally, we targeted a third chromosomal locus to generate a knock-in. We strategically selected the downstream region of the enolase gene, as a stable and highly expressed locus, which we previously used for antigen expression in *L. acidophilus* (58) using a upp-plasmid based cloning system (59, 60). We designed a repair template containing the green fluorescent protein (GFP) gene flanked by 2 kb homologous arms, cloned into SalI-PvuI digested pTRK1190 to generate pTRK1191 (Table 1, FIG. 10, panel C). In this case, PCR screening of the transformants revealed the intended GFP integration (730 bp) with 23% efficiency (3/13 colonies) (FIG. 13, panel B). Prophage-curing, leading to the enhancement of strain genetic stability, was demonstrated under the selective induction of mitomycin C (0.75 µg/ml), with the deletion mutant NCK2662 being able to grow, whereas cell lysis occurred in the wild type strain NCK1350, due to prophage excision from the chromosome (FIG. 13, panel B). The fluorescence signal of the chromosomal inserted GFP was detected in the derivative mutant NCK2665 using fluorescence microscopy, enabling monitoring of probiotic strains in future characterization through in vitro and in vivo analyses (FIG. 13, panel D). Overall, these results show that various loci can be targeted by the endogenous Type I-E machinery to generate deletions and insertions flexibly and efficiently.

Discussion

The advent of CRISPR-based technologies has revolutionized genome editing and enabled the alteration of virtually any sequence in any organism of interest. Much of this success is due to the portability, ease of delivery and accessibility of materials and protocols for genome editing and transcriptional control (61). However, the current toolbox is limited to only a few Cas9, Cas12 and Cas13 effector proteins, predominantly optimized for use in eukaryotes. With thousands of native CRISPR-Cas systems widely occurring in bacteria and archaea, we have the opportunity to repurpose endogenous systems in their native host for genome editing, provided we can characterize their guide RNAs and targeting PAM sequences (15). Harnessing the endogenous machinery enables efficient genome editing simply by delivering a CRISPR array, together with desired repair templates. The development of such a potent tool has the potential to facilitate the engineering of many valuable bacteria that play critical roles in human health (62, 63) and important biological functions in the various habitats and niches they inhabit. Also, this opens new avenues for the functional enhancement of bacterial communities and rational design of beneficial microbes and probiotics to promote host health.

Recent studies have established *L. crispatus* as a key commensal species for women's health and poultry intestinal health (29, 31-33), though it is unclear what the genetic basis of those probiotic features are. Furthermore, research in this species has been limited by the paucity of molecular tools available for functional studies, and limited transformation efficiencies in this genetically recalcitrant species (64, 65). Indeed, the lack of molecular tools for *L. crispatus* represents a bottle neck for a more comprehensive understanding of its physiology and further enhancement of its probiotic features through genome editing.

The methods we used to edit various chromosomal loci in *L. crispatus* NCK1350 using the native CRISPR-Cas3 system illustrated how endogenous CRISPR-Cas systems can be easily repurposed for precise genome editing encompassing insertions, deletions and single base alterations. Similar approaches have been used previously for transcriptional control in the model bacterium *E. coli* (66, 67) and in archaea (68), for genome editing in archaea (69, 70) and also for genome engineering of bacteriophage (71) and *Clostridium* (72, 73). However, this is the first time that an endogenous CRISPR-Cas system is being used successfully for genome editing in lactobacilli. The only unique tool available previously was based on the heterologous expression of *S. pyogenes* Cas9 in *L. reuteri*, *L. casei* and *L. plantarum* (74-76). While Cas3-based exonucleolytic activity can be toxic to bacterial cells (25, 77), the widespread homologous recombination machinery mediated by RecBCD resects DNA ends. Subsequently RecA is recruited to drive recombination (26, 78), or RecA is recruited via the RecF pathway with RecFOR at the initial steps (79), to assist with DNA repair and genesis of the desired genome editing outcomes encoded on the repair template. In this study, we show that providing an adequately designed repair template (e.g., about 2 kb size) in the targeting plasmid constitutes an efficient means to carry out various editing outcomes (e.g., insertion, deletion, substitution), even in a recalcitrant species such as *L. crispatus*. The flexible genetic manipulation of the commensal *L. crispatus* uncovers tremendous potential to develop next generation probiotics for women's health and poultry health, including but not limited to enhancing the probiotic features or the development of vaccines against infectious diseases and sexually transmitted diseases. These findings also open new avenues for engineering other *Lactobacillus* species by repurposing their endogenous active CRISPR-Cas systems (80, 81) to enhance bacterial applications, microbiome targeting and modulation in humans and animals. Indeed, this technology relies on the use of a single plasmid conveniently designed for easy cloning, thus enabling potent CRISPR targeting and programmable genome editing, without the necessity of a large heterologous Cas nuclease which usually requires complex plasmid engineering, leading to stability artifacts and cloning challenges.

Overall, this study provides a framework to characterize endogenous CRISPR-Cas systems, based on in silico examination, transcriptomic analyses and plasmid interference assays. We have demonstrated how endogenous Type I CRISPR-Cas systems can be repurposed for efficient genome editing of bacteria in situ, opening new avenues for next-generation engineering of industrial workhorses, commensal microbes and beneficial probiotic bacteria for the development of engineered biotherapeutics.

REFERENCES

1. Barrangou R, et al. (2007) CRISPR provides acquired resistance against viruses in prokaryotes. *Science* 315 (5819): 1709-1712.
2. Crawley A B, Henriksen E D, & Barrangou R (2018) CRISPRdisco: An Automated Pipeline for the Discovery and Analysts of CRISPR-Cas Systems. *The CRISPR Journal* 1(2):171-181.
3. Makarova K S, Wolf Y I, & Koonin E V (2018) Classification and Nomenclature of CRISPR-Cas Systems: Where from Here? *The CRISPR Journal* 1(5):325-336.
4. Gasiunas G, Sinkunas T, & Siksnys V (2014) Molecular mechanisms of CRISPR-mediated microbial immunity. *Cell Mol Life Sci* 71(3) 449-465.
5. Abudayyeh O O, et al. (2016) C2c2 is a single-component programmable RNA-guided RNA-targeting CRISPR effector. *Science* 353(6299):aaf5573.
6. Mojica F J, Diez-Villasenor C, Garcia-Martinez J, & Almendros C (2009) Short motif sequences determine the targets of the prokaryotic CRISPR defence system. *Microbiology* 155(Pt 3):733-740.
7. Marraffini L A & Sontheimer E J (2010) Self versus non-self discrimination during CRISPR RNA-directed immunity. *Nature* 463(7280):568-571.
8. Deveau H, et al. (2008) Phage response to CRISPR-encoded resistance in *Streptococcus thermophilus*. *J Bacteriol* 190(4):1390-1400.
9. Barrangou R & Doudna J A (2016) Applications of CRISPR technologies in research and beyond. *Nat Biotechnol* 34(9):933-941.
10. Zetsche B, et al. (2015) Cpf1 is a single RNA-guided endonuclease of a class 2 CRISPR-Cas system. *Cell* 163(3):759-771.
11. Cong L, et al. (2013) Multiplex genome engineering using CRISPR/Cas systems. *Science* 339(6121):819-823.
12. Jinek M, et al. (2012) A programmable dual-RNA-guided DNA endonuclease in adaptive bacterial immunity. *Science* 337(6096):816-821.
13. Mall P, et al. (2013) RNA-guided human genome engineering via Cas9. *Science* 339(6121):823-826.
14. Sinkunas T, et al. (2011) Cas3 is a single-stranded DNA nuclease and ATP-dependent helicase in the CRISPR/Cas immune system. *EMBO J* 30(7): 1335-1342.
15. Hidalgo-Cantabrana C, Goh Y J, & Barrangou R (2019) Characterization and Repurposing of Type I and Type II CRISPR-Cas Systems in Bacteria. *J Mol Biol* 431(1):21-33.
16. Ishino Y, Shinagawa H, Makino K, Amemura M, & Nakata A (1987) Nucleotide sequence of the iap gene, responsible for alkaline phosphatase isozyme conversion in *Escherichia coli*, and identification of the gene product. *J Bacteriol* 169(12):5429-5433.
17. Brouns S J, et al. (2008) Small CRISPR RNAs guide antiviral defense in prokaryotes *Science* 321 (5891):960-964.
18. Marraffini L A & Sontheimer E J (2010) CRISPR interference: RNA-directed adaptive immunity in bacteria and archaea. *Nat Rev Genet* 11(3):181-190.
19. Jore M M, et al. (2011) Structural basis for CRISPR RNA-guided DNA recognition by Cascade. *Nat Struct Mol Biol* 18(5):529-536.

20. Xiao Y, et al. (2017) Structure Basis for Directional R-loop Formation and Substrate Handover Mechanisms in Type I CRISPR-Cas System. *Cell* 170(1):48-60 e11.
21. Sinkunas T, et al. (2013) In vitro reconstitution of Cascade-mediated CRISPR immunity in *Streptococcus thermophilus* EMBO J 32(3):385-394.
22. Loeff L, Brouns S J J, & Joo C (2018) Repetitive DNA Reeling by the Cascade-Cas3 Complex in Nucleotide Unwinding Steps. *Mol Cell* 70(3):385-394 e383.
23. Mulepati S & Bailey S (2013) In vitro reconstitution of an *Escherichia coli* RNA-guided immune system reveals unidirectional, ATP-dependent degradation of DNA target. *J Biol Chem* 288(31):22184-22192.
24. Huo Y, et al. (2014) Structures of CRISPR Cas3 offer mechanistic insights into Cascade-activated DNA unwinding and degradation. *Nat Struct Mol Biol* 21(9): 771-777.
25. Gomaa A A, et al. (2014) Programmable removal of bacterial strains by use of genome-targeting CRISPR-Cas systems. *MBio* 5(1):e00928-00913.
26. Selle K & Barrangou R (2015) Harnessing CRISPR-Cas systems for bacterial genome editing. *Trends Microbiol* 23(4):225-232.
27. Human Microbiome Project C (2012) Structure, function and diversity of the healthy human microbiome. *Nature* 486(7402):207-214.
28. Integrative HMPRNC (2014) The Integrative Human Microbiome Project: dynamic analysis of microbiome-host omics profiles during periods of human health and disease. *Cell Host Microbe* 16(3):276-289.
29. Wei S, Morrison M, & Yu Z (2013) Bacterial census of poultry intestinal microbiome. *Poult Sci* 92(3):671-683.
30. Dec M, Nowaczek A, Stepien-Pysniak D, Wawrzykowski J, & Urban-Chmiel R (2018) Identification and antibiotic susceptibility of lactobacilli isolated from turkeys. *BMC Microbiol* 18(1):168.
31. Ravel J, et al. (2011) Vaginal microbiome of reproductive-age women. *Proc Natl Acad Sci USA* 108 Suppl 1:4680-4687.
32. Liu M B, et al. (2013) Diverse vaginal microbiomes in reproductive-age women with vulvovaginal candidiasis. *PloS One* 8(11):e79812.
33. Arokiyaraj S, Seo S S, Kwon M, Lee J K, & Kim M K (2018) Association of cervical microbial community with persistence, clearance and negativity of Human Papillomavirus in Korean women: a longitudinal study. *Sci Rep* 8(1):15479.
34. Donnarumma G, et al. (2014) *Lactobacillus crispatus* L1: high cell density cultivation and exopolysaccharide structure characterization to highlight potentially beneficial effects against vaginal pathogens. *BMC Microbiol* 14:137.
35. Nardini P, et al. (2016) *Lactobacillus crispatus* inhibits the infectivity of *Chlamydia trachomatis* elementary bodies, in vitro study. *Sci Rep* 6:29024.
36. Parolin C, et al. (2018) *Lactobacillus crispatus* BC5 Interferes With *Chlamydia trachomatis* Infectivity Through Integrin Modulation in Cervical Cells. *Front Microbiol* 9:2630.
37. Rizzo A, et al. (2015) *Lactobacillus crispatus* mediates anti-inflammatory cytokine interleukin-10 induction in response to *Chlamydia trachomatis* infection in vitro. *Int J Med Microbiol* 305(8):815-827.
38. Sun Z, et al. (2015) Expanding the biotechnology potential of lactobacilli through comparative genomics of 213 strains and associated genera. *Nat Commun* 6:8322.
39. Koonin E V, Makarova K S, & Zhang F (2017) Diversity, classification and evolution of CRISPR-Cas systems. *Curr Opin Microbiol* 37:67-78.
40. Makarova K S, et al. (2015) An updated evolutionary classification of CRISPR-Cas systems. *Nat Rev Microbiol* 13(11):722-736.
41. Hidalgo-Cantabrana C, Crawley A B, Sanchez B, & Barrangou R (2017) Characterization and Exploitation of CRISPR Loci in *Bifidobacterium longum. Front Microbiol* 8:1851.
42. Horvath P, et al. (2009) Comparative analysis of CRISPR loci in lactic acid bacteria genomes. *Int J Food Microbiol* 131(1):62-70.
43. Briner A E, et al. (2015) Occurrence and Diversity of CRISPR-Cas Systems in the Genus *Bifidobacterium. PLoS One* 10(7):e0133661.
44. Horvath P, et al. (2008) Diversity, activity, and evolution of CRISPR loci in *Streptococcus thermophilus. J Bacteriol* 190(4):1401-1412.
45. Magadan A H, Dupuis M E, Villion M, & Moineau S (2012) Cleavage of phage DNA by the *Streptococcus thermophilus* CRISPR3-Cas system. *PLoS One* 7(7): e40913.
46. Chylinski K, Le Rhun A, & Charpentier E (2013) The tracrRNA and Cas9 families of type II CRISPR-Cas immunity systems. *RNA Biol* 10(5):726-737.
47. Briner A E, Henriksen E D, & Barrangou R (2016) Prediction and Validation of Native and Engineered Cas9 Guide Sequences. *Cold Spring Harb Protoc* 2016(7):pdb prot086785.
48. Briner A E & Barrangou R (2016) Guide RNAs: A Glimpse at the Sequences that Drive CRISPR-Cas Systems. *Cold Spring Harb Protoc* 2016(7):pdb top090902.
49. Li H (2015) Structural Principles of CRISPR RNA Processing. *Structure* 23(1):13-20.
50. Wang R, Preamplume G, Terns M P, Terns R M, & Li H (2011) interaction of the Cas6 riboendonuclease with CRISPR RNAs: recognition and cleavage. *Structure* 19(2):257-264.
51. Lebeer S. et al. (2009) Identification of a Gene Cluster for the Biosynthesis of a Long, Galactose-Rich Exopolysaccharide in *Lactobacillus rhamnosus* GG and Functional Analysis of the Priming Glycosyltransferase. *Appl Environ Microbiol* 75(11):3554-3563.
52. Fanning S, et al. (2012) Bifidobacterial surface-exopolysaccharide facilitates commensal-host interaction through immune modulation and pathogen protection. *Proc Natl Acad Sci USA* 109(6):2108-2113.
53. van Kranenburg R, Vos H R, van S, II, Kleerebezern M. & de Vos W M (1999) Functional analysis of glycosyltransferase genes from *Lactococcus lactis* and other gram-positive cocci: complementation, expression, and diversity. *J Bacteriol* 181(20):6347-6353.
54. Hidalgo-Cantabrana C, et al. (2012) Immune Modulation Capability of Exopolysaccharides Synthesised by Lactic Acid Bacteria and Bifidobacteria. *Probiotics Antimicrob Proteins* 4(4):227-237.
55. Castro-Bravo N, Wells J M, Margolles A & Ruas-Madledo P (2018) Interactions of Surface Exopolysaccharides From *Bifidobacterium* and *Lactobacillus* Within the Intestinal Environment. *Front Microbiol* 9:2426.
56. Hidalgo-Cantabrana C, et al. (2015) A single mutation in the gene responsible for the mucoid phenotype of *Bifidobacterium animalis* subsp. *lactis* confers surface and functional characteristics. *Appl Environ Microbiol* 81(23): 7960-7968.

57. Kawaharada Y, et al. (2015) Receptor-mediated exopolysaccharide perception controls bacterial infection. *Nature* 523(7560):308-312.
58. O'Flaherty S & Klaenhammer T R (2016) Multivalent Chromosomal Expression of the *Clostridium botulinum* Serotype A Neurotoxin Heavy-Chain Antigen and the *Bacillus anthracis* Protective Antigen in *Lactobacillus acidophilus*. *Appl Environ Microbiol* 82(20):6091-6101.

59. Douglas G L & Klaenhammer T R (2011) Directed chromosomal integration and expression of the reporter gene gusA3 in *Lactobacillus acidophilus* NCFM. *Appl Environ Microbiol* 77(20):7365-7371.

60. Goh Y J, et al. (2009) Development and application of a upp-based counterselective gene replacement system for the study of the S-layer protein SlpX of *Lactobacillus acidophilus* NCFM. *Appl Environ Microbiol* 75(10): 3093-3105.

61. LaManna C M & Barrangou R (2018) Enabling the Rise of a CRISPR World. *The CRISPR Journal* 1(3):4.

62. Goh Y J & Barrangou R (2018) Harnessing CRISPR-Cas systems for precision engineering of designer probiotic lactobacilli. *Curr Opin Biotechnol* 56:163-171.

63. Klotz C & Barrangou R (2018) Engineering Components of the *Lactobacillus* S-Layer for Biotherapeutic Applications. *Front Microbiol* 9:2264.

64. Beasley S S, Takala T M, Reunanen J. Apajalahti J, & Saris P E (2004) Characterization and electrotransformation of *Lactobacillus crispatus* isolated from chicken crop and intestine. *Poult Sci* 83(1):45-48.

65. Heravi R M, Nasiraii L R, Sankian M, Kermanshahi H, & Varasteh A R (2012) Optimization and Comparison of Two Electrotransformation Methods for Lactobacilli. *Biotechnology* 11:5.

66. Chang Y, Su T, Qi Q, & Liang Q (2016) Easy regulation of metabolic flux in *Escherichia coli* using an endogenous type I-E CRISPR-Cas system. *Microb Cell Fact* 15(1): 195.

67. Luo M L, Mullis A S, Leenay R T, & Beisel C L (2015) Repurposing endogenous type I CRISPR-Cas systems for programmable gene repression. *Nucleic Acids Res* 43(1): 674-681.

68. Stachler A E & Marchfelder A (2016) Gene Repression in Haloarchaea Using the CRISPR (Clustered Regularly Interspaced Short Palindromic Repeats)-Cas I-B System. *J Biol Chem* 291(29): 15226-15242.

69. Li Y, et al. (2016) Harnessing Type I and Type III CRISPR-Cas systems for genome editing. *Nucleic Acids Res* 44(4) e34.

70. Cheng F, et al. (2017) Harnessing the native type I-B CRISPR-Cas for genome editing in a polyploid archaeon. *J Genet Genomics* 44(11):541-548.

71. Kiro R, Shitrit D, & Qimron U (2014) Efficient engineering of a bacteriophage genome using the type I-E CRISPR-Cas system. *RNA Biol* 11(1):42-44.

72. Pyne M E, Bruder M R, Moo-Young M, Chung D A, & Chou C P (2016) Harnessing heterologous and endogenous CRISPR-Cas machineries for efficient markerless genome editing in *Clostridium*. *Sci Rep* 6:25666.

73. Zhang J, Zong W, Hong W, Zhang Z T, & Wang Y (2018) Exploiting endogenous CRISPR-Cas system for multiplex genome editing in *Clostridium tyrobutyricum* and engineer the strain for high-level butanol production. *Metab Eng* 47:49-59.

74. Leenay R T, et al. (2018) Genome Editing with CRISPR-Cas9 in *Lactobacillus plantarum* Revealed That Editing Outcomes Can Vary Across Strains and Between Methods. *Biotechnol J*:e1700583.

75. Oh J H & van Pijkeren J P (2014) CRISPR-Cas9-assisted recombineering in *Lactobacillus reuteri*. *Nucleic Acids Res* 42(17):e131.

76. Song X, Huang H, Xiong Z, Ai L, & Yang S (2017) CRISPR-Cas9(D10A) Nickase-Assisted Genome Editing in *Lactobacillus casei, Appl Environ Microbiol* 83(22).

77. Vercoe R B, et al. (2013) Cytotoxic chromosomal targeting by CRISPR/Cas systems can reshape bacterial genomes and expel or remodel pathogenicity islands. *PLoS Genet* 9(4):e1003454.

78. Wigley D B (2013) Bacterial DNA repair: recent insights into the mechanism of RecBCD, AddAB and AdnAB. *Nat Rev Microbiol* 11(1):9-13.

79. Morimatsu K & Kowalczykowski S C (2003) RecFOR proteins load RecA protein onto gapped DNA to accelerate DNA strand exchange: a universal step of recombinational repair. *Mol Cell* 11(5):1337-1347.

80. Crawley A B, Henriksen E D, Stout E, Brandt K, & Barrangou R (2018) Characterizing the activity of abundant, diverse and active CRISPR-Cas systems in lactobacilli. *Sci Rep* 8(1):11544.

81. Sanozky-Dawes R, Selle K, O'Flaherty S, Klaenhammer T, & Barrangou R (2015) Occurrence and activity of a type II CRISPR-Cas system in *Lactobacillus gasseri*. *Microbiology* 161(9):1752-1761.

82. Altschul S F, et al. (1997) Gapped BLAST and PSI-BLAST: a new generation of protein database search programs. *Nucleic Acids Res* 25(17):3389-3402.

83. Bland C, et al. (2007) CRISPR recognition tool (CRT): a tool for automatic detection of clustered regularly interspaced palindromic repeats. *BMC Bioinformatics* 8:209.

84. Kearse M, Moir, R., Wilson, A., Stones-Havas, S., Cheung, M., Sturrock, S., Buxton, S., Cooper, A., Markowitz, S., Duran, C., Thierer, T., Ashton, B., Mentjies, P., & Drummond, A. (2012) Geneious Basic: an integrated and extendable desktop software platform for the organization and analysis of sequence data. *Bioinformatics* 28:1647-1649.

85. Biswas A, Gagnon J N, Brouns S J, Fineran P C, & Brown C M (2013) CRISPRTarget: bioinformatic prediction and analysis of crRNA targets. *RNA Biol* 10(5):817-827.

86. Crooks G E, Hon G, Chandonia J M, & Brenner S E (2004) WebLogo: a sequence logo generator. *Genome Res* 14(6):1188-1190.

87. Zadeh J N, et al. (2011) NUPACK: Analysis and design of nucleic acid systems. *J Comput Chem* 32(1):170-173.

88. Theilmann M C, et al. (2017) *Lactobacillus acidophilus* Metabolizes Dietary Plant Glucosides and Externalizes Their Bioactive Phytochemicals. *MBio* 8(6).

89. Wagner G P, Kin K, & Lynch V J (2012) Measurement of mRNA abundance using RNA-seq data: RPKM measure is inconsistent among samples. *Theory Biosci* 131 (4):281-285.

90. O'Sullivan D J & Klaenhammer T R (1993) High- and low-copy-number *Lactococcus* shuttle cloning vectors with features for clone screening. *Gene* 137(2):227-231.

The foregoing is illustrative of the present invention, and is not to be construed as limiting thereof. The invention is defined by the following claims, with equivalents of the claims to be included therein.

TABLE 1

Strains and plasmids

| | Description |
|---|---|
| Strains | |
| *L. crispatus* NCK1350 | *Lactobacillus crispatus* isolated from a human endoscopy with CRISPR-Cas systems subtype I-E |
| NCK2635 | *L. crispatus* NCK1350 mutant with the deletion (643 bp) of the exopolysaccharide gene priming-glycosyltransferase (p-gtf) (EC 2.7.8.6) |
| NCK2656 | *L. crispatus* NCK1350 mutant with three stop codons inserted (p-gtf15_16::taatagtga) in the p-gtf gene and the protospacer sequence deleted |
| NCK2659 | *L. crispatus* NCK1350 mutant with a single base substitution altering the PAM sequence (14A > G) (K5R) in the p-gtf gene |
| NCK2662 | *L. crispatus* NCK1350 mutant with the prophage DNA packaging Nu1 deleted (308 bp) |
| NCK2665 | *L. crispatus* NCK1350 mutant with the GFP inserted in the chromosome downstream the enolase (EC 4.2.1.11) |
| Plasmids | |
| pTRKH2 | High copy Gram+ shuttle vector: Erm$^r$ |
| pS6 | Spacer 6 from CRISPR-1 cloned into BglII-SalI digested pTRKH2 |
| pPS6 | PAM + Spacer 6 from CRISPR-1 cloned into BglII-SalI digested pTRKH2 |
| pS21 | Spacer 18 from CRISPR-2 cloned into BglII-SalI digested pTRKH2 |
| pPS21 | PAM + Spacer 18 from CRISPR-2 cloned into BglII-SalI digested pTRKH2 |
| pS26 | Spacer 26 from CRISPR-3 cloned into BglII-SalI digested pTRKH2 |
| pPS26 | PAM + Spacer 26 from CRISPR-3 cloned into BglII-SalI digested pTRKH2 |
| pTRK1183 (pcrRNA) | Plasmid-based technology with an artificial crRNA (leader + 2 repeats + rhc-terminator) cloned into BglII-SalI digested pTRKH2 |
| pTRK1184 (pcrRNA_T1) | Targeting plasmid on the exopolysaccharide p-gtf gene obtained after cloning with annealing oligonucleotides a 33 nt spacer into BsaI digested pTRK1183 |
| pTRK1185 (pcrRNA_T1_RTdef) | Editing plasmid containing the repair template (RT$_{KO}$) to generate a knock out of the p-gtf gene, cloned into SalI-PvuI digested pTRK1184 |
| pTRKH2-RT | Control plasmid containing the repair template (RT$_{KO}$) used to generate a knock out of the p-gtf gene, cloned into SalI-PvuI digested pTRKH2 |
| pTRK1186 | Editing plasmid containing the repair template (RT$_{STOP}$) to generate the insertion of three stop codons in the p-gtf gene, cloned into SalI-PvuI digested pTRK1184 |
| pTRK1187 | Editing plasmid containing the repair template (RT$_{SNP}$) to perform single nucleotide substitution altering the PAM sequence in the p-gtf gene, cloned into SalI-PvuI digested pTRK1184 |
| pTRK1188 (pcrRNA_T3) | Targeting plasmid on the prophage DNA packaging Nu1 gene obtained after cloning with annealing oligonucleotides a 33 nt spacer into BsaI digested pTRK1183 |
| pTRK1189 | Editing plasmid containing the repair template (RT$_{KO}$) to generate a knock out of the Nu1 gene, cloned into SalI-PvuI digested pTRK1188 |
| pTRK1190 | Targeting plasmid on the enolase gene obtained after cloning with annealing oligonucleotides a 33 nt spacer into BsaI digested pTRK1183 |
| pTRK1191 | Editing plasmid containing the repair template (RT$_{GFP}$) to generate the chromosomal insertion of the GFP gene, cloned into SalI-PvuI digested pTRK1188 |

TABLE 2

*Lactobacillus crispalus* genomes available at NCBI

| Source | Strain | Isolation source | GenBank genome |
|---|---|---|---|
| Human isolates | 125-2-CHN | Vaginal isolate | ACPV00000000 |
| | 214-1 | Vaginal isolate | ADGR00000000 |
| | 2029 | Healthy women genital tract | AVFH00000000 |
| | C037 | Adult female bladder | MAKH00000000 |
| | CTV-05 | Vaginal isolate | ADML00000000 |
| | FB049-03 | Vaginal isolate | AGZF00000000 |
| | FB077-07 | Vaginal isolate | AGZG00000000 |
| | JV-V01 | Normal human vaginal flora | ACKR00000000 |
| | MV-1A-US | Vaginal isolate | ACOG00000000 |
| | MV-3A-US | Vaginal isolate | ACQC00000000 |
| | OAB24-B | Human urine | MAMR00000000 |
| | PSS7772C | Human urine | LSQY00000000 |
| | SJ-3C-US | Vaginal isolate | ADDT00000000 |
| | VMC1 | Mid-vaginal wall from BV | LJCZ00000000 |
| | VMC2 | Mid-vaginal wall from BV | LJDA00000000 |
| | VMC3 | Mid-vaginal wall from BV | LJGP00000000 |

TABLE 2-continued

*Lactobacillus crispalus* genomes available at NCBI

| Source | Strain | Isolation source | GenBank genome |
|---|---|---|---|
| | VMC4 | Mid-vaginal wall from BV | LJGQ00000000 |
| | VMC5 | Mid-vaginal wall healthy women | LJOK00000000 |
| | VMC6 | Mid-vaginal wall healthy women | LJOL00000000 |
| | VMC7 | Mid-vaginal wall healthy women | LJOM00000000 |
| | VMC8 | Mid-vaginal wall healthy women | LJON00000000 |
| | DSM 20584* | Human Eye | AZCW00000000 |
| | EM-LC1 | Human fecal sample | AXLM00000000 |
| | DISK12 | Human oral cavity | MKXG01 |
| | NCK1350 | Human endoscopy | SGWL00000000 |
| Chicken/ | C25 | Chicken cecum | MCJG00000000 |
| Turkey | JCM 5810 | Chicken feces | LSVK00000000 |
| isolates | ST1 | Chicken crop isolate | NC-014106 |
| | UMNLC1 | Turkey Ileum | LYQR00000000 |
| | UMNLC2 | Turkey Ileum | LYQS00000000 |
| | UMNLC3 | Turkey Ileum | LYQT00000000 |
| | UMNLC4 | Turkey Ileum | LYQU00000000 |
| | UMNLC5 | Turkey Ileum | LYQV00000000 |
| | UMNLC6 | Turkey Ileum | LYQW00000000 |
| | UMNLC7 | Turkey Ileum | LYQX00000000 |
| | UMNLC8 | Turkey Ileum | LYQY00000000 |
| | UMNLC9 | Turkey Ileum | LYQZ00000000 |
| | UMNLC10 | Turkey Ileum | LYRA00000000 |
| | UMNLC11 | Turkey Ileum | LYRB00000000 |
| | UMNLC12 | Turkey Ileum | LYRC00000000 |
| | UMNLC13 | Turkey Ileum | LYRD00000000 |
| | UMNLC14 | Turkey Ileum | LYRE00000000 |
| | UMMLC15 | Turkey Ileum | LYRF00000000 |
| | UMNLC16 | Turkey Ileum | LYRG00000000 |
| | UMNLC18 | Turkey Ileum | LYRH00000000 |
| | UMNLC19 | Turkey Ileum | LYRI00000000 |
| | UMNLC20 | Turkey Ileum | LYRK00000000 |
| | UMNLC21 | Turkey Ileum | LYRK00000000 |
| | UMNLC22 | Turkey Ileum | LYRL00000000 |
| | UMNLC23 | Turkey Ileum | LYRM00000000 |
| | UMNLC24 | Turkey Ileum | LYRN00000000 |
| | UMNCL25 | Turkey Ileum | LYRO00000000 |

*DSM 20584 = ATCC 33820 = JCM1185

TABLE 3

CRISPR-Cas systems in *Lactobacillus crispatus* genomes available at NCBI

| Isolation source | Strain | CRISPR Subtype | Repeat sequence* | SEQ ID NO | Repeat Length | No. spacers | cas1 | cas3 | cas9 |
|---|---|---|---|---|---|---|---|---|---|
| Human | 125-2-CHN | II-A | GTTTTAGATGATTGTTAGATCAATGAGGTTTAGATC | 153 | 36 | 3 | — | — | — |
| Isolates | 214-1 | II-A | GTTTTAGATGATTGTTAGATCAATGAGGTTTAGATC | 153 | 36 | 6 | Y | — | Y |
| | 2029 | II-A | GTTTTAGATGGTTGTTAGATCAATGAGGTTTAGATC | 153 | 36 | 7 | Y | — | Y |
| | C037 | II-A | GTTTTAGATGATTGTTAGATCAATGAGGTTTAGATC | 153 | 36 | 3 | Y | — | Y |
| | | II-E | GTATTCTCCACGCATGTGGAGGTGTGTGGAGGTGATCC | 154 | 28 | 2 | — | — | — |
| | CTV-05 | II-A | GTTTTAGATGATTGTTAGATCAATGAGGTTTAGATC | 153 | 36 | 5 | Y | — | Y |
| | FB049-03 | II-A | GTTTTAGATGATTGTTAGATCAATGAGGTTTAGATC | 153 | 36 | 7 | Y | — | Y |
| | | II-E | GTATTCTCCACACATGTGGAGGTGATCC | 155 | 28 | 4 | — | — | — |
| | FB077-07 | II-A | GTTTTAGATGATTGTTAGATCAATGAGGTTTAGATC | 153 | 36 | 7 | Y | — | Y |
| | JV-V01 | II-A | GTTTTAGATGATTGTTAGATCAATGAGGTTTAGATC | 153 | 36 | 4 | Y | — | Y |

TABLE 3-continued

CRISPR-Cas systems in *Lactobacillus crispatus* genomes available at NCBI

| Isolation source | Strain | CRISPR Subtype | Repeat sequence* | SEQ ID NO | Repeat Length | No. spacers | cas1 | cas3 | cas9 |
|---|---|---|---|---|---|---|---|---|---|
| | MV-1A-US | II-A | GTTTTAGATGATTGTTAGATCAATGAGGTTTAGATC | 153 | 36 | 3 | Y | — | Y |
| | MV-3A-US | II-A | GTTTTAGATGATTGTTAGATCAATGAGGTTTAGATC | 153 | 36 | 4 | Y | — | Y |
| | OAB24-B | II-A | — | | | | Y | — | Y |
| | | II-E | GTATTCTCCACGTGTGTGGAGGTGATCC | 154 | 28 | 2 | — | — | — |
| | PSS7772C | II-A | GTTTTAGATGATTGTTAGATCAATGAGGTTTAGATC | 153 | 36 | 6 | Y | — | Y |
| | SJ-3C-US | II-A | GTTTTAGATGATTGTTAGATCAATGAGGTTTAGATC | 153 | 36 | 7 | Y | — | Y |
| | VMC1 | II-A | GTTTTAGATGATTGTTAGATCAATGAGGTTTAGATC | 153 | 36 | 7 | Y | — | Y |
| | | II-E | GTATTCTCCACACATGTGGAGGTGATCC | 155 | 28 | 4 | — | — | — |
| | VMC2 | II-A | GTTTTAGATGATTGTTAGATCAATGAGGTTTAGATC | 153 | 36 | 6 | Y | — | Y |
| | VMC3 | I-B | GTATTTATTTATCTTAAGAGAAATGTAAAT | 156 | 30 | 13 | Y | Y | — |
| | | I-E | GTATTCTCCACGCATGTGGAGGTGATCC | 157 | 28 | 35 | Y | Y | — |
| | | | GTATTCTCCACGAGTGTGGGGATCCTAT | 158 | 28 | | | | |
| | VMC4 | II-A | GTTTTAGATGATTGTTAGATCAATGAGGTTTAGATC | 153 | 36 | 4 | Y | — | Y |
| | VMC5 | II-A | GTTTTAGATGATTGTTAGATCAATGAGGTTTAGATC | 153 | 36 | 4 | Y | — | Y |
| | | II-E | GTATTCTCCACGTGTGTGGAGGTGATCC | 154 | 28 | 4 | — | — | — |
| | VMC6 | II-A | GTTTTAGATGATTGTTAGATCAATGAGGTTTAGATC | 153 | 36 | 7 | Y | — | Y |
| | | II-E | GTATTCTCCACACATGTGGAGGTGATCC | 155 | 28 | 4 | — | — | — |
| | VMC7 | II-A | GTTTTAGATGGTTGTTAGATCAATGAGGTTTAGATC | 153 | 36 | 5 | Y | — | Y |
| | VMC8 | II-A | GTTTTAGATGGTTGTTAGATCAATGAGGTTTAGATC | 153 | 36 | 7 | Y | — | Y |
| | DSM 20584 | I-E | GTATTCTCCACGTGTGTGGAGGTGATCC | 154 | 28 | 5 | Y | Y | — |
| | EM-LC1 | — | — | | | | — | — | — |
| | DISK12 | I-E | GTATTCTCCACGTATGTGGAGGTGATCC | 159 | 28 | 10 | — | — | — |
| | NCK1350 | I-E | GTATTCTCCACGTATGTGGAGGTCATCC | 160 | 28 | 53 | Y | Y | — |
| | | | GTATTCTCCACGTATGTGGAGGTGATCC | 159 | | | | | |
| | | | GTATTCTCCACACATGTGGAGGTGATCC | 155 | | | | | |
| | | | GTATTCTCCACGTGTGTGGAGGTGATCC | 154 | | | | | |

TABLE 3-continued

CRISPR-Cas systems in *Lactobacillus crispatus* genomes available at NCBI

| Isolation source | Strain | CRISPR Subtype | Repeat sequence* | SEQ ID NO | Repeat Length | No. spacers | cas1 | cas3 | cas9 |
|---|---|---|---|---|---|---|---|---|---|
| Chicken/ | C25 | I-E | GTATTCTCCACGTGTGTGGAGGTGATCC | 154 | 28 | 37 | Y | Y | — |
| Turkey | JCM 5810 | I-E | GTATTCTCCACGCCGTGTGGAGGTGATCC | 161 | 28 | 55 | Y | Y | — |
| Isolates | ST1 | I-E | GTATTCTCCACGTGTGTGGAGGTGATCC | 154 | 28 | 38 | Y | Y | — |
| | | | GTATTCTCCACGTATGTGGAGGTGATCCC | 162 | 29 | | | | |
| | UMNLC1 | I-E | GTATTCTCCACGTGTGTGGAGGTGATCC | 154 | 28 | 49 | Y | Y | — |
| | UMNLC2 | I-E | GTATTCTCCACACATGTGGAGGTGATCC | 155 | 28 | 40 | Y | Y | — |
| | UMNLC3 | I-E | GTATTCTCCACACATGTGGAGGTGATCC | 155 | 28 | 40 | Y | Y | — |
| | UMNLC4 | I-E | GTATTCTCCACGTATGTGGAGGTGATCC | 159 | 28 | 40 | Y | Y | — |
| | UMNLC5 | I-E | GTATTCTCCACGTATGTGGAGGTGATCC | 159 | 28 | 39 | Y | Y | — |
| | UMNLC6 | I-E | GTATTCTCCACGTATGTGGAGGTGATCC | 159 | 28 | 64 | Y | Y | — |
| | UMNLC7 | I-E | GTATTCTCCACGTATGTGGAGGTGATCC | 159 | 28 | 36 | Y | Y | — |
| | UMNLC8 | I-E | GTATTCTCCACGTATGTGGAGGTGATCC | 159 | 28 | 46 | Y | Y | — |
| | UMNLC9 | I-E | GTATTCTCCACGTATGTGGAGGTGATCC | 159 | 28 | 76 | Y | Y | — |
| | UMNLC10 | I-E | GTATTCTCCACGTATGTGGAGGTGATCC | 159 | 28 | 56 | Y | Y | — |
| | UMNLC11 | I-E | GTATTCTCCACGTGTGTGGAGGTGATCC | 163 | 28 | 47 | Y | Y | — |
| | | | GTATTCTCCACGTGTGTGGAGGTGATCCT | 164 | 29 | | | | |
| | UMNLC12 | I-E | GTATTCTCCACGTATGTGGAGGTGATCC | 159 | 28 | 56 | Y | Y | — |
| | UMNLC13 | I-E | GTATTCTCCACGTATGTGGAGGTGATCC | 159 | 28 | 43 | Y | Y | — |
| | UMNLC14 | I-E | GTATTCTCCACGTATGTGGAGGTGATCC | 159 | 28 | 63 | Y | Y | — |
| | UMNLC15 | I-E | GTATTCTCCACGTATGTGGAGGTGATCC | 159 | 28 | 40 | Y | Y | — |
| | UMNLC16 | I-E | GTATTCTCCACGTATGTGGAGGTGATCC | 159 | 28 | 50 | Y | Y | — |
| | UMNLC18 | I-E | GTATTCTCCACGTATGTGGAGGTGATCC | 159 | 28 | 66 | Y | Y | — |
| | UMNLC19 | I-E | GTATTCTCCACGTATGTGGAGGTGATCC | 159 | 28 | 66 | Y | Y | — |
| | UMNLC20 | I-E | GTATTCTCCACGTATGTGGAGGTGATCC | 159 | 28 | 62 | Y | Y | — |
| | UMNLC21 | I-E | GTATTCTCCACGTATGTGGAGGTGATCC | 159 | 28 | 62 | Y | Y | — |
| | | | GTATTCTCCACGTATGTGGAGGTGATCCT | 164 | 29 | | | | |

TABLE 3-continued

CRISPR-Cas systems in *Lactobacillus crispatus* genomes available at NCBI

| Isolation source | Strain | CRISPR Subtype | Repeat sequence* | SEQ ID NO | Repeat Length | No. spacers | cas1 | cas3 | cas9 |
|---|---|---|---|---|---|---|---|---|---|
| | UMNLC22 | I-E | GTATTCTCCACGTATGTGGAGGTGATCC | 159 | 28 | 62 | Y | Y | — |
| | UMNLC23 | I-E | GTATTCTCCACGTATGTGGAGGTGATCC | 159 | 28 | 62 | Y | Y | — |
| | | | GTATTCTCCACGTATGTGGAGGTGATCCT | 164 | 29 | | | | |
| | UMNLC24 | I-E | GTATTCTCCACGTATGTGGAGGTGATCC | 159 | 28 | 62 | Y | Y | — |
| | | | GTATTCTCCACGTATGTGGAGGTGATCCT | 164 | 29 | | | | |
| | UMNLC25 | I-E | GTATTCTCCACGTATGTGGAGGTGATCC | 159 | 28 | 64 | Y | Y | — |
| | | | GTATTCTCCACGTATGTGGAGGTGATCCT | 164 | 29 | | | | |

*Highlighted nucleotides indicate SNP variants in the repeat sequence within the same CRISPR subtype

TABLE 4

Protospacers targeted by *L. crispatus* spacers from CRISPR subtype II-A

| Isolation Source | Strain | Spacer Contig | PAM_protospacers | SEQ ID NO | Plasmid/phage | Strain |
|---|---|---|---|---|---|---|
| Human | 125 | 3- | TTCGTGATTAGTTTGATCTCGTTGTTGTAA<u>GCGACGAA</u> | 165 | rudivirus | *Sulfolobales* Mexican rudivirus |
| | 214 | 5-82 | AAATTAACACCTCTATTATTTTTTTCTGTA<u>AGATACTT</u> | 166 | pDF308 | *Deferribacier desulfuricans* SSM1 |
| | CTV-05 | 1-49 | CCCACGTTGGTACCTTCGCAAAAGCTATT<u>GGGCGCCAC</u> | 167 | Phage EFDG1 | *Enterococcus faecalis* |
| | JVV01 | 4-84 | AAAAAAAGGATTATCTGTACCATCATCTAA<u>CGGCGTA</u> | 168 | pXNC1 | *Xenorhabdus nematophila* ATCC 19061 |
| | | 4-84 | CAGAAAATGGTTTATTTGTCATTTCTTCAT<u>GGCGGGCT</u> | 169 | phage vB-PmiM-Pm5461 | |
| | MV-1A US | 1-65 | CAGAAAATGGTTTATTTGTCATTTCTTCAT<u>GGCGGGCT</u> | 170 | phage vB-PmiM-Pm5461 | |
| | MV-3A-US | 4-60 | TAAAAAAGGATTATCTGTACCATCATCTA<u>ACGGCGTA</u> | 171 | pXNC1 | *Xenorhabdus nematophila* ATCC 19061 |
| | | | CAGAAAATGGTTTATTTGTCATTTCTTCAT<u>GGCGGGCT</u> | 172 | pXNC2 phage vB-PmiM-Pm5461 | *Xenorhabdus nematophila* AN61 Proteus phage |
| | PSS7772 | 1-21 | TAAAAAAGGATTATCTGTACCATCATCTA<u>ACGGCGTA</u> | 171 | pXNC1 | *Xenorhabdus nematophila* |
| | | | | | pXNC2 | ATCC 19061 *Xenorhabdus nematophila* AN61 |
| | SJ-3C-US | 5-67 | CCCACGTTGGTACCTTCGCAAAAGCTATTG<u>GGCGCCAC</u> | 173 | Phage EFDG1 | *Enterococcus faecalis* |

TABLE 4-continued

Protospacers targeted by *L. crispatus* spacers from CRISPR subtype II-A

| Isolation Source | Strain | Spacer Contig | PAM_protospacers | SEQ ID NO | Plasmid/phage | Strain |
|---|---|---|---|---|---|---|
| | VMC1 | 3-15 | CCCACGTTGGTACCTTCGCAAAAGCTATTGGGCGCCAC | 173 | Phage EFDG1 | *Enterococcus faecalis* |
| | VMC2 | 5-153 | CCCACGTTGGTACCTTCGCAAAAGCTATTGGGCGCCAC | 173 | Phage EFDG1 | *Enterococcus faecalis* |
| | VMC4 | 4-76 | TAAAAAAAGGATTATCTGTACCATCATCTAACGGCGTA | 171 | pXNC1 | *Xenorhabdus nematophila* |
| | | | | | pXNC2 | ATCC 19061 *Xenorhabdus nematophila* AN61 |
| | | | CAGAAAATGGTTTATTTGTCATTTCTTCATGGCGGGCT | 172 | phage vB-PmiM-Pm5461 | Proteus phage |
| | VMC5 | 3-117 | CCCACGTTGGTACCTTCGCAAAAGCTATTGGGCGCCAC | 173 | Phage EFDG1 | *Enterococcus faecalis* |
| | | 4-117 | AAATTAACACCTCTATTATTTTTTTCTGTAAGATACTT | 166 | pDF308 | *Deferribacter desulfuricans* SSM1 |
| | VMC6 | 5-50 | CCCACGTTGGTACCTTCGCAAAAGCTATTGGGCGCCAC | 173 | Phage EFDG1 | *Enterococcus faecalis* |

*Underlined nucleotides indicate the predicted PAM

TABLE 5

Protospacers targeted by *L. crispatus* spacers from CRISPR subtype I-B

| Isolation Source | Strain | Spacer Contig | PAM_protospacers | SEQ ID NO | Plasmid/Phage | Strain |
|---|---|---|---|---|---|---|
| Human | VMC3 | 1 | GTCCACCGTAACTAAGAACGACAGGATCTTTTTCTAGGTCAA | 174 | Phage KC5a | *Lactobacillus* |
| | | 1 | TTTATGGTGTATCAAGAACAACAGATTCAGTTTTTAGTTCAA | 175 | pLM1 | *L. muscosae* LM1 |
| | | 2 | GTTGATGGGTTATGGGAAAATGCCCGTTCAAAAAATCTTTATAA | 176 | Phage e112 | *E. coli* O157:H7 |
| | | 2 | GTTGATGGGAAAATGCCCGTTCAAAAAATCTCTATAA | 177 | phage-vB_EcoM_ACG C40 | |
| | | 4 | ACCTGGTGCAACAGCAACTACTCCTGTAACTCTGCCTGCAAAC | 178 | phage vB_CsaM_GAP31 | |
| | | 5 | CCTGCCGGGGATGGTGAATCCCTCGGCAGGGCGCATTTACAGTCG | 179 | Phage Job42 | |
| | | 6 | GATTTACCGTTAATAGAATCTGGCGATAAAGTCAACATTGTTCTGC | 180 | Phage 0507-KN2-1 | *Klebsiella* |

*Underlined nucleotides indicate the predicted PAM

TABLE 6

Protospacers targeted by L. crispatus spacers from CRISPR subtype I-E

| Isolation Source | Strain | Spacer Contig | PAM_protospacers | SEQ ID NO | Plasmid/ Phage | Strain |
|---|---|---|---|---|---|---|
| Human | VMC3 | 2-36 | GCTTCAAACATGGGTGAGATTATCCGGAAAGGATAAGATATG | 181 | pUMNLJ22 | *L. johnsonii* UMNLJ22 |
| | | 16-36 | AGCCTTAACAGATGGATTAAACAATTTTTAACGGCTGGTTT | 182 | pL11995-5 | *L. paracollinoides* TMW1.1995 |
| | | | | | pR2 pPC892-4 | *L. salivarius* Ren *P. pentosaceus* SRCM100892 |
| | NCK1350 | 1-18 | AATCGAAAGTCCGCATGACTTCGTTGACAATAGCTCTCA | 183 | pL1481-4 | *L. lindneri* TMW1.481 |
| | | | | | pL11991-8 plca36 (repA) | *L. backii* TMW1.1991 *L. casei* Zhang |
| Poultry | C25 | 1-18 | TCAATTAACTAACAATGCTCAAACGTTAAATATGGTTGATA | 184 | plasmid1 | *L. amylovorus* GRL1112 |
| | | 1-18 | AAAATTAACTAACAACGCACAAACGTTAAATTTGGTTGATA | 185 | PLH1 | *L. helveticus* DSM20075 |
| | JCM5810 | 3-4 | AAGCACAAACCTTGCATAAATCGAGCGATCCGACCAGCATA | 186 | pUMNLJ22 | *L. johnsonii* UMNLJ22 |
| | | 3-4 | AAGCACAAACCTTGCATAAATCGAGCGATCCGACCAGCATA | 186 | pUMNLJ21 | *L. johnsonii* UMNLJ21 |
| | | 15-4 | TGCCGTAACAATTGACATGGCAAAAGAGCTTTGCATGATGT | 187 | phiJB | *L. delbrueckii bulgaricus* |
| | ST1 | 8-2 | TTAACTAACAATGCTCAAACGTTAAATATGGTTGATAAAGA | 188 | plasmid1 | *L. amylovorus* GRL1112 |
| | UMNLC1 | 13-19 | ATAAAAAATAGGCGATTCCGCAATACTTGCGAACCTATCG | 189 | phage AQ113 | *L. helveticus* |
| | UMNLC6 | 13-32 | TTAACTAACAATGCTCAAACGTTAAATATGGTTGATAAAGA | 190 | plasmid1 | *L. amylovorus* GRL1112 |
| | | 11-32 | GGGCTTAATTGTATCAATGCTAATAAGAATGTTCTGCCCGG | 191 | phage phi hlb1 | *L. gasseri* |
| | | 12-38 | CATGAAAATAATCTGCTACTTTTGCTAAATCTTCAGCTTTT | 192 | Phage PLgT-1 | *Lactococcus* |
| | UMNLC9 | 22-09 | GAAATTAATGTTGGTGCATTAATGGAAGATGCATATTTAGA | 193 | Phage AQ113 | *L. helveticus* |
| | | 6-50 | CTGCTCAATTAGTTAAAGGTTTTGGTGGTTTGGCTTCTGCG | 194 | Phage AQ113 | *L. helveticus* |
| | | 17-09 | TTAACTAACAATGCTCAAACGTTAAATATGGTTGATAAAGA | 188 | plasmid1 | *L. amylovorus* GRL1112 |

*Underlined nucleotides indicate the predicted PAM

That which is claimed is:

1. A recombinant nucleic acid construct comprising a Clustered Regularly Interspaced Short Palindromic Repeats (CRISPR) array comprising two or more repeat sequences and one or more spacer sequence(s), wherein each of the one or more spacer sequences is linked at its 5' end and at its 3' end to a repeat sequence, and each of the one or more spacer sequences is complementary to one or more target sequences in a target DNA of a target organism, wherein the target DNA is located immediately adjacent (3') to a protospacer adjacent motif (PAM), wherein the two or more repeat sequences comprise 20 to 28 consecutive nucleotides of any one of the nucleotide sequences of SEQ ID NOs:1, 10, 19, 28, 37, 42, 51, or 60.

2. The recombinant nucleic acid construct of claim 1, wherein the PAM comprises a nucleotide sequence of 5'-NAA-,3' 5'-AAA-3' or 5'-AA-3' that is immediately adjacent to and 5' of the target sequence.

3. The recombinant nucleic acid construct of claim 1, wherein the spacer sequence is about 80 to 100% complementary to the target sequence.

4. The recombinant nucleic acid construct of claim 1, wherein the one or more spacer sequence(s) each have a length of about 25 nucleotides to about 40 nucleotides.

5. The recombinant nucleic acid construct of claim 1, wherein the one or more spacer sequence(s) each comprise a 5' region and a 3' region, wherein the 5' region comprises a seed sequence and the 3' region comprises a remaining portion of the one or more spacer sequence(s).

6. The recombinant nucleic acid construct of claim 5, wherein the seed sequence comprises the first 8 nucleotides of the 5' end of each of the one or more spacer sequence(s), and is fully complementary to the target sequence, and the remaining portion of the one or more spacer sequence(s) is at least 80% complementary to the target sequence.

7. The recombinant nucleic acid construct of claim 1, wherein the target sequence is located in a gene, optionally in the sense or coding strand or in the antisense or non-coding strand.

8. The recombinant nucleic acid construct of claim 7, wherein the target sequence is located in an intragenic region of the gene, optionally located in the sense or coding strand or in the antisense or non-coding strand.

9. The recombinant nucleic acid construct of claim 1, wherein the target sequence is located in an intergenic region.

10. The recombinant nucleic acid construct of claim 7, wherein the target sequence is located on a chromosome, a mobile element, an extrachromosomal nucleic acid or a plasmid.

11. The recombinant nucleic acid construct of claim 7, wherein the gene encodes a transcription factor or a promoter.

12. The recombinant nucleic acid construct of claim 7, wherein the gene encodes non-coding RNA (e.g., miRNA, siRNA, piwi-interacting RNA (piRNA) and long non-coding RNA (lncRNA).

13. The recombinant nucleic acid construct of claim 1, wherein the target organism is a prokaryote or a eukaryote.

14. A recombinant cell comprising the recombinant nucleic acid construct of claim 1.

15. A vector encoding the recombinant nucleic acid of claim 1.

16. The vector of claim 15, further comprising a recombinant nucleic acid encoding a Type I-E CRISPR associated complex for antiviral defense complex (Cascade complex) comprising a Cse1 polypeptide, a Cse2 polypeptide, a Cas7 polypeptide, a Cas5 polypeptide and a Cas6 polypeptide.

17. The vector of claim 16, wherein the Cse1 polypeptide is encoded by the nucleotide sequence of SEQ ID NO:82, the Cse2 polypeptide is encoded by the nucleotide sequence of SEQ ID NO:83, the Cas7 polypeptide is encoded by the nucleotide sequence of SEQ ID NO:84, the Cas5 polypeptide is encoded by the nucleotide sequence of SEQ ID NO:85, and the Cas6 polypeptide is encoded by the nucleotide sequence of SEQ 11) NO:86.

18. The vector of claim 16, further comprising a polynucleotide encoding a Cas3 polypeptide, wherein the polynucleotide encoding the Cas3 comprises the nucleotide sequence of SEQ ID NO:87 or wherein the polynucleotide encoding the Cas3 encodes the amino acid sequence of SEQ ID NO:119.

19. The vector of claim 15, wherein the vector is a plasmid, bacteriophage, and/or retrovirus.

* * * * *

UNITED STATES PATENT AND TRADEMARK OFFICE
CERTIFICATE OF CORRECTION

PATENT NO. : 10,711,267 B2
APPLICATION NO. : 16/582269
DATED : July 14, 2020
INVENTOR(S) : Barrangou et al.

It is certified that error appears in the above-identified patent and that said Letters Patent is hereby corrected as shown below:

On the Title Page

Item (56) References Cited, OTHER PUBLICATIONS, Page 2, Column 1, Line 59, Bhaya et al. cite: Please correct "Acrhaea" to read -- Archaea --

Item (56) References Cited, OTHER PUBLICATIONS, Page 2, Column 2, Line 5, Carte et al. cite: Please correct "pp. 98.112" to read -- pp. 98-112 --

Item (56) References Cited, OTHER PUBLICATIONS, Page 3, Column 1, Line 5, Grissa et al. cite: Please correct "CRISPIRs" to read -- CRISPRs --

Item (56) References Cited, OTHER PUBLICATIONS, Page 3, Column 1, Lines 20-21: Please correct "PCT/US2015/047138" to read -- PCT/US2015/047136 --

Item (56) References Cited, OTHER PUBLICATIONS, Page 3, Column 2, Line 44, Selle K. cite: Please correct "bacterual" to read -- bacterial --

Item (56) References Cited, OTHER PUBLICATIONS, Page 3, Column 2, Line 54, Semenova et al. cite: Please correct "108:205" to read -- 108:25 --

Item (56) References Cited, OTHER PUBLICATIONS, Page 4, Column 1, Line 15: Please correct "PCT/US2016/037493." to read -- PCT/US2016/037493, mailed Sep. 15, 2016, 8 pages. --

Item (56) References Cited, OTHER PUBLICATIONS, Page 4, Column 2, Line 3: Please correct "Serach" to read -- Search --

Item (56) References Cited, OTHER PUBLICATIONS, Page 4, Column 2, Line 10: Please correct "PCT/US219/52861, dated Feb. 1, 2020" to read -- PCT/US2019/52861, dated Feb. 12, 2020 --

Signed and Sealed this
First Day of December, 2020

Andrei Iancu
*Director of the United States Patent and Trademark Office*

CERTIFICATE OF CORRECTION (continued)
U.S. Pat. No. 10,711,267 B2

Item (56) References Cited, OTHER PUBLICATIONS, Page 4, Column 2, Line 11, Ojala et al. cite: Please correct "cirspatus" to read -- crispatus --

In the Specification

Column 4, Line 51: Please correct "(AAA≤AGA)" to read -- (AAA>AGA) --

Column 14, Line 45: Please correct "W. T. and X" to read -- W, T, and X --

Column 21, Line 49: Please correct "(Psctin)" to read -- (Pactin) --

Column 26, Lines 51-55: Please delete the sequence and replace with the following sequence:
(GUAUUCUCCACGUGUGUGGAGGUGAUCC*CUACAAGUUAAUCCGGCAAA GC UAAAUGGCCGG*GUAUUCUCCACGUGUGUGGAGGUGAUCC)

Column 26, Lines 56-58: Please delete the sequence and replace with the following sequence:
(GUGAUCC*CUACAAGUAAUCCGGCAAAGCUAAAUG GCCGG*GUAUUCUCCACGUG UGUGGAG)

Column 27, Line 7: Please correct "85,88," to read -- 85,86, --

Column 27, Line 39: Please correct "bole" to read -- bold --

Column 38, Line 8: Please correct "doi: 1.1038" to read -- doi: 10.1038 --

Column 47, Line 3: Please correct "pTRK1167." to read -- pTRK1187. --

Column 48, Line 19: Please correct "Slate" to read -- State --

Column 51, Line 50: Please correct "panel B Table 1" to read -- panel B, Table 1 --

Column 52, Lines 9-15: Please delete the sequence and replace with the following sequence:
AATGGAAT*TTAAATTAGATGAATCACAAGAAACCGAGATTAAAACTTTTGTTAT GGGCGTGGTTAAAGACGCTATTAAACAAGCCACTACCACCAGCAAACCATATTT GAACCGCAAAGAAATTGCTAAGTATTTTGGCGTGGCTGAATCAACTATTACATA TTGGGCTTCTTTAGGGATGCCTGTCGCTGTCATAGACGGG*CGCAAA*CTCTATG GCAAGCAATCTATAACTAACTGGCT*AAAATT Column 67, final line of Table 4: Please correct "GGCGCCAC" to read -- GGCGCCAC --

In the Claims

Column 152, Line 34, Claim 17: Please correct "SEQ 11) NO:86." to read -- SEQ ID NO:86 --

SEQUENCE LISTING

<160> NUMBER OF SEQ ID NOS: 195

<210> SEQ ID NO 1
<211> LENGTH: 28
<212> TYPE: DNA

<213> ORGANISM: Lactobacillus crispatus

<400> SEQUENCE: 1
gtattctcca cgtgtgtgga ggtgatcc                                        28

<210> SEQ ID NO 2
<211> LENGTH: 27
<212> TYPE: DNA
<213> ORGANISM: Lactobacillus crispatus

<400> SEQUENCE: 2
gtattctcca cgtgtgtgga ggtgatc                                         27

<210> SEQ ID NO 3
<211> LENGTH: 26
<212> TYPE: DNA
<213> ORGANISM: Lactobacillus crispatus

<400> SEQUENCE: 3
gtattctcca cgtgtgtgga ggtgat                                          26

<210> SEQ ID NO 4
<211> LENGTH: 25
<212> TYPE: DNA
<213> ORGANISM: Artificial
<220> FEATURE:
<223> OTHER INFORMATION: repeat sequence

<400> SEQUENCE: 4
gtattctcca cgtgtgtgga ggtga                                           25

<210> SEQ ID NO 5
<211> LENGTH: 24
<212> TYPE: DNA
<213> ORGANISM: Artificial
<220> FEATURE:
<223> OTHER INFORMATION: repeat sequence

<400> SEQUENCE: 5
gtattctcca cgtgtgtgga ggtg                                            24

<210> SEQ ID NO 6
<211> LENGTH: 23
<212> TYPE: DNA
<213> ORGANISM: Artificial
<220> FEATURE:
<223> OTHER INFORMATION: repeat sequence

<400> SEQUENCE: 6
gtattctcca cgtgtgtgga ggt                                             23

<210> SEQ ID NO 7
<211> LENGTH: 22
<212> TYPE: DNA
<213> ORGANISM: Artificial
<220> FEATURE:
<223> OTHER INFORMATION: repeat sequence

<400> SEQUENCE: 7
gtattctcca cgtgtgtgga gg                                              22

<210> SEQ ID NO 8
<211> LENGTH: 21
<212> TYPE: DNA
<213> ORGANISM: Artificial

<220> FEATURE:
<223> OTHER INFORMATION: repeat sequence

<400> SEQUENCE: 8
gtattctcca cgtgtgtgga g                                          21

<210> SEQ ID NO 9
<211> LENGTH: 20
<212> TYPE: DNA
<213> ORGANISM: Artificial
<220> FEATURE:
<223> OTHER INFORMATION: repeat sequence

<400> SEQUENCE: 9
gtattctcca cgtgtgtgga                                            20

<210> SEQ ID NO 10
<211> LENGTH: 28
<212> TYPE: DNA
<213> ORGANISM: Lactobacillus crispatus

<400> SEQUENCE: 10
gtattctcca cacatgtgga ggtgatcc                                   28

<210> SEQ ID NO 11
<211> LENGTH: 27
<212> TYPE: DNA
<213> ORGANISM: Artificial
<220> FEATURE:
<223> OTHER INFORMATION: repeat sequence

<400> SEQUENCE: 11
gtattctcca cacatgtgga ggtgatc                                    27

<210> SEQ ID NO 12
<211> LENGTH: 26
<212> TYPE: DNA
<213> ORGANISM: Artificial
<220> FEATURE:
<223> OTHER INFORMATION: repeat sequence

<400> SEQUENCE: 12
gtattctcca cacatgtgga ggtgat                                     26

<210> SEQ ID NO 13
<211> LENGTH: 25
<212> TYPE: DNA
<213> ORGANISM: Artificial
<220> FEATURE:
<223> OTHER INFORMATION: repeat sequence

<400> SEQUENCE: 13
gtattctcca cacatgtgga ggtga                                      25

<210> SEQ ID NO 14
<211> LENGTH: 24
<212> TYPE: DNA
<213> ORGANISM: Artificial
<220> FEATURE:
<223> OTHER INFORMATION: repeat sequence

<400> SEQUENCE: 14
gtattctcca cacatgtgga ggtg                                       24

<210> SEQ ID NO 15

```
<211> LENGTH: 23
<212> TYPE: DNA
<213> ORGANISM: Artificial
<220> FEATURE:
<223> OTHER INFORMATION: repeat sequence

<400> SEQUENCE: 15
gtattctcca cacatgtgga ggt                                              23

<210> SEQ ID NO 16
<211> LENGTH: 22
<212> TYPE: DNA
<213> ORGANISM: Artificial
<220> FEATURE:
<223> OTHER INFORMATION: repeat sequence

<400> SEQUENCE: 16
gtattctcca cacatgtgga gg                                               22

<210> SEQ ID NO 17
<211> LENGTH: 21
<212> TYPE: DNA
<213> ORGANISM: Artificial
<220> FEATURE:
<223> OTHER INFORMATION: repeat sequence

<400> SEQUENCE: 17
gtattctcca cacatgtgga g                                                21

<210> SEQ ID NO 18
<211> LENGTH: 20
<212> TYPE: DNA
<213> ORGANISM: Artificial
<220> FEATURE:
<223> OTHER INFORMATION: repeat sequence

<400> SEQUENCE: 18
gtattctcca cacatgtgga                                                  20

<210> SEQ ID NO 19
<211> LENGTH: 28
<212> TYPE: DNA
<213> ORGANISM: Lactobacillus crispatus

<400> SEQUENCE: 19
gtattctcca cgcatgtgga ggtgatcc                                         28

<210> SEQ ID NO 20
<211> LENGTH: 27
<212> TYPE: DNA
<213> ORGANISM: Artificial
<220> FEATURE:
<223> OTHER INFORMATION: repeat sequence

<400> SEQUENCE: 20
gtattctcca cgcatgtgga ggtgatc                                          27

<210> SEQ ID NO 21
<211> LENGTH: 26
<212> TYPE: DNA
<213> ORGANISM: Artificial
<220> FEATURE:
<223> OTHER INFORMATION: repeat sequence

<400> SEQUENCE: 21
gtattctcca cgcatgtgga ggtgat                                           26
```

<210> SEQ ID NO 22
<211> LENGTH: 25
<212> TYPE: DNA
<213> ORGANISM: Artificial
<220> FEATURE:
<223> OTHER INFORMATION: repeat sequence

<400> SEQUENCE: 22
gtattctcca cgcatgtgga ggtga                                   25

<210> SEQ ID NO 23
<211> LENGTH: 24
<212> TYPE: DNA
<213> ORGANISM: Artificial
<220> FEATURE:
<223> OTHER INFORMATION: repeat sequence

<400> SEQUENCE: 23
gtattctcca cgcatgtgga ggtg                                    24

<210> SEQ ID NO 24
<211> LENGTH: 23
<212> TYPE: DNA
<213> ORGANISM: Artificial
<220> FEATURE:
<223> OTHER INFORMATION: repeat sequence

<400> SEQUENCE: 24
gtattctcca cgcatgtgga ggt                                     23

<210> SEQ ID NO 25
<211> LENGTH: 22
<212> TYPE: DNA
<213> ORGANISM: Artificial
<220> FEATURE:
<223> OTHER INFORMATION: repeat sequence

<400> SEQUENCE: 25
gtattctcca cgcatgtgga gg                                      22

<210> SEQ ID NO 26
<211> LENGTH: 21
<212> TYPE: DNA
<213> ORGANISM: Artificial
<220> FEATURE:
<223> OTHER INFORMATION: repeat sequence

<400> SEQUENCE: 26
gtattctcca cgcatgtgga g                                       21

<210> SEQ ID NO 27
<211> LENGTH: 20
<212> TYPE: DNA
<213> ORGANISM: Artificial
<220> FEATURE:
<223> OTHER INFORMATION: repeat sequence

<400> SEQUENCE: 27
gtattctcca cgcatgtgga                                         20

<210> SEQ ID NO 28
<211> LENGTH: 28
<212> TYPE: DNA
<213> ORGANISM: Lactobacillus crispatus

```
<400> SEQUENCE: 28
gtattctcca cgtatgtgga ggtgatcc                                     28

<210> SEQ ID NO 29
<211> LENGTH: 27
<212> TYPE: DNA
<213> ORGANISM: Artificial
<220> FEATURE:
<223> OTHER INFORMATION: repeat sequence

<400> SEQUENCE: 29
gtattctcca cgtatgtgga ggtgatc                                      27

<210> SEQ ID NO 30
<211> LENGTH: 26
<212> TYPE: DNA
<213> ORGANISM: Artificial
<220> FEATURE:
<223> OTHER INFORMATION: repeat sequence

<400> SEQUENCE: 30
gtattctcca cgtatgtgga ggtgat                                       26

<210> SEQ ID NO 31
<211> LENGTH: 25
<212> TYPE: DNA
<213> ORGANISM: Artificial
<220> FEATURE:
<223> OTHER INFORMATION: repeat sequence

<400> SEQUENCE: 31
gtattctcca cgtatgtgga ggtga                                        25

<210> SEQ ID NO 32
<211> LENGTH: 24
<212> TYPE: DNA
<213> ORGANISM: Artificial
<220> FEATURE:
<223> OTHER INFORMATION: repeat sequence

<400> SEQUENCE: 32
gtattctcca cgtatgtgga ggtg                                         24

<210> SEQ ID NO 33
<211> LENGTH: 23
<212> TYPE: DNA
<213> ORGANISM: Artificial
<220> FEATURE:
<223> OTHER INFORMATION: repeat sequence

<400> SEQUENCE: 33
gtattctcca cgtatgtgga ggt                                          23

<210> SEQ ID NO 34
<211> LENGTH: 22
<212> TYPE: DNA
<213> ORGANISM: Artificial
<220> FEATURE:
<223> OTHER INFORMATION: repeat sequence

<400> SEQUENCE: 34
gtattctcca cgtatgtgga gg                                           22

<210> SEQ ID NO 35
<211> LENGTH: 21
```

```
<212> TYPE: DNA
<213> ORGANISM: Artificial
<220> FEATURE:
<223> OTHER INFORMATION: repeat sequence

<400> SEQUENCE: 35
gtattctcca cgtatgtgga g                                           21

<210> SEQ ID NO 36
<211> LENGTH: 20
<212> TYPE: DNA
<213> ORGANISM: Artificial
<220> FEATURE:
<223> OTHER INFORMATION: repeat sequence

<400> SEQUENCE: 36
gtattctcca cgtatgtgga                                             20

<210> SEQ ID NO 37
<211> LENGTH: 28
<212> TYPE: DNA
<213> ORGANISM: Lactobacillus crispatus

<400> SEQUENCE: 37
gtattctcca cgtatgtgga ggtcatcc                                    28

<210> SEQ ID NO 38
<211> LENGTH: 27
<212> TYPE: DNA
<213> ORGANISM: Artificial
<220> FEATURE:
<223> OTHER INFORMATION: repeat sequence

<400> SEQUENCE: 38
gtattctcca cgtatgtgga ggtcatc                                     27

<210> SEQ ID NO 39
<211> LENGTH: 26
<212> TYPE: DNA
<213> ORGANISM: Artificial
<220> FEATURE:
<223> OTHER INFORMATION: repeat sequence

<400> SEQUENCE: 39
gtattctcca cgtatgtgga ggtcat                                      26

<210> SEQ ID NO 40
<211> LENGTH: 25
<212> TYPE: DNA
<213> ORGANISM: Artificial
<220> FEATURE:
<223> OTHER INFORMATION: repeat sequence

<400> SEQUENCE: 40
gtattctcca cgtatgtgga ggtca                                       25

<210> SEQ ID NO 41
<211> LENGTH: 24
<212> TYPE: DNA
<213> ORGANISM: Artificial
<220> FEATURE:
<223> OTHER INFORMATION: repeat sequence

<400> SEQUENCE: 41
gtattctcca cgtatgtgga ggtc                                        24
```

<210> SEQ ID NO 42
<211> LENGTH: 28
<212> TYPE: DNA
<213> ORGANISM: Lactobacillus crispatus

<400> SEQUENCE: 42
gtattctcca cgagtgtggg gatcctat                                28

<210> SEQ ID NO 43
<211> LENGTH: 27
<212> TYPE: DNA
<213> ORGANISM: Artificial
<220> FEATURE:
<223> OTHER INFORMATION: repeat sequence

<400> SEQUENCE: 43
gtattctcca cgagtgtggg gatccta                                 27

<210> SEQ ID NO 44
<211> LENGTH: 26
<212> TYPE: DNA
<213> ORGANISM: Artificial
<220> FEATURE:
<223> OTHER INFORMATION: repeat sequence

<400> SEQUENCE: 44
gtattctcca cgagtgtggg gatcct                                  26

<210> SEQ ID NO 45
<211> LENGTH: 25
<212> TYPE: DNA
<213> ORGANISM: Artificial
<220> FEATURE:
<223> OTHER INFORMATION: repeat sequence

<400> SEQUENCE: 45
gtattctcca cgagtgtggg gatcc                                   25

<210> SEQ ID NO 46
<211> LENGTH: 24
<212> TYPE: DNA
<213> ORGANISM: Artificial
<220> FEATURE:
<223> OTHER INFORMATION: repeat sequence

<400> SEQUENCE: 46
gtattctcca cgagtgtggg gatc                                    24

<210> SEQ ID NO 47
<211> LENGTH: 23
<212> TYPE: DNA
<213> ORGANISM: Artificial
<220> FEATURE:
<223> OTHER INFORMATION: repeat sequence

<400> SEQUENCE: 47
gtattctcca cgagtgtggg gat                                     23

<210> SEQ ID NO 48
<211> LENGTH: 22
<212> TYPE: DNA
<213> ORGANISM: Artificial
<220> FEATURE:
<223> OTHER INFORMATION: repeat sequence

<400> SEQUENCE: 48

```
gtattctcca cgagtgtggg ga                                              22

<210> SEQ ID NO 49
<211> LENGTH: 21
<212> TYPE: DNA
<213> ORGANISM: Artificial
<220> FEATURE:
<223> OTHER INFORMATION: repeat sequence

<400> SEQUENCE: 49
gtattctcca cgagtgtggg g                                               21

<210> SEQ ID NO 50
<211> LENGTH: 20
<212> TYPE: DNA
<213> ORGANISM: Artificial
<220> FEATURE:
<223> OTHER INFORMATION: repeat sequence

<400> SEQUENCE: 50
gtattctcca cgagtgtggg                                                 20

<210> SEQ ID NO 51
<211> LENGTH: 29
<212> TYPE: DNA
<213> ORGANISM: Lactobacillus crispatus

<400> SEQUENCE: 51
gtattctcca cgtatgtgga ggtgatccc                                       29

<210> SEQ ID NO 52
<211> LENGTH: 28
<212> TYPE: DNA
<213> ORGANISM: Artificial
<220> FEATURE:
<223> OTHER INFORMATION: repeat sequence

<400> SEQUENCE: 52
gtattctcca cgtatgtgga ggtgatcc                                        28

<210> SEQ ID NO 53
<211> LENGTH: 27
<212> TYPE: DNA
<213> ORGANISM: Artificial
<220> FEATURE:
<223> OTHER INFORMATION: repeat sequence

<400> SEQUENCE: 53
gtattctcca cgtatgtgga ggtgatc                                         27

<210> SEQ ID NO 54
<211> LENGTH: 26
<212> TYPE: DNA
<213> ORGANISM: Artificial
<220> FEATURE:
<223> OTHER INFORMATION: repeat sequence

<400> SEQUENCE: 54
gtattctcca cgtatgtgga ggtgat                                          26

<210> SEQ ID NO 55
<211> LENGTH: 25
<212> TYPE: DNA
<213> ORGANISM: Artificial
<220> FEATURE:
```

<223> OTHER INFORMATION: repeat sequence

<400> SEQUENCE: 55
gtattctcca cgtatgtgga ggtga                                          25

<210> SEQ ID NO 56
<211> LENGTH: 24
<212> TYPE: DNA
<213> ORGANISM: Artificial
<220> FEATURE:
<223> OTHER INFORMATION: repeat sequence

<400> SEQUENCE: 56
gtattctcca cgtatgtgga ggtg                                           24

<210> SEQ ID NO 57
<211> LENGTH: 23
<212> TYPE: DNA
<213> ORGANISM: Artificial
<220> FEATURE:
<223> OTHER INFORMATION: repeat sequence

<400> SEQUENCE: 57
gtattctcca cgtatgtgga ggt                                            23

<210> SEQ ID NO 58
<211> LENGTH: 22
<212> TYPE: DNA
<213> ORGANISM: Artificial
<220> FEATURE:
<223> OTHER INFORMATION: repeat sequence

<400> SEQUENCE: 58
gtattctcca cgtatgtgga gg                                             22

<210> SEQ ID NO 59
<211> LENGTH: 21
<212> TYPE: DNA
<213> ORGANISM: Artificial
<220> FEATURE:
<223> OTHER INFORMATION: repeat sequence

<400> SEQUENCE: 59
gtattctcca cgtatgtgga g                                              21

<210> SEQ ID NO 60
<211> LENGTH: 29
<212> TYPE: DNA
<213> ORGANISM: Lactobacillus crispatus

<400> SEQUENCE: 60
gtattctcca cgtgtgtgga ggtgatcct                                      29

<210> SEQ ID NO 61
<211> LENGTH: 28
<212> TYPE: DNA
<213> ORGANISM: Artificial
<220> FEATURE:
<223> OTHER INFORMATION: repeat sequence

<400> SEQUENCE: 61
gtattctcca cgtgtgtgga ggtgatcc                                       28

<210> SEQ ID NO 62
<211> LENGTH: 27

```
<212> TYPE: DNA
<213> ORGANISM: Artificial
<220> FEATURE:
<223> OTHER INFORMATION: repeat sequence

<400> SEQUENCE: 62
gtattctcca cgtgtgtgga ggtgatc                                    27

<210> SEQ ID NO 63
<211> LENGTH: 26
<212> TYPE: DNA
<213> ORGANISM: Artificial
<220> FEATURE:
<223> OTHER INFORMATION: repeat sequence

<400> SEQUENCE: 63
gtattctcca cgtgtgtgga ggtgat                                     26

<210> SEQ ID NO 64
<211> LENGTH: 25
<212> TYPE: DNA
<213> ORGANISM: Artificial
<220> FEATURE:
<223> OTHER INFORMATION: repeat sequence

<400> SEQUENCE: 64
gtattctcca cgtgtgtgga ggtga                                      25

<210> SEQ ID NO 65
<211> LENGTH: 24
<212> TYPE: DNA
<213> ORGANISM: Artificial
<220> FEATURE:
<223> OTHER INFORMATION: repeat sequence

<400> SEQUENCE: 65
gtattctcca cgtgtgtgga ggtg                                       24

<210> SEQ ID NO 66
<211> LENGTH: 23
<212> TYPE: DNA
<213> ORGANISM: Artificial
<220> FEATURE:
<223> OTHER INFORMATION: repeat sequence

<400> SEQUENCE: 66
gtattctcca cgtgtgtgga ggt                                        23

<210> SEQ ID NO 67
<211> LENGTH: 22
<212> TYPE: DNA
<213> ORGANISM: Artificial
<220> FEATURE:
<223> OTHER INFORMATION: repeat sequence

<400> SEQUENCE: 67
gtattctcca cgtgtgtgga gg                                         22

<210> SEQ ID NO 68
<211> LENGTH: 21
<212> TYPE: DNA
<213> ORGANISM: Artificial
<220> FEATURE:
<223> OTHER INFORMATION: repeat sequence

<400> SEQUENCE: 68
```

```
gtattctcca cgtgtgtgga g                                               21
```

<210> SEQ ID NO 69
<211> LENGTH: 200
<212> TYPE: DNA
<213> ORGANISM: Lactobacillus crispatus

<400> SEQUENCE: 69

```
acaaaaaaga actttagttg aattactgtt gtataagcgt tgtcgaaaga tgacgtcttt    60
tttgtatgtt tagggagaca agaaaattct attcgttgga tgactaatga gacagaaata   120
gatacaatag taattgacaa agtgatgaaa ttttgggatc tattgttttg tgattgttgt   180
tatattggga tttgtttact                                              200
```

<210> SEQ ID NO 70
<211> LENGTH: 200
<212> TYPE: DNA
<213> ORGANISM: Lactobacillus crispatus

<400> SEQUENCE: 70

```
cttgatatat aaggatttat aaatgaaatt tgaatcctag gggcactttg ggagcaaaac    60
tattcaaaaa gaagcagaaa tgcttctttt ttatttggag tggcttttttg taattatggc   120 tttattattg gtctttgtta aaagtgatta aaaatgatat tatttcgatt gagcgatgct   180
gatatattgt ggatcattta                                              200
```

<210> SEQ ID NO 71
<211> LENGTH: 200
<212> TYPE: DNA
<213> ORGANISM: Lactobacillus crispatus

<400> SEQUENCE: 71

```
gcagacaaat aatatttttc tttatttgtt taggaggaat catagcagaa tgatattatg    60
attcctcttt ttatttgaat attatgtcta gcagatattg tctatttaat aaaaatcgat   120
atacttggta gtaggatcaa agtgatgaaa aaatggtgtt tgcgtatttt catttggcgc   180
tataaaggga tttgtttact                                              200
```

<210> SEQ ID NO 72
<211> LENGTH: 201
<212> TYPE: DNA
<213> ORGANISM: Lactobacillus crispatus

<400> SEQUENCE: 72

```
atattcccaa accaatccag caccacttga tggttcatct aagggcggaa aatgggaaga    60
ttttagcatt tgggattatg ataaatatga tcaagtaata aaagacatcg attatccctat   120 gtatataaat aaaaatagat tgtaaaataa aaagtaatta taaatattag attaagcaga   180
tagtataaat ttaggagaaa c                                            201
```

<210> SEQ ID NO 73
<211> LENGTH: 212
<212> TYPE: DNA
<213> ORGANISM: Lactobacillus crispatus

<400> SEQUENCE: 73

```
taaactgtat taagtgtatt cctcacttag gtgagggtga tcctgttaat tatttattta    60
ttgaagtaat ccccatcaaa gtggggttta gcggtttcag tatatgaaac cgcttttttat   120 tttattgaaa aagtattgta aataaaataa ataagcttta atataaatat gaatgttaaa   180
```

```
tatttattta atgaggaaag aaacggtgat at                                    212
```

<210> SEQ ID NO 74
<211> LENGTH: 189
<212> TYPE: DNA
<213> ORGANISM: Lactobacillus crispatus

<400> SEQUENCE: 74

```
aaaataagta aaaaggtttt acattttcaa actatttagt ataattagca aaggatattt      60
tcgttaggca atttcgctta agcttttta ctaggcattt gccgaagaaa gtagtacaat       120
attcaacaga gaattatccg ttaacttatc tcaacggact tcttgcaaat ttacaggagg     180
gtcatttta                                                              189
```

<210> SEQ ID NO 75
<211> LENGTH: 214
<212> TYPE: DNA
<213> ORGANISM: Lactobacillus crispatus

<400> SEQUENCE: 75

```
tttagattcc ttattttttg tatttatttt aatacatata ttatagtcct ttgatataga      60
gttttttagg ctgctttact aattttaaa atgtaaaccg ctttcatatg tttacaccgt       120
cacaaagtta ggctaaaatt tgagatgtaa agcggagcaa aaattgttcc gtatggtatg    180
aaaaacatac cataattttt gaggaggttt atta                                 214
```

<210> SEQ ID NO 76
<211> LENGTH: 451
<212> TYPE: DNA
<213> ORGANISM: Lactobacillus acidophilus

<400> SEQUENCE: 76

```
atcttaagga attagctaat gaagcttgtt ttgtttcaga aactgctgaa gaaaacgaaa      60
aattagttaa cgacttaatg aagaaaatta acaagtaatt ttcaaaaaga gaccatctgg     120
tctctttttt tatatttta agtaaaacaa ataatttctt cacaaataat tcacgctttta    180 tttttagaat ataagtagtt gtaagtataa aagataaaat gagtacttac aaaaaagaag    240
ttagtatgtt atactgatta taagttaaag aacgtataca aatatttgtt ctgaggagcg    300 tgattttta ggtagattta tatgtctctc ctagttgtac ctcatgtcgt aaggcaagag     360
catggcttga aaacataat attccattta aggaaagaaa cattttttct gagccattaa      420
ctaaagaaga attattaaag atcctctaga g                                   451
```

<210> SEQ ID NO 77
<211> LENGTH: 39
<212> TYPE: DNA
<213> ORGANISM: Artificial
<220> FEATURE:
<223> OTHER INFORMATION: rho independent terminator

<400> SEQUENCE: 77

```
aaaaaaaaac cccgccctg acagggcggg gttttttt                              39
```

<210> SEQ ID NO 78
<211> LENGTH: 39
<212> TYPE: DNA
<213> ORGANISM: Lactobacillus crispatus

<400> SEQUENCE: 78

```
caaaaaaagc atgagaatta attttctcat gcttttttg                              39
```

<210> SEQ ID NO 79
<211> LENGTH: 38
<212> TYPE: DNA
<213> ORGANISM: Lactobacillus crispatus

<400> SEQUENCE: 79

```
aaaaaagatg cacttcttca caggagcgca tcttttt                                38
```

<210> SEQ ID NO 80
<211> LENGTH: 32
<212> TYPE: DNA
<213> ORGANISM: Lactobacillus crispatus

<400> SEQUENCE: 80

```
caaaaagagc ggctataggc cgcttttttt gc                                     32
```

<210> SEQ ID NO 81
<211> LENGTH: 37
<212> TYPE: DNA
<213> ORGANISM: Lactobacillus crispatus

<400> SEQUENCE: 81

```
gtaaaaatgg cttgcgtgtt gcaagccatt tttttac                                37
```

<210> SEQ ID NO 82
<211> LENGTH: 1730
<212> TYPE: DNA
<213> ORGANISM: Lactobacillus crispatus

<400> SEQUENCE: 82

```
atgaataatg atttaagctt caatctggtt actgatcctt ggattaaagt cctgaaaaag         60
gattataccg aaagtgaggt ctctttgaat gaacttttta gtaattctga agagtatctt        120
cagcttgctg gtgatatgaa atcacaagac ttagcgattc tcagattatt gttggctatt        180
ttactgtcag tttatactag attcgatgca gatgatacgc catactcatg gctggattta        240
gatgacaaat ggcgagtgac tcggacagat aatgatggct tcaactctca aaaactaaaa        300
ctgggagaca cttggagaag tctatatgat caaaaaactt tttcaaaaaa agtatttgat        360
tatctaaatc tttatcaggc taagttaaat ttatttggtg aagatccttt ttatcaagtt        420
aatcgtcaag tctatgacca aaatgtgccg aaaataaaa aggtagctaa aggtgcgggt         480
acagtatcag ttaaacaaat taatcgactt atttctgaaa gcaataacag cccggcactg        540
ttttcaccta aatcaggtat tgaaaaagat agtgttaata atgcggaatt agttcgctgg        600
ttaattactt accaaaactt cacaggtgtt actgataaga ccaaagttaa gtcaaaggat        660
aagttctctg tttctcctgg ttggttgtat tcaattaatc ctgtttatat taaaggtaaa        720
actttatttg acacgttgat gttaaatcta agcttagtta ccaatgattc tgcagatgga        780
acaaactggc taaactcaca aagaccagtg tgggaatacg atgatattaa tgattatctt        840
caacaaagat tgaatggagt gtatcctgac aatttgtctg aattatatac tgtctggtct        900
agaatgattc atattgattg gcaaaatggt cagccagtta tatttagcgc aggactgcct        960
aagttagata gtgaaaaaca attcctagag ccaatgacga cttggcgtaa aaataaagat       1020
ggtgttgtat atccagctgc caagaataaa aataatataa atgtcgctat gtggcgtaat       1080
tttggtcagt atataaggac taagaagat aataacaacg aaaaaagat aaaaataatc        1140
acagaattcc aggagttatt ggttggattc aggaattgaa aatgcataat caaatttcca       1200
```

```
agcatactaa catcaatata gttacagtag ctatgataag tgatggaaat gctacatctc    1260 aatcaccta tgcggaaatc actgataata tgcaagctaa ggcagggatc cttttttgatg    1320 atgagcctat gtttgaaaat cggtggcaag ataagattga agaagaagta ttattagcac    1380
aaaaggttgt ggcttatttc tattggtttg caaaagatat atcgaacatt caaacccata    1440
gcgagaagaa aaaagtaat gatgattggg caagtcgaaa ggtagcgcaa ctttatgacg    1500
aactgaatca gccattttac acttggcttt ctggattaga tataaatcaa gaccgtaatg    1560
tcaaaattaa agaatggcgt gaaactttaa atcgtcttgt tgcaacgcaa gctaaaaata    1620 ttttatcaa tgcaactgct gatgaaatca ttggcgggaa ggaagacaat atttttacaa    1680
tttataataa actacgcaga aacgtctatg tttgtctcgg attaaaataa                1730

<210> SEQ ID NO 83
<211> LENGTH: 606
<212> TYPE: DNA
<213> ORGANISM: Lactobacillus crispatus

<400> SEQUENCE: 83
atgagtgatg cttatactgc tacggcacga ataattaatc agctgtatgg tgatggaact      60
cctgataaag gtgctttggc tgaacttaga aggacaacag ctatcaccga taaaggcgct     120
gaaaaaatct ggcctttaat tttttcagtc gtgcctaaat taagtacaaa tggaaagcct     180
acaaagcttg aaacagcagt ttatactgct cttcactgtt atgctgcatt tcaacaaggg     240
aatgattcat ttgtctttgg tcaaattcct agatcaaaag ataaggaaga atctggagaa     300
aatggtgtat ctcttttac tgcactgagg aaaatgaaaa taaacgactc taacgaaaag     360
aaggctttag ataggcgagt aacagcttta ttagcaacta caaatatcag cagtgccacc     420
aattcaatta atcatctagt aagtattctt aaaggaaaga aatgggtgga aaagattgac     480
tttgctcaat tggcggaaga cttgtataac tttcagtgga gtacgaaaaa tgcaagattc     540
gttgccttga agtggggaaa agattactac tggaacgttt ataagctggc atcagacaac     600
gattag                                                                606

<210> SEQ ID NO 84
<211> LENGTH: 1110
<212> TYPE: DNA
<213> ORGANISM: Lactobacillus crispatus

<400> SEQUENCE: 84
atgaataaga atctttatat ggacattaat gtattgcaaa ctgtaccatc atcaaatatc      60
aatagagatg acactggttc acctaaaaca gctatttatg gtggcgtgac tcggtcaaga    120
gtttcttcac aaagctggaa gagagcaatg cgtttagcct ttaaacaaga ctcagaaaat    180
gaagagtggc ttaagagcta tagaactttg aaaacagcta gtcttttggc gaataagtta    240
caagaactag attcaaattt aagtgaagaa gatgctttaa agaaagttga agaagtctttt    300 aaagtagctg gaatcaaatt aaaaaaggac aagaaaacgg gcgaaatgtt aactggagca    360
ctactactag taagtgaagg gcaactcgaa aagatcgcta aacttgcttt gtctgttgat    420
caaatagata aagatacagc taagaaaatt aagaaaaatt tgatgggaga tcaatctcta    480
gatttagctt tatttggaag aatggtggca gataatccag aattgaatgt ggatgcttct    540
agtcaagtgg ctcatgcaat ttccactcat gaagttactc cagaatttga ttattacact    600
gcagttgatg atgcaaatac gaaaagccaa acaggttctg caatgcttgg tacgattgaa    660
```

```
tataattcat ctactttata cagatatgcc aatgttaaca ttcttgattt attgcacaat    720
cttggtaata aagatttgac tattgaggga attaagcttt ttatcaaga atttgttttg    780 acaatgccga ctggtaagga aaatactttt gctaataaaa cactccctca atacgttatg    840
attaatgttc gtactgatac acctgttaac ctagtatctg catttgaaac accagttaga    900
tctgaaggcg atacgttga taaatctatc aatcgattag aggatgaata taaaaattct    960
ttgaaatttg tagataagcc tgtgtttaat gtcgaattga cgaatagtga gaatatagtc   1020
gacaatcagg ctgaaaatat tgatgattta attaatcaaa ctgctgaatt cgtaaaacag   1080
gagttagaaa atgaagacag caacgattag                                    1110

<210> SEQ ID NO 85
<211> LENGTH: 726
<212> TYPE: DNA
<213> ORGANISM: Lactobacillus crispatus

<400> SEQUENCE: 85
atgaagacag caacgattag attgactgcg ccacttcagt cttatggcaa tcccgcatct     60
tttaaccaaa gaactagtga tagttatcca actaaaagcg ctattgtagg tatgattgca    120
gctgcattgg gctacgcaag agaagataat gaaaaaactt tggagctaaa taatttatta    180
tttgctgttc gaattgagca atcaggcaaa atgttgacag agtttcaaac agtggaatac    240
agaaagagtg caagcaagac tgctcgaaag ttaacgtatc gtgattttat tcaagatgga    300
gttttcatgg tagcaattgg cagcgatgat gatcaattga tcgaaaacat caagaagca    360 cttgaacatc caaaatttca gctttatta ggaagacggt ctaatccgcc agctggtcca    420
cttaaaattg atattttaa tggaagaaat ccctacaag tactagaaga tttgccttgg    480
caagcttcag attggtataa gaggagcttt aagacgtcac aatttctaac tagaataatt    540
gctgatgcta gtttagattc tgaaagtacc cccttaatga aaaagataa agtgggctct    600 tttgatcaaa aagatagata ttatcaatat cgtcctgtcg taatcaaaaa agcagttaaa    660
cttaaaaatt cagaaaataa tcagacagca gataatactg attgggattt ttggtcattt    720
gtgtag                                                              726

<210> SEQ ID NO 86
<211> LENGTH: 657
<212> TYPE: DNA
<213> ORGANISM: Lactobacillus crispatus

<400> SEQUENCE: 86
atgtatattt cgagagttga aattgatact aacaaccgac aaaaaattag ggatttgtat     60
catttaggtg cttatcataa ttgggttgaa aattgctttc cagatgaatt aaagaaaaaa    120
gtaagattac gccatttatg gagaattgat gaattaaatg gtaaaaagta tttacttgtt    180
ttaagtgaag aaaagccaaa attagataag cttgaaagat atggtcttgc caatacggca    240
gagacgaaag actatgatca tttttaagt agtttaaatc aaggaaaaaa atatcgcttt    300
aaactaacgg ctaatccttc atatagaatt acagatgcaa aaaccggtaa atcaaaagta    360
gtaccgcata ttactgtttt gcagcaaact aagtggttat tagatcgatc agaaaaatat    420
ggttttgatt tagttaaatc agaagatgac gaagaaacat atgaaatgaa tattacgtca    480
agagattggc cacgattacg ccgcaagggc aataaaatag taaattaag tcgtgttact    540 tttgaaggct tattagagat taaggattg caacaattta agcaggcaat ggtaactggt    600 ataggcgtg aaaaagcttt tgggatggga ctactcactg taattccaat ggaataa      657
```

<210> SEQ ID NO 87
<211> LENGTH: 2751
<212> TYPE: DNA
<213> ORGANISM: Lactobacillus crispatus

<400> SEQUENCE: 87

| | | | | | |
|---|---|---|---|---|---|
| atgacaaatt | tatcaaatac | caccctgtct | ttatggggta | aaagaatat | taatgaagat | 60 |
| agcgaagaag | tatggttacc | cttaatcgct | cacttaattg | acacaaaaaa | tgttattgga | 120 |
| tggttatata | atcattggct | taatgacggc | caaagatgca | ttttgagtca | gggttttgaa | 180 |
| aactcaaatg | aagttcagaa | tcttgttgaa | tttattggat | acattcatga | tattggtaag | 240 |
| gctacgcctg | cttttcaaat | taagcaatcg | tttatccata | tgaagatttt | agaccaggat | 300 |
| ctgttagaga | gattattaca | aaatggattt | gataatttag | aagaattaaa | ggcaaatatg | 360 |
| gatactagac | actggctcca | cgctctggct | ggtgaagtga | tcttagaaaa | tagtgggcta | 420 |
| aatgaaagta | ttggcgctat | agttggcggg | caccatggta | aaccacaaaa | taagtatttt | 480 |
| gactatgaag | atcaactgat | ggatgatact | tctaaatatt | atcaatcaga | ttcttgggcc | 540 |
| gaaaatccaa | ctagagaaaa | atgggaaaat | gtacaaaaag | agatcatcaa | ttatggttta | 600 |
| gatttgtgta | attttaaaaa | tttagaagat | atacctacag | ttactgactc | acaagcagta | 660 |
| attttagaag | gcctagtcat | tatggccgac | tggttggcat | ctagtgaata | tacaattaaa | 720 |
| gatggtaagc | gtgttagcat | gtttccatta | atctcgatgg | atcaaggttt | tagcgatatt | 780 |
| gatatgacat | caagatatca | acaaggaatt | ttaaattggc | ttaaaacaga | ttcctggacg | 840 |
| cctcaattga | tagtcgatac | taaagagcaa | tatcaaaaac | gctggaatttt | tgatccaaga | 900 |
| caagttcagg | aacaaatgtc | tcaagcaatc | ggagatagtg | tggatcctag | catgattatc | 960 |
| gttgaagccc | cgatgggtat | tggtaaaact | gaaatagctt | taaccgctgt | tgagcaatta | 1020 |
| gctgctaaga | ccggtatcaa | tggcctgttt | tttggcttgc | caactcaggc | tactgcaaat | 1080 |
| gcaatgtttg | atagagtaga | taactggctg | gggaatattg | ccaaagaaca | gagcgaaaat | 1140 |
| ctttctatta | aattgatgca | tggaaaggca | cagtttaatc | aaaaatatca | caatattcct | 1200 |
| gatgctgatg | atattgaaac | cgatgaaggt | gcagttgttg | ttaatcagtg | gtttaatggt | 1260 |
| aaaaagtcaa | tattaactga | ctttgtaatt | ggaactattg | atcaattgct | tttgatgggc | 1320 |
| ttgaagcaaa | agcatctggc | cttaagacat | ttagggctaa | gcggaaaaat | agttgtaatt | 1380 |
| gacgaggttc | atgcttatga | cgtatatatg | agttcctatc | ttgaaaaggc | aatagagtgg | 1440 |
| ttgggggcat | atcatgtacc | agttgttgct | ttgtcggcta | cgcttccagt | tgataaaaga | 1500 |
| aatgaacttc | ttacagcata | ttgtagagga | aaatatggca | gtgaaaaatt | taaagctcaa | 1560 |
| aatactaatt | ggcaaacttg | tcaagcatat | cccttattaa | gtattttgga | tggcaaagtt | 1620 |
| ttaaaacaaa | agtcagactt | ttctactaaa | gctgatgata | ctacagttaa | agttactcgc | 1680 |
| ttaagcattg | aaaattacga | tttaattgaa | aagattaatg | atcaaattga | agatggcggt | 1740 |
| gtcgcaggtg | tcatagttaa | tacggtaaag | cgagcacaag | aattggcaaa | aattgctgaa | 1800 |
| aaagagtgct | ctgaagatac | gcaaattttg | gtgcttcatt | ccgcatttt | ggctaatgat | 1860 |
| cgtagtaatt | tagagtccaa | attggaaaag | tcaattggaa | atcaccaaaa | acgtccaaag | 1920 |
| aaaatgatag | taattggcac | gcaagtgctc | gaacaatctt | tggatatcga | ttttgatgtt | 1980 |
| atgtatacgg | atattgcacc | aatagacttg | attttacaaa | gagcgggtcg | tttgcatcgt | 2040 |
| catcaagtta | agcgcccaga | caaattaatt | gagcctcaac | tattcattat | gggtattaat | 2100 |

```
tctaatgggg actatgggga tgcaaatcaa gcaatatatg agaaatatct tttaattaag    2160
acggatcatt tcttaaaaga caatatcaaa ttacctagtg atatttctaa tttggttcaa    2220
aaggtatatt cagcggatac tgataatgaa gtacaagatc ttcaggaagc ggaagttaag    2280
aaattcaaca ttgatcagga aaaggcagaa caaaaatcga aagggtatca aattagagcc    2340
ccaagagttg aaaaaacttt acacggttgg cttgataatg atagtgacac tgatctaaat    2400
gatgttaaag cagaggctgc tgtcagagat acgaatgaaa caatcgaggt tcttttgcta    2460
aaaaaagatg ccgatggatt ttatttaatg gatgggcgaa aagtggatga agaagttcct    2520
gatagcgttg ttgctcagca gttgattagg ctgccccatg cattaacgat ggatataaac    2580
caatctatac gaaatttgga acgagatact attagtaatt ttcctgaatg gcagaacagt    2640
tcctggttaa agggctcggt agctttaatt cttgatgcca ataatgagac agaatttaat    2700
ggatataaaa ttaagtattc atctgacttg gggttatcgt acgaaaaata g             2751

<210> SEQ ID NO 88
<211> LENGTH: 53
<212> TYPE: DNA
<213> ORGANISM: Artificial
<220> FEATURE:
<223> OTHER INFORMATION: target sequence

<400> SEQUENCE: 88
atgctaatgg agaaactaca agttaatccg gcaaagctaa atggccggcc cgt           53

<210> SEQ ID NO 89
<211> LENGTH: 89
<212> TYPE: DNA
<213> ORGANISM: Artificial
<220> FEATURE:
<223> OTHER INFORMATION: Pre-crRNA

<400> SEQUENCE: 89
gtattctcca cgtgtgtgga ggtgatccta caatatgac cgctactgaa ttgttgaagc     60
agtattctcc acgtgtgtgg aggtgatcc                                      89

<210> SEQ ID NO 90
<211> LENGTH: 61
<212> TYPE: DNA
<213> ORGANISM: Artificial
<220> FEATURE:
<223> OTHER INFORMATION: Mature crRNA

<400> SEQUENCE: 90
gtgatcctaa caatatgacc gctactgaat tgttgaagca gtattctcca cgtgtgtgga    60
g                                                                    61

<210> SEQ ID NO 91
<211> LENGTH: 61
<212> TYPE: RNA
<213> ORGANISM: Artificial
<220> FEATURE:
<223> OTHER INFORMATION: crRNA boundary

<400> SEQUENCE: 91
gugauccuaa caauaugacc gcuacugaau uguugaagca guauucucca cgugugugga    60
g                                                                    61

<210> SEQ ID NO 92
<211> LENGTH: 33
```

```
<212> TYPE: DNA
<213> ORGANISM: Artificial
<220> FEATURE:
<223> OTHER INFORMATION: plasmid sequence

<400> SEQUENCE: 92
cagtttaggt accatttttt gacgatcaaa atc                                    33

<210> SEQ ID NO 93
<211> LENGTH: 36
<212> TYPE: DNA
<213> ORGANISM: Artificial
<220> FEATURE:
<223> OTHER INFORMATION: plasmid sequence

<400> SEQUENCE: 93
aaacagttta ggtaccattt tttgacgatc aaaatc                                 36

<210> SEQ ID NO 94
<211> LENGTH: 33
<212> TYPE: DNA
<213> ORGANISM: Artificial
<220> FEATURE:
<223> OTHER INFORMATION: plasmid sequence

<400> SEQUENCE: 94
cagttcaaat gttacttggc cacgcaaata taa                                    33

<210> SEQ ID NO 95
<211> LENGTH: 36
<212> TYPE: DNA
<213> ORGANISM: Artificial
<220> FEATURE:
<223> OTHER INFORMATION: plasmid sequence

<400> SEQUENCE: 95
aaacagttca aatgttactt ggccacgcaa atataa                                 36

<210> SEQ ID NO 96
<211> LENGTH: 33
<212> TYPE: DNA
<213> ORGANISM: Artificial
<220> FEATURE:
<223> OTHER INFORMATION: plasmid sequence

<400> SEQUENCE: 96
cgtgttgttt ccatattcat tagataaaac atc                                    33

<210> SEQ ID NO 97
<211> LENGTH: 36
<212> TYPE: DNA
<213> ORGANISM: Artificial
<220> FEATURE:
<223> OTHER INFORMATION: plasmid sequence

<400> SEQUENCE: 97
aaacgtgttg tttccatatt cattagataa aacatc                                 36

<210> SEQ ID NO 98
<211> LENGTH: 116
<212> TYPE: DNA
<213> ORGANISM: Artificial
<220> FEATURE:
<223> OTHER INFORMATION: plasmid sequence

<400> SEQUENCE: 98
```

```
ttactgtatt ctccacgtgt gtggaggtga tcctgagacc aaaggtctcg tattctccac    60
gtgtgtggag gtgatccaaa aaaaaacccc gcccctgaca gggcggggtt tttttt       116
```

<210> SEQ ID NO 99
<211> LENGTH: 29
<212> TYPE: DNA
<213> ORGANISM: Artificial
<220> FEATURE:
<223> OTHER INFORMATION: sequence

<400> SEQUENCE: 99

```
ttactgtatt ctccacgtgt gtggaggtg                                      29
```

<210> SEQ ID NO 100
<211> LENGTH: 66
<212> TYPE: DNA
<213> ORGANISM: Artificial
<220> FEATURE:
<223> OTHER INFORMATION: sequence

<400> SEQUENCE: 100

```
tattctccac gtgtgtggag gtgatccaaa aaaaaacccc gcccctgaca gggcggggtt    60
tttttt                                                               66
```

<210> SEQ ID NO 101
<211> LENGTH: 32
<212> TYPE: DNA
<213> ORGANISM: Artificial
<220> FEATURE:
<223> OTHER INFORMATION: sequence

<400> SEQUENCE: 101

```
atgacataag aggtgcacac acctccacta gg                                  32
```

<210> SEQ ID NO 102
<211> LENGTH: 62
<212> TYPE: DNA
<213> ORGANISM: Artificial
<220> FEATURE:
<223> OTHER INFORMATION: sequence

<400> SEQUENCE: 102

```
gaggtgcaca cacctccact aggtttttt ttggggcggg gactgtcccg ccccaaaaaa     60
aa                                                                   62
```

<210> SEQ ID NO 103
<211> LENGTH: 38
<212> TYPE: DNA
<213> ORGANISM: Artificial
<220> FEATURE:
<223> OTHER INFORMATION: Annealing oligonucleotide

<400> SEQUENCE: 103

```
atccctacaa gttaatccgg caaagctaaa tggccggg                            38
```

<210> SEQ ID NO 104
<211> LENGTH: 38
<212> TYPE: DNA
<213> ORGANISM: Artificial
<220> FEATURE:
<223> OTHER INFORMATION: Annealing oligonucleotide

<400> SEQUENCE: 104

```
gatgttcaat taggccgttt cgatttaccg gcccataa                            38
```

<210> SEQ ID NO 105
<211> LENGTH: 36
<212> TYPE: DNA
<213> ORGANISM: Lactobacillus crispatus

<400> SEQUENCE: 105
aaactacaag ttaatccggc aaagctaaat ggccgg                                    36

<210> SEQ ID NO 106
<211> LENGTH: 133
<212> TYPE: DNA
<213> ORGANISM: Artificial
<220> FEATURE:
<223> OTHER INFORMATION: plasmid sequence

<400> SEQUENCE: 106
ttactgtatt ctccacgtgt gtggaggtga tccctacaag ttaatccggc aaagctaaat          60
ggccgggtat tctccacgtg tgtggaggtg atccaaaaaa aaaccccgcc cctgacaggg         120
cggggttttt ttt                                                           133

<210> SEQ ID NO 107
<211> LENGTH: 61
<212> TYPE: RNA
<213> ORGANISM: Artificial
<220> FEATURE:
<223> OTHER INFORMATION: crRNA

<400> SEQUENCE: 107
gugaucccua caaguuaauc cggcaaagcu aaauggccgg guauucucca cgugugugga         60
g                                                                         61

<210> SEQ ID NO 108
<211> LENGTH: 54
<212> TYPE: DNA
<213> ORGANISM: Artificial
<220> FEATURE:
<223> OTHER INFORMATION: target sequence

<400> SEQUENCE: 108
tacgattacc tctttgatgt tcaattaggc cgtttcgatt taccggccgg gcat               54

<210> SEQ ID NO 109
<211> LENGTH: 102
<212> TYPE: DNA
<213> ORGANISM: Lactobacillus crispatus

<400> SEQUENCE: 109
agtaattagg agagtaagag gcaatgatgc taatggagaa actacaagtt aatccggcaa         60
agctaaatgg ccggcccgta tatcatacag ttaagcgagt at                           102

<210> SEQ ID NO 110
<211> LENGTH: 78
<212> TYPE: DNA
<213> ORGANISM: Lactobacillus crispatus

<400> SEQUENCE: 110
agtaattagg agagtaagag gcaatgatgc taatggagaa ataatagtga cccgtatatc         60
atacagttaa gcgagtat                                                       78

<210> SEQ ID NO 111

<211> LENGTH: 102
<212> TYPE: DNA
<213> ORGANISM: Lactobacillus crispatus

<400> SEQUENCE: 111
agtaattagg agagtaagag gcaatgatgc taatggagag actacaagtt aatccggcaa    60
agctaaatgg ccggcccgta tatcatacag ttaagcgagt at                      102

<210> SEQ ID NO 112
<211> LENGTH: 392
<212> TYPE: PRT
<213> ORGANISM: Lactobacillus crispatus

<400> SEQUENCE: 112

Met Asn Asn Asp Leu Ser Phe Asn Leu Val Thr Asp Pro Trp Ile Lys
1               5                   10                  15

Val Leu Lys Lys Asp Tyr Thr Glu Ser Glu Val Ser Leu Asn Glu Leu
            20                  25                  30

Phe Ser Asn Ser Glu Glu Tyr Leu Gln Leu Ala Gly Asp Met Lys Ser
        35                  40                  45

Gln Asp Leu Ala Ile Leu Arg Leu Leu Leu Ala Ile Leu Leu Ser Val
    50                  55                  60

Tyr Thr Arg Phe Asp Ala Asp Thr Pro Tyr Ser Trp Leu Asp Leu
65                  70                  75                  80

Asp Asp Lys Trp Arg Val Thr Arg Thr Asp Asn Asp Gly Phe Asn Ser
                85                  90                  95

Gln Lys Leu Lys Leu Gly Asp Thr Trp Arg Ser Leu Tyr Asp Gln Lys
            100                 105                 110

Thr Phe Ser Lys Lys Val Phe Asp Tyr Leu Asn Leu Tyr Gln Ala Lys
        115                 120                 125

Phe Asn Leu Phe Gly Glu Asp Pro Phe Tyr Gln Val Asn Arg Gln Val
    130                 135                 140

Tyr Asp Gln Asn Val Pro Glu Asn Lys Lys Val Ala Lys Gly Ala Gly
145                 150                 155                 160

Thr Val Ser Val Lys Gln Ile Asn Arg Leu Ile Ser Glu Ser Asn Asn
                165                 170                 175

Ser Pro Ala Leu Phe Ser Pro Lys Ser Gly Ile Glu Lys Asp Ser Val
            180                 185                 190

Asn Asn Ala Glu Leu Val Arg Trp Leu Ile Thr Tyr Gln Asn Phe Thr
        195                 200                 205

Gly Val Thr Asp Lys Thr Lys Val Lys Ser Lys Asp Lys Phe Ser Val
    210                 215                 220

Ser Pro Gly Trp Leu Tyr Ser Ile Asn Pro Val Tyr Ile Lys Gly Lys
225                 230                 235                 240

Thr Leu Phe Asp Thr Leu Met Leu Asn Leu Ser Leu Val Thr Asn Asp
                245                 250                 255

Ser Ala Asp Gly Thr Asn Trp Leu Asn Ser Gln Arg Pro Val Trp Glu
            260                 265                 270

Tyr Asp Asp Ile Asn Asp Tyr Leu Gln Gln Arg Leu Asn Gly Val Tyr
        275                 280                 285

Pro Asp Asn Leu Ser Glu Leu Tyr Thr Val Trp Ser Arg Met Ile His
    290                 295                 300

Ile Asp Trp Gln Asn Gly Gln Pro Val Ile Phe Ser Ala Gly Leu Pro
305                 310                 315                 320

Lys Leu Asp Ser Glu Lys Gln Phe Leu Glu Pro Met Thr Thr Trp Arg

```
                 325                 330                 335
Lys Asn Lys Asp Gly Val Val Tyr Pro Ala Ala Lys Asn Lys Asn Asn
            340                 345                 350

Ile Asn Val Ala Met Trp Arg Asn Phe Gly Gln Tyr Ile Arg Thr Lys
        355                 360                 365

Glu Asp Asn Asn Asn Glu Lys Lys Ile Lys Ile Ile Thr Glu Phe Gln
370                 375                 380

Glu Leu Leu Val Gly Phe Arg Asn
385                 390

<210> SEQ ID NO 113
<211> LENGTH: 201
<212> TYPE: PRT
<213> ORGANISM: Lactobacillus crispatus

<400> SEQUENCE: 113

Met Ser Asp Ala Tyr Thr Ala Thr Ala Arg Ile Ile Asn Gln Leu Tyr
1               5                   10                  15

Gly Asp Gly Thr Pro Asp Lys Gly Ala Leu Ala Glu Leu Arg Arg Thr
            20                  25                  30

Thr Ala Ile Thr Asp Lys Gly Ala Glu Lys Ile Trp Pro Leu Ile Phe
        35                  40                  45

Ser Val Val Pro Lys Leu Ser Thr Asn Gly Lys Pro Thr Lys Leu Glu
    50                  55                  60

Thr Ala Val Tyr Thr Ala Leu His Cys Tyr Ala Ala Phe Gln Gln Gly
65                  70                  75                  80

Asn Asp Ser Phe Val Phe Gly Gln Ile Pro Arg Ser Lys Asp Lys Glu
                85                  90                  95

Glu Ser Gly Glu Asn Gly Val Ser Leu Phe Thr Ala Leu Arg Lys Met
            100                 105                 110

Lys Ile Asn Asp Ser Asn Glu Lys Lys Ala Leu Asp Arg Arg Val Thr
        115                 120                 125

Ala Leu Leu Ala Thr Thr Asn Ile Ser Ser Ala Thr Asn Ser Ile Asn
    130                 135                 140

His Leu Val Ser Ile Leu Lys Gly Lys Lys Met Gly Glu Lys Ile Asp
145                 150                 155                 160

Phe Ala Gln Leu Ala Glu Asp Leu Tyr Asn Phe Gln Trp Ser Thr Lys
                165                 170                 175

Asn Ala Arg Phe Val Ala Leu Lys Trp Gly Lys Asp Tyr Tyr Trp Asn
            180                 185                 190

Val Tyr Lys Leu Ala Ser Asp Asn Asp
        195                 200

<210> SEQ ID NO 114
<211> LENGTH: 369
<212> TYPE: PRT
<213> ORGANISM: Lactobacillus crispatus

<400> SEQUENCE: 114

Met Asn Lys Asn Leu Tyr Met Asp Ile Asn Val Leu Gln Thr Val Pro
1               5                   10                  15

Ser Ser Asn Ile Asn Arg Asp Asp Thr Gly Ser Pro Lys Thr Ala Ile
            20                  25                  30

Tyr Gly Gly Val Thr Arg Ser Arg Val Ser Ser Gln Ser Trp Lys Arg
        35                  40                  45

Ala Met Arg Leu Ala Phe Lys Gln Asp Ser Glu Asn Glu Glu Trp Leu
```

```
                  50                  55                  60
Lys Ser Tyr Arg Thr Leu Lys Thr Ala Ser Leu Leu Ala Asn Lys Leu
 65                  70                  75                  80

Gln Glu Leu Asp Ser Asn Leu Ser Glu Glu Asp Ala Leu Lys Lys Val
                 85                  90                  95

Glu Glu Val Phe Lys Val Ala Gly Ile Lys Leu Lys Lys Asp Lys Lys
                100                 105                 110

Thr Gly Glu Met Leu Thr Gly Ala Leu Leu Val Ser Glu Gly Gln
                115                 120                 125

Leu Glu Lys Ile Ala Lys Leu Ala Leu Ser Val Asp Gln Ile Asp Lys
130                 135                 140

Asp Thr Ala Lys Glu Ile Lys Lys Asn Leu Met Glu Asp Gln Ser Leu
145                 150                 155                 160

Asp Leu Ala Leu Phe Gly Arg Met Val Ala Asp Asn Pro Glu Leu Asn
                165                 170                 175

Val Asp Ala Ser Ser Gln Val Ala His Ala Ile Ser Thr His Glu Val
                180                 185                 190

Thr Pro Glu Phe Asp Tyr Tyr Thr Ala Val Asp Asp Ala Asn Thr Lys
                195                 200                 205

Ser Gln Thr Gly Ser Ala Met Leu Gly Thr Ile Glu Tyr Asn Ser Ser
210                 215                 220

Thr Leu Tyr Arg Tyr Ala Asn Val Asn Ile Leu Asp Leu Leu His Asn
225                 230                 235                 240

Leu Gly Asn Lys Asp Leu Thr Ile Glu Gly Ile Lys Leu Phe Ile Lys
                245                 250                 255

Glu Phe Val Leu Thr Met Pro Thr Gly Lys Glu Asn Thr Phe Ala Asn
                260                 265                 270

Lys Thr Leu Pro Gln Tyr Val Met Ile Asn Val Arg Thr Asp Thr Pro
                275                 280                 285

Val Asn Leu Val Ser Ala Phe Glu Thr Pro Val Arg Ser Glu Gly Gly
                290                 295                 300

Tyr Val Asp Lys Ser Ile Asn Arg Leu Glu Asp Glu Tyr Lys Asn Ser
305                 310                 315                 320

Leu Lys Phe Val Asp Lys Pro Val Phe Asn Val Glu Leu Thr Asn Ser
                325                 330                 335

Glu Asn Ile Val Asp Asn Gln Ala Glu Asn Ile Asp Asp Leu Ile Asn
                340                 345                 350

Gln Thr Ala Glu Phe Val Lys Gln Glu Leu Glu Asn Glu Asp Ser Asn
                355                 360                 365

Asp

<210> SEQ ID NO 115
<211> LENGTH: 241
<212> TYPE: PRT
<213> ORGANISM: Lactobacillus crispatus

<400> SEQUENCE: 115

Met Lys Thr Ala Thr Ile Arg Leu Thr Ala Pro Leu Gln Ser Tyr Gly
1               5                   10                  15

Asn Pro Ala Ser Phe Asn Gln Arg Thr Ser Asp Ser Tyr Pro Thr Lys
                20                  25                  30

Ser Ala Ile Val Gly Met Ile Ala Ala Leu Gly Tyr Ala Arg Glu
                35                  40                  45

Asp Asn Glu Lys Thr Leu Glu Leu Asn Asn Leu Leu Phe Ala Val Arg
```

```
                    50                  55                  60
Ile Glu Gln Ser Gly Lys Met Leu Thr Glu Phe Gln Thr Val Glu Tyr
 65                  70                  75                  80

Arg Lys Ser Ala Ser Lys Thr Ala Arg Lys Leu Thr Tyr Arg Asp Phe
                 85                  90                  95

Ile Gln Asp Gly Val Phe Met Val Ala Ile Gly Ser Asp Asp Asp Gln
            100                 105                 110

Leu Ile Glu Asn Ile Lys Glu Ala Leu Glu His Pro Lys Phe Gln Leu
        115                 120                 125

Tyr Leu Gly Arg Arg Ser Asn Pro Pro Ala Gly Pro Leu Lys Ile Asp
130                 135                 140

Ile Phe Asn Gly Arg Asn Pro Leu Gln Val Leu Glu Asp Leu Pro Trp
145                 150                 155                 160

Gln Ala Ser Asp Trp Tyr Lys Arg Ser Phe Lys Thr Ser Gln Phe Leu
                165                 170                 175

Thr Arg Ile Ile Ala Asp Ala Ser Leu Asp Ser Glu Ser Thr Pro Leu
            180                 185                 190

Met Lys Lys Asp Lys Val Gly Ser Phe Asp Gln Lys Asp Arg Tyr Tyr
        195                 200                 205

Gln Tyr Arg Pro Val Val Ile Lys Lys Ala Val Lys Leu Lys Asn Ser
210                 215                 220

Glu Asn Asn Gln Thr Ala Asp Asn Thr Asp Trp Asp Phe Trp Ser Phe
225                 230                 235                 240

Val

<210> SEQ ID NO 116
<211> LENGTH: 218
<212> TYPE: PRT
<213> ORGANISM: Lactobacillus crispatus

<400> SEQUENCE: 116

Met Tyr Ile Ser Arg Val Glu Ile Asp Thr Asn Asn Arg Gln Lys Ile
  1               5                  10                  15

Arg Asp Leu Tyr His Leu Gly Ala Tyr His Asn Trp Val Glu Asn Cys
                 20                  25                  30

Phe Pro Asp Glu Leu Lys Lys Lys Val Arg Leu Arg His Leu Trp Arg
             35                  40                  45

Ile Asp Glu Leu Asn Gly Lys Lys Tyr Leu Leu Val Leu Ser Glu Glu
         50                  55                  60

Lys Pro Lys Leu Asp Lys Leu Glu Arg Tyr Gly Leu Ala Asn Thr Ala
 65                  70                  75                  80

Glu Thr Lys Asp Tyr Asp His Phe Leu Ser Ser Leu Asn Gln Gly Lys
                 85                  90                  95

Lys Tyr Arg Phe Lys Leu Thr Ala Asn Pro Ser Tyr Arg Ile Thr Asp
            100                 105                 110

Ala Lys Thr Gly Lys Ser Lys Val Val Pro His Ile Thr Val Leu Gln
        115                 120                 125

Gln Thr Lys Trp Leu Leu Asp Arg Ser Glu Lys Tyr Gly Phe Asp Leu
    130                 135                 140

Val Lys Ser Glu Asp Asp Glu Glu Thr Tyr Glu Met Asn Ile Thr Ser
145                 150                 155                 160

Arg Asp Trp Pro Arg Leu Arg Arg Lys Gly Asn Lys Ile Val Lys Leu
                165                 170                 175

Ser Arg Val Thr Phe Glu Gly Leu Leu Glu Ile Lys Asp Leu Gln Gln
```

```
              180                 185                 190
Phe Lys Gln Ala Met Val Thr Gly Ile Gly Arg Glu Lys Ala Phe Gly
            195                 200                 205

Met Gly Leu Leu Thr Val Ile Pro Met Glu
            210                 215

<210> SEQ ID NO 117
<211> LENGTH: 315
<212> TYPE: PRT
<213> ORGANISM: Lactobacillus crispatus

<400> SEQUENCE: 117

Met Lys Asn Asn Tyr Gly Ala Lys Lys Pro Glu Arg Gln Glu Leu Gly
1               5                   10                  15

Arg Val Ser Asp Arg Ile Ser Phe Ile Tyr Val Glu His Ala Arg Ile
            20                  25                  30

Asn Arg Gln Asp Ser Ala Ile Gln Val Val Asp Tyr Arg Gly Ile Ile
        35                  40                  45

Asn Ile Pro Val Ala Leu Val Ser Val Leu Leu Gly Pro Gly Val
    50                  55                  60

Asp Val Thr His Arg Ala Met Glu Leu Met Gly Asp Ser Ser Leu Ala
65                  70                  75                  80

Val Val Trp Val Gly Glu Cys Gly Val Arg Gln Tyr Ala His Gly Arg
                85                  90                  95

Ser Leu Asn His Ser Ser Arg Leu Leu Glu Ala Gln Ala Lys Leu Val
            100                 105                 110

Ser Asn Arg Arg Ser Arg Leu Ala Thr Ala Arg Gln Met Tyr Glu Met
        115                 120                 125

Arg Phe Pro Asn Glu Asp Phe Ser Asn Leu Thr Met Glu Glu Leu Arg
    130                 135                 140

Gly Lys Glu Gly Ser Arg Val Arg Arg Ile Tyr Arg Glu Gln Ser Lys
145                 150                 155                 160

Leu Thr Gly Val Ser Trp Asn Lys Arg Glu Tyr Lys Val Asp Asn Phe
                165                 170                 175

Glu Asp Gly Thr Pro Ile Asn Lys Ala Leu Thr Ala Ala His Gln Ala
            180                 185                 190

Leu Tyr Gly Leu Ser Tyr Ser Val Ile Val Ala Leu Gly Ala Ser Pro
        195                 200                 205

Gly Leu Gly Phe Ile His Thr Gly His Asp Leu Ala Phe Val Tyr Asp
    210                 215                 220

Phe Ala Asp Leu Tyr Lys Ala Lys Tyr Ser Ile Pro Ile Ala Phe Lys
225                 230                 235                 240

Met Thr Ala Lys Tyr Gly Asn Gln Asp Ile Ala Thr His Thr Arg Ile
                245                 250                 255

Ala Met Arg Asp Glu Phe Lys Lys Gly Lys Leu Leu Ala Lys Met Val
            260                 265                 270

Lys Asp Leu Lys Thr Leu Leu Leu Lys Asp Ser Thr Ala Asp Ile Glu
        275                 280                 285

Ser Pro Gln Val Ile Met Ser Leu Trp Asp Asp Arg Glu Gly Leu Gln
    290                 295                 300

Lys Phe Gly Val Gln Tyr His Glu Ala Gln Ser
305                 310                 315

<210> SEQ ID NO 118
<211> LENGTH: 298
```

<212> TYPE: PRT
<213> ORGANISM: Lactobacillus crispatus

<400> SEQUENCE: 118

Met Ile Val Ile Thr Leu Ser Lys Thr Pro Gln Ser Leu Arg Gly Asp
1               5                   10                  15

Leu Thr Lys Trp Cys Gln Glu Val Gln Thr Gly Val Tyr Val Gly Asn
            20                  25                  30

Phe Ser Ala Arg Ile Arg Asp Leu Ile Trp Gln Arg Ile Ile Ser Asn
        35                  40                  45

Ile Gly Gln Gly Glu Ala Thr Leu Ile Tyr Ser Thr Asn Asn Glu Leu
50                  55                  60

Gly Phe Asp Phe Lys Thr Thr Arg Gln Asp Lys Met Val Ala Asp Phe
65                  70                  75                  80

Asp Gly Ile Pro Leu Met Val His Leu Asn Ser Gln Asn Lys Leu Ser
                85                  90                  95

Ser Lys Lys Lys Leu Gly Phe Ser Lys Ala Ala Gln His His Lys Val
            100                 105                 110

Asn Thr Phe Arg Ser Gln Val Gln Asp Lys Ala Asp Ser Leu Thr Ser
        115                 120                 125

Leu Ala Val Leu Asp Ile Glu Thr Thr Gly Leu Asn Leu Glu Lys Asp
130                 135                 140

Lys Ile Ile Ser Ile Gly Ala Ile Lys Tyr Leu Glu Asn Asn Asp Cys
145                 150                 155                 160

Glu Lys Phe Tyr Arg Leu Ile Lys Val Asp Thr Glu Val Pro Asp Asn
                165                 170                 175

Ile Glu Lys Ile Thr Gln Leu Asn Lys Gly Val Leu Ala Asn Lys Gly
            180                 185                 190

Ile Asp Ile Lys Thr Ala Leu Leu Asp Leu Arg Lys Phe Leu Ala Asp
        195                 200                 205

Arg Ile Val Val Gly Tyr Asn Leu Pro Phe Asp Ile Asn Phe Leu Asn
210                 215                 220

Arg Asp Phe Lys Lys Tyr Cys His Tyr Ser Leu Leu Asn Glu Cys Val
225                 230                 235                 240

Asp Leu Leu Ser Ala Val Lys Lys Lys Asn Val Phe Leu Asp Asn Tyr
                245                 250                 255

His Leu Ser Thr Val Leu Glu Asn Tyr Asn Ile Lys Asn Ser Asn Pro
            260                 265                 270

His Asn Ser Leu Ala Asp Ala Val Ala Thr Met Glu Leu Leu Lys Lys
        275                 280                 285

Leu Ile Lys Asn Asp Asn Tyr Lys Ile Lys
290                 295

<210> SEQ ID NO 119
<211> LENGTH: 916
<212> TYPE: PRT
<213> ORGANISM: Lactobacillus crispatus

<400> SEQUENCE: 119

Met Thr Asn Leu Ser Asn Thr Thr Leu Ser Leu Trp Gly Lys Lys Asn
1               5                   10                  15

Ile Asn Glu Asp Ser Glu Glu Val Trp Leu Pro Leu Ile Ala His Leu
            20                  25                  30

Ile Asp Thr Lys Asn Val Ile Gly Trp Leu Tyr Asn His Trp Leu Asn
        35                  40                  45

Asp Gly Gln Arg Cys Ile Leu Ser Gln Gly Phe Glu Asn Ser Asn Glu
     50                  55                  60

Val Gln Asn Leu Val Glu Phe Ile Gly Tyr Ile His Asp Ile Gly Lys
 65                  70                  75                  80

Ala Thr Pro Ala Phe Gln Ile Lys Gln Ser Phe Ile His Asn Glu Asp
                 85                  90                  95

Leu Asp Gln Asp Leu Leu Glu Arg Leu Leu Gln Asn Gly Phe Asp Asn
            100                 105                 110

Leu Glu Glu Leu Lys Ala Asn Met Asp Thr Arg His Trp Leu His Ala
            115                 120                 125

Leu Ala Gly Glu Val Ile Leu Glu Asn Ser Gly Leu Asn Glu Ser Ile
    130                 135                 140

Gly Ala Ile Val Gly Gly His His Gly Lys Pro Gln Asn Lys Tyr Phe
145                 150                 155                 160

Asp Tyr Glu Asp Gln Leu Met Asp Asp Thr Ser Lys Tyr Tyr Gln Ser
                165                 170                 175

Asp Ser Trp Ala Glu Asn Pro Thr Arg Glu Lys Trp Glu Asn Val Gln
            180                 185                 190

Lys Glu Ile Ile Asn Tyr Gly Leu Asp Leu Cys Asn Phe Lys Asn Leu
            195                 200                 205

Glu Asp Ile Pro Thr Val Thr Asp Ser Gln Ala Val Ile Leu Glu Gly
    210                 215                 220

Leu Val Ile Met Ala Asp Trp Leu Ala Ser Glu Tyr Thr Ile Lys
225                 230                 235                 240

Asp Gly Lys Arg Val Ser Met Phe Pro Leu Ile Ser Met Asp Gln Gly
                245                 250                 255

Phe Ser Asp Ile Asp Met Thr Ser Arg Tyr Gln Gln Gly Ile Leu Asn
            260                 265                 270

Trp Leu Lys Thr Asp Ser Trp Thr Pro Gln Leu Ile Val Asp Thr Lys
            275                 280                 285

Glu Gln Tyr Gln Lys Arg Trp Asn Phe Asp Pro Arg Gln Val Gln Glu
    290                 295                 300

Gln Met Ser Gln Ala Ile Gly Asp Ser Val Asp Pro Ser Met Ile Ile
305                 310                 315                 320

Val Glu Ala Pro Met Gly Ile Gly Lys Thr Glu Ile Ala Leu Thr Ala
                325                 330                 335

Val Glu Gln Leu Ala Ala Lys Thr Gly Ile Asn Gly Leu Phe Phe Gly
            340                 345                 350

Leu Pro Thr Gln Ala Thr Ala Asn Ala Met Phe Asp Arg Val Asp Asn
            355                 360                 365

Trp Leu Gly Asn Ile Ala Lys Glu Gln Ser Glu Asn Leu Ser Ile Lys
    370                 375                 380

Leu Met His Gly Lys Ala Gln Phe Asn Gln Lys Tyr His Asn Ile Pro
385                 390                 395                 400

Asp Ala Asp Asp Ile Glu Thr Asp Glu Gly Ala Val Val Asn Gln
                405                 410                 415

Trp Phe Asn Gly Lys Lys Ser Ile Leu Thr Asp Phe Val Ile Gly Thr
            420                 425                 430

Ile Asp Gln Leu Leu Leu Met Gly Leu Lys Gln Lys His Leu Ala Leu
            435                 440                 445

Arg His Leu Gly Leu Ser Gly Lys Ile Val Ile Asp Glu Val His
    450                 455                 460

Ala Tyr Asp Val Tyr Met Ser Ser Tyr Leu Glu Lys Ala Ile Glu Trp

```
            465                 470                 475                 480
Leu Gly Ala Tyr His Val Pro Val Val Ala Leu Ser Ala Thr Leu Pro
                    485                 490                 495

Val Asp Lys Arg Asn Glu Leu Leu Thr Ala Tyr Cys Arg Gly Lys Tyr
                500                 505                 510

Gly Ser Glu Lys Phe Lys Ala Gln Asn Thr Asn Trp Gln Thr Cys Gln
                515                 520                 525

Ala Tyr Pro Leu Leu Ser Ile Leu Asp Gly Lys Val Leu Lys Gln Lys
            530                 535                 540

Ser Asp Phe Ser Thr Lys Ala Asp Thr Thr Val Lys Val Thr Arg
545                 550                 555                 560

Leu Ser Ile Glu Asn Tyr Asp Leu Ile Glu Lys Ile Asn Asp Gln Ile
                    565                 570                 575

Glu Asp Gly Gly Val Ala Gly Val Ile Val Asn Thr Val Lys Arg Ala
                580                 585                 590

Gln Glu Leu Ala Lys Ile Ala Glu Lys Glu Cys Ser Glu Asp Thr Gln
            595                 600                 605

Ile Leu Val Leu His Ser Ala Phe Leu Ala Asn Asp Arg Ser Asn Leu
        610                 615                 620

Glu Ser Lys Leu Glu Lys Ser Ile Gly Asn His Gln Lys Arg Pro Lys
625                 630                 635                 640

Lys Met Ile Val Ile Gly Thr Gln Val Leu Glu Gln Ser Leu Asp Ile
                    645                 650                 655

Asp Phe Asp Val Met Tyr Thr Asp Ile Ala Pro Ile Asp Leu Ile Leu
                660                 665                 670

Gln Arg Ala Gly Arg Leu His Arg His Gln Val Lys Arg Pro Asp Lys
            675                 680                 685

Leu Ile Glu Pro Gln Leu Phe Ile Met Gly Ile Asn Ser Asn Gly Asp
        690                 695                 700

Tyr Gly Asp Ala Asn Gln Ala Ile Tyr Glu Lys Tyr Leu Leu Ile Lys
705                 710                 715                 720

Thr Asp His Phe Leu Lys Asp Asn Ile Lys Leu Pro Ser Asp Ile Ser
                    725                 730                 735

Asn Leu Val Gln Lys Val Tyr Ser Ala Asp Thr Asp Asn Glu Val Gln
                740                 745                 750

Asp Leu Gln Glu Ala Glu Val Lys Lys Phe Asn Ile Asp Gln Glu Lys
            755                 760                 765

Ala Glu Gln Lys Ser Lys Gly Tyr Gln Ile Arg Ala Pro Arg Val Glu
        770                 775                 780

Lys Thr Leu His Gly Trp Leu Asp Asn Asp Ser Asp Thr Asp Leu Asn
785                 790                 795                 800

Asp Val Lys Ala Glu Ala Val Arg Asp Thr Asn Glu Thr Ile Glu
                    805                 810                 815

Val Leu Leu Leu Lys Lys Asp Ala Asp Gly Phe Tyr Leu Met Asp Gly
                820                 825                 830

Arg Lys Val Asp Glu Glu Val Pro Asp Ser Val Val Ala Gln Gln Leu
            835                 840                 845

Ile Arg Leu Pro His Ala Leu Thr Met Asp Ile Asn Gln Ser Ile Arg
        850                 855                 860

Asn Leu Glu Arg Asp Thr Ile Ser Asn Phe Pro Glu Trp Gln Asn Ser
865                 870                 875                 880

Ser Trp Leu Lys Gly Ser Val Ala Leu Ile Leu Asp Ala Asn Asn Glu
                    885                 890                 895
```

Thr Glu Phe Asn Gly Tyr Lys Ile Lys Tyr Ser Ser Asp Leu Gly Leu
        900                 905                 910

Ser Tyr Glu Lys
        915

<210> SEQ ID NO 120
<211> LENGTH: 103
<212> TYPE: DNA
<213> ORGANISM: Lactobacillus crispatus

<400> SEQUENCE: 120
actcttaacc ttattgatct aacaatcata atttaaaatc aagcaatgcg ttttagtacg    60
cagagtttca acacttgtcc cgagctatcg agggactttt ttt                    103

<210> SEQ ID NO 121
<211> LENGTH: 66
<212> TYPE: DNA
<213> ORGANISM: Artificial
<220> FEATURE:
<223> OTHER INFORMATION: crRNA/crDNA

<400> SEQUENCE: 121
tagaaaatgg tttatttgta ccatcttcta gttttagatg attgttagat caatgaggtt    60
tagatc                                                              66

<210> SEQ ID NO 122
<211> LENGTH: 66
<212> TYPE: DNA
<213> ORGANISM: Artificial
<220> FEATURE:
<223> OTHER INFORMATION: crRNA/crDNA

<400> SEQUENCE: 122
taccttgaat tactccagta actctgccgg aatacagtat ttatttatct taagagaaat    60
gtaaat                                                              66

<210> SEQ ID NO 123
<211> LENGTH: 66
<212> TYPE: DNA
<213> ORGANISM: Artificial
<220> FEATURE:
<223> OTHER INFORMATION: crRNA/crDNA

<400> SEQUENCE: 123
taccttgaat tactccagta actctgccgg aatacagtat ttatttatct taagagaaat    60
gtaaat                                                              66

<210> SEQ ID NO 124
<211> LENGTH: 37
<212> TYPE: DNA
<213> ORGANISM: Artificial
<220> FEATURE:
<223> OTHER INFORMATION: plasmid sequence

<400> SEQUENCE: 124
atctcagttt aggtaccatt ttttgacgat caaaatc                            37

<210> SEQ ID NO 125
<211> LENGTH: 40
<212> TYPE: DNA
<213> ORGANISM: Artificial
<220> FEATURE:

<223> OTHER INFORMATION: plasmid sequence

<400> SEQUENCE: 125
atctaaacag tttaggtacc atttttttgac gatcaaaatc                     40

<210> SEQ ID NO 126
<211> LENGTH: 37
<212> TYPE: DNA
<213> ORGANISM: Artificial
<220> FEATURE:
<223> OTHER INFORMATION: plasmid sequence

<400> SEQUENCE: 126
atctcagttc aaatgttact tggccacgca aatataa                         37

<210> SEQ ID NO 127
<211> LENGTH: 40
<212> TYPE: DNA
<213> ORGANISM: Artificial
<220> FEATURE:
<223> OTHER INFORMATION: plasmid sequence

<400> SEQUENCE: 127
atctaaacag ttcaaatgtt acttggccac gcaaatataa                      40

<210> SEQ ID NO 128
<211> LENGTH: 37
<212> TYPE: DNA
<213> ORGANISM: Artificial
<220> FEATURE:
<223> OTHER INFORMATION: plasmid sequence

<400> SEQUENCE: 128
atctcgtgtt gtttccatat tcattagata aacatc                          37

<210> SEQ ID NO 129
<211> LENGTH: 40
<212> TYPE: DNA
<213> ORGANISM: Artificial
<220> FEATURE:
<223> OTHER INFORMATION: plasmid sequence

<400> SEQUENCE: 129
atctaaacgt gttgtttcca tattcattag ataaacatc                       40

<210> SEQ ID NO 130
<211> LENGTH: 60
<212> TYPE: DNA
<213> ORGANISM: Artificial
<220> FEATURE:
<223> OTHER INFORMATION: NCK1350 wt for p-gtf gene

<400> SEQUENCE: 130
atgatgctaa tggagaaact acaagttaat ccggcaaagc taaatggccg gcccgtatat    60

<210> SEQ ID NO 131
<211> LENGTH: 59
<212> TYPE: DNA
<213> ORGANISM: Artificial
<220> FEATURE:
<223> OTHER INFORMATION: NCK2635 (deletion of the p-gtf)

<400> SEQUENCE: 131
atgatgctaa tggagaaagc gaataaatga ataaagaat ctgcgttctt cacgttgca      59

```
<210> SEQ ID NO 132
<211> LENGTH: 60
<212> TYPE: DNA
<213> ORGANISM: Artificial
<220> FEATURE:
<223> OTHER INFORMATION: NCK2656 (insertion of stop codons)

<400> SEQUENCE: 132
atgatgctaa tggagaaata atagtgaccc gtatatcata cagttaagcg agtatttgat      60

<210> SEQ ID NO 133
<211> LENGTH: 60
<212> TYPE: DNA
<213> ORGANISM: Artificial
<220> FEATURE:
<223> OTHER INFORMATION: NCK2659 (single base substitution)

<400> SEQUENCE: 133
atgatgctaa tggagagact acaagttaat ccggcaaagc taaatggccg gcccgtatat      60

<210> SEQ ID NO 134
<211> LENGTH: 246
<212> TYPE: DNA
<213> ORGANISM: Artificial
<220> FEATURE:
<223> OTHER INFORMATION: NCK1350 wt for prophage DNA packaging NU1 gene

<400> SEQUENCE: 134
aatggaattt aaattagatg aatcacaaga aaccgagatt aaaacttttg ttatgggcgt      60
ggttaaagac gctattaaac aagccactac caccagcaaa ccatatttga accgcaaaga     120
aattgctaag tattttggcg tggctgaatc aactattaca tattgggctt ctttagggat     180
gcctgtcgct gtcatagacg ggcgcaaact ctatggcaag caatctataa ctaactggct     240
aaaatt                                                                246

<210> SEQ ID NO 135
<211> LENGTH: 59
<212> TYPE: DNA
<213> ORGANISM: Artificial
<220> FEATURE:
<223> OTHER INFORMATION: NCK2667

<400> SEQUENCE: 135
aacaagaaat attattacag cgtgcaagtg ggctaatctt aggtatttaa tacttaacc       59

<210> SEQ ID NO 136
<211> LENGTH: 60
<212> TYPE: DNA
<213> ORGANISM: Artificial
<220> FEATURE:
<223> OTHER INFORMATION: NCK1350 wt for enolase gene

<400> SEQUENCE: 136
gaaattgtac tcggttaact cgaaattaat cgtgatcaac atcgtctggg aagaaggcaa      60

<210> SEQ ID NO 137
<211> LENGTH: 60
<212> TYPE: DNA
<213> ORGANISM: Artificial
<220> FEATURE:
<223> OTHER INFORMATION: NCK2665 (chromosomal insertion of GFP
      downstream enolase)

<400> SEQUENCE: 137
tttacgcatt aataaacctc ctcacttaat cgtgatcaac atcgtctggg aagaaggcaa      60
```

```
<210> SEQ ID NO 138
<211> LENGTH: 57
<212> TYPE: DNA
<213> ORGANISM: Artificial
<220> FEATURE:
<223> OTHER INFORMATION: p-gtf sequence

<400> SEQUENCE: 138
atgatgctaa tggagaaact acaagttaat ccggcaaagc taaatggccg gcccgta      57

<210> SEQ ID NO 139
<211> LENGTH: 16
<212> TYPE: DNA
<213> ORGANISM: Artificial
<220> FEATURE:
<223> OTHER INFORMATION: p-gtf sequence

<400> SEQUENCE: 139
gccaataaat gaataa                                                    16

<210> SEQ ID NO 140
<211> LENGTH: 18
<212> TYPE: DNA
<213> ORGANISM: Artificial
<220> FEATURE:
<223> OTHER INFORMATION: repair template

<400> SEQUENCE: 140
atgatgctaa tggagaaa                                                  18

<210> SEQ ID NO 141
<211> LENGTH: 16
<212> TYPE: DNA
<213> ORGANISM: Artificial
<220> FEATURE:
<223> OTHER INFORMATION: repair template

<400> SEQUENCE: 141
gcgaataaat gaataa                                                    16

<210> SEQ ID NO 142
<211> LENGTH: 18
<212> TYPE: DNA
<213> ORGANISM: Artificial
<220> FEATURE:
<223> OTHER INFORMATION: repair template

<400> SEQUENCE: 142
atgatgctaa tggagaaa                                                  18

<210> SEQ ID NO 143
<211> LENGTH: 17
<212> TYPE: DNA
<213> ORGANISM: Artificial
<220> FEATURE:
<223> OTHER INFORMATION: repair template

<400> SEQUENCE: 143
taatagtgac ccgtata                                                   17

<210> SEQ ID NO 144
<211> LENGTH: 58
<212> TYPE: DNA
<213> ORGANISM: Artificial
<220> FEATURE:
```

<223> OTHER INFORMATION: repair template

<400> SEQUENCE: 144
atgatgctaa tggagagact acaagttaat ccggcaaagc taaatggccg gccctata          58

<210> SEQ ID NO 145
<211> LENGTH: 20
<212> TYPE: DNA
<213> ORGANISM: Artificial
<220> FEATURE:
<223> OTHER INFORMATION: Nu1 sequence

<400> SEQUENCE: 145
aatggaggac atcaaaaatg          20

<210> SEQ ID NO 146
<211> LENGTH: 46
<212> TYPE: DNA
<213> ORGANISM: Artificial
<220> FEATURE:
<223> OTHER INFORMATION: Nu1 sequence

<400> SEQUENCE: 146
gacggcgcaa actctatggc aagcaatcta taactaactg gctaaa          46

<210> SEQ ID NO 147
<211> LENGTH: 10
<212> TYPE: DNA
<213> ORGANISM: Artificial
<220> FEATURE:
<223> OTHER INFORMATION: Nu1 sequence

<400> SEQUENCE: 147
acaagaaata          10

<210> SEQ ID NO 148
<211> LENGTH: 17
<212> TYPE: DNA
<213> ORGANISM: Artificial
<220> FEATURE:
<223> OTHER INFORMATION: repair template

<400> SEQUENCE: 148
aatggaggac atcaaaa          17

<210> SEQ ID NO 149
<211> LENGTH: 10
<212> TYPE: DNA
<213> ORGANISM: Artificial
<220> FEATURE:
<223> OTHER INFORMATION: repair template

<400> SEQUENCE: 149
acaagaaata          10

<210> SEQ ID NO 150
<211> LENGTH: 87
<212> TYPE: DNA
<213> ORGANISM: Artificial
<220> FEATURE:
<223> OTHER INFORMATION: enolase

<400> SEQUENCE: 150
tttttttgaa attgtactcg gttaactcga aattaatcgt gatcaacatc gtctgggaag          60
aaggcaagac gttcaccatc gccaagt          87

<210> SEQ ID NO 151
<211> LENGTH: 13
<212> TYPE: DNA
<213> ORGANISM: Artificial
<220> FEATURE:
<223> OTHER INFORMATION: repair template

<400> SEQUENCE: 151
ctcggttaac tcg                                                              13

<210> SEQ ID NO 152
<211> LENGTH: 78
<212> TYPE: DNA
<213> ORGANISM: Artificial
<220> FEATURE:
<223> OTHER INFORMATION: repair template

<400> SEQUENCE: 152
tacgcattaa taaacctcct cacttaatcg tgatcaacat cgtctgggaa gaaggcaaga          60
cgttcaccat cgccaagt                                                        78

<210> SEQ ID NO 153
<211> LENGTH: 36
<212> TYPE: DNA
<213> ORGANISM: Lactobacillus crispatus

<400> SEQUENCE: 153
gttttagatg attgttagat caatgaggtt tagatc                                    36

<210> SEQ ID NO 154
<211> LENGTH: 38
<212> TYPE: DNA
<213> ORGANISM: Lactobacillus crispatus

<400> SEQUENCE: 154
gtattctcca cgcatgtgga ggtgtgtgga ggtgatcc                                  38

<210> SEQ ID NO 155
<211> LENGTH: 28
<212> TYPE: DNA
<213> ORGANISM: Lactobacillus crispatus

<400> SEQUENCE: 155
gtattctcca cacatgtgga ggtgatcc                                             28

<210> SEQ ID NO 156
<211> LENGTH: 30
<212> TYPE: DNA
<213> ORGANISM: Lactobacillus crispatus

<400> SEQUENCE: 156
gtatttattt atcttaagag aaatgtaaat                                           30

<210> SEQ ID NO 157
<211> LENGTH: 28
<212> TYPE: DNA
<213> ORGANISM: Lactobacillus crispatus

<400> SEQUENCE: 157
gtattctcca cgcatgtgga ggtgatcc                                             28

<210> SEQ ID NO 158

```
<210> SEQ ID NO 158
<211> LENGTH: 28
<212> TYPE: DNA
<213> ORGANISM: Lactobacillus crispatus

<400> SEQUENCE: 158
gtattctcca cgagtgtggg gatcctat                                       28

<210> SEQ ID NO 159
<211> LENGTH: 28
<212> TYPE: DNA
<213> ORGANISM: Lactobacillus crispatus

<400> SEQUENCE: 159
gtattctcca cgtatgtgga ggtgatcc                                       28

<210> SEQ ID NO 160
<211> LENGTH: 28
<212> TYPE: DNA
<213> ORGANISM: Lactobacillus crispatus

<400> SEQUENCE: 160
gtattctcca cgtatgtgga ggtcatcc                                       28

<210> SEQ ID NO 161
<211> LENGTH: 28
<212> TYPE: DNA
<213> ORGANISM: Lactobacillus crispatus

<400> SEQUENCE: 161
gtattctcca cgcgtgtgga ggtgatcc                                       28

<210> SEQ ID NO 162
<211> LENGTH: 29
<212> TYPE: DNA
<213> ORGANISM: Lactobacillus crispatus

<400> SEQUENCE: 162
gtattctcca cgtatgtgga ggtgatccc                                      29

<210> SEQ ID NO 163
<211> LENGTH: 28
<212> TYPE: DNA
<213> ORGANISM: Lactobacillus crispatus

<400> SEQUENCE: 163
gtattctcca cgtgtgtgga ggtgatcc                                       28

<210> SEQ ID NO 164
<211> LENGTH: 29
<212> TYPE: DNA
<213> ORGANISM: Lactobacillus crispatus

<400> SEQUENCE: 164
gtattctcca cgtgtgtgga ggtgatcct                                      29

<210> SEQ ID NO 165
<211> LENGTH: 38
<212> TYPE: DNA
<213> ORGANISM: Lactobacillus crispatus

<400> SEQUENCE: 165
ttcgtgatta gtttgatctc gttgttgtaa gcgacgaa                            38
```

-continued

```
<210> SEQ ID NO 166
<211> LENGTH: 38
<212> TYPE: DNA
<213> ORGANISM: Lactobacillus crispatus

<400> SEQUENCE: 166
aaattaacac ctctattatt tttttctgta agatactt                              38

<210> SEQ ID NO 167
<211> LENGTH: 38
<212> TYPE: DNA
<213> ORGANISM: Lactobacillus crispatus

<400> SEQUENCE: 167
cccacgttgg taccttcgca aaagctattg ggcgccac                              38

<210> SEQ ID NO 168
<211> LENGTH: 37
<212> TYPE: DNA
<213> ORGANISM: Lactobacillus crispatus

<400> SEQUENCE: 168
aaaaaaagga ttatctgtac catcatctaa cggcgta                               37

<210> SEQ ID NO 169
<211> LENGTH: 38
<212> TYPE: DNA
<213> ORGANISM: Lactobacillus crispatus

<400> SEQUENCE: 169
cagaaaatgg tttatttgtc atttcttcat ggcgggct                              38

<210> SEQ ID NO 170
<211> LENGTH: 38
<212> TYPE: DNA
<213> ORGANISM: Lactobacillus crispatus

<400> SEQUENCE: 170
cagaaaatgg tttatttgtc atttcttcat ggcgggct                              38

<210> SEQ ID NO 171
<211> LENGTH: 38
<212> TYPE: DNA
<213> ORGANISM: Lactobacillus crispatus

<400> SEQUENCE: 171
taaaaaaagg attatctgta ccatcatcta acggcgta                              38

<210> SEQ ID NO 172
<211> LENGTH: 38
<212> TYPE: DNA
<213> ORGANISM: Lactobacillus crispatus

<400> SEQUENCE: 172
cagaaaatgg tttatttgtc atttcttcat ggcgggct                              38

<210> SEQ ID NO 173
<211> LENGTH: 38
<212> TYPE: DNA
<213> ORGANISM: Lactobacillus crispatus

<400> SEQUENCE: 173
cccacgttgg taccttcgca aaagctattg ggcgccac                              38
```

<210> SEQ ID NO 174
<211> LENGTH: 42
<212> TYPE: DNA
<213> ORGANISM: Lactobacillus crispatus

<400> SEQUENCE: 174
gtccaccgta actaagaacg acaggatctt tttctaggtc aa                           42

<210> SEQ ID NO 175
<211> LENGTH: 42
<212> TYPE: DNA
<213> ORGANISM: Lactobacillus crispatus

<400> SEQUENCE: 175
tttatggtgt atcaagaaca acagattcag tttttagttc aa                           42

<210> SEQ ID NO 176
<211> LENGTH: 44
<212> TYPE: DNA
<213> ORGANISM: Lactobacillus crispatus

<400> SEQUENCE: 176
gttgatgggt tatgggaaaa tgcccgttca aaaaatcttt ataa                         44

<210> SEQ ID NO 177
<211> LENGTH: 37
<212> TYPE: DNA
<213> ORGANISM: Lactobacillus crispatus

<400> SEQUENCE: 177
gttgatggga aaatgcccgt tcaaaaaatc tctataa                                 37

<210> SEQ ID NO 178
<211> LENGTH: 43
<212> TYPE: DNA
<213> ORGANISM: Lactobacillus crispatus

<400> SEQUENCE: 178
acctggtgca acagcaacta ctcctgtaac tctgcctgca aac                          43

<210> SEQ ID NO 179
<211> LENGTH: 45
<212> TYPE: DNA
<213> ORGANISM: Lactobacillus crispatus

<400> SEQUENCE: 179
cctgccgggg atggtgaatc cctcggcagg gcgcatttac agtcg                        45

<210> SEQ ID NO 180
<211> LENGTH: 46
<212> TYPE: DNA
<213> ORGANISM: Lactobacillus crispatus

<400> SEQUENCE: 180
gatttaccgt taatagaatc tggcgataaa gtcaacattg ttctgc                       46

<210> SEQ ID NO 181
<211> LENGTH: 42
<212> TYPE: DNA
<213> ORGANISM: Lactobacillus crispatus

<400> SEQUENCE: 181
gcttcaaaca tgggtgagat tatccggaaa ggataagata tg                           42

<210> SEQ ID NO 182
<211> LENGTH: 41
<212> TYPE: DNA
<213> ORGANISM: Lactobacillus crispatus

<400> SEQUENCE: 182
agccttaaca gatggattaa acaatttta acggctggtt t                41

<210> SEQ ID NO 183
<211> LENGTH: 39
<212> TYPE: DNA
<213> ORGANISM: Lactobacillus crispatus

<400> SEQUENCE: 183
aatcgaaagt ccgcatgact tcgttgacaa tagctctca                  39

<210> SEQ ID NO 184
<211> LENGTH: 41
<212> TYPE: DNA
<213> ORGANISM: Lactobacillus crispatus

<400> SEQUENCE: 184
tcaattaact aacaatgctc aaacgttaaa tatggttgat a                41

<210> SEQ ID NO 185
<211> LENGTH: 41
<212> TYPE: DNA
<213> ORGANISM: Lactobacillus crispatus

<400> SEQUENCE: 185
aaaattaact aacaacgcac aaacgttaaa tttggttgat a                41

<210> SEQ ID NO 186
<211> LENGTH: 41
<212> TYPE: DNA
<213> ORGANISM: Lactobacillus crispatus

<400> SEQUENCE: 186
aagcacaaac cttgcataaa tcgagcgatc cgaccagcat a                41

<210> SEQ ID NO 187
<211> LENGTH: 41
<212> TYPE: DNA
<213> ORGANISM: Lactobacillus crispatus

<400> SEQUENCE: 187
tgccgtaaca attgacatgg caaaagagct ttgcatgatg t                41

<210> SEQ ID NO 188
<211> LENGTH: 41
<212> TYPE: DNA
<213> ORGANISM: Lactobacillus crispatus

<400> SEQUENCE: 188
ttaactaaca atgctcaaac gttaaatatg gttgataaag a                41

<210> SEQ ID NO 189
<211> LENGTH: 40
<212> TYPE: DNA
<213> ORGANISM: Lactobacillus crispatus

<400> SEQUENCE: 189
ataaaaaata ggcgattccg caatacttgc gaacctatcg         40

<210> SEQ ID NO 190
<211> LENGTH: 41
<212> TYPE: DNA
<213> ORGANISM: Lactobacillus crispatus

<400> SEQUENCE: 190
ttaactaaca atgctcaaac gttaaatatg gttgataaag a        41

<210> SEQ ID NO 191
<211> LENGTH: 41
<212> TYPE: DNA
<213> ORGANISM: Lactobacillus crispatus

<400> SEQUENCE: 191
gggcttaatt gtatcaatgc taataagaat gttctgcccg g        41

<210> SEQ ID NO 192
<211> LENGTH: 41
<212> TYPE: DNA
<213> ORGANISM: Lactobacillus crispatus

<400> SEQUENCE: 192
catgaaaata atctgctact tttgctaaat cttcagcttt t        41

<210> SEQ ID NO 193
<211> LENGTH: 41
<212> TYPE: DNA
<213> ORGANISM: Lactobacillus crispatus

<400> SEQUENCE: 193
gaaattaatg ttggtgcatt aatggaagat gcatatttag a        41

<210> SEQ ID NO 194
<211> LENGTH: 41
<212> TYPE: DNA
<213> ORGANISM: Lactobacillus crispatus

<400> SEQUENCE: 194
ctgctcaatt agttaaaggt tttggtggtt tggcttctgc g        41

<210> SEQ ID NO 195
<211> LENGTH: 246
<212> TYPE: DNA
<213> ORGANISM: Escherichia coli

<400> SEQUENCE: 195
aatggaattt aaattagatg aatcacaaga aaccgagatt aaaacttttg ttatgggcgt    60
ggttaaagac gctattaaac aagccactac caccagcaaa ccatatttga accgcaaaga   120
aattgctaag tattttggcg tggctgaatc aactattaca tattgggctt ctttagggat   180
gcctgtcgct gtcatagacg ggcgcaaact ctatggcaag caatctataa ctaactggct   240
aaaatt                                                              246